(12) United States Patent
Scarpaci et al.

(10) Patent No.: US 10,881,778 B2
(45) Date of Patent: Jan. 5, 2021

(54) MEDICAL TREATMENT SYSTEM AND METHODS USING A PLURALITY OF FLUID LINES

(71) Applicant: DEKA Products Limited Partnership, Manchester, NH (US)

(72) Inventors: Jacob W. Scarpaci, Manchester, NH (US); Robert J. Bryant, Jr., Manchester, NH (US); Geoffrey P. Spencer, Manchester, NH (US); David J. Hibbard, Bedford, NH (US); James D. Dale, Nashua, NH (US); John M. Kerwin, Manchester, NH (US); Andrew S. Coll, Goffstown, NH (US); David A. Beavers, Manchester, NH (US); David W. McGill, Woodstock, GA (US); Simon C. Helmore, Cambridge, MA (US)

(73) Assignee: DEKA Products Limited Partnership, Manchester, NH (US)

(*) Notice: Subject to any disclaimer, the term of this patent is extended or adjusted under 35 U.S.C. 154(b) by 204 days.

(21) Appl. No.: 15/992,037

(22) Filed: May 29, 2018

(65) Prior Publication Data
US 2018/0361048 A1    Dec. 20, 2018

Related U.S. Application Data

(62) Division of application No. 15/432,265, filed on Feb. 14, 2017, now Pat. No. 9,981,079, which is a division
(Continued)

(51) Int. Cl.
*H05B 1/02* (2006.01)
*A61M 1/28* (2006.01)
(Continued)

(52) U.S. Cl.
CPC .......... *A61M 1/28* (2013.01); *A61M 1/1006* (2014.02); *A61M 1/1664* (2014.02);
(Continued)

(58) Field of Classification Search
CPC .... A61M 1/28; A61M 1/1006; A61M 1/1614; A61M 1/282; A61M 1/288;
(Continued)

(56) References Cited

U.S. PATENT DOCUMENTS

| 3,656,873 A | 4/1972 | Schiff |
| 4,155,852 A | 5/1979 | Fischel et al. |

(Continued)

FOREIGN PATENT DOCUMENTS

| CA | 1119971 A | 3/1982 |
| CA | 2341993 A1 | 3/2000 |

(Continued)

OTHER PUBLICATIONS

[No Author Listed] Homechoice Patient At-Home Guide, Jun. 1998. 84 pages.
(Continued)

*Primary Examiner* — Mark H Paschall
(74) *Attorney, Agent, or Firm* — Wolf, Greenfield & Sacks, P.C.

(57) ABSTRACT

A medical treatment system, such as peritoneal dialysis system, may include control and other features to enhance patient comfort and ease of use. For example, a peritoneal dialysis system may include a control system that can adjust the volume of fluid infused into the peritoneal cavity to prevent the intraperitoneal fluid volume from exceeding a pre-determined amount. The control system can adjust by adding one or more therapy cycles, allowing for fill volumes during each cycle to be reduced. The control system may continue to allow the fluid to drain from the peritoneal cavity
(Continued)

as completely as possible before starting the next therapy cycle. The control system may also adjust the dwell time of fluid within the peritoneal cavity during therapy cycles in order to complete a therapy within a scheduled time period. The cycler may also be configured to have a heater control system that monitors both the temperature of a heating tray and the temperature of a bag of dialysis fluid in order to bring the temperature of the dialysis fluid rapidly to a specified temperature, with minimal temperature overshoot.

7 Claims, 106 Drawing Sheets

Related U.S. Application Data of application No. 13/667,679, filed on Nov. 2, 2012, now Pat. No. 9,861,732.

(60) Provisional application No. 61/555,926, filed on Nov. 4, 2011.

(51) Int. Cl.
  A61M 1/16  (2006.01)
  A61M 1/10  (2006.01)
  F04B 43/02  (2006.01)
  F16L 53/00  (2018.01)
  F17D 1/00  (2006.01)
  H02J 7/00  (2006.01)

(52) U.S. Cl.
  CPC .......... *A61M 1/282* (2014.02); *A61M 1/288* (2014.02); *F04B 43/02* (2013.01); *F16L 53/00* (2013.01); *F17D 1/00* (2013.01); *H02J 7/007* (2013.01); *H05B 1/025* (2013.01); *A61M 2205/122* (2013.01); *A61M 2205/128* (2013.01); *A61M 2205/15* (2013.01); *A61M 2205/3368* (2013.01); *A61M 2205/36* (2013.01); *A61M 2205/50* (2013.01); *A61M 2205/8206* (2013.01); *A61M 2205/8212* (2013.01); *Y10T 137/6416* (2015.04); *Y10T 137/85978* (2015.04)

(58) Field of Classification Search
  CPC ...... A61M 2205/122; A61M 2205/128; A61M 1/15; A61M 2205/3368; A61M 2205/36; A61M 2205/50; A61M 2205/8206; F04B 43/02; F16L 53/00; H05B 1/02; H05B 3/085; H05B 1/025
  USPC ................ 219/497, 486, 483, 505, 494, 507
  See application file for complete search history.

(56) References Cited

U.S. PATENT DOCUMENTS

| | | |
|---|---|---|
| 4,381,545 A | 4/1983 | Biddle, III et al. |
| 4,574,876 A | 3/1986 | Aid |
| 4,628,186 A | 12/1986 | Bergemann et al. |
| 4,731,072 A | 3/1988 | Aid |
| 4,844,072 A | 7/1989 | French et al. |
| 4,906,816 A | 3/1990 | van Leerdam |
| 5,293,028 A | 3/1994 | Payne |
| 5,324,422 A | 6/1994 | Colleran et al. |
| 5,350,357 A | 9/1994 | Kamen et al. |
| 5,420,962 A | 5/1995 | Bakke |
| 5,421,823 A | 6/1995 | Kamen et al. |
| 5,427,509 A | 6/1995 | Chapman et al. |
| 5,476,444 A | 12/1995 | Keeling et al. |
| 5,482,440 A | 1/1996 | Dennehey et al. |
| 5,486,286 A | 1/1996 | Peterson et al. |
| 5,609,572 A | 3/1997 | Lang |
| 5,645,531 A | 7/1997 | Thompson et al. |
| 5,676,644 A | 10/1997 | Toays et al. |
| 5,722,947 A | 3/1998 | Jeppsson et al. |
| 5,795,317 A | 8/1998 | Brierton et al. |
| 5,906,978 A | 5/1999 | Ash |
| 5,925,011 A | 7/1999 | Faict et al. |
| 5,938,634 A | 8/1999 | Packard |
| 6,228,047 B1 | 5/2001 | Dadson |
| 6,264,680 B1 | 7/2001 | Ash |
| 6,382,923 B1 | 5/2002 | Gray |
| 6,416,293 B1 | 7/2002 | Bouchard et al. |
| 6,481,980 B1 | 11/2002 | Vandlik et al. |
| 6,491,656 B1 | 12/2002 | Morris |
| 6,520,747 B2 | 2/2003 | Gray et al. |
| 6,522,844 B2 | 2/2003 | Yamane et al. |
| RE38,203 E | 7/2003 | Kelly |
| 6,638,478 B1 | 10/2003 | Treu et al. |
| 6,758,975 B2 | 7/2004 | Peabody et al. |
| 6,814,547 B2 | 11/2004 | Childers et al. |
| 6,852,090 B2 | 2/2005 | Burbank et al. |
| 6,860,846 B2 | 3/2005 | Odak et al. |
| 6,905,479 B1 | 6/2005 | Bouchard et al. |
| 6,940,047 B2 | 9/2005 | van Kesteren et al. |
| 6,949,079 B1 | 9/2005 | Westberg et al. |
| 6,953,323 B2 | 10/2005 | Childers et al. |
| 7,041,076 B1 | 5/2006 | Westberg et al. |
| 7,153,285 B2 | 12/2006 | Lauman et al. |
| 7,153,286 B2 | 12/2006 | Busby et al. |
| 7,175,606 B2 | 2/2007 | Bowman, Jr. et al. |
| 7,238,164 B2 | 7/2007 | Childers et al. |
| 7,364,563 B2 | 4/2008 | Lucke et al. |
| 7,473,238 B2 | 1/2009 | Brugger et al. |
| 7,476,209 B2 | 1/2009 | Gara et al. |
| 7,544,179 B2 | 6/2009 | Distler et al. |
| 7,559,524 B2 | 7/2009 | Gray et al. |
| 7,563,248 B2 | 7/2009 | Smisson, III et al. |
| 7,727,220 B2 | 6/2010 | Wieslander et al. |
| 7,736,328 B2 | 6/2010 | Childers et al. |
| 7,758,532 B2 | 7/2010 | Mori et al. |
| 7,776,006 B2 | 8/2010 | Childers et al. |
| 7,780,619 B2 | 8/2010 | Brugger et al. |
| 7,794,141 B2 | 9/2010 | Perry et al. |
| 7,867,214 B2 | 1/2011 | Childers et al. |
| 7,935,074 B2 | 5/2011 | Plahey et al. |
| 7,955,295 B2 | 6/2011 | Lee et al. |
| 8,027,572 B2 | 9/2011 | Bedingfield et al. |
| 8,029,454 B2 | 10/2011 | Kelly et al. |
| 8,105,265 B2 | 1/2012 | Demers et al. |
| 8,113,244 B2 | 2/2012 | Kamen et al. |
| 8,197,439 B2 | 6/2012 | Wang et al. |
| 8,219,196 B2 | 7/2012 | Torgerson |
| 8,330,579 B2 | 12/2012 | Kneip et al. |
| 8,350,195 B2 | 1/2013 | Hedmann et al. |
| 8,366,316 B2 | 2/2013 | Kamen et al. |
| 8,366,655 B2 | 2/2013 | Kamen et al. |
| 8,512,553 B2 | 8/2013 | Cicchello et al. |
| 8,535,525 B2 | 9/2013 | Heyes et al. |
| 8,597,229 B2 | 12/2013 | Pan |
| 8,597,505 B2 | 12/2013 | Fulkerson et al. |
| 8,612,055 B2 | 12/2013 | Ali et al. |
| 8,673,139 B2 | 3/2014 | Hedmann et al. |
| 8,708,950 B2 | 4/2014 | Scarpaci et al. |
| 8,764,702 B2 | 7/2014 | Childers et al. |
| 8,803,044 B2 | 8/2014 | Kienman et al. |
| 8,821,475 B2 | 9/2014 | Distler et al. |
| 8,840,581 B2 | 9/2014 | McGill et al. |
| 8,858,787 B2 | 10/2014 | Muller et al. |
| 8,870,812 B2 | 10/2014 | Alberti et al. |
| 8,882,700 B2 | 11/2014 | Chapman et al. |
| 8,968,232 B2 | 3/2015 | Kamen et al. |
| 9,022,969 B2 | 5/2015 | Helmore et al. |
| 9,028,440 B2 | 5/2015 | Helmore et al. |
| 9,066,668 B2 | 6/2015 | McGrath et al. |
| 9,072,831 B2 | 7/2015 | Kelly et al. |
| 9,078,971 B2 | 7/2015 | Scarpaci et al. |
| 9,084,566 B2 | 7/2015 | Zdeblick |
| 9,121,403 B2 | 9/2015 | Lanigan et al. |
| 9,248,225 B2 | 2/2016 | Demers et al. |

(56) References Cited

U.S. PATENT DOCUMENTS

| | | | |
|---|---|---|---|
| 9,302,039 B2 | 4/2016 | Kelly et al. |
| 9,358,332 B2 | 6/2016 | McGill et al. |
| 9,366,781 B2 | 6/2016 | Scarpaci et al. |
| 9,514,283 B2 | 12/2016 | Childers et al. |
| 9,561,317 B2 | 2/2017 | Distler et al. |
| 9,561,318 B2 | 2/2017 | Distler et al. |
| 9,713,667 B2 | 7/2017 | Distler et al. |
| 9,750,865 B2 | 9/2017 | Vasta et al. |
| 9,770,546 B2 | 9/2017 | Vasta |
| 9,839,775 B2 | 12/2017 | McGill et al. |
| 9,839,776 B2 | 12/2017 | Helmore et al. |
| 9,861,732 B2 | 1/2018 | Scarpaci et al. |
| 9,907,972 B2 | 3/2018 | Kameli |
| 9,981,079 B2 | 5/2018 | Scarpaci et al. |
| 9,987,410 B2 | 6/2018 | Helmore et al. |
| 10,058,694 B2 | 8/2018 | Norris et al. |
| 10,098,996 B2 | 10/2018 | Scarpaci et al. |
| 10,172,988 B2 | 1/2019 | McGill et al. |
| 10,195,330 B2 | 2/2019 | Coll et al. |
| 10,201,647 B2 | 2/2019 | Norris et al. |
| 10,265,451 B2 | 4/2019 | McGill et al. |
| 10,485,914 B2 | 11/2019 | Scarpaci et al. |
| 10,576,194 B2 | 3/2020 | Distler et al. |
| 2003/0220607 A1 | 11/2003 | Busby et al. |
| 2005/0095141 A1 | 5/2005 | Lanigan et al. |
| 2005/0209563 A1 | 9/2005 | Hopping et al. |
| 2007/0278155 A1 | 12/2007 | Lo et al. |
| 2008/0015493 A1 | 1/2008 | Childers et al. |
| 2008/0058697 A1 | 3/2008 | Kamen et al. |
| 2008/0058712 A1 | 3/2008 | Plahey |
| 2008/0240929 A1 | 10/2008 | Kamen et al. |
| 2009/0008331 A1* | 1/2009 | Wilt .......... A61M 1/3672 210/647 |
| 2009/0012450 A1 | 1/2009 | Shah et al. |
| 2009/0213521 A1* | 8/2009 | Bedingfield .......... A61M 5/445 361/194 |
| 2009/0294359 A1 | 12/2009 | Hopping et al. |
| 2010/0076516 A1 | 3/2010 | Padiy et al. |
| 2010/0191181 A1 | 7/2010 | Childers et al. |
| 2011/0005992 A1 | 1/2011 | Kelly et al. |
| 2011/0071465 A1* | 3/2011 | Wang .......... G16H 20/40 604/67 |
| 2011/0092893 A1 | 4/2011 | Demers et al. |
| 2011/0218600 A1 | 9/2011 | Kamen et al. |
| 2011/0303598 A1 | 12/2011 | Lo et al. |
| 2013/0165847 A1 | 6/2013 | Scarpaci et al. |
| 2013/0184638 A1 | 7/2013 | Scarpaci et al. |
| 2013/0193041 A1 | 8/2013 | Rohde |
| 2014/0288488 A1 | 9/2014 | Distler et al. |
| 2014/0288489 A1 | 9/2014 | Distler et al. |
| 2014/0288490 A1 | 9/2014 | Distler et al. |
| 2015/0151047 A1 | 6/2015 | Anderson et al. |
| 2016/0030657 A1 | 2/2016 | Kelly et al. |
| 2016/0082173 A1 | 3/2016 | Coll et al. |
| 2016/0101227 A1 | 4/2016 | Norris et al. |
| 2016/0101278 A1 | 4/2016 | Norris et al. |
| 2016/0144093 A1 | 5/2016 | Demers et al. |
| 2018/0256803 A1 | 9/2018 | Helmore et al. |
| 2018/0361048 A1 | 12/2018 | Scarpaci et al. |
| 2019/0060629 A1 | 2/2019 | Norris et al. |
| 2019/0099534 A1 | 4/2019 | McGill et al. |
| 2019/0167883 A1 | 6/2019 | Girouard et al. |
| 2019/0314565 A1 | 10/2019 | McGill et al. |
| 2019/0321535 A1 | 10/2019 | Beavers et al. |
| 2019/0344002 A1 | 11/2019 | McGill et al. |
| 2020/0086030 A1 | 3/2020 | Scarpaci et al. |

FOREIGN PATENT DOCUMENTS

| | | |
|---|---|---|
| CA | 2704411 A1 | 5/2009 |
| DE | 19704564 A1 | 8/1998 |
| EP | 1 195 171 A2 | 4/2002 |
| JP | H06-207845 A | 7/1994 |
| JP | 2004-147721 A | 5/2004 |
| WO | WO 2000/057935 A1 | 10/2000 |
| WO | WO 01/19430 A1 | 3/2001 |
| WO | WO 2001/37895 A2 | 5/2001 |
| WO | WO 03/099353 A2 | 12/2003 |

OTHER PUBLICATIONS

[No Author Listed] Patient At-Home Guide, HomeChoice Automated PD System. Version 2.0 (published May 1997); Baxter Healthcare Corporation. Copyright 1994. 61 pages.

[No Author Listed] 2008K2 Hemodialysis Machine Operator's Manual. Fresenius Medical Care. https://laz3qm2bxvodlae4oellp3es-wpengine.netdna-ssl.com/wp-content/uploads/2018/09/490136_Rev_K.pdf. 2000-2018. 240 pages.

Choppy et al., Architectural patterns for problem frames—relating software requirements and architectures. IEEE Proceedings: Software, IEE. Stevenage, GB. Aug. 5, 2005;52(4):198-208.

Krasner et al., A cookbook for using the model-view-controller user interface paradigm in smalltalk-80. JOOP. Aug. 1, 1988;1(3):26-49.

Harel et al., Statecharts: A visual formalism for complex systems. Retrieved from the Internet: http://www.wisdom.weizmann.ac.il/~harel/Statecharts87.pdf> Retrieved on Jul. 2, 2002.

Office Action for AU Application No. 2017200700 filed Feb. 2, 2017, which Office Action is dated Feb. 8, 2018, and claims as pending for AU Application No. 2017200700 as of Feb. 8, 2018.

Extended European Search Report for EP Application No. 17157596.2 filed Feb. 23, 2017, which Extended European Search Report is dated Aug. 4, 2017, and claims as pending for EP Application No. 17157596.2 as of Aug. 4, 2017.

Extended European Search Report for EP Application No. 19150706.0 filed Nov. 2, 2012, which Search Report is dated Mar. 7, 2019 and claims as pending for EP Application No. 19150706.0 as of Mar. 7, 2019.

Office Action for JP Application No. 2016-202018 filed Oct. 13, 2016, which Office Action is dated Sep. 19, 2017, and claims as pending for JP Application No. 2016-202018 as of Sep. 19, 2017.

U.S. Appl. No. 15/012,764, filed Feb. 1, 2016, Demers et al.
U.S. Appl. No. 16/207,349. filed Dec. 3, 2018, McGill et al.
U.S. Appl. No. 16/863,454, filed Apr, 30, 2020, Scarpaci et al.
U.S. Appl. No. 16/112,287, filed Aug. 24, 2018, Norris et al.
U.S. Appl. No. 16/247,204, filed Jan. 14, 2019, Beavers et al.
AU 2017200700, Feb. 8, 2018, Office Action.
EP 17157596.2, Aug. 4, 2017, Extended European Search Report.
EP 19150706.0, Mar. 7, 2019, Extended European Search Report.
JP 2016-202018, Sep. 19, 2017, Office Action.

* cited by examiner

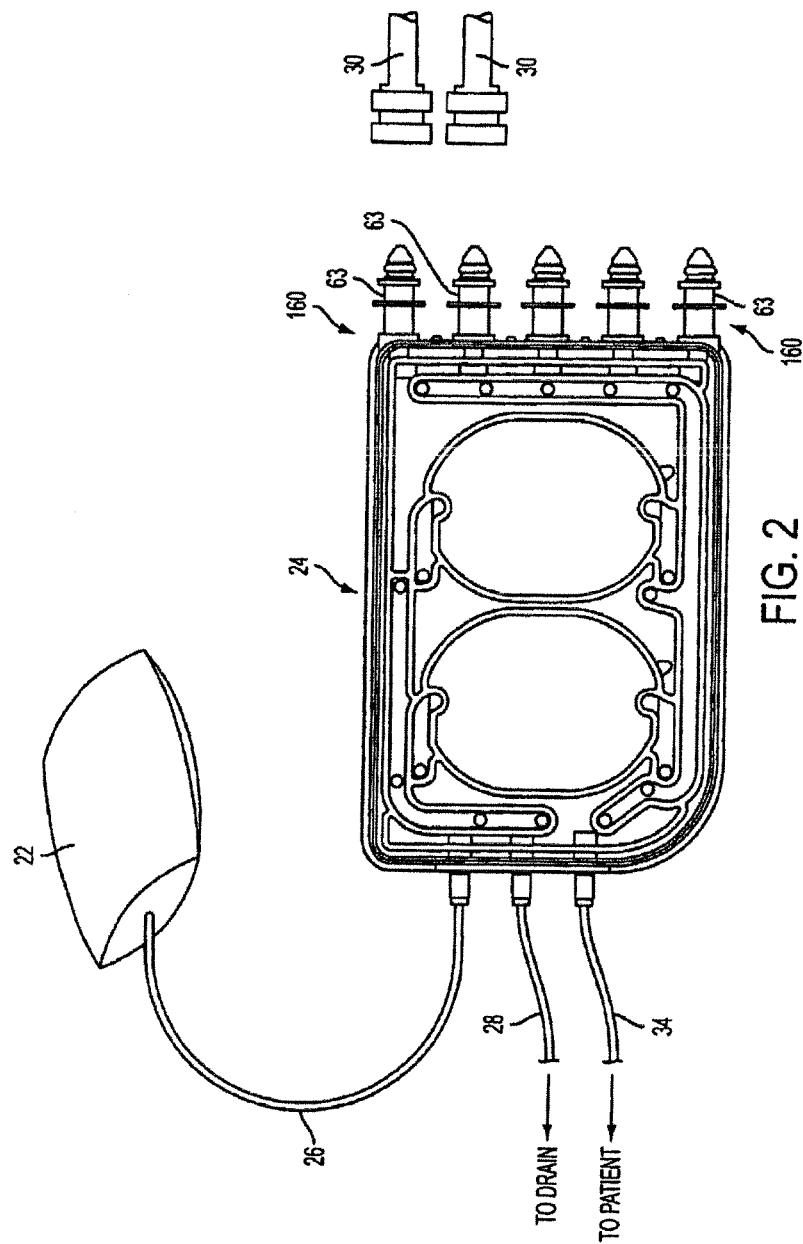

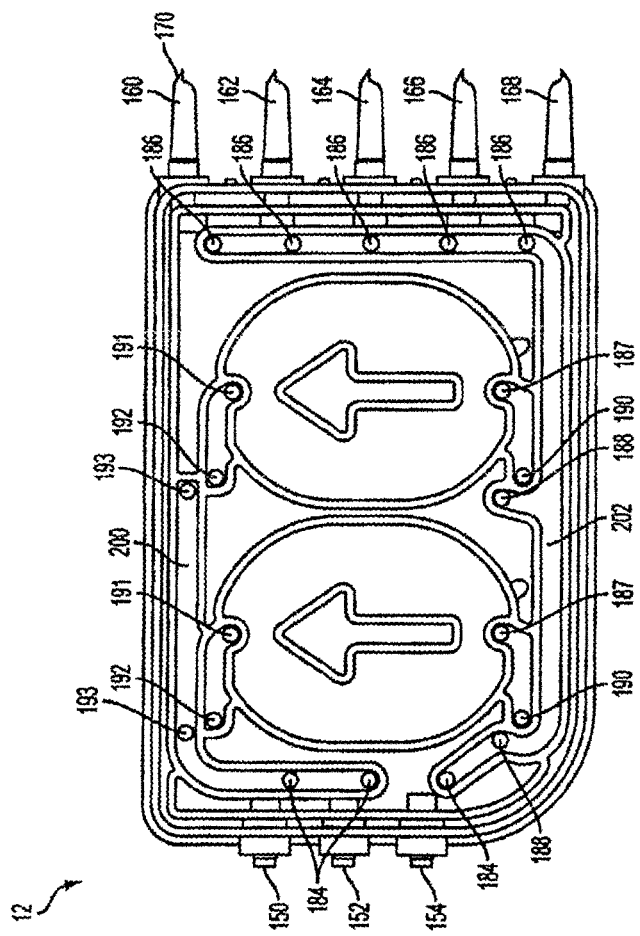

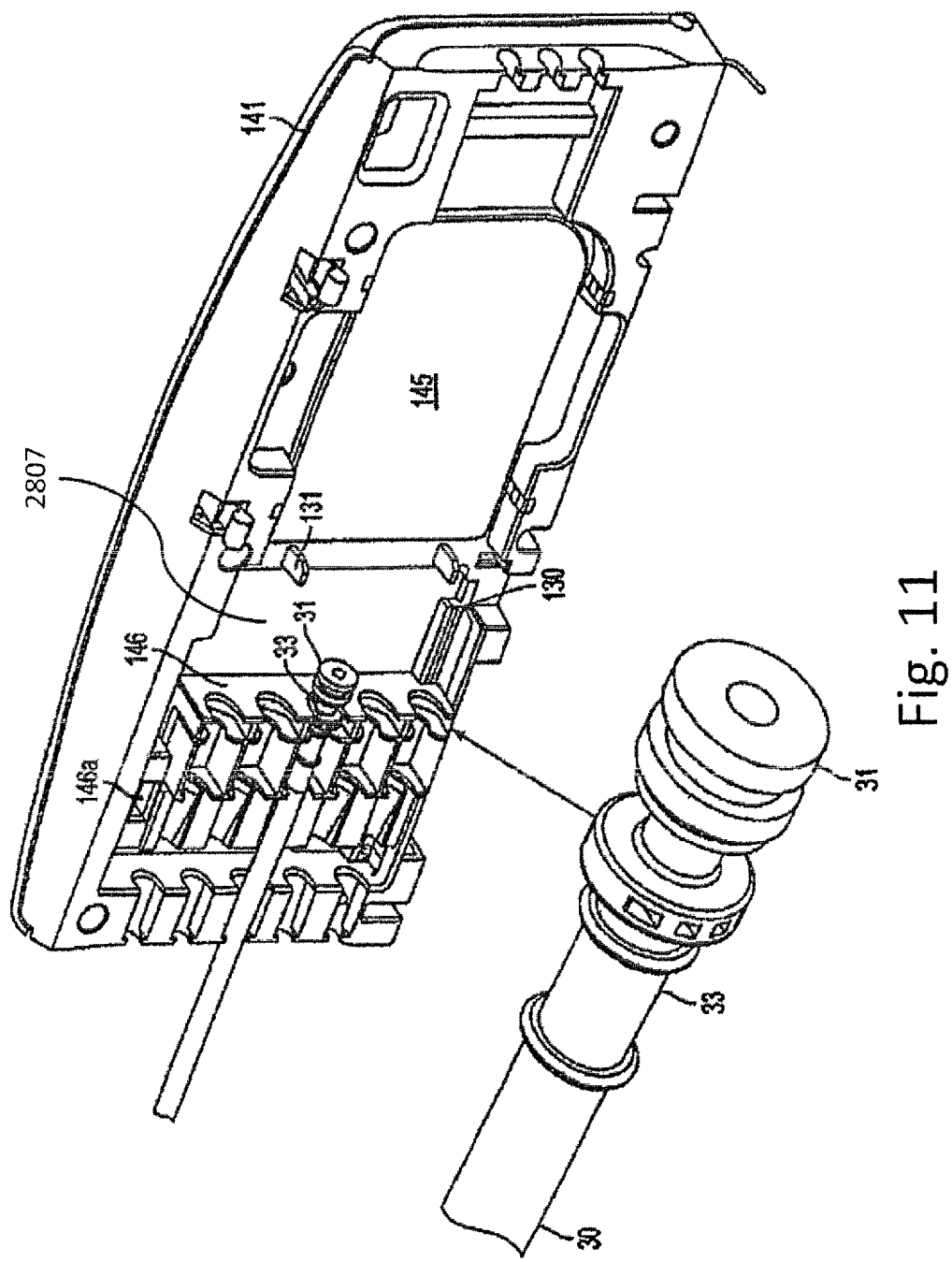

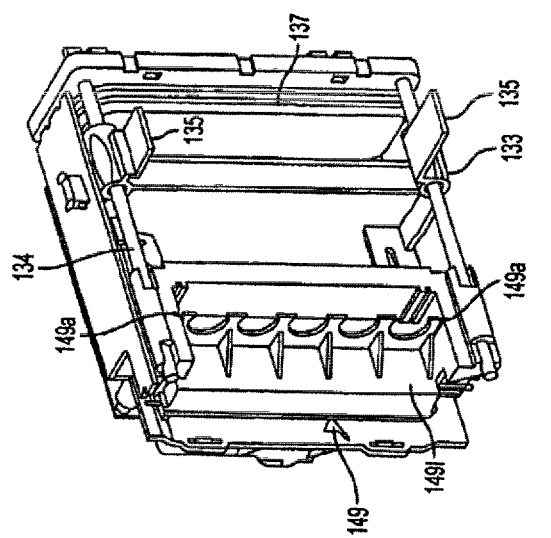

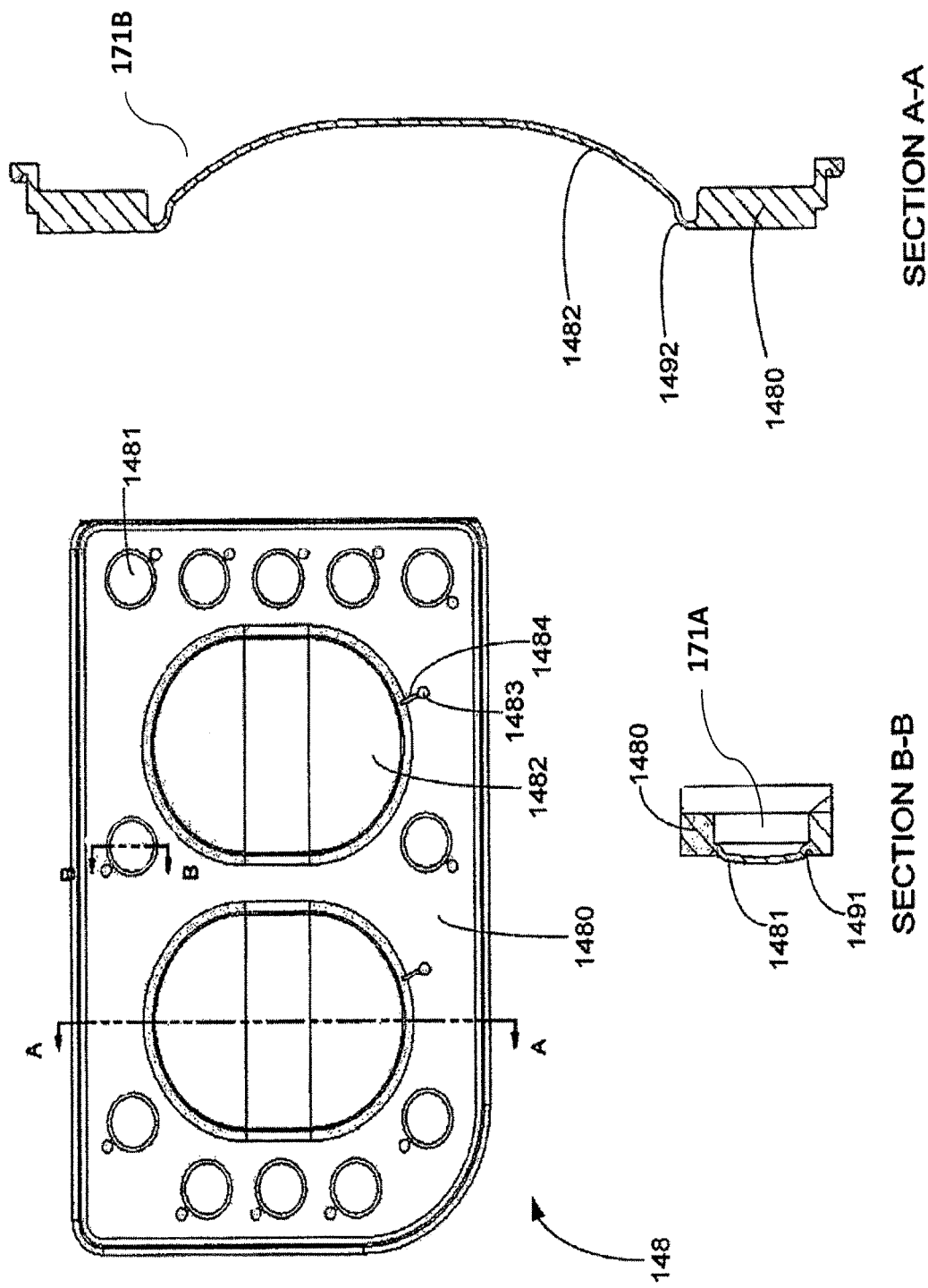

MEDICAL TREATMENT SYSTEM AND METHODS USING A PLURALITY OF FLUID LINES

This application is a division of U.S. patent application Ser. No. 15/432,265, filed Feb. 14, 2017, now U.S. Pat. No. 9,981,079, which is a division of U.S. patent application Ser. No. 13/667,679, filed Nov. 2, 2012, now U.S. Pat. No. 9,861,732, which claims the benefit of U.S. Provisional Application No. 61/555,926, filed Nov. 4, 2011, all of which are hereby incorporated by reference in their entireties.

BACKGROUND

Peritoneal Dialysis (PD) involves the periodic infusion of sterile aqueous solution (called peritoneal dialysis solution, or dialysate) into the peritoneal cavity of a patient. Diffusion and osmosis exchanges take place between the solution and the bloodstream across the natural body membranes. These exchanges transfer waste products to the dialysate that the kidneys normally excrete. The waste products typically consist of solutes like sodium and chloride ions, and other compounds normally excreted through the kidneys like urea, creatinine, and water. The diffusion of water across the peritoneal membrane during dialysis is called ultrafiltration.

Conventional peritoneal dialysis solutions include dextrose in concentrations sufficient to generate the necessary osmotic pressure to remove water from the patient through ultrafiltration.

Continuous Ambulatory Peritoneal Dialysis (CAPD) is a popular form of PD. A patient performs CAPD manually about four times a day. During a drain/fill procedure for CAPD, the patient initially drains spent peritoneal dialysis solution from his/her peritoneal cavity, and then infuses fresh peritoneal dialysis solution into his/her peritoneal cavity. This drain and fill procedure usually takes about 1 hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours.

The APD sequence typically lasts for several hours. It often begins with an initial drain phase to empty the peritoneal cavity of spent dialysate. The APD sequence then proceeds through a succession of fill, dwell, and drain phases that follow one after the other. Each fill/dwell/drain sequence is called a cycle.

During the fill phase, the cycler transfers a predetermined volume of fresh, warmed dialysate into the peritoneal cavity of the patient. The dialysate remains (or "dwells") within the peritoneal cavity for a period of time. This is called the dwell phase. During the drain phase, the cycler removes the spent dialysate from the peritoneal cavity.

The number of fill/dwell/drain cycles that are required during a given APD session depends upon the total volume of dialysate prescribed for the patient's APD regimen, and is either entered as part of the treatment prescription or calculated by the cycler.

APD can be and is practiced in different ways.

Continuous Cycling Peritoneal Dialysis (CCPD) is one commonly used APD modality. During each fill/dwell/drain phase of CCPD, the cycler infuses a prescribed volume of dialysate. After a prescribed dwell period, the cycler completely drains this liquid volume from the patient, leaving the peritoneal cavity empty, or "dry." Typically, CCPD employs 4-8 fill/dwell/drain cycles to achieve a prescribed therapy volume.

After the last prescribed fill/dwell/drain cycle in CCPD, the cycler infuses a final fill volume. The final fill volume dwells in the patient for an extended period of time. It is drained either at the onset of the next CCPD session in the evening, or during a mid-day exchange. The final fill volume can contain a different concentration of dextrose than the fill volume of the successive CCPD fill/dwell/drain fill cycles the cycler provides.

Intermittent Peritoneal Dialysis (IPD) is another APD modality. IPD is typically used in acute situations, when a patient suddenly enters dialysis therapy. IPD can also be used when a patient requires PD, but cannot undertake the responsibilities of CAPD or otherwise do it at home.

Like CCPD, IPD involves a series of fill/dwell/drain cycles. Unlike CCPD, IPD does not include a final fill phase. In IPD, the patient's peritoneal cavity is left free of dialysate (or "dry") in between APD therapy sessions.

Tidal Peritoneal Dialysis (TPD) is another APD modality. Like CCPD, TPD includes a series of fill/dwell/drain cycles. Unlike CCPD, TPD does not completely drain dialysate from the peritoneal cavity during each drain phase. Instead, TPD establishes a base volume during the first fill phase and drains only a portion of this volume during the first drain phase. Subsequent fill/dwell/drain cycles infuse and then drain a replacement volume on top of the base volume. The last drain phase removes all dialysate from the peritoneal cavity.

There is a variation of TPD that includes cycles during which the patient is completely drained and infused with a new full base volume of dialysis.

TPD can include a final fill cycle, like CCPD. Alternatively, TPD can avoid the final fill cycle, like IPD.

APD offers flexibility and quality of life enhancements to a person requiring dialysis. APD can free the patient from the fatigue and inconvenience that the day to day practice of CAPD represents to some individuals. APD can give back to the patient his or her waking and working hours free of the need to conduct dialysis exchanges.

Still, the complexity and size of past machines and associated disposables for various APD modalities have dampened widespread patient acceptance of APD as an alternative to manual peritoneal dialysis methods.

SUMMARY OF INVENTION

Aspects of the invention relate to various components, systems and methods for use in medical applications, including medical infusion operations such as peritoneal dialysis. In some cases, aspects of the invention are limited to applications in peritoneal dialysis, while others to more general dialysis applications (e.g., hemodialysis) or infusion applications, while others to more general methods or processes. Thus, aspects of the invention are not necessarily limited to APD systems and methods, although many of the illustrative embodiments described relate to APD.

In one aspect of the invention, a tubing state detector may be included with a dialysis system for detecting the presence or absence of a tubing segment, such as a portion of a patient line to be connected to a patient access for delivering dialysate to the peritoneal cavity. The tubing state detector may include a first light emitter having a first optical axis directed toward a space in which a tubing segment is to be positioned, and a second light emitter, adjacent to the first light emitter and having a second optical axis directed toward the space. An optical sensor may be positioned on a side of the space opposite the first and second light emitters and arranged to receive light emitted by the first and second light emitters to determine a presence or absence of a tubing segment in the space.

In one embodiment, the first optical axis may be approximately collinear with a sensor optical axis of the optical sensor, and may pass approximately through a center of a tubing segment when the tubing segment is positioned in the space. In contrast, the second optical axis may be approximately parallel to the first optical axis, and thus, the second optical axis may be offset from the center of the tubing segment and sensor optical axis.

The optical sensor may be arranged to detect a range of light levels when a tubing segment is in the space, e.g., a light level that is higher and/or lower that a light level detected when the tubing segment is absent from the space. However, the optical sensor may detect a lower light level from the second light emitter when a tubing segment is in the space that is detected when the tubing segment it absent from the space. For example, with a tubing segment in the space, a detected light level for both the first and second light emitters may be within about 15-20% of a calibration light level for the first and second light emitters, where the calibration light level is a level detected when a tubing segment is known to be absent from the space. However, with a tubing segment not in the space, a detected light level for the second light emitter may be less than about 15-20% of the calibration light level for the second light emitter. This lower light level detection may be used to determine that a tubing segment is in the space.

In another embodiment, the tubing state detector may be arranged to detect whether there is liquid present in the tubing segment, e.g., whether the patient line is properly primed for use. For example, the detector may include a third light emitter having a third optical axis that is arranged at an oblique angle relative to the sensor optical axis. The oblique angle may be between 90 and 180 degrees, e.g., about 110-120 degrees. The optical sensor and third light emitter may be arranged such that with a tubing segment in the space and the tubing segment containing no liquid, a light level detected by the optical sensor may be over about 150% of a calibration light level detected with no tubing segment in the space. In addition, with a tubing segment in the space and containing liquid, the optical sensor may detect a light level from the third light emitter that is less than about 125% of the calibration light level. Thus, the optical sensor and third light emitter may be arranged such that with a tubing segment in the space and the tubing segment containing no liquid, a light level detected by the optical sensor may be over a threshold level, and with a tubing segment in the space and the tubing segment containing liquid, a light level detected by the optical sensor is less than the threshold level. This arrangement may allow the detector to determine whether liquid is contained in the patient line, e.g., whether the patient line is properly primed. In one embodiment, the third light emitter and the optical sensor may be arranged such that the optical sensor receives light from the third light emitter both when a tubing segment in the space is filled with liquid and when a tubing segment in the space is empty of liquid. Thus, the presence or absence of liquid in the tubing segment may be determined based on a detected light intensity rather than the presence or absence of light. This may help the system avoid false condition detection that might result if the detector were to use the absence of detected light to indicate a condition, such as the presence of liquid in the tubing segment. That is, since the optical sensor detects light from the third light emitter regardless of the presence of liquid, the optical sensor may be able to determine whether the third light emitter is operating properly (or at all). The space in which the tubing segment is held may be arranged to receive and hold the tubing segment, which may have a cylindrical outer surface, without substantially deforming the tubing segment. Thus, the detector may operate without deforming the tubing segment, thereby avoiding potential problems such as pinching, reduced flow in the tubing segment, etc.

In another aspect of the invention, a tubing state detector for detecting whether liquid is contained in a tubing segment may include a fill state light emitter having an optical axis that is arranged to pass through a space in which a tubing segment is to be positioned. The space may be arranged to receive a tubing segment having a cylindrical outer surface and to hold the tubing segment without substantially deforming the tubing segment. Thus, the detector may be useable with common tubing frequently used in dialysis systems and without requiring special purpose fittings or other components. An optical sensor may be positioned on a side of the space opposite the fill state light emitter and arranged to receive light emitted by the fill state light emitter to determine a presence or absence of liquid in the tubing segment. In one embodiment, the optical sensor may have a sensor optical axis that is arranged at an oblique angle to the optical axis of the fill state light emitter, and may be arranged to detect whether liquid is present in the tubing segment or not. The oblique angle may be between 90 and 180 degrees, e.g., about 110-120 degrees, and the optical sensor may be arranged to receive light from the fill state light emitter whether there is liquid present in the tubing segment or not.

The optical sensor and fill state light emitter may be arranged such that with a tubing segment in the space and the tubing segment containing no liquid, a light level detected by the optical sensor is over a threshold level, and such that with a tubing segment in the space and the tubing segment containing liquid, a light level detected by the optical sensor is less than the threshold level. Thus, if the optical sensor detects a light level below a threshold, e.g., below about 125-150% of a light level detected with no tubing segment in the space, a determination may be made that the tubing segment is filled with liquid. The fill state light emitter (as with other light emitters) may be a light emitting diode or other electromagnetic radiation emitting component, such as a device that emits infrared, UV, visible light, or other light in the visible and/or invisible spectrum.

In one embodiment, the tubing state detector may include a first light emitter having a first optical axis directed toward the space, and a second light emitter having a second optical axis directed toward the space. The second light emitter may be adjacent the first light emitter, and the second optical axis may be parallel to the first optical axis. The optical sensor may be positioned on a side of the space opposite the first and second light emitters and arranged to receive light emitted by the first and second light emitters to determine a presence or absence of a tubing segment in the space. For example, the first and second light emitters may be arranged with respect to each other and the optical sensor as described above, e.g., the first optical axis may pass through a center of a tubing segment in the space, the second optical axis may be offset from the tubing segment center, etc.

In another aspect of the invention, a peritoneal dialysis system may include at least one pump arranged to pump dialysate for delivery to a peritoneal cavity of a patient, and a patient line fluidly coupled to the at least one pump such that dialysate delivered from the pump is directed to the patient line. The patient line may have a distal end arranged for connection to a patient, e.g., for connection to a patient access to deliver dialysate to a peritoneal cavity of the patient. A patient line state detector may be arranged to be associated with the patient line and to detect both a presence of the patient line and a priming condition of the patient line. For example, the patient line state detector may be arranged to receive the distal end of the patient line to detect the presence of the distal end and whether the distal end of the patient line is filled with fluid. This arrangement may be useful to allow the system and a patient to confirm that the patient line is sufficiently full of dialysate before connecting the patient line to the patient access connection.

The patient line state detector may include a cavity to receive the distal end of the patient line, one or more light emitters associated with the cavity arranged to direct light into the cavity, and one or more light detectors arranged to detect light emitted by the one or more light emitters. In one embodiment, a single light detector may be used to determine both the presence or absence of the patient line, as well as whether liquid is present in the patient line. The patient line state detector may be arranged in any of the ways that the tubing state detectors described above may be arranged. For example, first and second light emitters may be arranged adjacent each other and on a side of a cavity to receive the patient line that is opposite an optical sensor. A third light emitter may be arranged to have its optical axis arranged at an oblique angle to a sensor axis of the optical sensor, and thereby enable detection of liquid in the patient line. Other features of the tubing state detectors described above may be incorporated into the patient line state detector, including the detection and use of relative light levels to indicate a presence of the patient line and/or liquid in the patient line, and so on.

In another aspect of the invention, a method for detecting a presence of a tubing segment includes emitting first light along a first optical axis toward a space in which a tubing segment is to be optionally positioned, and emitting second light along a second optical axis toward the space, wherein the first and second light are emitted from a first side of the space. At least portions of the first and second light may be sensed on a second side of the space opposite the first side, and a presence or absence of a tubing segment in the space may be determined based on the sensed portions of the first and second light. The second optical axis may be approximately parallel to the first optical axis, and the first optical axis may pass through a center of the tubing segment. In one embodiment, a first calibration level of the first light may be detected with no tubing segment in the space, and a first light level may be detected of the first light when a tubing segment is in the space. The first light level may be higher, or lower, than the first calibration level. However, a second calibration level of the second light may be detected with no tubing segment in the space, and a second light level may be detected of the second light when a tubing segment is in the space, where the second light level is lower than the second calibration level. Thus, the detection of a second light level that is lower than the second calibration level may indicate the presence of a tubing segment in the space. In one embodiment, a detected second light level for the second light may be less than about 15-20% of the second calibration level with a tubing segment in the space.

In another aspect of the invention, a method for detecting a presence of liquid in a tubing segment may include emitting light along an optical axis toward a space in which a tubing segment is positioned, where the tubing segment has a cylindrical outer surface, and sensing light along a sensor optical axis that extends into the space, where the sensor optical axis is arranged at an oblique angle (e.g., about 110-120 degrees) relative to the optical axis. A presence or absence of liquid in the tubing segment in the space may be determined based on a sensed light level sensed along the sensor optical axis. For example, a determination may be made that fluid is not present in the tubing segment if a light level detected along the sensor optical axis is over a threshold level, and a determination may be made that fluid is present in the tubing segment if a light level detected along the sensor optical axis is below a threshold level. The threshold level may be approximately equal to about 125-150% of a light level detected along the sensor optical axis with no tubing segment in the space.

In one aspect of the invention, a disposable fluid handling cassette, such as that useable with an APD cycler device or other infusion apparatus, includes a generally planar body having at least one pump chamber formed as a depression in a first side of the body and a plurality of flowpaths for fluid that includes a channel. A patient line port may be arranged for connection to a patient line and be in fluid communication with the at least one pump chamber via at least one flowpath, and a membrane may be attached to the first side of the body over the at least one pump chamber. In one embodiment, the membrane may have a pump chamber portion with an unstressed shape that generally conforms to the pump chamber depression in the body and is arranged to be movable for movement of fluid in the useable space of the pump chamber. If the cassette body include two or more pump chamber depressions, the membrane may likewise include two or more pre-shaped pump portions. In other embodiments, the membrane need not be included with the cassette, e.g., where a control surface of the cycler interacts with the cassette to control pumping and/or valve functions.

In another embodiment, the pump chamber may include one or more spacer elements that extend from an inner wall of the depression, e.g., to help prevent the membrane from contacting the inner wall, thereby preventing blocking of an inlet/outlet of the pump chamber, helping remove or trap air in the pump chamber, and/or preventing sticking of the membrane to the inner wall. The spacer elements may be arranged to minimize deformation of the membrane at edges of the spacer elements when the membrane is forced against the spacer elements.

In another embodiment, a patient line port and a drain line port may be located at a first end of the body and be in fluid communication with the at least one pump chamber via at least one flowpath. A plurality of solution line spikes may, on the other hand, be located at a second end of the body opposite the first end, with each of the solution line spikes being in fluid communication with the at least one pump chamber via at least one flowpath. This arrangement may enable automated connection of solution lines to the cassette, and/or separate occlusion of the patient and/or drain lines relative to the solution lines. In one embodiment, a heater bag line port may also be located at the first end of the body and be in fluid communication with the at least one pump chamber via at least one flowpath. Flexible patient, drain and heater bag lines may be respectively connected to the patient line port, drain line port and heater bag line port.

In another embodiment, the body may include a vacuum vent clearance depression formed adjacent the at least one pump chamber. This depression may aid in the removal of fluid (gas and/or liquid) between the membrane and a corresponding control surface of the cycler, e.g., by way of a vacuum port in the control surface. That is, the depression may help ensure that the membrane is not forced against the vacuum port, leaving the port open to draw fluid into a collection chamber as necessary.

In one embodiment, one or more ports, such as a drain line port and heater bag line port, and/or one or more solution line spikes may communicate with a common flowpath channel of the cassette base. As needed, a plurality of valves may each be arranged to control flow in a respective flowpath between the at least one pump chamber and the patient line port, the drain line port, and the plurality of solution line spikes. In one embodiment, portions of the membrane may be positioned over respective valves and be movable to open and close the respective valve. Similarly, flow through openings into the pump chamber(s) may be controlled by corresponding valves that are opened and closed by movement of one or more portions of the membrane.

In some embodiments, the membrane may close at least some of the flowpaths of the body. That is, the body may be formed with open flow channels that are closed on at least one side by the membrane. In one embodiment, the body may include flowpaths formed on opposite planar sides, and at least some of the flowpaths on a first side may communicate with flowpaths on the second side.

In one embodiment, one or more spikes on the cassette (e.g., for receiving dialysate solution) may be covered by a spike cap that seals the spike closed and is removable.

In another aspect of the invention, a disposable fluid handling cassette, for use with a reusable automated peritoneal dialysis cycler device, includes a generally planar body having at least one pump chamber formed as a depression in a first side of the body and a plurality of flowpaths for fluid that includes a channel, a patient line port arranged for connection to a patient line, the patient line port being in fluid communication with the at least one pump chamber via at least one flowpath, and a flexible membrane attached to the first side of the body over the at least one pump chamber. A pump chamber portion of the membrane over the at least one pump chamber may have an unstressed shape that generally conforms to usable area of the pump chamber depression in the body and be arranged to be movable for movement of fluid in the pump chamber. In one embodiment, the cassette is configured for operative engagement with a reusable automated peritoneal dialysis cycler device.

The cassette may include a drain line port arranged for connection to a drain line, the drain line port being in fluid communication with the at least one pump chamber via at least one flowpath, and/or a plurality of solution line spikes that are in fluid communication with the at least one pump chamber via at least one flowpath. The pump chamber portion of the membrane may be generally dome shaped, and may include two pump chamber portions that have a shape that generally conforms to usable area of a corresponding pump chamber depression. In one embodiment, a volume of the pump chamber portion may be between 85-110% of the useable volume of the pump chamber depression. In another embodiment, the pump chamber portion may be arranged to be 85-110% of the depth of the useable area of the pump chamber depression. In another embodiment, the pump chamber portion may be arranged to have a size that is between 85-100% of the circumference of the useable area of the pump chamber depression. The useable area of the pump chamber may be defined at least in part by one or more spacer elements that extend from an inner wall of the depression. In one embodiment, a plurality of spacer elements may be of graduated lengths or varying height that define a generally dome-shaped region or other shape. The spacer elements may be arranged in a concentric elliptical pattern or other shape when viewed in plan. One or more breaks in the pattern may be provided, e.g., to allow communication between voids. In one embodiment, the spacer elements may be arranged to minimize deformation of the membrane at edges of the spacer elements when the membrane is forced against the spacer elements. In another embodiment, one or more spacers may be configured to inhibit the membrane from covering the fluid inlet and/or outlet of the pump chamber.

In another aspect of the invention, a fluid handling cassette for use with a fluid handling system of a medical infusion device includes a generally planar body having at least one pump chamber formed as a depression in a first side of the body and a plurality of flowpaths for fluid that includes a channel, the at least one pump chamber including one or more spacer elements that extend from an inner wall of the depression, a patient line port arranged for connection to a patient line, the patient line port being in fluid communication with the at least one pump chamber via at least one flowpath, a drain line port arranged for connection to a drain line, the drain line port being in fluid communication with the at least one pump chamber via at least one flowpath, and a plurality of solution line spikes being in fluid communication with the at least one pump chamber via at least one flowpath.

In one aspect of the invention, a disposable component system for use with a fluid line connection system of a peritoneal dialysis system includes a fluid handling cassette having a generally planar body with at least one pump chamber formed as a depression in a first side of the body and a plurality of flowpaths for fluid, a solution line spike located at a first end of the body, the solution line spike being in fluid communication with the at least one pump chamber via at least one flowpath, and a spike cap configured to removably cover the solution line spike, wherein the cap includes at least one raised feature (e.g., an asymmetrical or symmetrical flange) to aid in removal of the cap for connection to a solution line prior to the commencement of a peritoneal dialysis therapy.

In one embodiment, the cassette includes a skirt arranged around the spike to receive the end of the spike cap, and there may be a recess between the skirt and the spike that are arranged to aid in forming a seal between the spike cap and skirt.

In another embodiment, a solution line cap may be removably connected to a solution line, and the solution line cap may include a recessed feature (such as a symmetrical or asymmetrical groove). At least a portion of the solution line cap may include a flexible material, such as silicone rubber. The recessed feature may aid in the removal of a spike cap from the cassette.

In another embodiment, the spike cap includes a second raised feature that may function as a stop for the solution line cap.

In another embodiment, a main axis of one or more spikes is in substantially a same plane as the generally planar body of the fluid handling cassette.

In another aspect of the invention, a fluid handling cassette for use with a peritoneal dialysis system includes a generally planar body with at least one pump chamber formed as a depression in a first side of the body and a plurality of flowpaths for fluid, and a spike located at a first end of the body for engagement with a dialysate solution line. The spike may be in fluid communication with the at least one pump chamber via at least one flowpath and include a distal tip and a lumen arranged so that the distal tip of the spike is positioned substantially near the longitudinal axis of the spike. In one embodiment, the lumen may be positioned substantially off the longitudinal axis.

In another aspect of the invention, a disposable component system for use with a fluid line connection system of a peritoneal dialysis system includes a spike cap configured to removably cover a spike of a fluid handling cassette. The cap may include at least one feature to aid in removal of the cap for connection to a solution line prior to the commencement of a peritoneal dialysis therapy. The feature may be a raised feature, or a recessed feature, and may be configured for engagement with a solution line cap.

In another aspect of the invention, a disposable component system for use with a fluid line connection system of a peritoneal dialysis system includes a solution line cap for removable attachment to a solution line, wherein the solution line cap includes at least one feature to aid in removal of a spike cap to enable connection between a solution line and a spike prior to the commencement of a peritoneal dialysis therapy. The feature may be a raised feature, or a recessed feature, and may be configured for engagement with a spike cap. Indicia may e associated with a solution line, e.g., so that a solution associated with the line may be identified and affect at least one function of the peritoneal dialysis system.

In another aspect of the invention, a medical infusion fluid handling system, such as an APD system, may be arranged to de-cap and connect one or more lines (such as solution lines) with one or more spikes or other connection ports on a fluid handling cassette. This feature may provide advantages, such as a reduced likelihood of contamination since no human interaction is required to de-cap and connect the lines and spikes. For example, an APD system may include a carriage arranged to receive a plurality of solution lines each having a connector end and a cap. The carriage may be arranged to move along a first direction so as to move the connector ends of the solution lines along the first direction, and a cap stripper may be arranged to engage with caps on the solution lines on the carriage. The cap stripper may be arranged to move in a second direction transverse to the first direction, as well as to move with the carriage along the first direction. For example, the carriage may move toward a cassette in an APD cycler in a first direction so as to engage caps on the solution lines with caps on spikes of the cassette. The cap stripper may engage the caps (e.g., by moving in a direction transverse to the motion of the carriage) and then move with the carriage as the carriage pulls away from the cassette to remove the caps from the spikes. The carriage may then pull the connector ends of the solution lines from the caps on the cap stripper, which may retract to allow the carriage to engage the now exposed solution line connector ends with the exposed spikes on the cassette.

In one embodiment, the carriage may include a plurality of grooves that each receive a corresponding solution line. By positioning solution lines in corresponding grooves, each of the lines may be more easily individually identified, e.g., by reading a barcode or other identifier on the line, and controlling the system accordingly. The carriage may be mounted to a door of a cycler housing, and a carriage drive may move the carriage along the first direction. In one embodiment, the carriage drive may engage the carriage when the door is moved to a closed position, and disengage from the carriage when the door is moved to an open position.

In one embodiment, the cap stripper may include a plurality of fork-shaped elements arranged to engage with a corresponding cap on a solution line carried by the carriage. The fork-shaped elements may hold the caps when they are removed from the solution lines, and each of the solution line caps may itself hold a spike cap. In another embodiment, the cap stripper may include a plurality of rocker arms each associated with a fork-shaped element. Each of the rocker arms may be arranged to move to engage a spike cap, e.g., to assist in removing the spike cap from the corresponding spike. Each of the rocker arms may be arranged to engage with a corresponding spike cap only when the associated fork-shaped element engages with a cap on a solution line. Thus, the cap stripper may not engage or remove spike caps from the cassette in locations where there is no corresponding solution line to connect with the spike.

In another aspect of the invention, a method for connecting fluid lines in a medical infusion fluid handling system, such as an APD cycler, may involve locating solution lines and spikes of a cassette in an enclosed space away from human touch. The solution lines and/or spikes may have caps removed and the lines connected to spikes while in the enclosed space, thus providing the connection while minimizing potential contamination at the connection, e.g., by fingers carrying pathogens or other potentially harmful substances. For example, one method in accordance with this aspect of the invention includes providing a plurality of solution lines each having a connector end and a cap, providing a fluid handling cassette having a plurality of spikes each covered by a spike cap, enclosing the connector ends of the plurality of solution lines with caps covering the connector ends and the plurality of spikes with spike caps covering the spikes in a space that prevents human touch of the caps or spike caps, removing the caps from the connector ends of the plurality of solution lines without removing the caps or connector ends from the space, removing the spike caps from the spikes without removing the spike caps or spikes from the space, engaging the caps with respective ones of the spike caps, and fluidly connecting the plurality of connector ends to corresponding spikes while maintaining the connector ends and spikes in the space and protected from human touch.

In one embodiment, the solution line caps and spike caps may be engaged with each other before their removal from the lines or spikes, and then may be removed from both the lines and the spikes while engaged with each other. This technique may simplify the de-capping/capping process, as well as allow for easier storage of the caps.

In another embodiment, the solution lines may be disconnected from the spikes, and the connector ends of the lines and the spikes may be re-capped, e.g., after a treatment is completed.

In another aspect of the invention, a dialysis machine may include a fluid handling cassette having a plurality of spikes and a plurality of spike caps covering a respective spike, a plurality of solution lines each having a cap covering a connector end of the respective line, and a cap stripper arranged to remove one or more caps from a connector end of a solution line, and remove one or more spike caps from a spike on the cassette while the one or more caps are secured to a corresponding one of the spike caps. As discussed above, the machine may be arranged to automatically fluidly connect a connector end of a solution line with a corresponding spike after the caps are removed.

In another aspect of the invention, a dialysis machine, such as an APD system, may include a cassette having a plurality of fluid spikes and a plurality of spike caps covering a respective spike, a carriage arranged to receive a plurality of solution lines each having a cap covering a connector end of the respective line, and a cap stripper arranged to engage one or more caps covering a connector end of a line. The carriage and cap stripper may be configured to engage one or more caps on a connector end of a line while the one or more caps are engaged with a corresponding spike cap covering a spike on the cassette, and to remove the spike cap from the spike and the cap from the connector end of the solution line, and to fluidly connect the spike and the connector end of the solution line after the caps are removed.

In another aspect of the invention, a dialysis machine may include a cap stripper that is arranged to remove one or more caps on a connector end of a solution line, remove one or more spike caps from spikes on a fluid handling cassette, and to retain and reattach the caps to the solution lines and the spike caps to the spikes on the cassette.

In another aspect of the invention, a fluid line connection system for a peritoneal dialysis system includes a fluid handling cassette having a generally planar body with at least one pump chamber formed as a depression in a first side of the body and a plurality of flowpaths for fluid, a plurality of dialysate solution line spikes located at a first end of the body, the solution line spikes being in fluid communication with the at least one pump chamber via at least one flowpath and arranged so that the spikes are generally co-planar with the generally planar body of the fluid handing cassette, and a carriage arranged to receive a plurality of solution lines, where each solution line has a connector end. The carriage may be arranged to automatically fluidly connect a connector end of a solution line with a corresponding spike.

In one embodiment, the carriage is arranged to move the solution lines and respective caps along a first direction substantially parallel to the generally planar body of the fluid handling cassette. A carriage drive that moves the carriage only the first direction may include a drive element and a pneumatic bladder or screw drive to move the drive element along the first direction. A cap stripper may be provided that is arranged to remove one or more caps from a connector end of a solution line, and remove one or more spike caps from a spike on the cassette while the one or more caps are secured to a corresponding one of the spike caps. In one embodiment, the cap stripper may be arranged to r retain and reattach the caps to the solution lines and the spike caps to the spikes on the cassette.

In another aspect of the invention, a peritoneal dialysis system may include a cycler device with components suitable for controlling delivery of dialysate to the peritoneal cavity of a patient. The cycler device may have a housing that encloses at least some of the components and have a heater bag receiving section. (The term "heater bag" is used herein to refer to any suitable container to heat dialysate, such as a flexible or rigid container, whether made of polymer, metal or other suitable material.) A lid may be mounted to the housing and be movable between an open position in which a heater bag is placeable in the heater bag receiving section and a closed position in which the lid covers the heater bag receiving section. Such an arrangement may allow for faster or more efficient heating of dialysate in the heater bag, e.g., because heat may be retained by the lid. Also, the lid may help prevent human touch of potentially hot surfaces.

In one embodiment, the dialysis system may include a fluid handling cassette with a heater bag port attached to a heater bag line, a patient port attached to a patient line, and at least one pump chamber to move fluid in the patient line and the heater bag line. A heater bag may be attached to the heater bag line and be arranged for placement in the heater bag receiving section.

In another embodiment, the system may include an interface (such as a visual display with a touch screen component) that is movably mounted to the housing and is movable between a first position in which the interface is received in the heater bag receiving section, and a second position in which the interface is located out of the heater bag receiving section (e.g., a position in which a user may interact with the interface). Thus, the interface may be hidden from view when the system is idle, allowing the interface to be protected. Also, storing the interface in the heater bag receiving section may make the system more compact, at least in an "as stored" condition.

In another aspect of the invention, a dialysis system includes a supply of pneumatic pressure and/or vacuum suitable for controlling pneumatically-operated components of the system, a pneumatically-operated component that is fluidly connected to the supply of pneumatic pressure and/or vacuum, and a control system that provides pneumatic pressure or vacuum to the pneumatically-operated component and subsequently isolates the pneumatically-operated component from the supply of pneumatic pressure or vacuum for a substantial period of time before again providing pneumatic pressure or vacuum to the pneumatically-operated component. Such an arrangement may be useful for components that are actuated relatively infrequently, such as the occluder arrangement described herein. Small motions of some components may cause the component to emit noise that may be found bothersome by a patient. By isolating the component from the pneumatic pressure/vacuum, the component may avoid slight movement caused by variations in the supply pressure/vacuum, e.g., resulting from draws on the pressure/vacuum by other system components. In one embodiment, the substantial period of time may be 5 minutes or more, 1 hour or more, 50% or more of a time period required to deliver or remove a volume of dialysate suitable for a dialysis treatment with respect to a patient's peritoneal cavity, or other suitable periods.

In another aspect of the invention, a dialysis system includes a supply of pneumatic pressure and/or vacuum suitable for controlling pneumatically-operated components of the system, a pneumatically-operated component that is fluidly connected to the supply of pneumatic pressure and/or vacuum, and a control system that provides pneumatic pressure or vacuum to the pneumatically-operated component and controls the pneumatic pressure or vacuum so as to reduce noise generated by the pneumatically-operated component. For example, the pneumatically-operated component may include at least one moving part (such as a pump diaphragm), and the control system may reduce the pneumatic pressure or vacuum provided to the pneumatically-operated component so as to slow movement of the moving part as the moving part stops and/or changes direction (e.g., the pressure/vacuum may be controlled to slow movement of the diaphragm before the diaphragm changes direction). In another embodiment, a pulse width modulation control of a pressure/vacuum supply valve may be used, e.g., to reduce noise emitted by moving parts of the valve.

In another aspect of the invention, a dialysis system includes a supply of pneumatic pressure and vacuum suitable for controlling pneumatically-operated components of the system. A first pneumatically-operated component may be fluidly connected to the supply of pneumatic pressure and/or vacuum, and have a first output line to release pneumatic pressure. A second pneumatically-operated component may be fluidly connected to the supply of pneumatic pressure and/or vacuum, and have a second output line to release pneumatic vacuum. A space, such as that defined by an accumulator, manifold or sound-insulated chamber, may be fluidly connected to both the first and second output lines. A control system may provide pneumatic pressure or vacuum to the pneumatically-operated components so that when the first and second components release pressure/vacuum during operation, the released pressure/vacuum may be received into the common space (e.g., a manifold). In some circumstances, gas under positive pressure released by components may be balanced by negative pressure released by other components, thus reducing noise generated.

In another aspect of the invention, a peritoneal dialysis system may include a fluid handling cassette having a patient line fluidly connected to and leading from the peritoneal cavity of a patient, and which includes at least one pump chamber to move dialysate solution in the patient line. A cycler device may be arranged to receive and interact with the fluid handling cassette and cause the at least one pump chamber to move dialysate solution in the patient line. The cycler may include a control system arranged to control the at least one pump chamber to operate in a priming operation to force dialysate solution into the patient line so as to remove any air in the patient line, and may be adapted to interact with two types of fluid handling cassettes that differ with respect to a volume of the patient line connected to the cassette body. A first type of cassette may have a relatively low volume patient line (e.g., for pediatric applications), and a second type of cassette may have a relatively high volume patient line (e.g., for adult applications), and the control system may detect whether a cassette received by the cycler is a first type or a second type and to adjust cycler operation accordingly.

In one embodiment, the control system may detect whether a cassette received by the cycler is a first type or a second type by determining the volume of the patient line during priming, and to adjust the amount of fluid moved through the cassette during operation of the system. In another embodiment, indicia, such as a barcode, on the cassette may be detected by the cycler and cause the cycler to adjust a pumping operation based on the type of cassette.

In another aspect of the invention, a dialysis machine includes a fluid handling cassette having a plurality of spikes and at least one pump chamber to move fluid in the spikes, a plurality of solution lines each engaged with a respective spike on the cassette, and a control system that reads indicia on each of the solution lines to determine a type for each of the solution lines. The control system may adjust a pumping operation or other cycler operation based in the identity of one or more of the solution lines. For example, a solution line may be identified as being an effluent sampling line and the pumping operation may be adjusted to direct used dialysate from a patient to the effluent sampling line during a drain cycle.

In another aspect of the invention, a method of automatically recovering from a tilt condition in a dialysis system may include (A) detecting an angle of tilt of at least a portion of a dialysis system, the portion of the dialysis system including machinery for performing a dialysis therapy, (B) determining that a tilt condition exists in which the angle of tilt exceeds a predetermined threshold, (C) in response to (B), pausing the dialysis therapy, (D) monitoring the angle of tilt while the dialysis therapy is paused, (E) determining that the tilt condition no longer exists, and (F) in response to (E), automatically resuming the dialysis therapy.

In another aspect of the invention, a patient data interface for a dialysis system includes a device port comprising a recess in a chassis of at least a portion of the dialysis system and a first connector disposed within the recess. A patient data storage device may include a housing and a second connector coupled to the housing, where the second connector is adapted to be selectively coupled to the first connector. The recess may have a first shape and the housing may have a second shape corresponding to the first shape such that when the first and second connectors are coupled, the housing of the patient data storage device is received at least partially within the recess. The first and second shapes may be irregular and the patient data storage device may have a verification code that is readable by the dialysis system to verify that the patient data storage device is of an expected type and/or origin.

In another aspect of the invention, a method for providing peritoneal dialysis includes delivering or withdrawing dialysate with respect to the patient's peritoneal cavity at a first pressure, and adjusting a pressure at which dialysate is delivered or withdrawn to minimize patient sensation of dialysate movement. In one embodiment, the pressure may be adjusted during a same fill or empty cycle of a peritoneal dialysis therapy, and/or within different fill or empty cycles of a peritoneal dialysis therapy. For example, when withdrawing dialysate from a patient, the pressure at which dialysate is withdrawn may be reduced when an amount of dialysate remaining in the peritoneal cavity drops below a threshold volume. Reducing the pressure (negative pressure or vacuum) near the end of a drain cycle may reduce the sensation the patient may have of the dialysate withdrawal.

In another aspect of the invention, a method for providing peritoneal dialysis includes providing a first solution to a patient's peritoneal cavity using a reusable cycler device during a first treatment of peritoneal dialysis, and providing a second solution to the patient's peritoneal cavity using the reusable cycler device during a second treatment of peritoneal dialysis immediately subsequent to the first treatment, where the second solution has a different chemical makeup relative to the first solution. The different solutions may be created by mixing liquid material from two or more solution containers that are connected to the cycler (e.g., via a cassette mounted to the cycler). The solution containers may be automatically identified by the cycler, e.g., by reading a barcode, RFID tag, or other indicia.

In another aspect of the invention, a medical infusion system includes a housing that encloses at least some of the components of the system, and a control surface attached to the housing and constructed and arranged to control the operation of a fluid handling cassette that may be removably mounted to the housing. The control surface may have a plurality of movable portions arranged to control fluid pumping and valve operations of the cassette, and at least one of the movable portions may have an associated vacuum port arranged to draw fluid from a region near the movable portion.

In one embodiment, the control surface includes a sheet of resilient polymer material, and each of the movable portions may have an associated vacuum port. In another embodiment, the cassette includes a membrane that is positionable adjacent the control surface, and the vacuum port is arranged to remove fluid from a space between the membrane and the control surface. A liquid sensor may be arranged to detect liquid drawn into the vacuum port, e.g., in case the membrane ruptures, allowing liquid to leak from the cassette.

In another aspect of the invention, a volume of fluid moved by a pump, such as a pump in an APD system, may be determined based on pressure measurement and certain known chamber and/or line volumes, but without direct measurement of the fluid, such as by flow meter, weight, etc. In one embodiment, a volume of a pump chamber having a movable element that varies the volume of the pump chamber may be determined by measuring pressure in the pump chamber, and a reference chamber both while isolated from each other, and after the two chambers are fluidly connected so that pressures in the chambers may equalize. In one embodiment, equalization of the pressures may be assumed to occur in an adiabatic way, e.g., a mathematical model of the system that is based on an adiabatic pressure equalization process may be used to determine the pump chamber volume. In another embodiment, pressures measured after the chambers are fluidly connected may be measured at a time before complete equalization has occurred, and thus the pressures for the pump and reference chambers measured after the chambers are fluidly connected may be unequal, yet still be used to determine the pump chamber volume. This approach may reduce a time between measurement of initial and final pressures, thus reducing a time during which heat transfer may take place and reducing error that may be introduced given the adiabatic model used to determine the pump chamber volume.

In one aspect of the invention, a method for determining a volume of fluid moved by a pump includes measuring a first pressure for a pump control chamber when the pump control chamber is isolated from a reference chamber. The pump control chamber may have a volume that varies at least in part based on movement of a portion of the pump, such as a pump membrane or diaphragm. A second pressure may be measured for the reference chamber when the reference chamber is isolated from the pump control chamber. The reference chamber may have a known volume. A third pressure associated with the pump control chamber after fluidly connecting the reference chamber and the pump control chamber may be measured, but the measurement may occur before substantial equalization of pressures between the pump control and reference chambers has occurred. Similarly, a fourth pressure associated with the reference chamber after fluidly connecting the reference chamber and the pump control chamber may be measured, but before substantial equalization of pressures between the pump control and reference chambers has occurred. A volume for the pump control chamber may be determined based on the first, second, third and fourth measured pressures.

In one embodiment, the third and fourth pressures are measured at approximately a same time and the third and fourth pressures are substantially unequal to each other. For example, equalization of the pressures in the pump control and reference chambers may occur after an equalization time period once the pump control and reference chambers are fluidly connected, but the third and fourth pressures may be measured at a time after the pump control and reference chambers are fluidly connected that is approximately 10% to 50% of the equalization time period. Thus, the third and fourth pressures may be measured long before (in time sense) the pressures in the chambers have fully equalized. In another embodiment, the third and fourth pressures may be measured at a time when the pressures in the chambers has reached approximately 50-70% equalization, e.g., the pressures in the chambers have changed from an initial value that is within about 50-70% of an equalized pressure value. Thus, a time period between measurement of the first and second pressures and measurement of the third and fourth pressures may be minimized.

In another embodiment, a model for determining the volume of the pump control chamber may incorporate an assumption that an adiabatic system exists from a point in time when the first and second pressures are measured for the isolated pump control chamber and the reference chamber until a point in time when the third and fourth pressures are measured.

To determine a volume of fluid moved by the pump, the steps of measuring the first, second, third and fourth pressures and the step of determining may be performed for two different positions of a pump membrane to determine two different volumes for the pump control chamber. A difference between the two different volumes may represent a volume of fluid delivered by the pump.

As mentioned above, this aspect of the invention may be used in any suitable system, such as a system in which the pump is part of a disposable cassette and the pump control chamber is part of a dialysis machine used in a dialysis procedure.

In one embodiment, the first and/or second pressure may be selected from a plurality of pressure measurements as coinciding with a point in time at which a pressure in the pump control chamber or reference chamber (as appropriate) first begins to change from a previously stable value. For example, the point in time may be identified based on a determination of when a best fit line for a plurality of consecutive sets of measured pressures first deviates from a constant slope. This approach may help identify initial pressures for the pump control and reference chambers that are as late in time as possible, while reducing error in the pump volume determination.

In another embodiment, a technique may be used to identify an optimal point in time at which the third and fourth pressures are measured. For example, a plurality of pressure values for the pump control chamber may be measured after the pump control and reference chambers are fluidly connected, and a plurality of change in volume values may be determined for the pump control chamber based on the plurality of pressure values for the pump control chamber. Each of the plurality of change in volume values may corresponding to a unique point in time and a measured pressure value for the pump chamber. In this case, the change in volume values are due to movement of an imaginary piston that is present at the valve or other component that initially isolates the pump control and reference chambers, but moves upon opening of the valve or other component. Thus, the pump chamber does not actually change size or volume, but rather the change in volume is an imaginary condition due to the pressures in the pump chamber and reference chamber being different from each other initially. Similarly, a plurality of pressure values for the reference chamber may be measured after the pump control and reference chambers are fluidly connected, and a plurality of change in volume values for the reference chamber may be determined based on the plurality of pressure values for the reference chamber. Each of the plurality of change in volume values may correspond to a unique point in time and a measured pressure value for the reference chamber, and like the change in volume values for the pump chamber, are a result of movement of an imaginary piston. A plurality of difference values between change in volume values for the pump control chamber and for the reference chamber may be determined, with each difference value being determined for corresponding change in volume values for the pump control chamber and change in volume values for the reference chamber, i.e., the pairs of change in volume values for which a difference value is determined correspond to a same or substantially same point in time. The difference values may be analyzed, and a minimum difference value (or a difference value that is below a desired threshold) may indicate a point in time for which the third and fourth pressures should be measured. Thus, the third and fourth pressure values may be identified as being equal to the pump control chamber pressure value and the reference chamber pressure value, respectively, that correspond to a difference value that is a minimum or below a threshold.

In another embodiment, the pressures measured are pressures of a gas within the pump control chamber and the reference chamber, the equalization of pressures within the pump control chamber and reference chamber is assumed to occur adiabatically, the equalization of pressures between the pump control chamber and reference chamber is assumed to include a change in the volume of a gas in the pump control chamber and reference chamber in equal but opposite directions, and the volume of gas in the reference chamber at the time of the fourth pressure measurement is calculated from the known volume of the reference chamber, and the second and fourth pressures. The change in volume of gas in the reference chamber may be assumed to be the difference between the known volume of the reference chamber and the calculated value of the volume of gas in the reference chamber at the time of the fourth pressure measurement. Also, the change in volume of gas in the pump control chamber may be assumed to be the difference between the initial volume of the pump control chamber and the volume of gas in the pump control chamber at the time of the third pressure measurement, wherein the change in volume of gas in the pump control chamber is equal to but opposite the change in volume of gas in the reference chamber.

In another aspect of the invention, a method for determining a volume of fluid moved by a pump includes providing a fluid pump apparatus having a pump chamber separated from a pump control chamber by a movable membrane, and a reference chamber that is fluidly connectable to the pump control chamber, adjusting a first pressure in the pump control chamber to cause the membrane to move and thereby move fluid in the pump chamber, isolating the reference chamber from the pump control chamber and establishing a second pressure in the reference chamber that is different from a pressure in the pump control chamber, fluidly connecting the reference chamber and the pump control chamber to initiate equalization of pressures in the pump control chamber and the reference chamber, and determining a volume for the pump control chamber based on the first and second pressures, and an assumption that the pressures in the pump control and reference chambers initiate equalization in an adiabatic way.

In one embodiment, third and fourth pressures for the pump control and reference chambers, respectively, may be measured after fluidly connecting the reference chamber and the pump control chamber, and the third and fourth pressures may be used to determine the volume for the pump control chamber. The third and fourth pressures may be substantially unequal to each other. Similar to that mentioned above, the adjusting, isolating, fluidly connecting and determining steps may be repeated, and a difference between the two determined volumes for the pump control chamber may be determined, where the difference represents a volume of fluid delivered by the pump.

In another embodiment, the pump is part of a disposable cassette and the pump control chamber is part of a dialysis machine used in a dialysis procedure.

In another aspect of the invention, a medical infusion system includes a pump control chamber, a control surface associated with the pump control chamber so that at least a portion of the control surface is movable in response to a pressure change in the pump control chamber, a fluid handling cassette having at least one pump chamber positioned adjacent the control surface and arranged so that fluid in the at least one pump chamber moves in response to movement of the portion of the control surface, a reference chamber that is fluidly connectable to the pump control chamber, and a control system arranged to adjust a pressure in the pump control chamber and thus control movement of fluid in the pump chamber of the fluid handling cassette. The control system may be arranged to measure a first pressure for the pump control chamber when the pump control chamber is isolated from the reference chamber, measure a second pressure for the reference chamber when the reference chamber is isolated from the pump control chamber, fluidly connect the pump control chamber and the reference chamber, measure third and fourth pressures associated with the pump control chamber and the reference chamber, respectively, after fluidly connecting the reference chamber and the pump control chamber, and determine a volume for the pump control chamber based on the first, second, third and fourth measured pressures and a mathematical model that defines equalization of pressure in the pump control and reference chambers as occurring adiabatically when the pump control and reference chambers are fluidly connected.

In one embodiment, the third and fourth pressures are substantially unequal to each other, e.g., the third and fourth pressures may be measured prior to substantial equalization of pressures in the pump control and reference chambers.

In another aspect of the invention, a method for determining a volume of fluid moved by a pump includes measuring a first pressure for a pump control chamber when the pump control chamber is isolated from a reference chamber, the pump control chamber having a volume that varies at least in part based on movement of a portion of the pump, measuring a second pressure for the reference chamber when the reference chamber is isolated from the pump control chamber, measuring a third pressure associated with both the pump control chamber and the reference chamber after fluidly connecting the reference chamber and the pump control chamber, and determining a volume for the pump control chamber based on the first, second and third measured pressures.

In one embodiment, the third pressure may be measured after complete equalization of pressures in the pump control and reference chambers is complete. In one embodiment, a model used to determine the pump chamber volume may assume an adiabatic system in equalization of pressure between the pump chamber and the reference chamber.

In one aspect of the invention, a method for determining a presence of air in a pump chamber includes measuring a pressure for a pump control chamber when the pump control chamber is isolated from a reference chamber, the pump control chamber having a known volume and being separated from a pump chamber, that is at least partially filled with liquid, by a membrane, measuring a pressure for the reference chamber when the reference chamber is isolated from the pump control chamber, the reference chamber having a known volume, measuring a pressure after fluidly connecting the reference chamber and the pump control chamber and prior to a time when the pressure in the chambers has equalized, and determining a presence or absence of an air bubble in the pump chamber based on the measured pressures and known volumes.

In one embodiment, a model used to determine the presence or absence of an air bubble assumes an adiabatic system from a point in time when the pressures are measured for the isolated pump control chamber and the reference chamber until a point in time after the chambers are fluidly connected. In another embodiment, the pressure for the pump control chamber is measured with the membrane drawn toward a wall of the pump control chamber.

In another aspect of the invention, an automated peritoneal dialysis system includes a reusable cycler that is constructed and arranged for coupling to a disposable fluid handling cassette containing at least one pumping chamber. The disposable fluid handling cassette may be configured to be connected in fluid communication with the peritoneum of a patient via a first collapsible tube and with a second source and/or destination (such as a solution container line) via a second collapsible tube. An occluder may be configured and positioned within the cycler to selectively occlude the first collapsible tube while not occluding the second collapsible tube. In one embodiment, the occluder can occlude a plurality of collapsible tubes, such as a patient line, a drain line and/or a heater bag line. The cassette may have a generally planar body with at least one pump chamber formed as a depression in a first side of the body and a plurality of flowpaths for fluid, a patient line port located at a first end of the body arranged for connection to the first collapsible tube, and a solution line port located at a second end of the body opposite the first end, and arranged for connection to the second collapsible tube. The occluder may be configured and positioned within the cycler to selectively occlude the first tube and a third collapsible tube (e.g., for a drain) while not occluding the second collapsible tube.

In another embodiment, the occluder includes first and second opposed occluding members pivotally connected to each other, a tube contacting member connected to, or comprising at least a portion of, at least one of the first and second occluding members, and a force actuator constructed and positioned to apply a force to at least one of the first and second occluding members. Application of the force by the force actuator may cause the tube contacting members to move between a tube occluding and an open position. The occluder may include a release member configured and positioned to enable an operator to manually move the tube contacting member from the tube occluding position to the open position even with no force applied to the occluding member by the force actuator. The force actuator may apply a force sufficient to bend both the first and second occluding members, so that upon application of the force by the force actuator to bend the first and second occluding members, the tube contacting member may move between a tube occluding and an open position. The occluding members may be spring plates pivotally connected together at opposite first and second ends, and the tube contacting member may be a pinch head connected to the spring plates at the first ends, while the second ends of the spring plates may be affixed directly or indirectly to a housing to which the occluder is connected. In one embodiment, the force actuator comprises an inflatable bladder positioned between the first and second occluding members. The force actuator may increase a distance between the first and second occluding members in a region where the first and second occluding members are in opposition so as to move the tube contacting member between a tube occluding and an open position. In one embodiment, the force actuator may bend one or both of the occluding members to move the tube contacting member from a tube occluding position to an open position.

Various aspects of the invention are described above and below with reference to illustrative embodiments. It should be understood that the various aspects of the invention may be used alone and/or in any suitable combination with other aspects of the invention. For example, the pump volume determination features described herein may be used with a liquid handling cassette having the specific features described, or with any other suitable pump configuration.

BRIEF DESCRIPTION OF THE DRAWINGS

Aspects of the invention are described below with reference to illustrative embodiments that are shown, at least in part, in the following figures, in which like numerals reference like elements, and wherein:

FIG. 9-1A is a front perspective view of an exemplary configuration of a patient line state detector or liquid level detector;

FIG. 9-1B is a rear perspective view of a patient line state detector or liquid level detector;

FIG. 9-2 is a perspective layout view of three LEDs and an optical detector surface-mounted on a printed circuit board;

FIG. 9-3 is a plan view of three LEDs and an optical detector mounted on a detector circuit board;

FIG. 9-4 is an exploded perspective view of the detector of FIG. 9-1 showing the printed circuit board and transparent or translucent plastic insert.

FIG. 9-5 is a perspective view of an alternative configuration of a liquid level detector;

FIG. 9-6 is a perspective view of the front of an unloaded organizer (absent any solution lines);

FIG. 9-7 is a back view of the organizer of FIG. 9-6;

FIG. 9-8 is a perspective view of an organizer including a plurality of solution lines, a patient line, and a drain line;

FIG. 9-9 is a perspective view of an organizer clip;

FIG. 9-10 is a perspective view of an organizer clip receiver;

FIG. 9-11 is a perspective view of a door latch sensor assembly associated with a cycler;

FIG. 9-11*a* is a cross-sectional view of the door latch sensor assembly of FIG. 9-11;

FIG. 9-12 is a graph showing the ability of the liquid level detector of FIG. 9-1 to distinguish between a primed and a non-primed patient line;

FIG. 9-12a is a graph showing the range of signals corresponding to a primed and a non-primed patient line for different cyclers using the liquid detector of FIG. 9.1;

FIG. 9-13 is a graph showing measurements collected by an optical sensor comparing liquid detection using an orthogonally oriented LED vs. an angled LED;

FIG. 9-14 is a graph showing the ability of the liquid level detector of FIG. 9-1 to distinguish between the presence and absence of a tubing segment within the detector;

FIG. 10 is a perspective view of the APD system of FIG. 1 with the door of the cycler in an open position;

FIG. 11 is a perspective view of the inner side of the door of the cycler show in FIG. 10;

FIG. 11-1 is a perspective view of a carriage in a first embodiment;

FIG. 11-2 is an enlarged perspective view of a solution line loaded into the carriage of FIG. 11-1;

FIG. 11-3 is a perspective view of an open identification tag;

FIG. 11-4 is a perspective view of a carriage drive assembly including an AutoID camera mounted to an AutoID camera board;

FIG. 11-5 is a perspective view of an embodiment for a stripper element of a cap stripper;

FIG. 11-6 is a front perspective view of the carriage drive assembly of FIG. 11-4 showing the position of the stripper element of FIG. 11-5 within the carriage drive assembly;

FIG. 11-7a shows a perspective view of a portion of the stripper element of FIG. 11-5, in which a spike cap is positioned;

FIG. 11-7b shows a perspective view of a portion of the stripper element of FIG. 11-5, in which a solution line cap is positioned over a spike cap;

FIG. 11-7c shows a perspective view of a portion of the stripper element of FIG. 11-5, showing a sensor element and rocker arm in the absence of a spike cap;

FIG. 12 is a right front perspective view of a carriage drive assembly and cap stripper in a first embodiment;

FIG. 13 a left front perspective view of the carriage drive assembly and cap stripper of FIG. 12;

FIG. 14 is a partial rear view of the carriage drive assembly of FIG. 12;

FIG. 36A shows a front view and selected cross-sectional views of an embodiment of a control surface of the cycler;

FIG. 49-1 shows a schematic cross section of the cycler illustrating the components of the heater system for the heater bag;

FIG. 49-2 shows the software processes interacting with the heater controller process;

FIG. 49-3 shows the block diagram of a nested feedback loop to control the heater bag temperature;

FIG. 49-4 shows the block diagram of an alternative nested feedback loop to control the heater bag temperature;

FIG. 49-5 shows the block diagram of another alternative nested feedback loop to control the heater bag temperature;

FIG. 49-6 shows the block diagram of the thermal model of the heater bag and heater tray;

FIG. 49-7 shows the temperature response of the heater bag and heater tray for nominal conditions;

FIG. 49-8 shows the temperature response of the heater bag and heater tray for warm conditions;

FIG. 49-9 shows the temperature response of the heater bag and heater tray for cold conditions;

FIG. 49-10 is a schematic block diagram of one embodiment of a heater control system;

FIG. 49-11 is a is a schematic block diagram illustrating a heater circuit configured with a pair of heating elements;

FIG. 49-12 is a is a schematic block diagram illustrating a heater circuit configured with a pair of heating elements with reduced potential for current leakage;

FIG. 49-13 is a circuit diagram of a heater circuit configured with a pair of heating elements;

FIG. 49-14 shows a flow chart diagram illustrating a method to select the heater configuration in an APD cycler, according to one embodiment of the present invention; and FIG. 49-15 shows a flow chart diagram illustrating a method to select the heater configuration in an APD cycler where a stored value of the AC mains voltage is queried during selection of the heater configuration, according to one embodiment of the present invention.

DETAILED DESCRIPTION

Although aspects of the invention are described in relation to a peritoneal dialysis system, certain aspects of the invention can be used in other medical applications, including infusion systems such as intravenous infusion systems or extracorporeal blood flow systems, and irrigation and/or fluid exchange systems for the stomach, intestinal tract, urinary bladder, pleural space or other body or organ cavity. Thus, aspects of the invention are not limited to use in peritoneal dialysis in particular, or dialysis in general.

APD System

Figure 1:
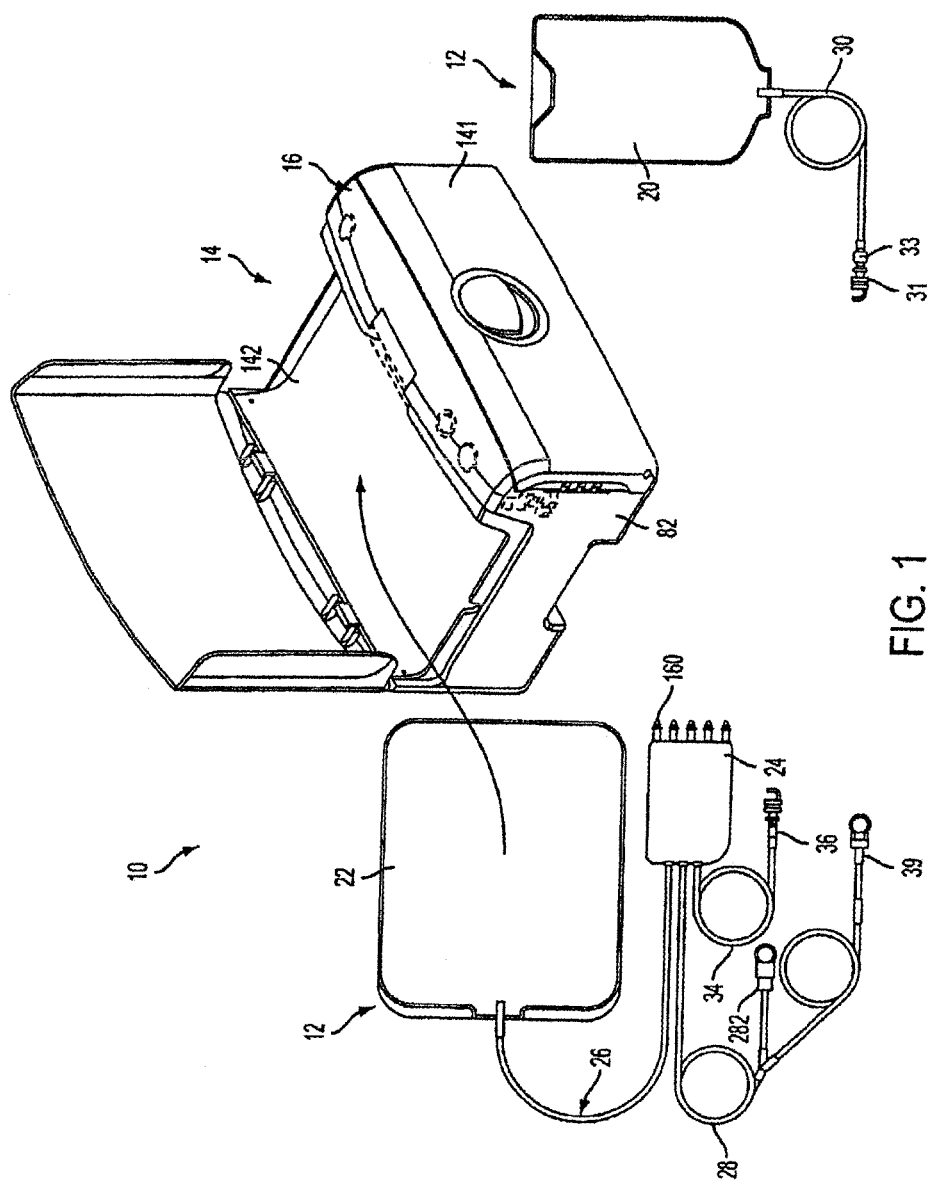
FIG. 1 shows a schematic view of an automated peritoneal dialysis (APD) system that incorporates one or more aspects of the invention.

FIG. 1 shows an automated peritoneal dialysis (APD) system 10 that may incorporate one or more aspects of the invention. As shown in FIG. 1, for example, the system 10 in this illustrative embodiment includes a dialysate delivery set 12 (which, in certain embodiments, can be a disposable set), a cycler 14 that interacts with the delivery set 12 to pump liquid provided by a solution container 20 (e.g., a bag), and a control system 16 (e.g., including a programmed computer or other data processor, computer memory, an interface to provide information to and receive input from a user or other device, one or more sensors, actuators, relays, pneumatic pumps, tanks, a power supply, and/or other suitable components—only a few buttons for receiving user control input are shown in FIG. 1, but further details regarding the control system components are provided below) that governs the process to perform an APD procedure. In this illustrative embodiment, the cycler 14 and the control system 16 are associated with a common housing 82, but may be associated with two or more housings and/or may be separate from each other. The cycler 14 may have a compact footprint, suited for operation upon a table top or other relatively small surface normally found in the home. The cycler 14 may be lightweight and portable, e.g., carried by hand via handles at opposite sides of the housing 82.

The set 12 in this embodiment is intended to be a single use, disposable item, but instead may have one or more reusable components, or may be reusable in its entirety. The user associates the set 12 with the cycler 14 before beginning each APD therapy session, e.g., by mounting a cassette 24 within a front door 141 of the cycler 14, which interacts with the cassette 24 to pump and control fluid flow in the various lines of the set 12. For example, dialysate may be pumped both to and from the patient to effect APD. Post therapy, the user may remove all or part of the components of the set 12 from the cycler 14.

As is known in the art, prior to use, the user may connect a patient line 34 of the set 12 to his/her indwelling peritoneal catheter (not shown) at a connection 36. In one embodiment, the cycler 14 may be configured to operate with one or more different types of cassettes 24, such as those having differently sized patient lines 34. For example, the cycler 14 may be arranged to operate with a first type of cassette with a patient line 34 sized for use with an adult patient, and a second type of cassette with a patient line 34 sized for an infant or pediatric use. The pediatric patient line 34 may be shorter and have a smaller inner diameter than the adult line so as to minimize the volume of the line, allowing for more controlled delivery of dialysate and helping to avoid returning a relatively large volume of used dialysate to the pediatric patient when the set 12 is used for consecutive drain and fill cycles. A heater bag 22, which is connected to the cassette 24 by a line 26, may be placed on a heater container receiving portion (in this case, a tray) 142 of the cycler 14. The cycler 14 may pump fresh dialysate (via the cassette 24) into the heater bag 22 so that the dialysate may be heated by the heater tray 142, e.g., by electric resistance heating elements associated with the tray 142 to a temperature of about 37 degrees C. Heated dialysate may be provided from the heater bag 22 to the patient via the cassette 24 and the patient line 34. In an alternative embodiment, the dialysate can be heated on its way to the patient as it enters, or after it exits, the cassette 24 by passing the dialysate through tubing in contact with the heater tray 142, or through an in-line fluid heater (which may be provided in the cassette 24). Used dialysate may be pumped from the patient via the patient line 34 to the cassette 24 and into a drain line 28, which may include one or more clamps to control flow through one or more branches of the drain line 28. In this illustrative embodiment, the drain line 28 may include a connector 39 for connecting the drain line 28 to a dedicated drain receptacle, and an effluent sample port 282 for taking a sample of used dialysate for testing or other analysis. The user may also mount the lines 30 of one or more containers 20 within the door 141. The lines 30 may also be connected to a continuous or real-time dialysate preparation system. (The lines 26, 28, 30, 34 may include a flexible tubing and/or suitable connectors and other components (such as pinch valves, etc.) as desired.) The containers 20 may contain sterile peritoneal dialysis solution for infusion, or other materials (e.g., materials used by the cycler 14 to formulate dialysate by mixing with water, or admixing different types of dialysate solutions). The lines 30 may be connected to spikes 160 of the cassette 24, which are shown in FIG. 1 covered by removable caps. In one aspect of the invention described in more detail below, the cycler 14 may automatically remove caps from one or more spikes 160 of the cassette 24 and connect lines 30 of solution containers 20 to respective spikes 160. This feature may help reduce the possibility of infection or contamination by reducing the chance of contact of non-sterile items with the spikes 160.

Figure 1A:
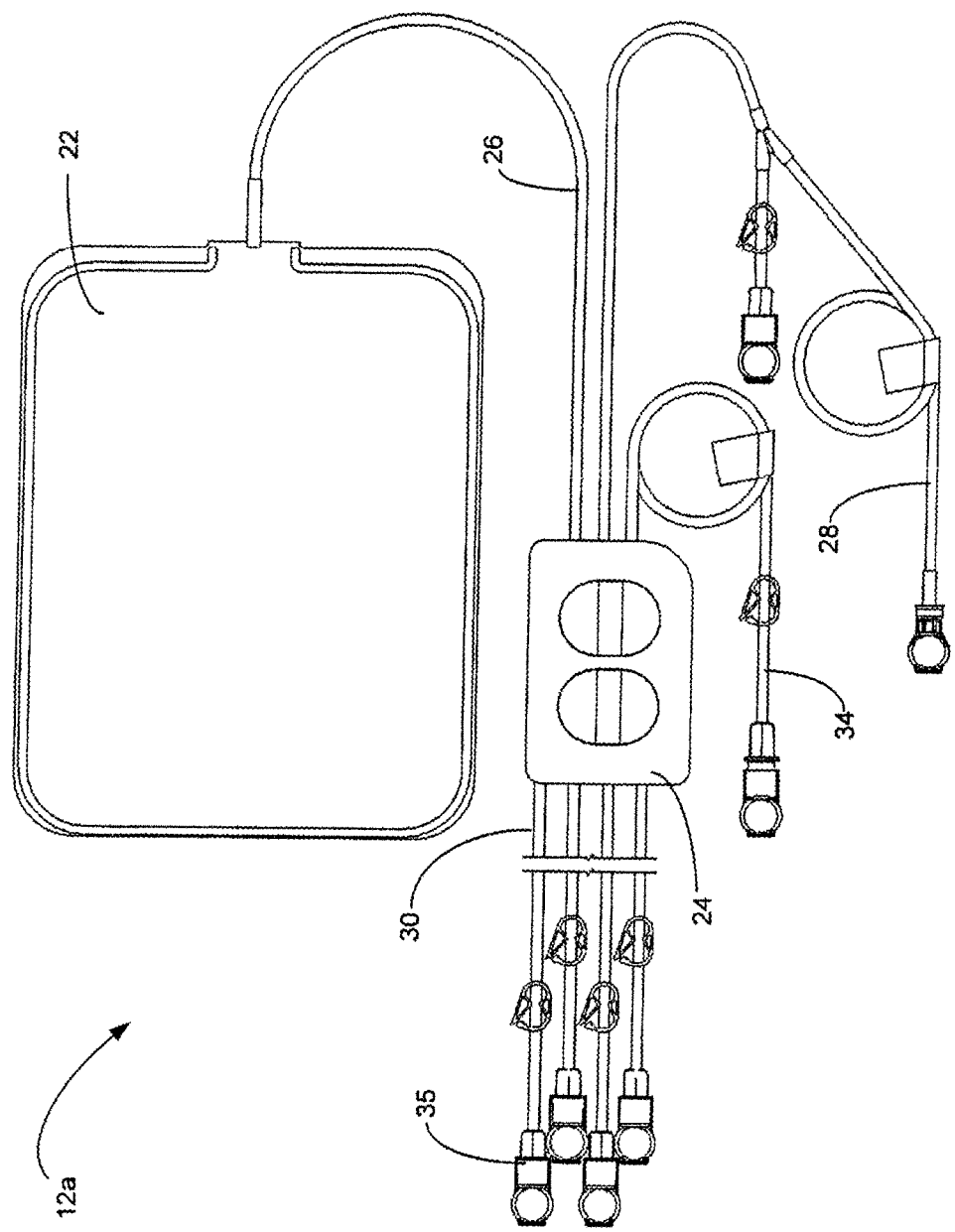
FIG. 1A shows an alternative arrangement for a dialysate delivery set shown in FIG. 1.

In another aspect, a dialysate delivery set 12a may not have cassette spikes 160. Instead, one or more solution lines 30 may be permanently affixed to the inlet ports of cassette 24, as shown in FIG. 1A. In this case, each solution line 30 may have a (capped) spike connector 35 for manual connection to a solution container or dialysate bag 20.

With various connections made, the control system 16 may pace the cycler 14 through a series of fill, dwell, and/or drain cycles typical of an APD procedure. For example, during a fill phase, the cycler 14 may pump dialysate (by way of the cassette 24) from one or more containers 20 (or other source of dialysate supply) into the heater bag 22 for heating. Thereafter, the cycler 14 may infuse heated dialysate from the heater bag 22 through the cassette 24 and into the patient's peritoneal cavity via the patient line 34. Following a dwell phase, the cycler 14 may institute a drain phase, during which the cycler 14 pumps used dialysate from the patient via the line 34 (again by way of the cassette 24), and discharges spent dialysis solution into a nearby drain (not shown) via the drain line 28.

The cycler 14 does not necessarily require the solution containers 20 and/or the heater bag 22 to be positioned at a prescribed head height above the cycler 14, e.g., because the cycler 14 is not necessarily a gravity flow system. Instead, the cycler 14 may emulate gravity flow, or otherwise suitably control flow of dialysate solution, even with the source solution containers 20 above, below or at a same height as the cycler 14, with the patient above or below the cycler, etc. For example, the cycler 14 can emulate a fixed head height during a given procedure, or the cycler 14 can change the effective head height to either increase or decrease pressure applied to the dialysate during a procedure. The cycler 14 may also adjust the rate of flow of dialysate. In one aspect of the invention, the cycler 14 may adjust the pressure and/or flow rate of dialysate when provided to the patient or drawn from the patient so as to reduce the patient's sensation of the fill or drain operation. Such adjustment may occur during a single fill and/or drain cycle, or may be adjusted across different fill and/or drain cycles. In one embodiment, the cycler 14 may taper the pressure used to draw used dialysate from the patient near the end of a drain operation. Because the cycler 14 may establish an artificial head height, it may have the flexibility to interact with and adapt to the particular physiology or changes in the relative elevation of the patient.

Cassette

In one aspect of the invention, a cassette 24 may include patient and drain lines that are separately occludable with respect to solution supply lines. That is, safety critical flow to and from patient line may be controlled, e.g., by pinching the lines to stop flow, without the need to occlude flow through one or more solution supply lines. This feature may allow for a simplified occluder device since occlusion may be performed with respect to only two lines as opposed to occluding other lines that have little or no effect on patient safety. For example, in a circumstance where a patient or drain connection becomes disconnected, the patient and drain lines may be occluded. However, the solution supply and/or heater bag lines may remain open for flow, allowing the cycler 14 to prepare for a next dialysis cycle; e.g., separate occlusion of patient and drain lines may help ensure patient safety while permitting the cycler 14 to continue to pump dialysate from one or more containers 20 to the heater bag 22 or to other solution containers 20.

In another aspect of the invention, the cassette may have patient, drain and heater bag lines at one side or portion of the cassette and one or more solution supply lines at another side or portion of the cassette, e.g., an opposite side of the cassette. Such an arrangement may allow for separate occlusion of patient, drain or heater bag lines with respect to solution lines as discussed above. Physically separating the lines attached to the cassette by type or function allows for more efficient control of interaction with lines of a certain type or function. For example, such an arrangement may allow for a simplified occluder design because less force is required to occlude one, two or three of these lines than all lines leading to or away from the cassette. Alternately, this arrangement may allow for more effective automated connection of solution supply lines to the cassette, as discussed in more detail below. That is, with solution supply lines and their respective connections located apart from patient, drain and/or heater bag lines, an automated de-capping and connection device may remove caps from spikes on the cassette as well as caps on solution supply lines, and connect the lines to respective spikes without interference by the patient, drain or heater bag lines.

Figures 1A, 9:
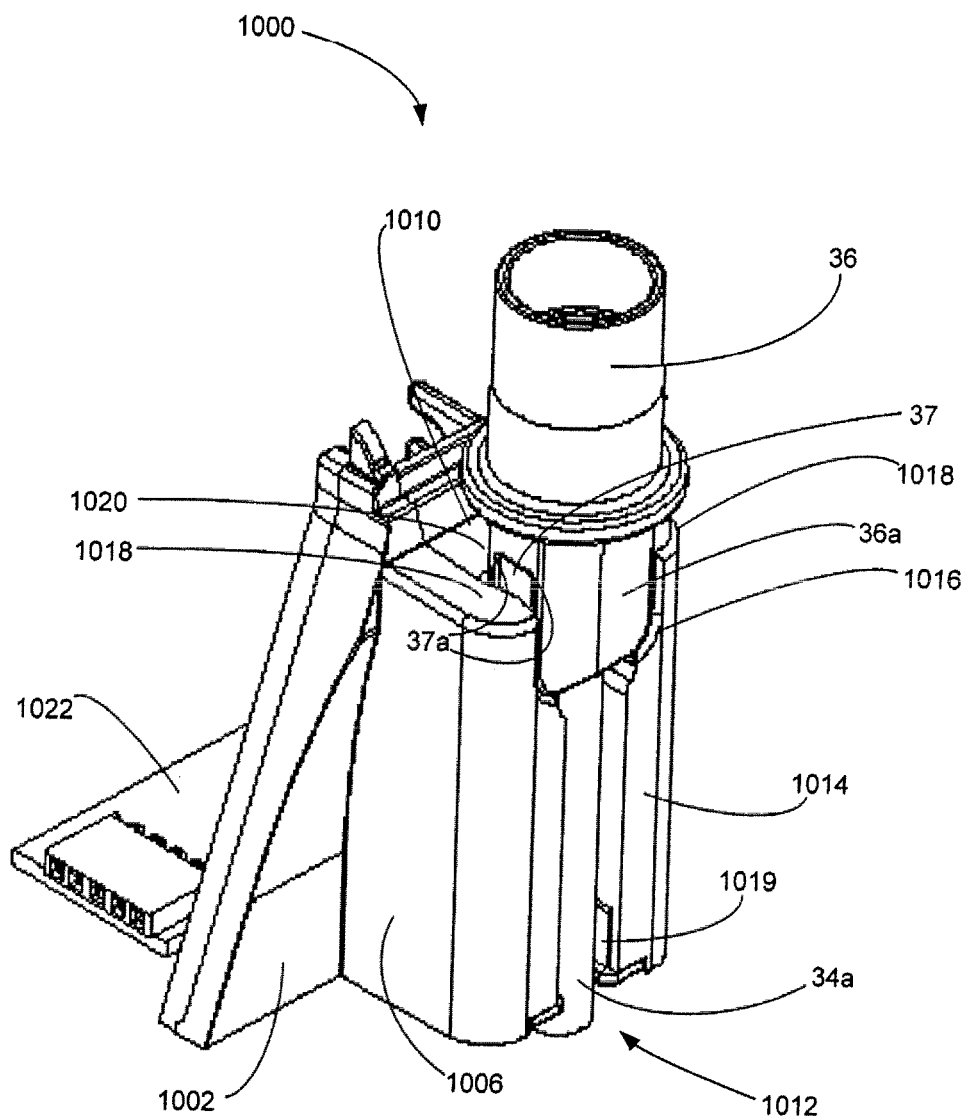
FIG. 9 is a rear view of the cassette body of FIG. 3.
Figures 1B, 9:
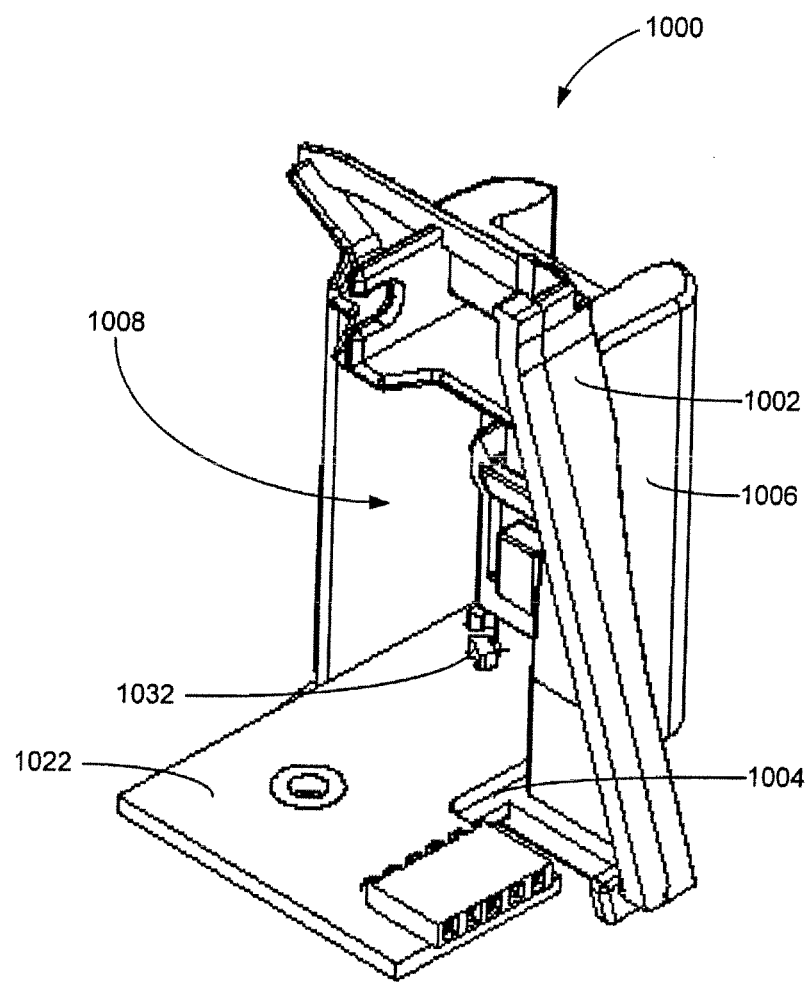
Figures 2, 9:
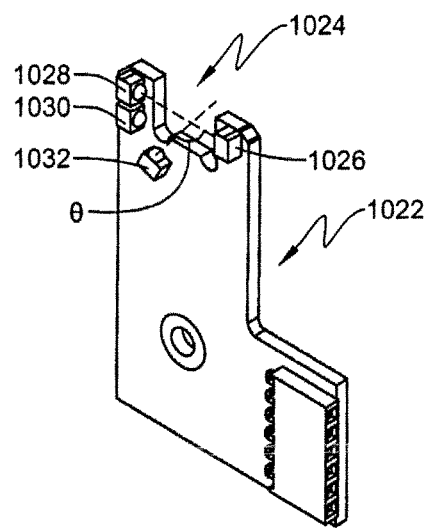
FIG. 2 is a schematic view of an illustrative set for use with the APD system of FIG. 1.
Figures 3, 9:
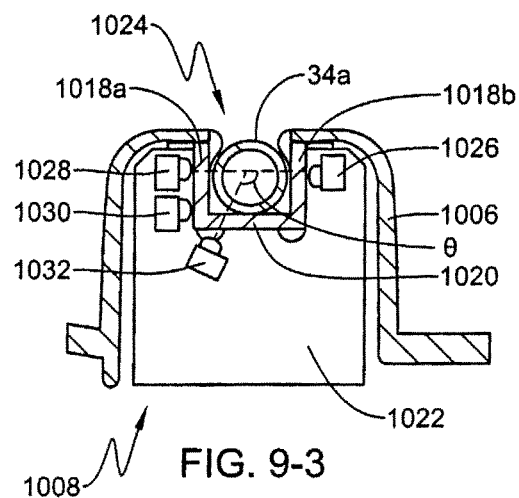
Figures 4, 9:
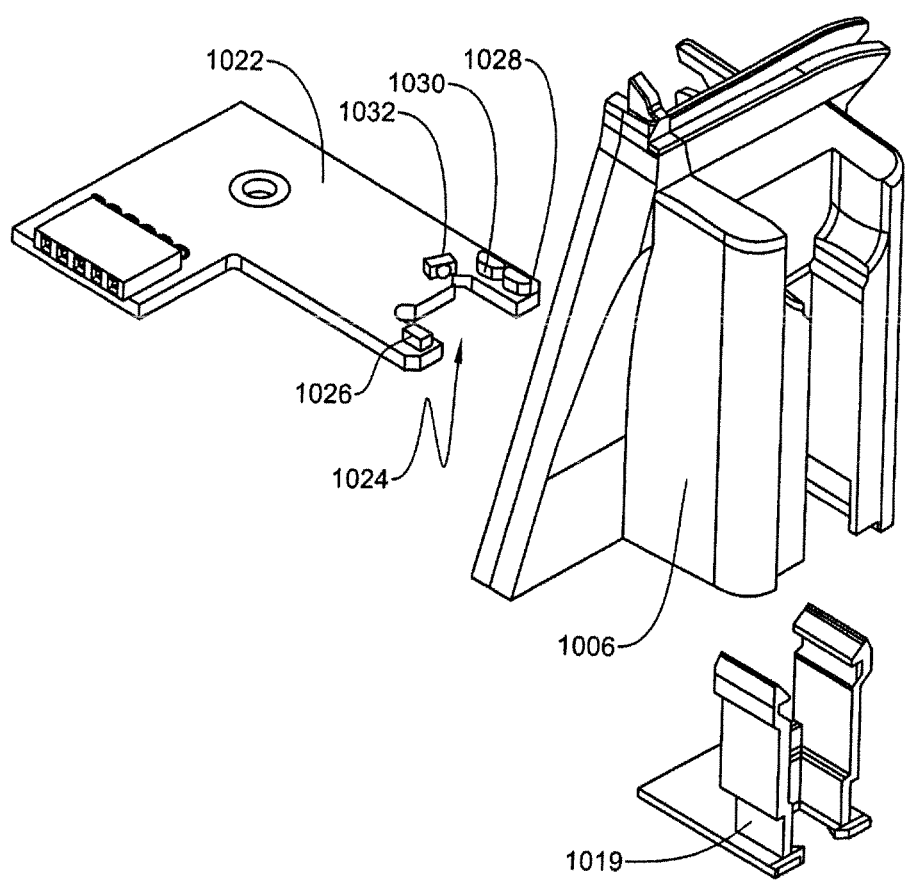
Figures 5, 9:
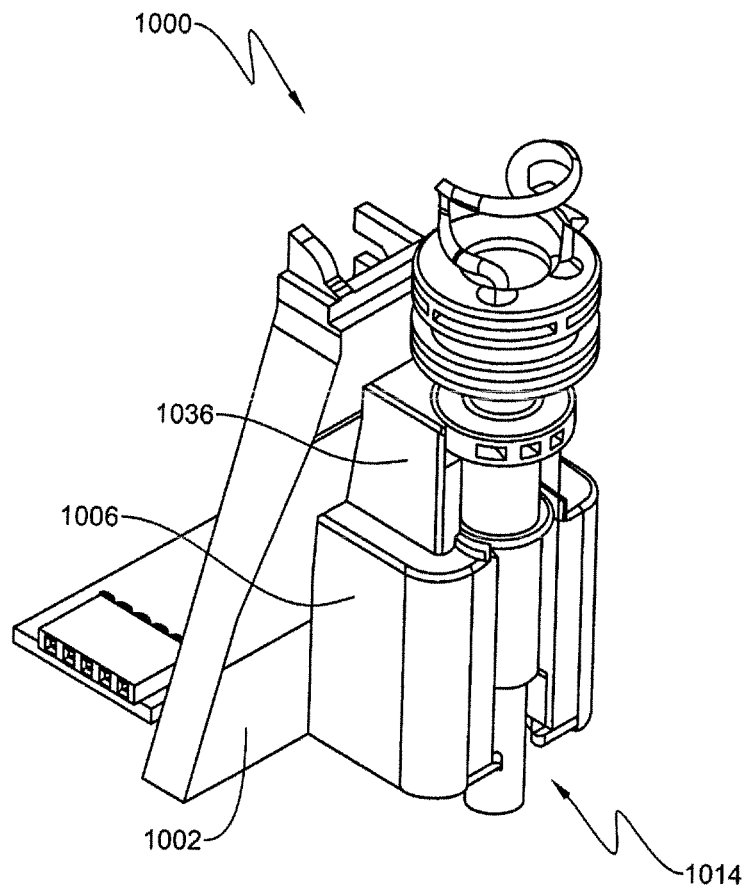
Figures 6, 9:
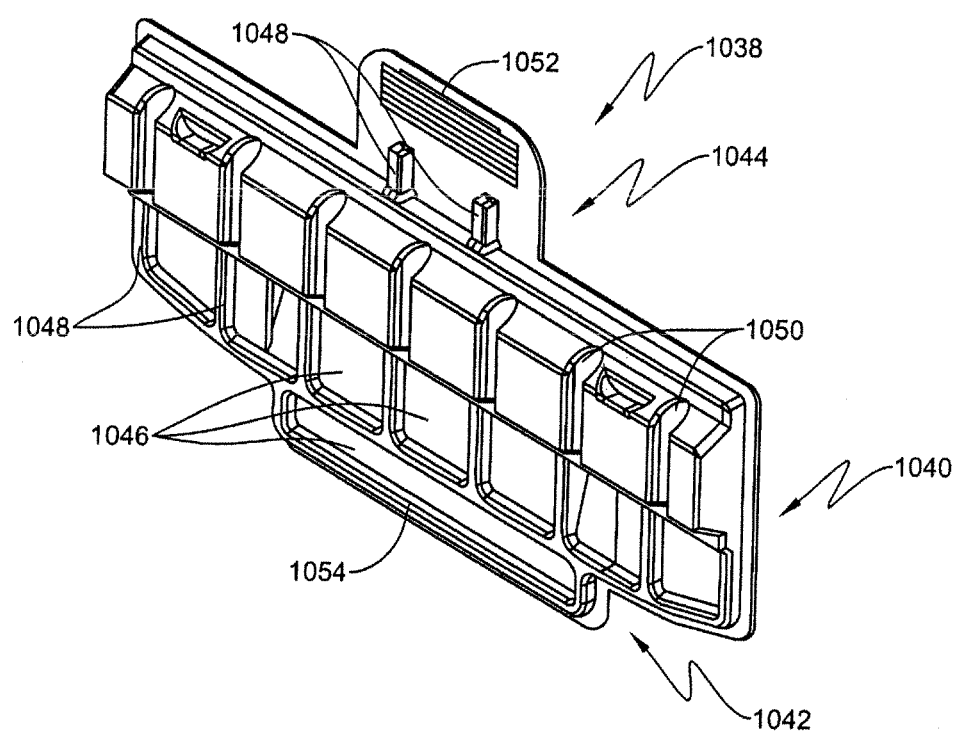
Figures 7, 9:
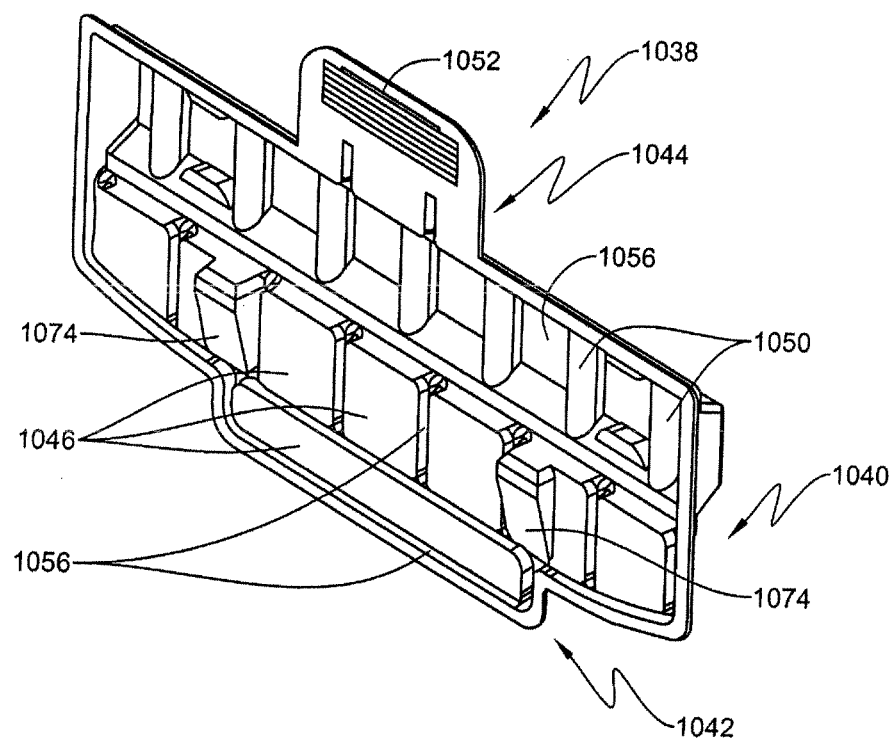
Figures 8, 9:
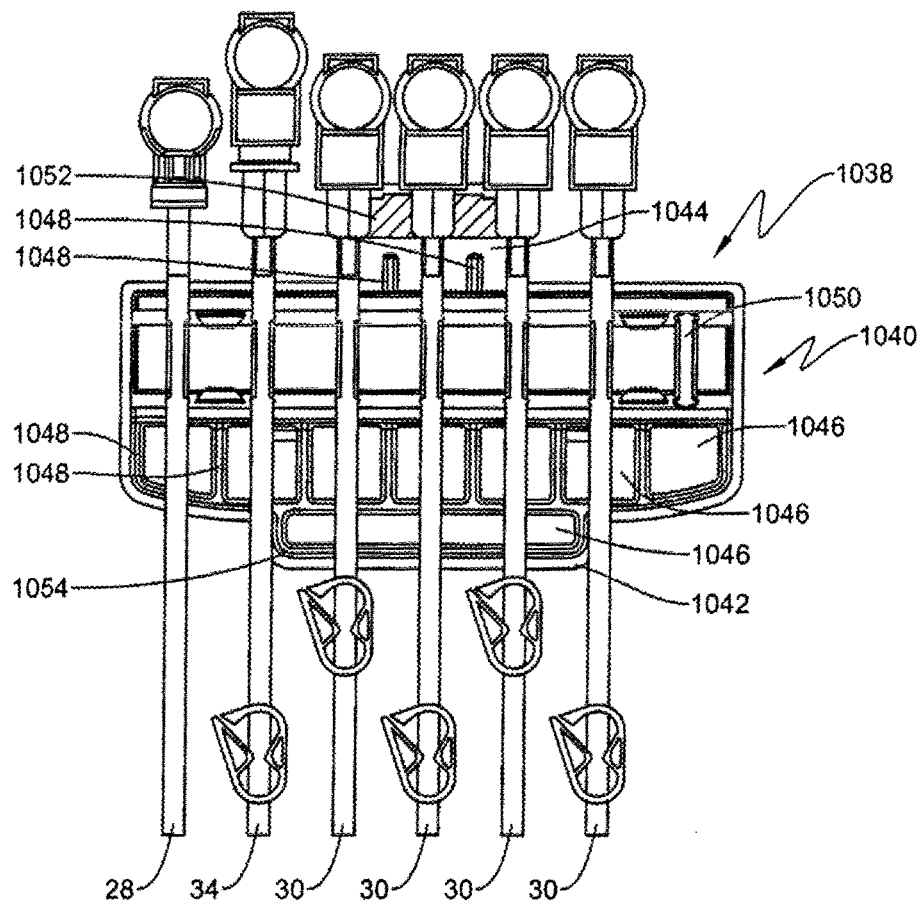
Figure 9:
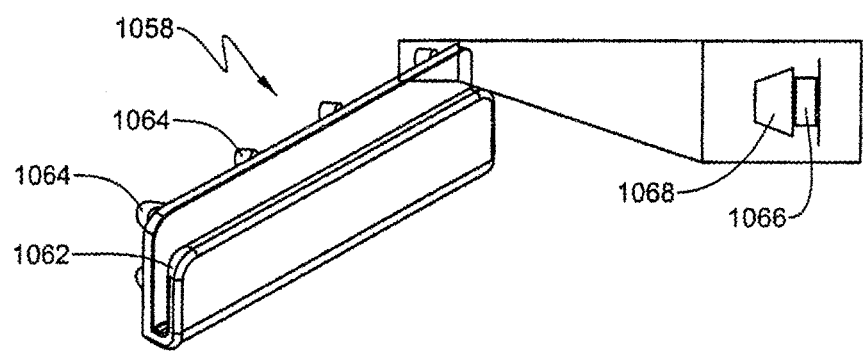

FIG. 2 shows an illustrative embodiment of a cassette 24 that incorporates aspects of the invention described above. In this embodiment, the cassette 24 has a generally planar body and the heater bag line 26, the drain line 28 and the patient line 34 are connected at respective ports on the left end of the cassette body, while the right end of the cassette body may include five spikes 160 to which solution supply lines 30 may be connected. In the arrangement shown in FIG. 2, each of the spikes 160 is covered by a spike cap 63, which may be removed, exposing the respective spike and allowing connection to a respective line 30. As described above, the lines 30 may be attached to one or more solution containers or other sources of material, e.g., for use in dialysis and/or the formulation of dialysate, or connected to one or more collection bags for sampling purposes or for peritoneal equilibration testing (PET test).

Figure 3:
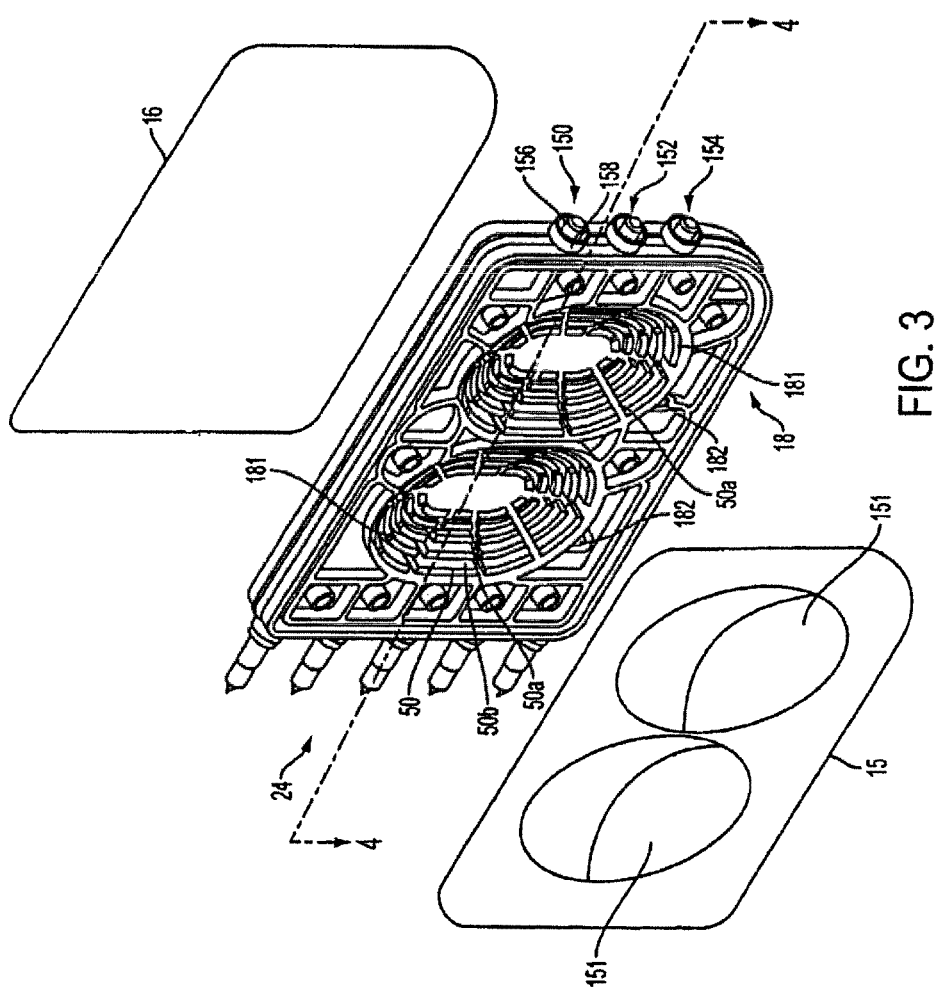
FIG. 3 is an exploded perspective view of a cassette in a first embodiment.
Figure 4:
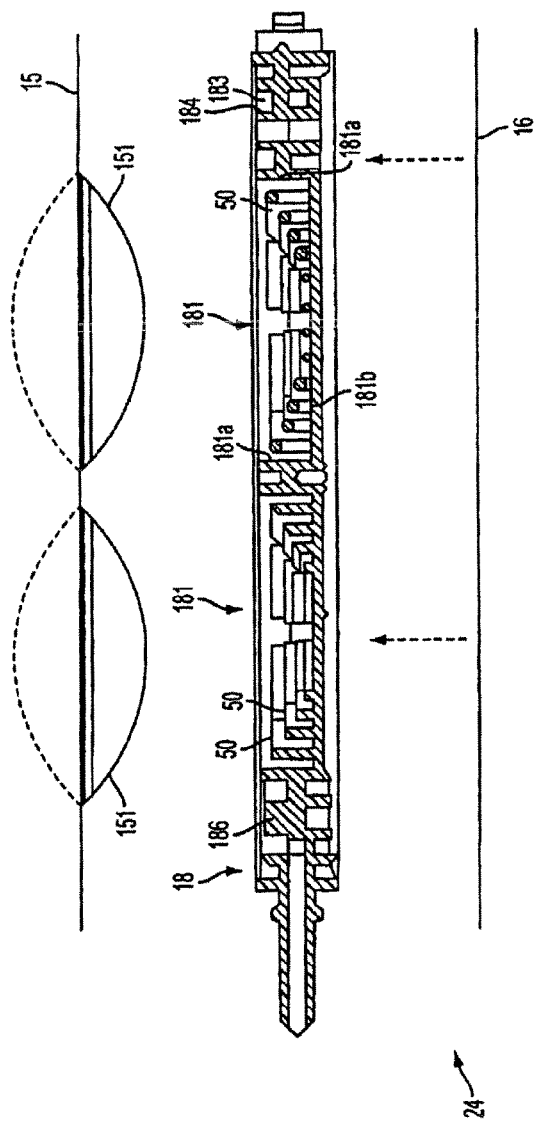
FIG. 4 is a cross sectional view of the cassette along the line 4-4 in FIG. 3.

FIGS. 3 and 4 show exploded views (perspective and top views, respectively) of the cassette 24 in this illustrative embodiment. The cassette 24 is formed as a relatively thin and flat member having a generally planar shape, e.g., may include components that are molded, extruded or otherwise formed from a suitable plastic. In this embodiment, the cassette 24 includes a base member 18 that functions as a frame or structural member for the cassette 24 as well as forming, at least in part, various flow channels, ports, valve portions, etc. The base member 18 may be molded or otherwise formed from a suitable plastic or other material, such as a polymethyl methacrylate (PMMA) acrylic, or a cyclic olefin copolymer/ultra low density polyethylene (COC/ULDPE), and may be relatively rigid. In an embodiment, the ratio of COC to ULDPE can be approximately 85%/15%. FIG. 3 also shows the ports for the heater bag (port 150), drain (port 152) and the patient (port 154) that are formed in the base member 18. Each of these ports may be arranged in any suitable way, such as, for example, a central tube 156 extending from an outer ring or skirt 158, or a central tube alone. Flexible tubing for each of the heater bag, drain and patient lines 26, 28, 34 may be connected to the central tube 156 and engaged by the outer ring 158, if present.

Both sides of the base member 18 may be covered, at least in part, by a membrane 15 and 16, e.g., a flexible polymer film made from, for example, polyvinyl chloride (PVC), that is cast, extruded or otherwise formed. Alternatively, the sheet may be formed as a laminate of two or more layers of poly-cyclohexylene dimethylene cyclohexanedicarboxylate (PCCE) and/or ULDPE, held together, for example, by a coextrudable adhesive (CXA). In some embodiments, the membrane thickness may be in the range of approximately 0.002 to 0.020 inches thick. In a preferred embodiment, the thickness of a PVC—based membrane may be in the range of approximately 0.012 to 0.016 inches thick, and more preferably approximately 0.014 inches thick. In another preferred embodiment, such as, for example, for laminate sheets, the thickness of the laminate may be in the range of approximately 0.006 to 0.010 inches thick, and more preferably approximately 0.008 inches thick.

Both membranes 15 and 16 may function not only to close or otherwise form a part of flowpaths of the cassette 24, but also may be moved or otherwise manipulated to open/close valve ports and/or to function as part of a pump diaphragm, septum or wall that moves fluid in the cassette 24. For example, the membranes 15 and 16 may be positioned on the base member 18 and sealed (e.g., by heat, adhesive, ultrasonic welding or other means) to a rim around the periphery of the base member 18 to prevent fluid from leaking from the cassette 24. The membrane 15 may also be bonded to other, inner walls of the base member 18, e.g., those that form various channels, or may be pressed into sealing contact with the walls and other features of the base member 18 when the cassette 24 suitably mounted in the cycler 14. Thus, both of the membranes 15 and 16 may be sealed to a peripheral rim of the base member 18, e.g., to help prevent leaking of fluid from the cassette 24 upon its removal from the cycler 14 after use, yet be arranged to lie, unattached, over other portions of the base member 18. Once placed in the cycler 14, the cassette 24 may be squeezed between opposed gaskets or other members so that the membranes 15 and 16 are pressed into sealing contact with the base member 18 at regions inside of the periphery, thereby suitably sealing channels, valve ports, etc., from each other.

Other arrangements for the membranes 15 and 16 are possible. For example, the membrane 16 may be formed by a rigid sheet of material that is bonded or otherwise made integral with the body 18. Thus, the membrane 16 need not necessarily be, or include, a flexible member. Similarly, the membrane 15 need not be flexible over its entire surface, but instead may include one or more flexible portions to permit pump and/or valve operation, and one or more rigid portions, e.g., to close flowpaths of the cassette 24. It is also possible that the cassette 24 may not include the membrane 16 or the membrane 15, e.g., where the cycler 14 includes a suitable member to seal pathways of the cassette, control valve and pump function, etc.

Figure 5:
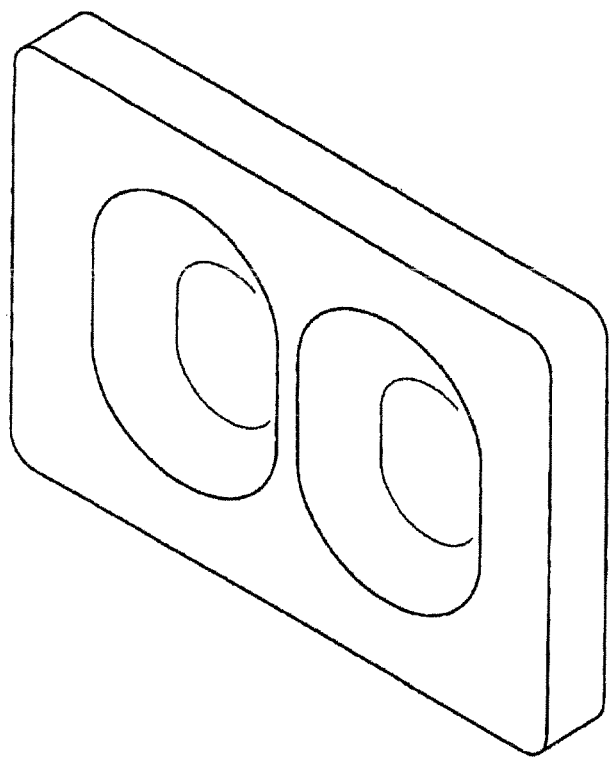
FIG. 5 is a perspective view of a vacuum mold that may be used to form a membrane having pre-formed pump chamber portions in an illustrative embodiment.

In accordance with another aspect of the invention, the membrane 15 may include a pump chamber portion 151 ("pump membrane") that is formed to have a shape that closely conforms to the shape of a corresponding pump chamber 181 depression in the base 18. For example, the membrane 15 may be generally formed as a flat member with thermoformed (or otherwise formed) dome-like shapes 151 that conform to the pump chamber depressions of the base member 18. The dome-like shape of the pre-formed pump chamber portions 151 may be constructed, for example, by heating and forming the membrane over a vacuum form mold of the type shown in FIG. 5. As shown in FIG. 5, the vacuum may be applied through a collection of holes along the wall of the mold. Alternatively, the wall of the mold can be constructed of a porous gas-permeable material, which may result in a more uniformly smooth surface of the molded membrane. In one example, the molded membrane sheet 15 is trimmed while attached to the vacuum form mold. The vacuum form mold then presses the trimmed membrane sheet 15 against the cassette body 18 and bonds them together. In one embodiment the membrane sheets 15, 16 are heat-welded to the cassette body 18. In this way, the membrane 15 may move relative to the pump chambers 181 to effect pumping action without requiring stretching of the membrane 15 (or at least minimal stretching of the membrane 15), both when the membrane 15 is moved maximally into the pump chambers 181 and (potentially) into contact with spacer elements 50 (e.g., as shown in solid line in FIG. 4 while pumping fluid out of the pump chamber 181), and when the membrane 15 is maximally withdrawn from the pump chamber 181 (e.g., as shown in dashed line in FIG. 4 when drawing fluid into the pump chamber 181). Avoiding stretching of the membrane 15 may help prevent pressure surges or other changes in fluid delivery pressure due to sheet stretch and/or help simplify control of the pump when seeking to minimize pressure variation during pump operation. Other benefits may be found, including reduced likelihood of membrane 15 failure (e.g., due to tears in the membrane 15 resulting from stresses place on the membrane 15 during stretching), and/or improved accuracy in pump delivery volume measurement, as described in more detail below. In one embodiment, the pump chamber portions 151 may be formed to have a size (e.g., a define a volume) that is about 85-110% of the pump chamber 181, e.g., if the pump chamber portions 151 define a volume that is about 100% of the pump chamber volume, the pump chamber portion 151 may lie in the pump chamber 181 and in contact with the spacers 50 while at rest and without being stressed.

Providing greater control of the pressure used to generate a fill and delivery stroke of liquid into and out of a pump chamber may have several advantages. For example, it may be desirable to apply the minimum negative pressure possible when the pump chamber draws fluid from the patient's peritoneal cavity during a drain cycle. A patient may experience discomfort during the drain cycle of a treatment in part because of the negative pressure being applied by the pumps during a fill stroke. The added control that a pre-formed membrane can provide to the negative pressure being applied during a fill stroke may help to reduce the patient's discomfort.

A number of other benefits may be realized by using pump membranes pre-formed to the contour of the cassette pump chamber. For example, the flow rate of liquid through the pump chamber can be made more uniform, because a constant pressure or vacuum can be applied throughout the pump stroke, which in turn may simplify the process of regulating the heating of the liquid. Moreover, temperature changes in the cassette pump may have a smaller effect on the dynamics of displacing the membrane, as well as the accuracy of measuring pressures within the pump chambers. In addition, pressure spikes within the fluid lines can be minimized. Also, correlating the pressures measured by pressure transducers on the control (e.g. pneumatic) side of the membrane with the actual pressure of the liquid on the pump chamber side of the membrane may be simpler. This in turn may permit more accurate head height measurements of the patient and fluid source bags prior to therapy, improve the sensitivity of detecting air in the pump chamber, and improve the accuracy of volumetric measurements. Furthermore, eliminating the need to stretch the membrane may allow for the construction and use of pump chambers having greater volumes.

In this embodiment, the cassette 24 includes a pair of pump chambers 181 that are formed in the base member 18, although one pump chamber or more than two pump chambers are possible. In accordance with an aspect of the invention, the inner wall of pump chambers 181 includes spacer elements 50 that are spaced from each other and extend from the inner wall of pump chamber 18 to help prevent portions of the membrane 15 from contacting the inner wall of pump chamber 181. (As shown on the right-side pump chamber 181 in FIG. 4, the inner wall is defined by side portions 181a and a bottom portion 181b. The spacers 50 extend upwardly from the bottom portion 181b in this embodiment, but could extend from the side portions 181a or be formed in other ways.) By preventing contact of the membrane 15 with the pump chamber inner wall, the spacer elements 50 may provide a dead space (or trap volume) which may help trap air or other gas in the pump chamber 181 and inhibit the gas from being pumped out of the pump chamber 181 in some circumstances. In other cases, the spacers 50 may help the gas move to an outlet of the pump chamber 181 so that the gas may be removed from the pump chamber 181, e.g., during priming. Also, the spacers 50 may help prevent the membrane 15 from sticking to the pump chamber inner wall and/or allow flow to continue through the pump chamber 181, even if the membrane 15 is pressed into contact with the spacer elements 50. In addition, the spacers 50 help to prevent premature closure of the outlet port of the pump chamber (openings 187 and/or 191) if the sheet happens to contact the pump chamber inner wall in a non-uniform manner. Further details regarding the arrangement and/or function of spacers 50 are provided in U.S. Pat. Nos. 6,302,653 and 6,382,923, both of which are incorporated herein by reference.

In this embodiment, the spacer elements 50 are arranged in a kind of "stadium seating" arrangement such that the spacer elements 50 are arranged in a concentric elliptical pattern with ends of the spacer elements 50 increasing in height from the bottom portion 181b of the inner wall with distance away from the center of the pump chamber 181 to form a semi-elliptical domed shaped region (shown by dotted line in FIG. 4). Positioning spacer elements 50 such that the ends of the spacer elements 50 form a semi-elliptical region that defines the domed region intended to be swept by the pump chamber portion 151 of the membrane 15 may allow for a desired volume of dead space that minimizes any reduction to the intended stroke capacity of pump chambers 181. As can be seen in FIG. 3 (and FIG. 6), the "stadium seating" arrangement in which spacer elements 50 are arranged may include "aisles" or breaks 50a in the elliptical pattern. Breaks (or aisles) 50a help to maintain an equal gas level throughout the rows (voids or dead space) 50b between spacer elements 50 as fluid is delivered from the pump chamber 181. For example, if the spacer elements 50 were arranged in the stadium seating arrangement shown in FIG. 6 without breaks (or aisles) 50a or other means of allowing liquid and air to flow between spacer elements 50, the membrane 15 might bottom out on the spacer element 50 located at the outermost periphery of the pump chamber 181, trapping whatever gas or liquid is present in the void between this outermost spacer element 50 and the side portions 181a of the pump chamber wall. Similarly, if the membrane 15 bottomed out on any two adjacent spacer elements 50, any gas and liquid in the void between the elements 50 may become trapped. In such an arrangement, at the end of the pump stroke, air or other gas at the center of pump chamber 181 could be delivered while liquid remains in the outer rows. Supplying breaks (or aisles) 50a or other means of fluidic communication between the voids between spacer elements 50 helps to maintain an equal gas level throughout the voids during the pump stroke, such that air or other gas may be inhibited from leaving the pump chamber 181 unless the liquid volume has been substantially delivered.

In certain embodiments, spacer elements 50 and/or the membrane 15 may be arranged so that the membrane 15 generally does not wrap or otherwise deform around individual spacers 50 when pressed into contact with them, or otherwise extend significantly into the voids between spacers 50. Such an arrangement may lessen any stretching or damage to membrane 15 caused by wrapping or otherwise deforming around one or more individual spacer elements 50. For example, it has also been found to be advantageous in this embodiment to make the size of the voids between spacers 50 approximately equal in width to the width of the spacers 50. This feature has shown to help prevent deformation of the membrane 15, e.g., sagging of the membrane into the voids between spacers 50, when the membrane 15 is forced into contact with the spacers 50 during a pumping operation.

In accordance with another aspect of the invention, the inner wall of pump chambers 181 may define a depression that is larger than the space, for example a semi-elliptical or domed space, intended to be swept by the pump chamber portion 151 of the membrane 15. In such instances, one or more spacer elements 50 may be positioned below the domed region intended to be swept by the membrane portion 151 rather than extending into that domed region. In certain instances, the ends of spacer elements 50 may define the periphery of the domed region intended to be swept by the membrane 15. Positioning spacer elements 50 outside of, or adjacent to, the periphery of the domed region intended to be swept by the membrane portion 151 may have a number of advantages. For example, positioning one or more spacer elements 50 such that the spacer elements are outside of, or adjacent to, the domed region intended to be swept by the flexible membrane provides a dead space between the spacers and the membrane, such as described above, while minimizing any reduction to the intended stroke capacity of pump chambers 181.

Figure 6:
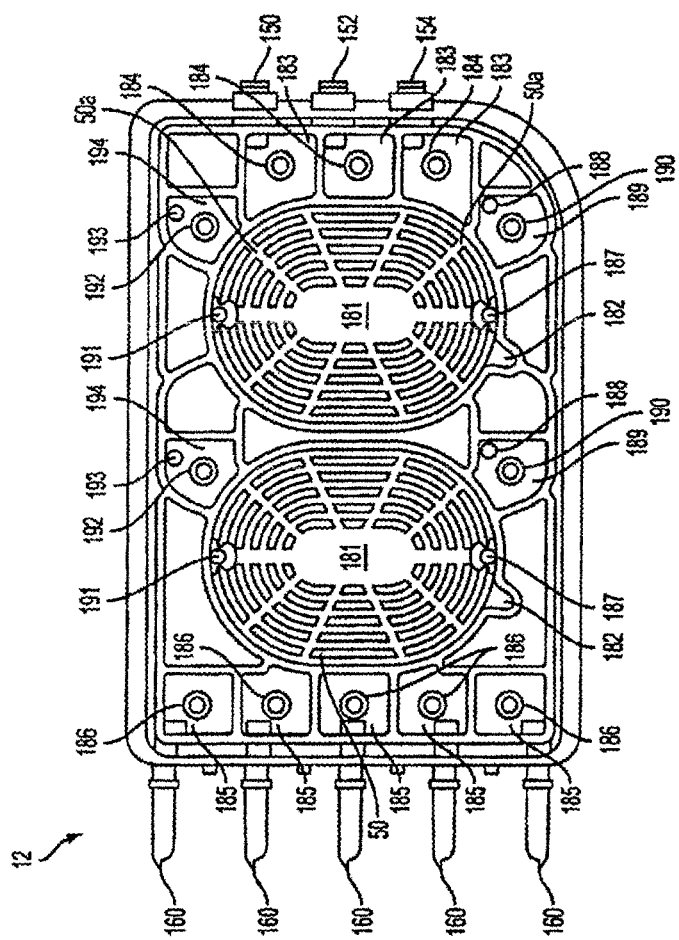
FIG. 6 shows a front view of the cassette body of FIG. 3.
Figure 7:
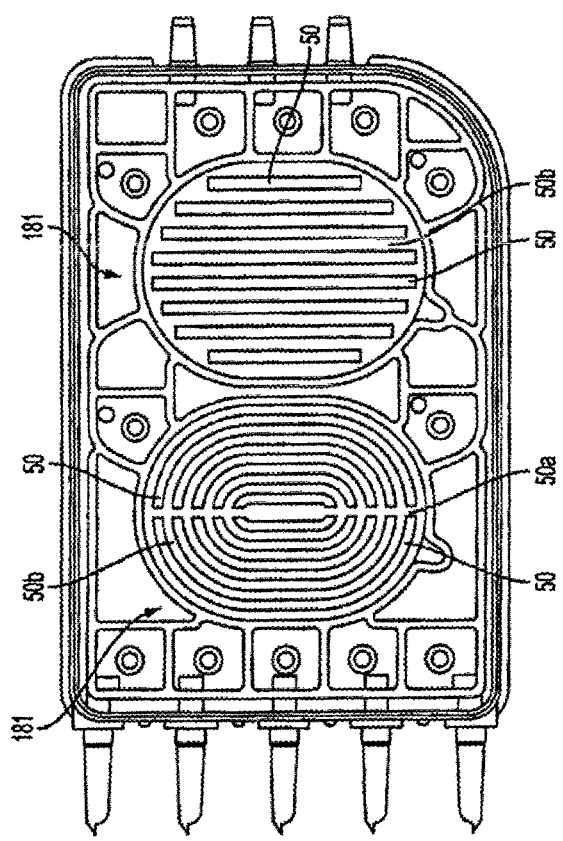
FIG. 7 is a front view of a cassette body including two different spacer arrangements in an illustrative embodiment.

It should be understood that the spacer elements 50, if present, in a pump chamber may be arranged in any other suitable way, such as for example, shown in FIG. 7. The left side pump chamber 181 in FIG. 7 includes spacers 50 arranged similarly to that in FIG. 6, but there is only one break or aisle 50a that runs vertically through the approximate center of the pump chamber 181. The spacers 50 may be arranged to define a concave shape similar to that in FIG. 6 (i.e., the tops of the spacers 50 may form the semi-elliptical shape shown in FIGS. 3 and 4), or may be arranged in other suitable ways, such as to form a spherical shape, a box-like shape, and so on. The right-side pump chamber 181 in FIG. 7 shows an embodiment in which the spacers 50 are arranged vertically with voids 50b between spacers 50 also arranged vertically. As with the left-side pump chamber, the spacers 50 in the right-side pump chamber 181 may define a semi-elliptical, spherical, box-like or any other suitably shaped depression. It should be understood, however, that the spacer elements 50 may have a fixed height, a different spatial pattern that those shown, and so on.

Also, the membrane 15 may itself have spacer elements or other features, such as ribs, bumps, tabs, grooves, channels, etc., in addition to, or in place of the spacer elements 50. Such features on the membrane 15 may help prevent sticking of the membrane 15, etc., and/or provide other features, such as helping to control how the sheet folds or otherwise deforms when moving during pumping action. For example, bumps or other features on the membrane 15 may help the sheet to deform consistently and avoid folding at the same area(s) during repeated cycles. Folding of a same area of the membrane 15 at repeated cycles may cause the membrane 15 to prematurely fail at the fold area, and thus features on the membrane 15 may help control the way in which folds occur and where.

Figure 8:
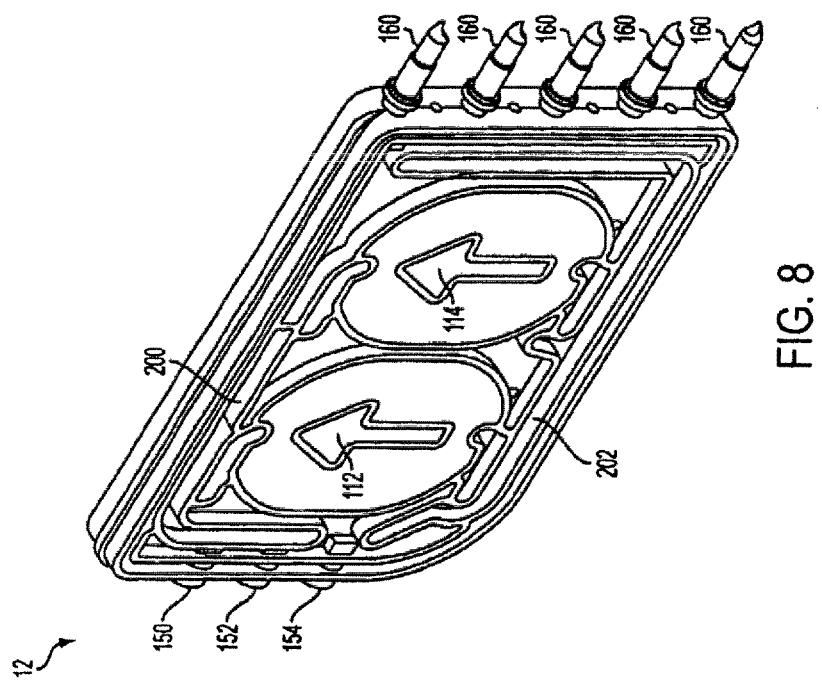
FIG. 8 is a rear perspective view of the cassette body of FIG. 3.

In this illustrative embodiment, the base member 18 of the cassette 24 defines a plurality of controllable valve features, fluid pathways and other structures to guide the movement of fluid in the cassette 24. FIG. 6 shows a plan view of the pump chamber side of the base member 18, which is also seen in perspective view in FIG. 3. FIG. 8 shows a perspective view of a back side of the base member 18, and FIG. 9 shows a plan view of the back side of the base member 18. The tube 156 for each of the ports 150, 152 and 154 fluidly communicates with a respective valve well 183 that is formed in the base member 18. The valve wells 183 are fluidly isolated from each other by walls surrounding each valve well 183 and by sealing engagement of the membrane 15 with the walls around the wells 183. As mentioned above, the membrane 15 may sealingly engage the walls around each valve well 183 (and other walls of the base member 18) by being pressed into contact with the walls, e.g., when loaded into the cycler 14. Fluid in the valve wells 183 may flow into a respective valve port 184, if the membrane 15 is not pressed into sealing engagement with the valve port 184. Thus, each valve port 184 defines a valve (e.g., a "volcano valve") that can be opened and closed by selectively moving a portion of the membrane 15 associated with the valve port 184. As will be described in more detail below, the cycler 14 may selectively control the position of portions of the membrane 15 so that valve ports (such as ports 184) may be opened or closed so as to control flow through the various fluid channels and other pathways in the cassette 24. Flow through the valve ports 184 leads to the back side of the base member 18. For the valve ports 184 associated with the heater bag and the drain (ports 150 and 152), the valve ports 184 lead to a common channel 200 formed at the back side of the base member 18. As with the valve wells 183, the channel 200 is isolated from other channels and pathways of the cassette 24 by the sheet 16 making sealing contact with the walls of the base member 18 that form the channel 200. For the valve port 184 associated with the patient line port 154, flow through the port 184 leads to a common channel 202 on the back side of the base member 18.

Returning to FIG. 6, each of the spikes 160 (shown uncapped in FIG. 6) fluidly communicates with a respective valve well 185, which are isolated from each other by walls and sealing engagement of the membrane 15 with the walls that form the wells 185. Fluid in the valve wells 185 may flow into a respective valve port 186, if the membrane 15 is not in sealing engagement with the port 186. (Again, the position of portions of the membrane 15 over each valve port 186 can be controlled by the cycler 14 to open and close the valve ports 186.) Flow through the valve ports 186 leads to the back side of the base member 18 and into the common channel 202. Thus, in accordance with one aspect of the invention, a cassette may have a plurality of solution supply lines (or other lines that provide materials for providing dialysate) that are connected to a common manifold or channel of the cassette, and each line may have a corresponding valve to control flow from/to the line with respect to the common manifold or channel. Fluid in the channel 202 may flow into lower openings 187 of the pump chambers 181 by way of openings 188 that lead to lower pump valve wells 189 (see FIG. 6). Flow from the lower pump valve wells 189 may pass through a respective lower pump valve port 190 if a respective portion of the membrane 15 is not pressed in sealing engagement with the port 190. As can be seen in FIG. 9, the lower pump valve ports 190 lead to a channel that communicates with the lower openings 187 of the pump chambers 181. Flow out of the pump chambers 181 may pass through the upper openings 191 and into a channel that communicates with an upper valve port 192. Flow from the upper valve port 192 (if the membrane 15 is not in sealing engagement with the port 192) may pass into a respective upper valve well 194 and into an opening 193 that communicates with the common channel 200 on the back side of the base member 18.

As will be appreciated, the cassette 24 may be controlled so that the pump chambers 181 can pump fluid from and/or into any of the ports 150, 152 and 154 and/or any of the spikes 160. For example, fresh dialysate provided by one of the containers 20 that is connected by a line 30 to one of the spikes 160 may be drawn into the common channel 202 by opening the appropriate valve port 186 for the proper spike 160 (and possibly closing other valve ports 186 for other spikes). Also, the lower pump valve ports 190 may be opened and the upper pump valve ports 192 may be closed. Thereafter, the portion of the membrane 15 associated with the pump chambers 181 (i.e., pump membranes 151) may be moved (e.g., away from the base member 18 and the pump chamber inner wall) so as to lower the pressure in the pump chambers 181, thereby drawing fluid in through the selected spike 160 through the corresponding valve port 186, into the common channel 202, through the openings 188 and into the lower pump valve wells 189, through the (open) lower pump valve ports 190 and into the pump chambers 181 through the lower openings 187. The valve ports 186 are independently operable, allowing for the option to draw fluid through any one or a combination of spikes 160 and associated source containers 20, in any desired sequence, or simultaneously. (Of course, only one pump chamber 181 need be operable to draw fluid into itself. The other pump chamber may be left inoperable and closed off to flow by closing the appropriate lower pump valve port 190.)

With fluid in the pump chambers 181, the lower pump valve ports 190 may be closed, and the upper pump valve ports 192 opened. When the membrane 15 is moved toward the base member 18, the pressure in the pump chambers 181 may rise, causing fluid in the pump chambers 181 to pass through the upper openings 191, through the (open) upper pump valve ports 192 and into the upper pump valve wells 194, through the openings 193 and into the common channel 200. Fluid in the channel 200 may be routed to the heater bag port 150 and/or the drain port 152 (and into the corresponding heater bag line or drain line) by opening the appropriate valve port 184. In this way, for example, fluid in one or more of the containers 20 may be drawn into the cassette 24, and pumped out to the heater bag 22 and/or the drain.

Fluid in the heater bag 22 (e.g., after having been suitably heated on the heater tray for introduction into the patient) may be drawn into the cassette 24 by opening the valve port 184 for the heater bag port 150, closing the lower pump valve ports 190, and opening the upper pump valve ports 192. By moving the portions of the membrane 15 associated with the pump chambers 181 away from the base member 18, the pressure in the pump chambers 181 may be lowered, causing fluid flow from the heater bag 22 and into the pump chambers 181. With the pump chambers 181 filled with heated fluid from the heater bag 22, the upper pump valve ports 192 may be closed and the lower pump valve ports 190 opened. To route the heated dialysate to the patient, the valve port 184 for the patient port 154 may be opened and valve ports 186 for the spikes 160 closed. Movement of the membrane 15 in the pump chambers 181 toward the base member 18 may raise the pressure in the pump chambers 181 causing fluid to flow through the lower pump valve ports 190, through the openings 188 and into the common channel 202 to, and through, the (open) valve port 184 for the patient port 154. This operation may be repeated a suitable number of times to transfer a desired volume of heated dialysate to the patient.

When draining the patient, the valve port 184 for the patient port 154 may be opened, the upper pump valve ports 192 closed, and the lower pump valve ports 190 opened (with the spike valve ports 186 closed). The membrane 15 may be moved to draw fluid from the patient port 154 and into the pump chambers 181. Thereafter, the lower pump valve ports 190 may be closed, the upper valve ports 192 opened, and the valve port 184 for the drain port 152 opened. Fluid from the pump chambers 181 may then be pumped into the drain line for disposal or for sampling into a drain or collection container. (Alternatively, fluid may also be routed to one or more spikes 160/lines 30 for sampling or drain purposes). This operation may be repeated until sufficient dialysate is removed from the patient and pumped to the drain.

The heater bag 22 may also serve as a mixing container. Depending on the specific treatment requirements for an individual patient, dialysate or other solutions having different compositions can be connected to the cassette 24 via suitable solution lines 30 and spikes 160. Measured quantities of each solution can be added to heater bag 22 using cassette 24, and admixed according to one or more predetermined formulae stored in microprocessor memory and accessible by control system 16. Alternatively, specific treatment parameters can be entered by the user via user interface 144. The control system 16 can be programmed to compute the proper admixture requirements based on the type of dialysate or solution containers connected to spikes 160, and can then control the admixture and delivery of the prescribed mixture to the patient.

In accordance with an aspect of the invention, the pressure applied by the pumps to dialysate that is infused into the patient or removed from the patient may be controlled so that patient sensations of "tugging" or "pulling" resulting from pressure variations during drain and fill operations may be minimized. For example, when draining dialysate, the suction pressure (or vacuum/negative pressure) may be reduced near the end of the drain process, thereby minimizing patient sensation of dialysate removal. A similar approach may be used when nearing the end of a fill operation, i.e., the delivery pressure (or positive pressure) may be reduced near the end of fill. Different pressure profiles may be used for different fill and/or drain cycles in case the patient is found to be more or less sensitive to fluid movement during different cycles of the therapy. For example, a relatively higher (or lower) pressure may be used during fill and/or drain cycles when a patient is asleep, as compared to when the patient is awake. The cycler 14 may detect the patient's sleep/awake state, e.g., using an infrared motion detector and inferring sleep if patient motion is reduced, or using a detected change in blood pressure, brain waves, or other parameter that is indicative of sleep, and so on. Alternately, the cycler 14 may simply "ask" the patient—"are you asleep?" and control system operation based on the patient's response (or lack of response).

Patient Line State Detection Apparatus

In one aspect, a patient line state detector detects when a fluid line to a patient, such as patient line 34, is adequately primed with fluid before it is connected to the patient. (It should be understood that although a patient line state detector is described in connection with a patient line, aspects of the invention include the detection of the presence any suitable tubing segment or other conduit and/or a fill state of the tubing segment or other conduit. Thus, aspects of the invention are not limited to use with a patient line, as a tubing state detector may be used with any suitable conduit.) In some embodiments, a patient line state detector can be used to detect adequate priming of a tubing segment of the patient-connecting end of a fluid line. The patient line 34 may be connected to an indwelling catheter in a patient's blood vessel, in a body cavity, subcutaneously, or in another organ. In one embodiment, the patient line 34 may be a component of a peritoneal dialysis system 10, delivering dialysate to and receiving fluid from a patient's peritoneal cavity. A tubing segment near the distal end of the line may be placed in an upright position in a cradle within which the sensor elements of the detector are located. FIG. 9-1A shows a front perspective view of an exemplary configuration of a patient line state detector 1000, which may be mounted on, or otherwise exposed at, the left side exterior of the housing 82, e.g., to the left of the front door 141. The patient line 34 should preferably be primed prior to being connected to the patient, because air could otherwise be delivered into the patient, raising the risk of complications. It may be permissible in some settings to allow up to 1 mL of air to be present in the patient line 34 prior to being connected to a patient's peritoneal dialysis catheter. The exemplary configurations of the patient line state detector 1000 described below will generally meet or exceed this standard, as they are capable of detecting a liquid level in a properly positioned tubing segment of line 34 so that at most about 0.2 mL of air remains in the distal end of line 34 after priming.

In one aspect, a first configuration patient line state detector 1000 may include a base member 1002. There may also be a patient line state detector housing 1006 affixed to (or co-molded with) the base member 1002, such that the detector housing 1006 may extend outwardly from the base member 1002. The detector housing 1006 defines a tube or connector holding channel 1012 within which a tubing segment 34a near the distal end of a patient line 34, or its associated connector 36 may be positioned. The portion of the detector housing 1006 facing the base member 1002 may be substantially hollow, and as a result an open cavity 1008 (shown in FIG. 9-3) may be created behind the detector housing 1006. The open cavity 1008 may accommodate the placement and positioning of sensor elements (1026, 1028, 1030 and 1032 shown in FIG. 9-3) next to the channel 1012 within which tubing segment 34a may be positioned. In an alternative embodiment, there may also optionally be a stabilizing tab 1010 extending outwardly from the base member 1002. The stabilizing tab 1010 may have a concave outer shape, so that it may substantially conform to the curvature of the patient line connector 36 when the patient line 34 is placed in the patient line state detector housing 1006. The stabilizing tab 1010 may help to prevent the connector 36 from moving during priming of the patient line 34, increasing the accuracy and efficiency of the priming process. The detector housing 1006 may have a shape that generally helps to define the tube or connector holding channel 1012, which in turn may have dimensions that vary to accommodate the transition from tubing segment 34a to tube connector 36.

In this illustrative embodiment, the channel 1012 may substantially conform to the shape of the patient line connector 36. As a result the channel 1012 may be "U-shaped" so as to encompass a portion of the connector 36 when it is placed into the channel 1012. The channel 1012 may be made up of two distinct features; a tube portion 1014 and a cradle 1016. In another aspect, the tube portion 1014 may be positioned below the cradle 1016. Additionally, the cradle 1016 may be formed by a pair of side walls 1018 and a back wall 1020. Both of the side walls 1018 may be slightly convex in shape, while the back wall 1020 may be generally flat or otherwise may have a contour generally matching the shape of the adjacent portion of connector 36. A generally convex shape of the side walls 1018 helps to lock the patient line connector 36 into place when positioned in the cradle 1016.

In an illustrative embodiment for a first configuration of patient line state detector 1000, a region 36a of the patient line connector 36 may have a generally planar surface that can rest securely against the opposing back wall 1020 of channel 1012. Additionally, this region 36a of the connector 36 may have recesses 37 on opposing sides, which can be positioned adjacent to the opposing side walls 1018 of channel 1012 when the connector 36 is positioned within the detector housing 1006. The recesses 37 can be defined by flanking raised elements 37a of connector 36. One of these recesses 37 is partially visible in FIG. 9-1. The two side walls 1018 may have a generally mating shape (such as, e.g. a convex shape) to engage recesses 37 and to help lock connector 36 into place within cradle 1016. This helps to prevent the connector 36 and tubing segment 34a from being inadvertently removed from the detector housing 1006 during priming of the patient line 34. If the raised elements 37a of connector 36 are made of sufficiently flexible material (such as, e.g., polypropylene, polyethylene, or other similar polymer-based material) a threshold pulling force against connector 36 will be capable of disengaging connector 36 and tubing segment 34a from the detector housing 1006.

In another aspect, the tube portion 1014 of the cavity 1012 may surround a majority of tubing segment 34a at a point just before tubing segment 34a attaches to the connector 36. The tube portion 1014 may contain a majority of tubing segment 34a using three structures: the two side walls 1018 and the back wall 1020. In an embodiment, the two side walls 1018 and back wall 1020 may be transparent or sufficiently translucent (constructed from, e.g. plexiglass) so as to allow the light from a plurality of LED's (such as, e.g., LED's 1028, 1030, and 1032 in FIG. 9-3) to be directed through the walls without being significantly blocked or diffused. An optical sensor 1026 (shown in FIG. 9-2), may also be positioned along one of the walls 1018, and can detect the light being emitted by the LED's. In the illustrated embodiment, a transparent or translucent plastic insert 1019 may be constructed to snap into the main detector housing 1006 in the region where the LED's have been positioned in the housing.

FIG. 9-2 shows a perspective layout view with LED's 1028, 1030, and 1032 and optical sensor 1026 surface-mounted on a patient line state detector printed circuit board 1022. FIG. 9-3 shows a plan view of LED's 1028, 1030, and 1032 and optical sensor 1026 mounted on detector circuit board 1022, where the detector circuit board 1022 can be positioned adjacent the back wall 1020 and side walls 1018 of detector housing 1006. FIG. 9-4 is an exploded perspective view of detection assembly 1000 showing the relative positions of the printed circuit board 1022 and the translucent or transparent plastic insert 1019 with respect to the housing 1006.

Referring also to the illustrative embodiment of FIG. 9-1B, the detector circuit board 1022 may be positioned on a support structure 1004 and inside open cavity 1008, which was formed from detector housing 1006 extending outwardly from base member 1002. The base member 1002 and support structure 1004 may be affixed to one another, or may be co-molded, so that the base member 1002 is generally perpendicular to the support structure 1004. This orientation generally permits the plane of the detector circuit board 1022 to be generally perpendicular to the long axis of tubing segment 34a when secured within channel 1012. The detector circuit board 1022 may conform generally to the cross-sectional shape of open cavity 1008, and it may also include a cutout 1024 (FIG. 9-2, 9-3) generally matching the cross-sectional shape of channel 1012 formed by back wall 1020 and side walls 1018 (FIG. 9-1A). The detector circuit board 1022 may then be positioned within open cavity 1008 with cutout 1024 nearly adjacent to side walls 1018 and back wall 1020 of detector housing 1006 in order to ensure proper alignment of the detector circuit board 1022 with tubing segment 34a or connector 36.

The detector circuit board 1022 may include a plurality of LED's and at least one optical sensor, which may be attached to circuit board 1022, and in one embodiment, the LED's and optical sensor may be surface-mounted to circuit board 1022. In one aspect, the detector circuit board 1022 may include a first LED 1028, a second LED 1030, a third LED 1032, and an optical sensor 1026. A first LED 1028 and a second LED 1030 may be positioned so as to direct light through the same side wall 1018a of channel 1012. The light emitted by the first LED 1028 and the second LED 1030 may be directed in a generally parallel direction, generally perpendicular to the side wall 1018a to which they are nearest. An optical sensor 1026 may be positioned along the opposite side wall 1018b of channel 1012. Furthermore, a third LED 1032 may be positioned along the back wall 1020 of channel 1012. In this illustrative embodiment, such a configuration of the LED's and the optical sensor 1026 allows the patient line state detector 1000 to detect three different states during the course of priming the patient line 34; a tubing segment 34a or connector 36 nearly completely filled with fluid (primed state), an incompletely filled tubing segment 34a or connector 36 (non-primed state), or the absence of a tubing segment 34a and/or connector 36 from channel 1012 (line-absent state).

When used in a peritoneal dialysis system such as, for example peritoneal dialysis system 10, configuring the detector circuit board 1022 in this fashion allows the appropriate control signal to be sent to the PD cycler controller system 16. Controller system 16 may then inform the user, via user interface 144, to position the distal end of line 34 in the patient line state detector 1000 prior to making a connection to the peritoneal dialysis catheter. The controller may then monitor for placement of tubing segment 34a within patient line state detector 1000. The controller may then proceed to direct the priming of line 34, to direct termination of priming once line 34 is primed, and then to instruct the user to disengage the distal end of line 34 from the patient line state detector 1000 and connect it to the user's peritoneal dialysis catheter.

Surface mounting the LED's 1028, 1030, and 1032 and the optical sensor 1026 to the circuit board 1022 can simplify manufacturing processes for the device, can allow the patient line state detector 1000 and circuit board 1022 to occupy a relatively small amount of space, and can help eliminate errors that may arise from movement of the LED's or the optical sensor relative to each other or to the channel 1012. Were it not for surface mounting of the sensor components, misalignment of the components could occur either during assembly of the device, or during its use.

In one aspect, the optical axis (or central optical axis) of LED 1032 may form an oblique angle with the optical axis of optical sensor 1026. In the illustrated embodiment, the optical axis of a first LED 1028, a second LED 1030, and an optical sensor 1026 are each generally parallel to each other and to back wall 1020 of channel 1012. Thus, the amount of light directed toward optical sensor 1026 from the LED's may vary depending on the presence or absence of (a) a translucent or transparent conduit within channel 1012 and/or (b) the presence of liquid within the conduit (which, for example, may be tubing segment 34a). Preferably, LED 1032 may be positioned near the side wall (e.g., 1018a) that is farthest from optical sensor 1026 in order for some of the light emitted by LED 1032 to be refracted by the presence of a translucent or transparent tubing segment 34a within channel 1012. The degree of refraction away from or toward optical sensor 1026 may depend on the presence or absence of fluid in tubing segment 34a.

In various embodiments, the oblique angle of LED 1032 with respect to optical sensor 1026 creates a more robust system for determining the presence or absence of liquid with a translucent or transparent conduit in channel 1012. LED 1032 may be positioned so that its optical axis can form any angle between 91° and 179° with respect to the optical axis of optical sensor 1026. Preferably the angle may be set within the range of about 95° to about 135° with respect to the optical sensor's optical axis. More preferably, LED 1032 may be set to have an optical axis of about 115°+/−5° with respect to the optical axis of optical sensor 1026. In an illustrative embodiment shown in FIG. 9-3, the angle θ of the optical axis of LED 1032 with respect to the optical axis of optical sensor 1026 was set to approximately 115°, +/−5°. (The optical axis of optical sensor 1026 in this particular embodiment is roughly parallel to back wall 1020, and roughly perpendicular to side wall 1018b). The advantage of angling LED 1032 with respect to the optical axis of optical sensor 1026 was confirmed in a series of tests comparing the performance of the optical sensor 1026 in distinguishing a fluid filled tube segment (wet tube) from an air filled tube segment (dry tube) using an LED 1032 oriented at about a 115° angle vs. an LED whose optical axis was directed either perpendicularly or parallel to the optical axis of optical sensor 1026. The results showed that an angled LED-based system was more robust in distinguishing the presence or absence of liquid in tubing segment 34a. Using an angled LED 1032, it was possible to select an optical sensor signal strength threshold above which an empty tubing segment 34a could reliably be detected. It was also possible to select an optical sensor signal strength threshold below which a liquid-filled tubing segment 34a could reliably be detected.

FIG. 9-12 shows a graph of test results demonstrating the ability of patient line state detector 1000 to distinguish between a liquid-filled tubing segment 34a (primed state) and an empty tubing segment 34a (non-primed state). The results were recorded with LED 1032 (third LED) oriented at an angle of about 115° with respect to the optical axis of optical sensor 1026, and LED 1030 (second LED) oriented roughly parallel to the optical axis of optical sensor 1026. The results plotted in FIG. 9-12 demonstrate that patient line state detector 1000 can reliably discriminate between a primed state and a non-primed state. When the relative signal strength associated with light received from LED 1030 was approximately 0.4 or above, it was possible to resolve an upper signal detection threshold 1027 and a lower signal detection threshold 1029 for a non-primed vs. primed state using only the light signal received from LED 1032. The upper threshold 1027 can be used to identify the non-primed state, and the lower threshold 1029 can be used to identify the primed state. The data points located above the upper-threshold 1027 are associated with an empty tubing segment 34a (non-primed state), and the data points located below the lower-threshold 1029 are associated with a liquid-filled tubing segment 34a (primed state). A relatively narrow region 1031 between these two threshold values defines a band of relative signal strength associated with light received from LED 1032 in which an assessment of the priming state of tubing segment 34a may be indeterminate. A controller (such as, e.g., control system 16) may be programmed to send the user an appropriate message whenever a signal strength associated with light received from LED 1032 falls within this indeterminate range. For example, the user may be instructed to assess whether tubing segment 34a and/or connector 36 are properly mounted in patient line state detector 1000. In the context of a peritoneal dialysis system, if optical sensor 1026 generates a signal corresponding with an empty tubing segment 34a, the controller can direct the cycler to continue to prime patient line 34 with dialysate. A signal corresponding to a liquid-filled tubing segment 34a can be used by the controller to stop further priming and instruct the user that the fluid line 34 is ready to be connected to a dialysis catheter.

In an embodiment, the cycler controller may continuously monitor the received signal from one of the LED's at the initiation of the priming procedure. Upon detection of a change in the received signal, the controller may halt further fluid pumping to carry out a full measurement using all of the LED's. If the received signals are well within the range indicating a wet tube, then further priming may be halted. However, if the received signals are within the indeterminate region 1031 or within the 'dry' region, then the cycler may command a series of small incremental pulses of fluid into the patient line by the pumping cassette, with a repeat reading of the LED signal strengths after each pulse of fluid. The priming can then be halted as soon as a reading is achieved that indicates a fluid-filled line at the level of the sensor. Incremental pulses of fluid may be accomplished by commanding brief pulses of the valve connecting the pressure reservoir to the pump actuation or control chamber. Alternatively, the controller may command the application of continuous pressure to the pump actuation or control chamber, and command the pump's outlet valve to open briefly and close to generate the series of fluid pulses.

FIG. 9-13 shows a graph of test results demonstrating the superiority of an angled LED 1032 (LEDc) when compared with an LED (LEDd) whose optical axis is roughly perpendicular to the optical axis of optical sensor 1026. In this case, the relative signal strength generated by optical sensor 1026 in response to light from LEDc was plotted against the signal strength associated with light from LEDd. Although some separation between a liquid-filled ('primed') and empty ('non-primed') tubing segment 34a was apparent at an LEDd relative signal strength of about 0.015, there remained a substantial number of 'non-primed' data points 1035 that cannot be distinguished from 'primed' data points based on this threshold value. On the other hand, a relative signal strength 1033 associated with light from LEDc of 0.028-0.03 can effectively discriminate between 'primed' tubing segment 34a (primed state) and 'non-primed' tubing segment 34a (non-primed state). Thus an angled LED (1032) can generate more reliable data than an orthogonally oriented LED.

In another embodiment, a patient line state detector 1000 can also determine whether a tubing segment 34a is present in channel 1012. In one aspect, a first LED 1028 and a second LED 1030 may be positioned next to one another. One LED (e.g., LED 1028) may be positioned so that its optical axis passes through approximately the center of a properly positioned translucent or transparent conduit or tubing segment 34a in channel 1012. The second LED (e.g. LED 1030) may be positioned so that its optical axis is shifted slightly off center with respect to conduit or tubing segment 34a in channel 1012. Such an on-center/off-center pairing of LED's on one side of channel 1012, with an optical sensor 1026 on the opposing side of channel 1012, has been shown to increase the reliability of determining whether a liquid conduit or tubing segment 34a is present or absent within channel 1012. In a series of tests in which a tubing segment 34a was alternately absent, present but improperly positioned, or present and properly positioned within channel 1012, signal measurements were taken by the optical sensor 1026 from the first LED and the second LED 1030. The signals received from each LED were plotted against each other, and the results are shown in FIG. 9-14.

As shown in FIG. 9-14, in the majority of cases in which tubing segment 34a was absent from channel 1012 (region 1039), the signal strength received by optical sensor 1026 attributable to LEDa (LEDa reception strength) was found not to be significantly different from the signal strength received from LEDa during a calibration step in which LEDa was illuminated in a known absence of any tubing in channel 1012. Similarly, the signal strength associated with LEDb (LEDb reception strength), was found not to be significantly different from LEDb during a calibration step in which LEDb was illuminated in a known absence of any tubing in channel 1012. Patient line state detector 1000 can reliably determine that no tube is present within channel 1012 if the ratio of LEDa to its calibration value, and the ratio of LEDb to its calibration value are each approximately 1±20%. In a preferred embodiment, the threshold ratio can be set at 1±15%. In an embodiment in which patient line state detector 1000 is used in conjunction with a peritoneal dialysis cycler, LEDa and LEDb values within region 1039 of FIG. 9-14, for example, can be used to indicate the absence of tube segment 34a from channel 1012. The cycler controller can be programmed to pause further pumping actions and inform the user via user interface 144 of the need to properly position the distal end of patient line 34 within patient line state detector 1000.

The configuration and alignment of the three LED's and the optical sensor 1026 described above is capable of generating the required data using translucent or transparent fluid conduits (e.g. tubing segment 34a) having a wide range of translucence. In additional testing, patient line state detector 1000 was found to be capable of providing reliable data to distinguish liquid from air in a fluid conduit, or the presence or absence of a fluid conduit, using samples of tubing having significantly different degrees of translucence. It was also capable of providing reliable data regardless of whether the PVC tubing being used was unsterilized, or sterilized (e.g., EtOx-sterilized).

The measurements taken by the optical sensor 1026 from the LED's can be used as inputs to a patient line state detector algorithm in order to detect the state of tubing segment 34a. Besides detecting a full, empty, or absent tubing segment 34a, the result of the algorithm may be indeterminate, possibly indicating movement or improper positioning of the tubing segment 34a within the patient line state detector 1000, or possibly the presence of a foreign object in channel 1012 of patient line state detector 1000. Manufacturing variations may cause the output from the LED's and the sensitivity of optical sensor 1026 to vary among different assemblies. Therefore, it may be advantageous to perform an initial calibration of the patient line state detector 1000. For example, the following procedure may be used to obtain calibration values of the LED's and sensor:
(1) Ensure that no tubing segment 34a is loaded in the patient line state detector 1000.
(2) Poll the optical sensor 1026 in four different states:
    (a) no LED illuminated
    (b) first LED 1028 (LEDa) illuminated
    (c) second LED 1030 (LEDb) illuminated
    (d) third LED 1032 (LEDc) illuminated
(3) Subtract the 'no LED illuminated' signal value from each of the other signal values to determine their ambient corrected values, and store these three readings as 'no-tube' calibration values.

Once calibration values for the LED's and sensor are obtained, the state of tubing segment 34a may then be detected. In this illustrative embodiment, the patient line state detector algorithm performs a state detection in a test as follows:

(1) Poll the optical sensor 1026 in four different states:
   (a) no LED illuminated
   (b) first LED 1028 (LEDa) illuminated
   (c) second LED 1030 (LEDb) illuminated
   (d) third LED 1032 (LEDc) illuminated
(2) Subtract the 'no LED illuminated' value from each of the other values to determine their ambient corrected values.
(3) Calculate the relative LED values by dividing the test values associated with each LED by their corresponding calibration ('no-tube') values.

Results:

If the ambient corrected LEDa value is less than 0.10, then there may be a foreign object in the detector, or an indeterminate result can be reported to the user.

If the ambient corrected LEDa and LEDb values fall within ±15% of their respective stored calibration (no-tube) values, then report to the user that no tubing segment is present in the detector.

If the ambient corrected LEDb value is equal to or greater than about 40% of its stored calibration ('no-tube') value,
   (a) check the signal associated with LEDc
      (i) if the ambient corrected signal associated with LEDc is equal or greater than about 150% of its calibration ('no-tube') value, then report to the user that the tubing segment is empty.
      (ii) If the ambient corrected signal associated with LEDc is equal to or less than about 125% of its calibration ('no-tube') value, then report to the user that the tubing segment is filled with liquid.
      (iii) Otherwise, the result is indeterminate, and either repeat the measurement (e.g., the tubing segment may be moving, may be indented, or otherwise obscured), or report to the user that the tubing segment should be checked to ensure that it is properly inserted in the detector.

If the ambient corrected LEDb value is less than about 40% of its stored calibration ('no-tube') value, then the LEDc threshold for determining the presence of a dry tube may be greater. In an embodiment, for example, the LEDc empty tube threshold was found empirically to follow the relationship: [LEDc empty tube threshold]=−3.75×[LEDb value]+3.

Once it is determined that the tubing segment 34*a* has been loaded in the patient line state detector 1000, the patient line state detector algorithm can perform the following:

a) Poll the optical sensor 1026 with no LED illuminated and store this as the no LED value.
b) Illuminate LEDc
c) Poll the optical sensor 1026, subtract the no LED value from the LEDc value, and store this as the initial value.
d) Begin pumping
e) Poll the optical sensor 1026 and subtract the no LED value from the subsequent LEDc value.
f) If this value is less than 75% of the initial value, then conclude that tubing segment 34*a* is filled with liquid, stop pumping, confirm the detector state using the above procedure, and when indicated, report to the user that priming is complete. Otherwise, keep repeating the poll, calculation, and comparison. In an embodiment, the system controller can be programmed to perform the polling protocol as frequently as desired, such as, for example, every 0.005 to 0.01 seconds. In an embodiment, the entire polling cycle can conveniently be performed every 0.5 seconds.

FIG. 9-12A shows the results of sample calibration procedures for six cyclers. The signal strength range that distinguishes a dry tube from a wet tube ('wet/dry threshold' ranges) is noted to vary among the different cyclers. (The variations in these ranges may be due to minor variations in manufacturing, assembly and positioning of the various components). Thus at calibration, each cycler may be assigned a wet/dry threshold signal strength range that optimally separates the data points generated with a dry tube from the data points generated with a wet tube.

FIG. 9-5 shows a perspective view of a second configuration of a patient line state detector 1000. Two or more different patient line state detector configurations may necessary to accommodate varying types of patient connectors. In this illustrative embodiment, the second configuration patient line state detector 1000 may include most of the same components as in the first configuration patient line state detector 1000. However, in order to accommodate a different type of connector, the second configuration may include a raised element 1036 above housing 1006, rather than the stabilizing tab 1010 found in the first configuration patient line state detector 1000. The raised element 1036 may generally conform to the shape of a standard patient line connector cap or connector flange.

In accordance with an aspect of the disclosure, detector housing 1006 may not include a tube portion 1014. Therefore, open cavity 1008 may be arranged to allow placement of detector circuit board 1022 so that the LED's and optical sensor may be positioned next to a translucent or transparent patient line connector 36 rather than a section of tubing. Channel 1012 consequently may be shaped differently to accommodate the transmission of LED light through connector 36.

Solution Line Organizer

FIG. 9-6, FIG. 9-7, and FIG. 9-8, show a perspective view of the front of an unloaded organizer 1038, a perspective view of the back of an unloaded organizer 1038, and a perspective view of a loaded organizer 1038 respectively. In this embodiment, the organizer 1038 may be substantially formed from a moderately flexible material (such as, e.g., PAXON AL55-003 HDPE resin). Forming the organizer 1038 from this or another relatively flexible polymer material increases the organizer's 1038 durability when attaching and removing solution lines or solution line connectors.

The organizer 1038 may conveniently be mounted or attached to an outer wall of the cycler housing 82. The organizer 1038 may include a tube holder section 1040, a base 1042, and a tab 1044. The tube holder section 1040, the base 1042, and the tab 1044 may all be flexibly connected, and may be substantially formed from the same HDPE-based material. The tube holder section 1040 may have a generally rectangular shape, and may include a generally flat top edge and a bottom edge that may be slightly curved in an outwardly direction. The tube holder section 1040 may include a series of recessed segments 1046 that extend horizontally along the bottom edge of the tube holder section 1040. Each of the recessed segments 1046 may be separated by a series of support columns 1048, which may also define the shape and size of the segments 1046. The tube holder section 1040 may also include a raised area that extends horizontally along the top edge of the tube holder section 1040. The raised area may include a plurality of slots 1050. The slots 1050 may be defined in a vertical orientation, and may extend from the top edge of the tube holder section 1040 to the top of the recessed segments 1046. The slots 1050 may have a generally cylindrical shape so as to conform to the shape of a drain line 28, solution line 30, or patient line 34. The depth of the slots 1050 may be such that the opening of the slot 1050 is narrower then the inner region of the slot 1050. Therefore, once a line is placed into the slot 1050 it becomes locked or snap-fit into place. The line may then require a pre-determined minimum amount of force to be removed from the slot 1050. This ensures that the lines are not unintentionally removed from the organizer 1050.

In one aspect, the tab 1044 may be flexibly connected to the top edge of the tube holder section 1040. The tab 1044 may have a generally rectangular shape. In another embodiment, the tab 1044 may also include two slightly larger radius corners. The tab 1044 may also include two vertically extending support columns 1048. The support columns 1048 may be connected to the top edge of the tube holder section 1040, and may extend in an upward direction into the tab 1044. In alternative embodiment, the length and number of the support columns 1048 may vary depending on the desired degree of flexibility of the tab 1044. In another aspect, the tab 1044 may include a ribbed area 1052. The purpose of the tab 1044 and the ribbed area 1052 is to allow the organizer 1038 to be easily grasped by a user so that the user can easily install, transport, or remove the solution lines 30 from the organizer 1038. Also, the tab 1044 provides an additional area of support when removing and loading the lines into the organizer 1038.

In another aspect, the base 1042 may be flexibly connected to the bottom edge of the tube holder section 1040. The base 1042 may have a generally rectangular shape. In another embodiment, the base 1042 may also include two slightly larger radius corners. The base 1042 may include an elongated recessed segment 1046, which may be defined by a support ring 1054 that surrounds the recessed segment 1046. The support columns 1050, the support ring 1054, and the raised area may all create a series of voids 1056 along the back of the organizer 1038 (shown, e.g., in FIG. 9-7).

Figures 9, 10:
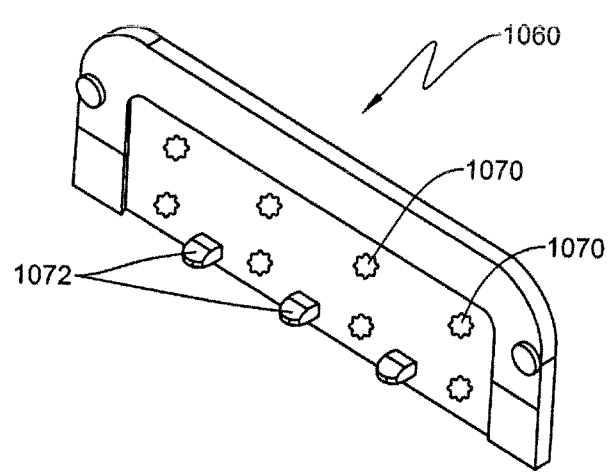

FIG. 9-9 and FIG. 9-10 show a perspective view of an organizer clip 1058, and a perspective view of an organizer clip receiver 1060 respectively. In these illustrative embodiments, the clip 1058 may be made from a relatively high durometer polyurethane elastomer, such as, for example, 80 Shore A durometer urethane. In an alternative embodiment, the clip 1058 may be made from any type of flexible and durable material that would allow the organizer 1038 to flex and pivot along the base 1042 when positioned in the clip 1058. The clip 1058 may be "U-shaped", and may include a back portion that extends slightly higher than a front portion. Additionally, there may be a lip 1062 that extends along the top edge of the front portion of the clip 1058. The lip 1062 extends slightly into the cavity of the clip 1058. The back portion of the clip 1058 may also include a plurality of elastomeric pegs 1064 connected to (or formed from) and extending away from the back portion of the clip 1058. The pegs 1064 may include both a cylindrical section 1066 and a cone 1068. The cylindrical section 1066 may connect to the back portion of the clip 1058, and the cone 1068 may be attached to an open end of the cylindrical section 1066. The pegs 1064 allow the clip 1058 to be permanently connected to the organizer clip receiver 1060, by engaging the pegs 1064 within a plurality of holes 1070 in the organizer clip receiver 1060.

The organizer clip receiver 1060 may include a plurality of chamfered tabs 1072. The chamfered tabs 1072 may mate with corresponding slots on the back portion of the clip 1058 when the pegs 1064 are engaged with the organizer clip receiver 1060. Once the chamfered tabs 1072 engage the slots, they can extend through the back portion of the clip 1058, and act as locking mechanisms to hold the organizer 1038 in place when positioned into the clip 1058. When the organizer 1038 is positioned within the clip 1058, the chamfers 1072 fit into the void 1056 on the back of the base 1042, which was created by the raised support ring 1054. Referring again to FIG. 9-7, and in accordance with another aspect of the present disclosure, there may be a plurality of ramps 1074 extending outwardly from the back of the organizer 1038. The ramps 1074 may be generally shaped as inclined planes. This allows the organizer 1038 to angle away from the cycler 14 when placed into the clip 1058, which provides numerous advantages over previous designs. For example, in this illustrative embodiment, the angle of the organizer 1038 ensures that neither the tab 1044, nor any of the lines (or line caps) connected to the organizer 1038 are allowed to interfere with the heater lid 143 when the lid 143 is being opened and closed. Additionally, the angle of the organizer 1038 in relation to the cycler 14, coupled with the flexibility of the organizer 1038, both encourage the user to remove the solution lines 30 from the bottom instead of from the connector end 30a of the solution lines. Preferably, the user should not remove the solution lines 30 by grasping the connector ends 30a, because in doing so the user could inadvertently remove one or more caps 31, which could cause contamination and spills. Another advantage of the organizer 1038 is that it aids the user in connecting color coded solution lines 30 to the correct containers 20 by helping to separate the color coded lines 30.

Door Latch Sensor

Figures 9, 10, 11:
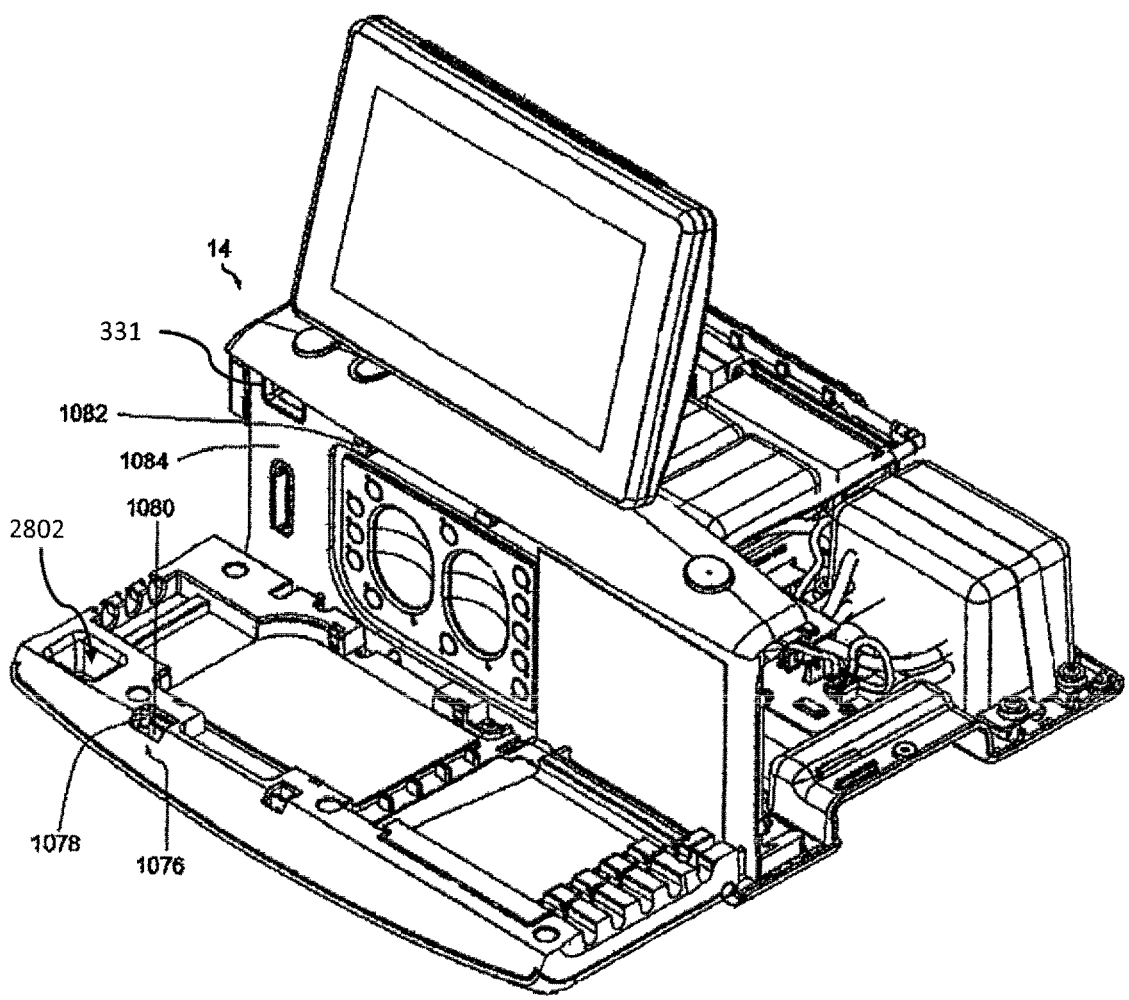
Figures 9, 10, 11, 11A:
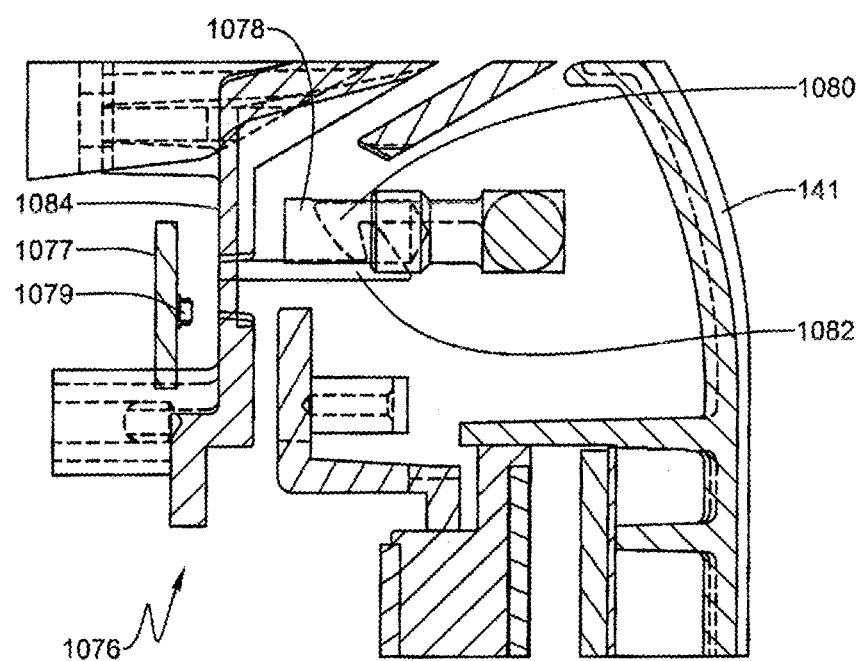

FIG. 9-11, shows a perspective view of a door latch sensor assembly 1076. In this illustrative embodiment, the door latch sensor assembly 1076 may include a magnet 1078 that is attached or connected to door latch 1080, and can pivot with door latch 1080 as it pivots into and our of a latching position with its mating base unit catch 1082. A sensor (not shown in FIG. 9-11) may be positioned behind the front panel 1084 of cycler 14, near base unit catch 1082, to detect the presence of magnet 1078 as door latch 1080 engages with base unit catch 1082. In one embodiment, the sensor may be an analog Hall effect sensor. The purpose of the door latch sensor assembly 1076 is to confirm both that the door 141 is closed and that the door latch 1080 is sufficiently engaged with catch 1082 to ensure a structurally sound connection. FIG. 9-11a shows a cross-sectional view of the door latch sensor assembly 1076. Sensor 1079 is positioned on a circuit board 1077 behind front panel 1084. Sensor 1079 is preferably oriented off-axis from the line of motion of magnet 1078, because in this orientation, sensor 1079 is better able to resolve a variety of positions of magnet 1078 as it approaches front panel 1084 as door 141 is closed.

In one example, the door 141 may be considered to be sufficiently engaged when the door latch 1080 has at least a 50% engagement with the catch 1082. In one embodiment, the door latch 1080 may engage to a degree of approximately 0.120 inch nominally. Additionally, the sensor 1079 may only sense a closed door 141 when the door latch 1080 is sufficiently engaged with the catch 1082. Therefore, the sensor 1082 may only sense a closed door 141 when the door latch 1080 is engaged to a degree of approximately 0.060 inch. These engagement thresholds for the door latch 1080 may be set approximately at the middle range for acceptable engagement between the door latch 1080 and the catch 1082. This can help to ensure a robust design by accounting for sensor drift due to time, temperature, and other variations. Testing was conducted to determine the robustness of the sensor 1082 by collecting numerous measurements both at room temperature (approximately 24° C.) and at an abnormally cold temperature (approximately −2° C. to 9° C.). The room temperature readings were repeatedly higher than the cold readings, but only by a small percentage of the 0 inch to 0.060 inch range. In one aspect, the output of the sensor 1079 may be ratiometric to the voltage supplied.

Therefore, both the supply voltage and the output of the sensor 1079 may be measured (see formulas below, where the supply voltage and the output of the sensor 1079 are represented by Door_Latch and Monitor_5V0 respectively). Both the output of the sensor 1079 as well as the voltage supplied may then pass through ¼ resistor dividers. Dividing the output of the sensor 1079 and the voltage supplied may allow for a stable output to be produced. This procedure may ensure that the output remains stable even if the supply voltage fluctuates.

In another aspect, the sensor 1079 may respond to both positive and negative magnetic fields. Consequently, if there is no magnetic field, the sensor 1079 may output half the supply voltage. Additionally, a positive magnetic field may cause the output of the sensor 1079 to increase, while a negative magnetic field may result in a decrease of the output of the sensor 1079. In order to obtain an accurate measurement of the output from the sensor 1079, the magnet polarity can be ignored, and the supply voltage can simultaneously be compensated for. The following formula may be used to calculate the latch sensor ratio:

Latch Sensor Ratio=absolute value((*V*Door_Latch/*V*Monitor_5*V*0)−noFieldRatio)   (1)

Where the noFieldRatio is calculated by (VDoor_Latch/VMonitor_5V0) with the door 141 fully open.

Using this formula:
Ratio=0.0 indicates no magnetic field
Ratio>0.0 indicates some magnetic field; direction indeterminate.

Shims of various thicknesses may be used between the inside of door 141 and front panel 1084 to vary the degree of engagement between latch 1080 and catch 1082, in order to calibrate the strength of the magnetic field detected by sensor 1079 with various positions of engagement of the door latch assembly 1076. In one embodiment, this data can be used to develop field strength ratios with and without a shim, or in other embodiments with several shims of varying thicknesses. In one example, the door latch sensor assembly 1076 may complete the procedure for determining if the door latch 1080 is sufficiently engaged with the catch 1082 by performing the following:

Calculate the nearRatio and the farRatio:

nearRatio=noShimRatio−(0.025/0.060)×(noShimRatio−withShimRatio)   (2)

farRatio=noShimRatio−(0.035/0.060)×(noShimRatio−withShimRatio)   (3)

In an embodiment, the door latch sensor assembly 1076 may save the noFieldRatio, nearRatio, and farRatio to a calibration file. The door latch sensor assembly 1076 may then load the noFieldRatio, nearRatio, and farRatio from the calibration file, and the sensor assembly 1076 may then use the nearRatio and farRatio as the hysteresis limits for the sensor 1079. The door latch sensor assembly 1076 may then begin with the initial condition that the door 141 is open, and then repeatedly calculate the Latch Sensor Ratio. If the Latch Sensor Ratio is greater than the nearRatio, the door latch sensor assembly 1076 will change the latch state to closed, and if the Latch Sensor Ratio is less than the farRatio, the door latch sensor assembly 1076 will change the latch state to open. In an alternative embodiment for the door latch sensor assembly 1076, a middleRatio can be calculated from the calibration data by averaging the noShimRatio and the withShimRatio. In this case, measurements greater than the middleRatio indicate that the door latch 1080 is engaged, and measurements less than the middleRatio indicate that the door latch 1080 is not engaged.

Set Loading and Operation

FIG. 10 shows a perspective view of the APD system 10 of FIG. 1 with the door 141 of the cycler 14 lowered into an open position, exposing a mounting location 145 for the cassette 24 and a carriage 146 for the solution lines 30. (In this embodiment, the door 141 is mounted by a hinge at a lower part of the door 141 to the cycler housing 82.) When loading the set 12, the cassette 24 is placed in the mounting location 145 with the membrane 15 and the pump chamber side of the cassette 24 facing upwardly, allowing the portions of the membrane 15 associated with the pump chambers and the valve ports to interact with a control surface 148 of the cycler 14 when the door 141 is closed. The mounting location 145 may be shaped so as to match the shape of the base member 18, thereby ensuring proper orientation of the cassette 24 in the mounting location 145. In this illustrative embodiment, the cassette 24 and mounting location 145 have a generally rectangular shape with a single larger radius corner which requires the user to place the cassette 24 in a proper orientation into the mounting location 145 or the door 141 will not close. It should be understood, however, that other shapes or orientation features for the cassette 24 and/or the mounting location 145 are possible.

In accordance with an aspect of the invention, when the cassette 24 is placed in the mounting location 145, the patient, drain and heater bag lines 34, 28 and 26 are routed through a channel 40 in the door 141 to the left as shown in FIG. 10. The channel 40, which may include guides 41 or other features, may hold the patient, drain and heater bag lines 34, 28 and 26 so that an occluder 147 may selectively close/open the lines for flow. Upon closing of door 141, occluder 147 can compress one or more of patient, drain and heater bag lines 34, 28 and 26 against occluder stop 29. Generally, the occluder 147 may allow flow through the lines 34, 28 and 26 when the cycler 14 is operating (and operating properly), yet occlude the lines when the cycler 14 is powered down (and/or not operating properly). (Occlusion of the lines may be performed by pressing on the lines, or otherwise pinching the lines to close off the flow path in the lines.) Preferably, the occluder 147 may selectively occlude at least the patient and drain lines 34 and 28.

When the cassette 24 is mounted and the door 141 is closed, the pump chamber side of the cassette 24 and the membrane 15 may be pressed into contact with the control surface 148, e.g., by an air bladder, spring or other suitable arrangement in the door 141 behind the mounting location 145 that squeezes the cassette 24 between the mounting location 145 and the control surface 148. This containment of the cassette 24 may press the membranes 15 and 16 into contact with walls and other features of the base member 18, thereby isolating channels and other flow paths of the cassette 24 as desired. The control surface 148 may include a flexible gasket or membrane, e.g., a sheet of silicone rubber or other material, that is associated with the membrane 15 and can selectively move portions of the membrane 15 to cause pumping action in the pump chambers 181 and opening/closing of valve ports of the cassette 24. The control surface 148 may be associated with the various portions of the membrane 15, e.g., placed into intimate contact with each other, so that portions of the membrane 15 move in response to movement of corresponding portions of the control surface 148. For example, the membrane 15 and control surface 148 may be positioned close together, and a suitable vacuum (or pressure that is lower relative to ambient) may be introduced through vacuum ports suitably located in the control surface 148, and maintained, between the membrane 15 and the control surface 148 so that the membrane 15 and the control surface 148 are essentially stuck together, at least in regions of the membrane 15 that require movement to open/close valve ports and/or to cause pumping action. In another embodiment, the membrane 15 and control surface 148 may be adhered together, or otherwise suitably associated.

In some embodiments, the surface of the control surface 148 or gasket facing the corresponding cassette membrane overlying the pump chambers and/or valves is textured or roughened. The texturing creates a plurality of small passages horizontally or tangentially along the surface of the gasket when the gasket is pulled against the surface of the corresponding cassette membrane. This may improve evacuation of air between the gasket surface and the cassette membrane surface in the textured locations. It may also improve the accuracy of pump chamber volume determinations using pressure-volume relationships (such as, for example, in the FMS procedures described elsewhere), by minimizing trapped pockets of air between the gasket and the membrane. It may also improve the detection of any liquid that may leak into the potential space between the gasket and the cassette membrane. In an embodiment, the texturing may be accomplished by masking the portions of the gasket mold that do not form the portions of the gasket corresponding to the pump membrane and valve membrane locations. A chemical engraving process such as the Mold-Tech® texturing and chemical engraving process may then be applied to the unmasked portions of the gasket mold. Texturing may also be accomplished by any of a number of other processes, such as, for example, sand blasting, laser etching, or utilizing a mold manufacturing process using electrical discharge machining.

Before closing the door 141 with the cassette 24 loaded, one or more solution lines 30 may be loaded into the carriage 146. The end of each solution line 30 may include a cap 31 and a region 33 for labeling or attaching an indicator or identifier. The indicator, for example, can be an identification tag that snaps onto the tubing at indicator region 33. In accordance with an aspect of the invention and as will be discussed in more detail below, the carriage 146 and other components of the cycler 14 may be operated to remove the cap(s) 31 from lines 30, recognize the indicator for each line 30 (which may provide an indication as to the type of solution associated with the line, an amount of solution, etc.) and fluidly engage the lines 30 with a respective spike 160 of the cassette 24. This process may be done in an automated way, e.g., after the door 141 is closed and the caps 31 and spikes 160 are enclosed in a space protected from human touch, potentially reducing the risk of contamination of the lines 30 and/or the spikes 160 when connecting the two together. For example, upon closing of the door 141, the indicator regions 33 may be assessed (e.g., visually by a suitable imaging device and software-based image recognition, by RFID techniques, etc.) to identify what solutions are associated with which lines 30. The aspect of the invention regarding the ability to detect features of a line 30 by way of an indicator at indicator region 33 may provide benefits such as allowing a user to position lines 30 in any location of the carriage 146 without having an affect on system operation. That is, since the cycler 14 can automatically detect solution line features, there is no need to ensure that specific lines are positioned in particular locations on the carriage 146 for the system to function properly. Instead, the cycler 14 may identify which lines 30 are where, and control the cassette 24 and other system features appropriately. For example, one line 30 and connected container may be intended to receive used dialysate, e.g., for later testing. Since the cycler 14 can identify the presence of the sample supply line 30, the cycler 14 can route used dialysate to the appropriate spike 160 and line 30. As discussed above, since the spikes 160 of the cassette 24 all feed into a common channel, the input from any particular spike 160 can be routed in the cassette 24 in any desired way by controlling valves and other cassette features.

With lines 30 mounted, the carriage 146 may be moved to the left as shown in FIG. 10 (again, while the door 141 is closed), positioning the caps 31 over a respective spike cap 63 on a spike 160 of the cassette 24 and adjacent a cap stripper 149. The cap stripper 149 may extend outwardly (toward the door 141 from within a recess in the cycler 14 housing) to engage the caps 31. (For example, the cap stripper 149 may include five fork-shaped elements that engage with a corresponding groove in the caps 31, allowing the cap stripper 149 to resist left/right movement of the cap 31 relative to the cap stripper 149.) By engaging the caps 31 with the cap stripper 149, the caps 31 may also grip the corresponding spike cap 63. Thereafter, with the caps 31 engaged with corresponding spike caps 63, the carriage 146 and cap stripper 149 may move to the right, removing the spike caps 63 from the spikes 160 that are engaged with a corresponding cap 31. (One possible advantage of this arrangement is that spike caps 63 are not removed in locations where no solution line 30 is loaded because engagement of the cap 31 from a solution line 30 is required to remove a spike cap 63. Thus, if a solution line will not be connected to a spike 160, the cap on the spike 160 is left in place.) The cap stripper 149 may then stop rightward movement (e.g., by contacting a stop), while the carriage 146 continues movement to the right. As a result, the carriage 146 may pull the terminal ends of the lines 30 from the caps 31, which remain attached to the cap stripper 149. With the caps 31 removed from the lines 30 (and the spike caps 63 still attached to the caps 31), the cap stripper 149 may again retract with the caps 31 into the recess in the cycler 14 housing, clearing a path for movement of the carriage 146 and the uncapped ends of the lines 30 toward the spikes 160. The carriage 146 then moves left again, attaching the terminal ends of the lines 30 with a respective spike 160 of the cassette 24. This connection may be made by the spikes 160 piercing an otherwise closed end of the lines 30 (e.g., the spikes may pierce a closed septum or wall in the terminal end), permitting fluid flow from the respective containers 20 to the cassette 24. In an embodiment, the wall or septum may be constructed of a flexible and/or self-sealing material such as, for example, PVC, polypropylene, or silicone rubber.

In accordance with an aspect of the invention, the heater bag 22 may be placed in the heater bag receiving section (e.g., a tray) 142, which is exposed by lifting a lid 143. (In this embodiment, the cycler 14 includes a user or operator interface 144 that is pivotally mounted to the housing 82, as discussed below. To allow the heater bag 22 to be placed into the tray 142, the interface 144 may be pivoted upwardly out of the tray 142.) As is known in the art, the heater tray 142 may heat the dialysate in the heater bag 22 to a suitable temperature, e.g., a temperature appropriate for introduction into the patient. In accordance with an aspect of the invention, the lid 143 may be closed after placement of the heater bag 22 in the tray 142, e.g., to help trap heat to speed the heating process, and/or help prevent touching or other contact with a relatively warm portion of the heater tray 142, such as its heating surfaces. In one embodiment, the lid 143 may be locked in a closed position to prevent touching of heated portions of the tray 142, e.g., in the circumstance that portions of the tray 142 are heated to temperatures that may cause burning of the skin. Opening of the lid 143 may be prevented, e.g., by a lock, until temperatures under the lid 143 are suitably low.

In accordance with another aspect of the invention, the cycler 14 includes a user or operator interface 144 that is pivotally mounted to the cycler 14 housing and may be folded down into the heater tray 142. With the interface 144 folded down, the lid 143 may be closed to conceal the interface 144 and/or prevent contact with the interface 144. The interface 144 may be arranged to display information, e.g., in graphical form, to a user, and receive input from the user, e.g., by using a touch screen and graphical user interface. The interface 144 may include other input devices, such as buttons, dials, knobs, pointing devices, etc. With the set 12 connected, and containers 20 appropriately placed, the user may interact with the interface 144 and cause the cycler 14 to start a treatment and/or perform other functions.

However, prior to initiating a dialysis treatment cycle, the cycler 14 must at least prime the cassette 24, the patient line 34, heater bag 22, etc., unless the set 12 is provided in a pre-primed condition (e.g., at the manufacturing facility or otherwise before being put into use with the cycler 14). Priming may be performed in a variety of ways, such as controlling the cassette 24 (namely the pumps and valves) to draw liquid from one or more solution containers 20 via a line 30 and pump the liquid through the various pathways of the cassette 24 so as to remove air from the cassette 24. Dialysate may be pumped into the heater bag 22, e.g., for heating prior to delivery to the patient. Once the cassette 24 and heater bag line 26 are primed, the cycler 14 may next prime the patient line 34. In one embodiment, the patient line 34 may be primed by connecting the line 34 (e.g., by the connector 36) to a suitable port or other connection point on the cycler 14 and causing the cassette 24 to pump liquid into the patient line 34. The port or connection point on the cycler 14 may be arranged to detect the arrival of liquid at the end of the patient line (e.g., optically, by conductive sensor, or other), thus detecting that the patient line is primed. As discussed above, different types of sets 12 may have differently sized patient lines 34, e.g., adult or pediatric size. In accordance with an aspect of the invention, the cycler 14 may detect the type of cassette 24 (or at least the type of patient line 34) and control the cycler 14 and cassette 24 accordingly. For example, the cycler 14 may determine a volume of liquid delivered by a pump in the cassette needed to prime the patient line 34, and based on the volume, determine the size of the patient line 34. Other techniques may be used, such as recognizing a barcode or other indicator on the cassette 24, patient line 34 or other component that indicates the patient line type.

FIG. 11 shows a perspective view of the inner side of the door 141 disconnected from the housing 82 of the cycler 14. This view more clearly shows how the lines 30 are received in corresponding grooves in the door 141 and the carriage 146 such that the indicator region 33 is captured in a specific slot of the carriage 146. With the indicator at indicator region 33 positioned appropriately when the tubing is mounted to the carriage 146, a reader or other device can identify indicia of the indicator, e.g., representing a type of solution in the container 20 connected to the line 30, an amount of solution, a date of manufacture, an identity of the manufacturer, and so on. The carriage 146 is mounted on a pair of guides 130 at top and bottom ends of the carriage 146 (only the lower guide 130 is shown in FIG. 11). Thus, the carriage 146 can move left to right on the door 141 along the guides 130. When moving toward the cassette mounting location 145 (to the right in FIG. 11), the carriage 146 can move until it contacts stops 131.

FIG. 11-1 and FIG. 11-2 show a perspective view of a carriage 146, and an enlarged perspective view of a solution line 30 loaded into the carriage 146. In these illustrative embodiments, the carriage 146 may have the ability to move on the door 141 along the guide 130. The carriage 146 may include five slots 1086, and therefore may have the ability to support up to five solution lines 30. Each slot 1086 may include three different sections; a solution line section 1088, an ID section 1090, and a clip 1092. The solution line section 1088 may have a generally cylindrical shaped cavity that allows the solution lines 30 to remain organized and untangled when loaded into the carriage 146. The clip 1092 may be located at the opposite end of each of the slots 1086, relative to the solution line section 1088. The purpose of the clip 1092 is to provide a secure housing for a membrane port 1094 located at the connector end 30*a* of the solution line 30, and to prevent the solution line 30 from moving during treatment.

In one embodiment of the present disclosure, the clip 1092 may have a semicircular shape, and may include a middle region that extends slightly deeper than the two surrounding edge regions. The purpose of including the deeper middle region is to accommodate a membrane port flange 1096. The flange 1096 may have a substantially greater radius than the rest of the membrane port. Therefore, the deeper middle region is designed to fit the wider flange 1096, while the two edge regions provide support so that the membrane port 1094 is immobilized. Additionally, the deep middle region may have two cutouts 1098 positioned on opposite sides of the semicircle. The cutouts 1098 may have a generally rectangular shape so as to allow a small portion of the flange 1096 to extend into each of the cutouts 1098 when positioned in the clip 1092. The cutouts 1098 may be formed so that the distance between the top edges of each cutout 1098 is slightly less than the radius of the flange 1096. Therefore, a sufficient amount of force is required to snap the flange 1096 into the clip 1092. Also, allowing for the distance between the top edges of the two cutouts 1098 to be less than the radius of the flange 1096 helps to keep the solution line 30 from inadvertently becoming dislodged during treatment.

In this illustrative embodiment, the carriage 146 may provide superior performance over previous designs because of its ability to counteract any deformation of the membrane ports 1094. The carriage 146 is designed to stretch the membrane ports 1094 between the front of the flange 1096 and the back of the sleeve. If the membrane port 1094 is further stretched at any point during treatment, a wall in the carriage 146 may support the flange 1096.

In accordance with another aspect of the present disclosure, the ID section 1090 may be positioned between the solution line section 1088 and the clip 1092. The ID section 1090 may have a generally rectangular shape, thus having the ability to house an identification tag 1100 that may snap onto the solution line 30 at the indicator region 33. The indicator region 33 may have an annular shape that is sized and configured to fit within the ID section 1090 when mounted in the carriage 146. The identification tag 1100 may provide an indication as to the type of solution associated with each line 30, the amount of solution, a date of manufacture, and an identity of the manufacturer. As shown in FIG. 11-1, the ID section 1090 may include a two dimensional (2-D) barcode 1102, which may be imprinted on the bottom of the ID section 1090. The barcode 1102 may be a Data Matrix symbol with 10 blocks per side, and may include an "empty" Data Matrix code. The barcode 1102 may be positioned on the carriage 146 underneath the identification tag 1100, when the solution lines 30 are loaded into the carriage 146. However, in an alternative embodiment, the barcode 1102 may be added to the ID section 1090 of the carriage 146 by way of a sticker or laser engraving. Also, in another embodiment, the barcode 1102 may include a Data Matrix that consists of varying dimensions of length and width, as well as varying numbers of blocks per side.

In this illustrative embodiment, however, the specific number of block per side, and the specific length and width of each barcode 1102 was specifically chosen in order to provide the most robust design under a variety of conditions. Using only 10 blocks per side may result in the barcode 1102 having larger blocks, which therefore ensures that the barcode 1102 is easily readable, even under the dark conditions that exist inside of the cycler housing 82.

FIG. 11-3 and FIG. 11-4 show a perspective view of a folded identification tag 1100, and a perspective view of a carriage drive assembly 132 including an AutoID camera 1104 mounted to an AutoID camera board 1106 respectively. In accordance with an aspect of the present disclosure, the identification tag 1100 may be formed from an injection mold, and it may then fold to snap around the indicator region 33. The identification tag 1100 may include edges that are rounded, which may prevent damage to the solution containers 20 during shipping. The identification tag 1100 may also include an 8×8 mm two dimensional (2-D) Data Matrix symbol 1103 with 18 blocks per side plus a quiet zone, which may be added by way of a sticker. The information contained in these Data Matrix symbols 1103 may be provided from the camera 1104 to the control system 16, which may then obtain indicia, through various processes such as by way of image analysis. Therefore, the AutoID camera 1104 will have the ability to detect slots 1086 that contain a solution line 30 that is correctly installed, a line 30 that is incorrectly installed, or the absence of a line 30. A solution line 30 that is correctly installed will allow the camera 1104 to detect the Data Matrix symbol 1103 located on the identification tag 1100, the absence of a solution line 30 will allow the camera 1104 to detect an "empty" Data Matrix barcode 1102 located on the carriage 146 underneath the membrane port 1094, and a solution line 30 that is incorrectly loaded will occlude the "empty" Data Matrix barcode 1102, resulting in no Data Matrix being decoded by the camera 1104 for that slot. Thus, the camera 1104 should always decode a Data Matrix in every slot 1086 on the carriage 146, baring an incorrectly loaded solution line 30.

In this illustrative embodiment, ability to detect features of a solution line 30 by way of an identification tag 1100 located at indicator region 33 may provide benefits such as allowing a user to position lines 30 in any location of the carriage 146 without having an effect on system operation. Additionally, since the cycler 14 can automatically detect solution line features, there is no need to ensure that specific lines 30 are positioned in particular locations on the carriage 146 for the system to function properly. Instead, the cycler 14 may identify which lines 30 are where, and control the cassette 24 and other system features appropriately.

In accordance with another aspect of the disclosure, the identification tag 1100 must face into the carriage drive assembly 132 in order to be decoded by the camera 1104. To ensure this, the carriage 146 and identification tag 1100 may have complementary alignment features. Additionally, the solution lines 30 with identification tags 1100 should also fit within the Cleanflash machine, thus, the solution line 30 with identification tag 1100 may be constructed to fit within a 0.53 inch diameter cylinder. In an embodiment, the alignment feature may be a simple flat bottomed bill on the identification tag 1100 and matching rib in the carriage 146. In one embodiment of the present disclosure, the bill and rib may slightly interfere, forcing the back of the identification tag 1100 in an upward direction. While this configuration may create a small amount of misalignment, it reduces misalignment in the other axis. Finally, to ensure that the identification tag 1100 is properly seated, the front of the carriage drive assembly 132 can be designed with only about 0.02 inch of clearance over the present carriage 146 and identification tag 1100 alignment.

In accordance with another aspect of the disclosure, the AutoID camera board 1106 may be mounted to the back of the carriage drive assembly 132. Additionally, the AutoID camera 1104 may be mounted to the camera board 1106. The camera board 1106 may be placed approximately 4.19 inches from the identification tag 1100. However, in an alternative embodiment, the camera board 1106 may be moved backward without any serious consequences. A plastic window 1108 may also be attached to the front of the carriage drive assembly 132, which may allow the identification tags 1100 to be imaged while also preventing fluid and finger ingress. The AutoID camera 1104 may include a camera lens, which may be any type of lens, such as those used for security applications, or lenses intended for camera phones with the IR filter removed. In accordance with an aspect of the present disclosure, the camera lens may consist of a small size, light weight, low cost, and high image quality.

Additionally, a single SMD IR LED 1110 may be attached to the camera board 1106. The LED 1110 may then illuminate the identification tags 1100 so that the camera 1104 may easily decode the Data Matrices. It is important that the identification tags 1100 be illuminated because the environment inside of the cycler housing 82 is mostly absent of light. Therefore, without the LED 1110 to illuminate the identification tags 1100 the camera 1104 would be unable to decode the Data Matrixes. Furthermore, to avoid creating glare in front of the identification tags 1100, the LED 1110 may be mounted 0.75 inch away from the camera 1104. An FPGA may also be mounted to the camera board 1106, and may act as an intermediary between the OV3640 image sensor and Voyager's UI processor. In addition to making the processor's job easier, this architecture may allow for a different image sensor to be used without a change to any other Voyager hardware or software. Finally, image decoding is handled by the open source package libdmtx, which is addressable from a number of programming languages and can run from a command line for testing.

Figures 9, 10, 11, 12:
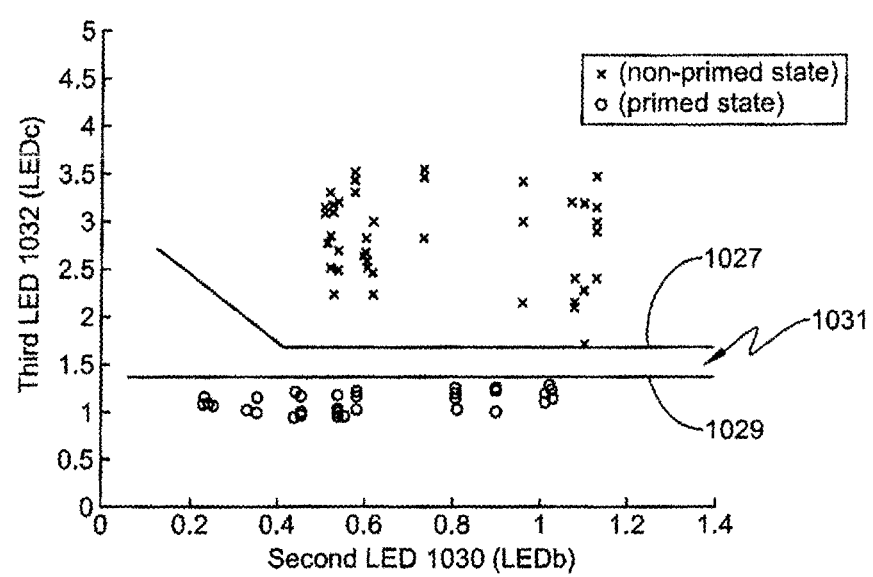
Figures 9, 10, 11, 12, 12A:
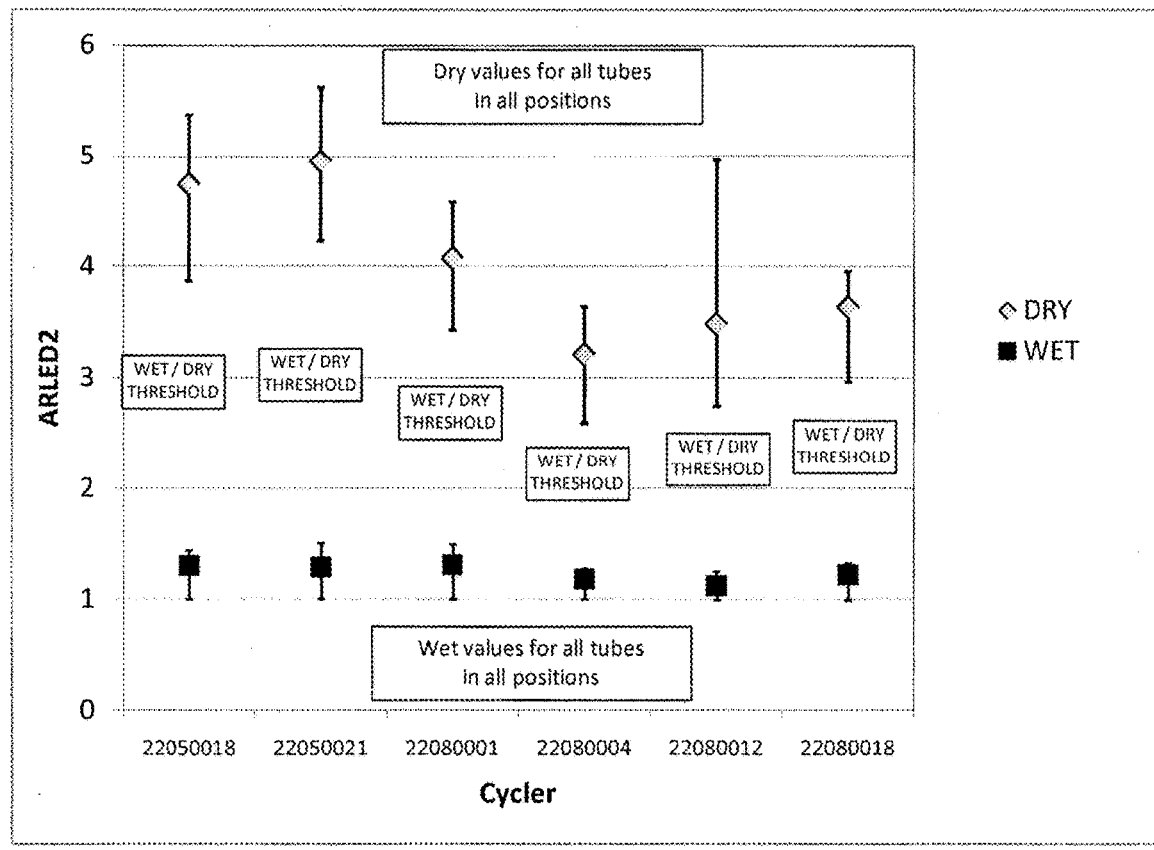

FIG. 12 shows a perspective view of a carriage drive assembly 132 in a first embodiment that functions to move the carriage 146 to remove the caps from spikes 160 on the cassette, remove caps 31 on the solution lines 30 and connect lines 30 to the spikes 160. A drive element 133 is arranged to move left to right along rods 134. In this illustrative embodiment, an air bladder powers the movement of the drive element 133 along the rods 134, but any suitable drive mechanism may be used, including motors, hydraulic systems, etc. The drive element 133 has forwardly extending tabs 135 that engage with corresponding slots 146a on the carriage 146 (see FIG. 11, which shows a top slot 146a on the carriage 146). Engagement of the tabs 135 with the slots 146a allow the drive element 133 to move the carriage 146 along the guides 130. The drive element 133 also includes a window 136, through which an imaging device, such as a CCD or CMOS imager, may capture image information of the indicators at indicator regions 33 on the lines 30 mounted to the carriage 146. Image information regarding the indicators at indicator regions 33 may be provided from the imaging device to the control system 16, which may obtain indicia, e.g., by image analysis. The drive element 133 can selectively move the cap stripper 149 both to the left and right along the rods 134. The cap stripper 149 extends forward and back using a separate drive mechanism, such as a pneumatic bladder.

Figures 9, 10, 11, 12, 13:
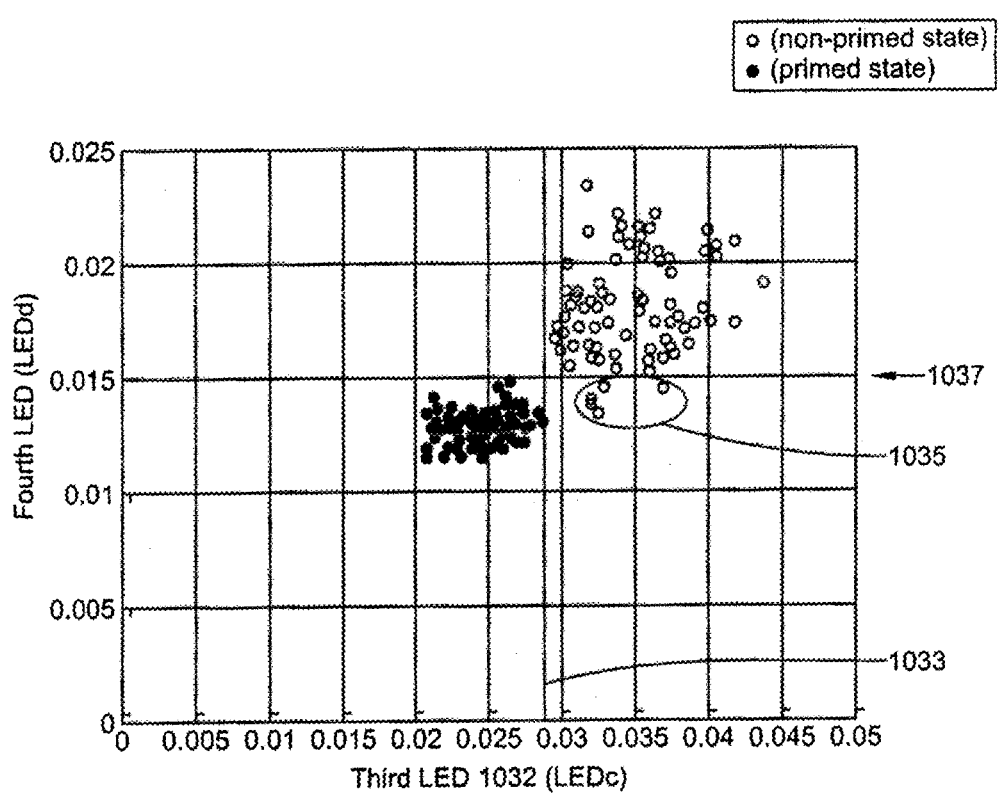
Figures 9, 10, 11, 12, 13, 14:
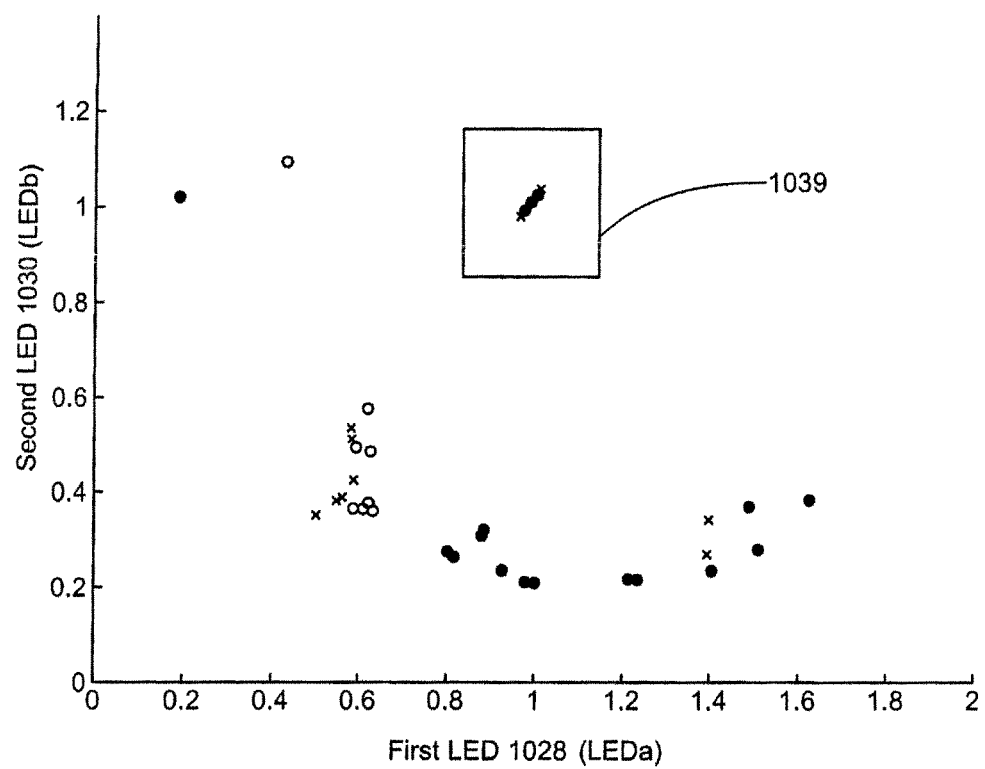
Figure 10:
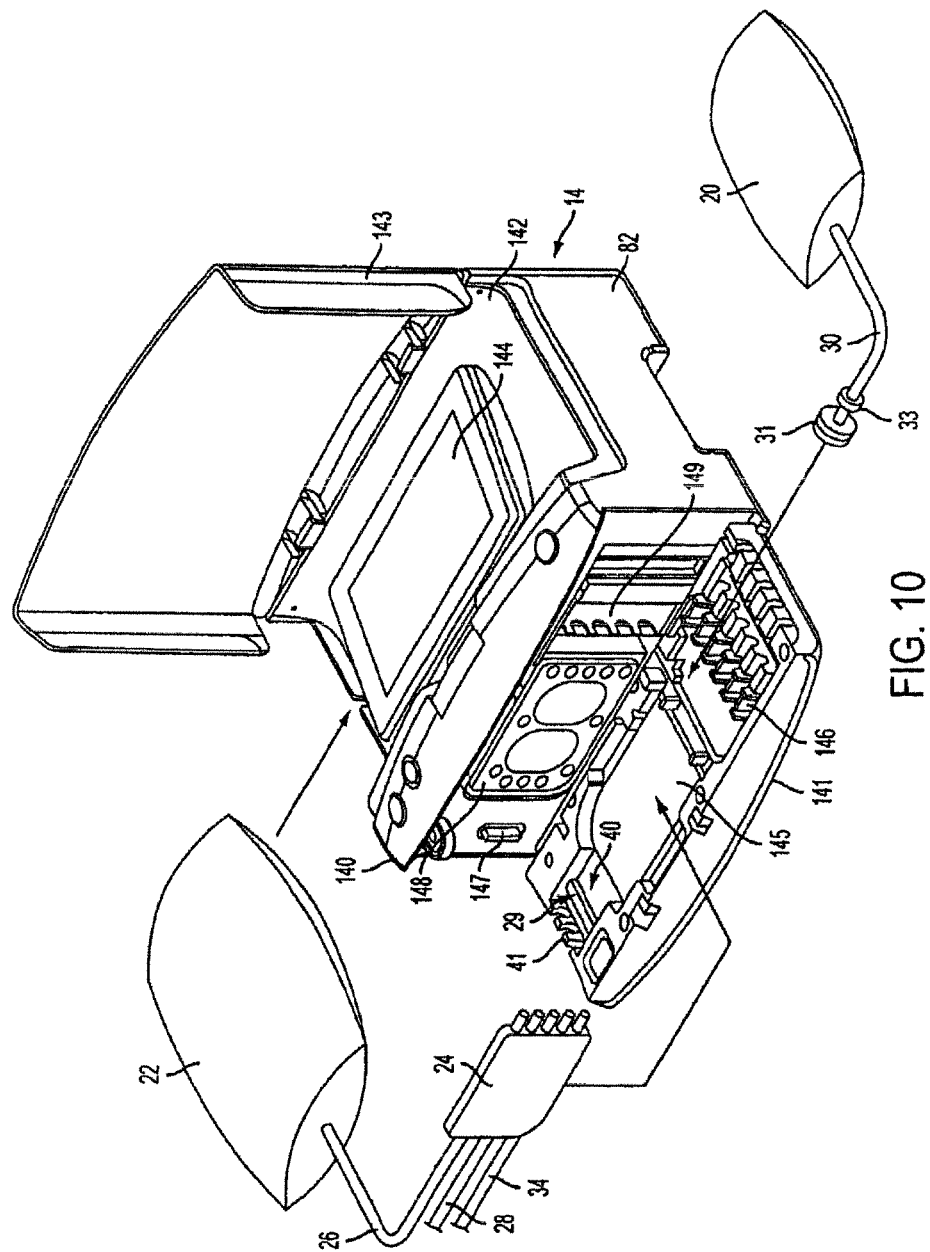

FIG. 13 shows a left side perspective view of the carriage drive assembly 132, which more clearly shows how a stripper element of the cap stripper 149 is arranged to move in and out (a direction generally perpendicular to the rods 134) along grooves 149a in the housing of the cap stripper 149. Each of the semicircular cut outs of the stripper element may engage a corresponding groove of a cap 31 on a line 30 by extending forwardly when the cap 31 is appropriately positioned in front of the stripper 149 by the drive element 133 and the carriage 146. With the stripper element engaged with the caps 31, the cap stripper 149 may move with the carriage 146 as the drive element 133 moves. FIG. 14 shows a partial rear view of the carriage drive assembly 132. In this embodiment, the drive element 133 is moved toward the cassette 24 mounting location 145 by a first air bladder 137 which expands to force the drive element 133 to move to the right in FIG. 14. The drive element can be moved to the left by a second air bladder 138. Alternatively, drive element 133 can be moved back and forth by means of one or more motors coupled to a linear drive gear assembly, such as a ball screw assembly (in which the carriage drive assembly is attached to a ball nut), or a rack and pinion assembly, for example. The stripper element 1491 of the cap stripper 149 can be moved in and out of the cap stripper housing by a third bladder, or alternatively, by a motor coupled to a linear drive assembly, as described previously.

FIGS. 15-18 show another embodiment of a carriage drive assembly 132 and cap stripper 149. As can be seen in the rear view of the carriage drive assembly 132 in FIG. 15, in this embodiment the drive element 133 is moved right and left by a screw drive mechanism 1321. As can be seen in the right rear perspective view of the carriage drive assembly 132 in FIG. 16, the stripper element is moved outwardly and inwardly by an air bladder 139, although other arrangements are possible as described above.

Figure 18:
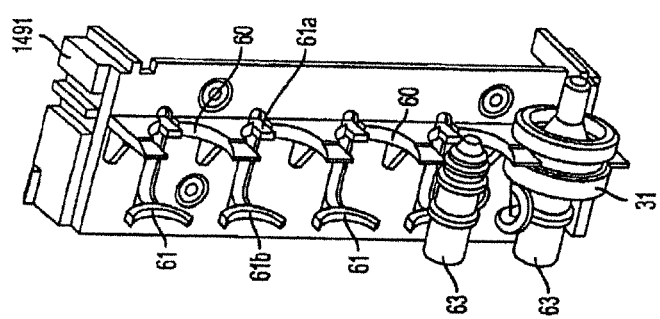
FIG. 18 is a right front perspective view of the cap stripper element of FIG. 17.
Figure 17:
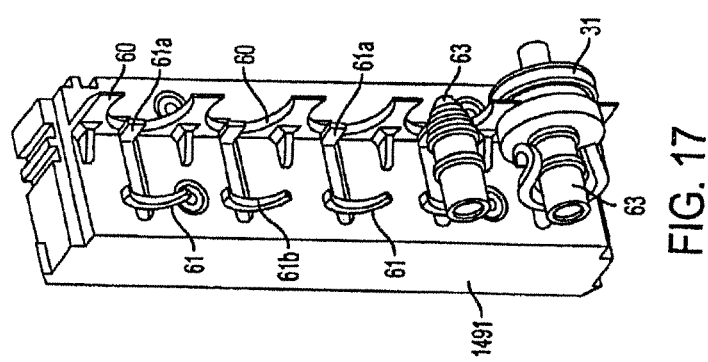
FIG. 17 is a left front perspective view of a cap stripper element in an illustrative embodiment.

FIGS. 17 and 18 show left and right front perspective views of another embodiment for the stripper element 1491 of the cap stripper 149. The stripper element 1491 in the embodiment shown in FIG. 13 included only fork-shaped elements arranged to engage with a cap 31 of a solution line 30. In the FIGS. 17 and 18 embodiment, the stripper element 1491 not only includes the fork-shaped elements 60, but also rocker arms 61 that are pivotally mounted to the stripper element 1491. As will be explained in more detail below, the rocker arms 61 assist in removing spike caps 63 from the cassette 24. Each of the rocker arms 61 includes a solution line cap engagement portion 61a and a spike cap engagement portion 61b. The rocker arms 61 are normally biased to move so that the spike cap engagement portions 61b are positioned near the stripper element 1491, as shown in the rocker arms 61 in FIG. 18. However, when a cap 31 is received by a corresponding fork-shaped element 60, the solution line cap engagement portion 61a contacts the cap 31, which causes the rocker arm 61 to pivot so that the spike cap engagement portion 61b moves away from the stripper element 1491, as shown in FIG. 17. This position enables the spike cap engagement portion 61b to contact a spike cap 63, specifically a flange on the spike cap 63.

Figure 19:
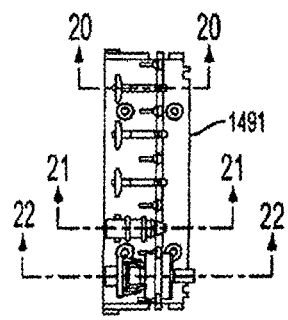
FIG. 19 is a front view of the cap stripper element of FIG. 17.
Figure 20:
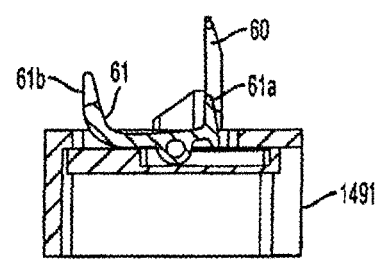
FIG. 20 is a cross sectional view along the line 20-20 in FIG. 19.
Figure 21:
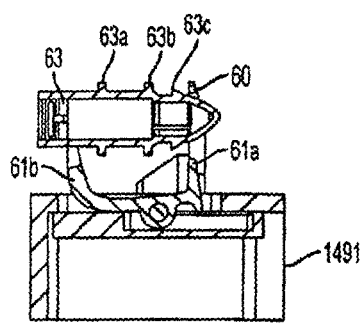
FIG. 21 is a cross sectional view along the line 21-21 in FIG. 19.
Figure 22:
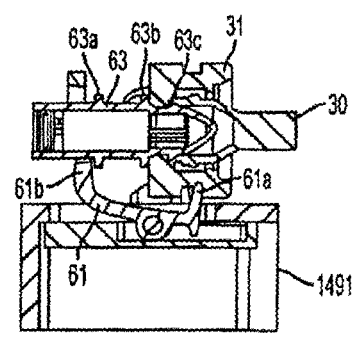
FIG. 22 is a cross sectional view along the line 22-22 in FIG. 19.

FIG. 19 shows a front view of the stripper element 1491 and the location of several cross-sectional views shown in FIGS. 20-22. FIG. 20 shows the rocker arm 61 with no spike cap 63 or solution line cap 31 positioned near the stripper element 1491. The rocker arm 61 is pivotally mounted to the stripper element 1491 at a point approximately midway between the spike cap engagement portion 61b and the solution cap engagement portion 61a. As mentioned above, the rocker arm 61 is normally biased to rotate in a counter-clockwise direction as shown in FIG. 20 so that the spike cap engagement portion 61b is positioned near the stripper element 1491. FIG. 21 shows that the rocker arm 61 maintains this position (i.e., with the spike cap engagement portion 61b located near the stripper element 1491) even when the stripper element 1491 advances toward a spike cap 63 in the absence of a solution line cap 31 engaging with the fork-shaped element 60. As a result, the rocker arm 61 will not rotate clockwise or engage the spike cap 63 unless a solution line cap 31 is present. Thus, a spike cap 63 that does not engage with a solution line cap 31 will not be removed from the cassette 24.

FIG. 22 shows an example in which a solution line cap 31 is engaged with the fork-shaped element 60 and contacts the solution line cap engagement portion 61a of the rocker arm 61. This causes the rocker arm 61 to rotate in a clockwise direction (as shown in the figure) and the spike cap engagement portion 61b to engage with the spike cap 63. In this embodiment, engagement of the portion 61b includes positioning the portion 61b adjacent a second flange 63a on the spike cap 63 so that when the stripper element 1491 moves to the right (as shown in FIG. 22), the spike cap engagement portion 61b will contact the second flange 63a and help pull the spike cap 63 from the corresponding spike 160. Note that the solution line cap 31 is made of a flexible material, such as silicone rubber, to allow a barb 63c of the spike cap 63 to stretch the hole 31b of cap 31 (see FIG. 23) and be captured by a circumferential inner groove or recess within cap 31. A first flange 63b on the spike cap 63 acts as a stop for the end of solution line cap 31. In another example, the spike cap 63 does not include a first flange 63b. The walls defining the groove or recess in the cap 31 hole 31b may be symmetrical, or preferably asymmetrically arranged to conform to the shape of the barb 63c. (See FIG. 33 for a cross sectional view of the cap 31 and the groove or recess.) The second flange 63a on spike cap 63 acts as a tooth with which the spike cap engagement portion 61b of the rocker arm 61 engages in order to provide an additional pulling force to disengage the spike cap 63 from the spike 160, if necessary.

FIG. 11-5 and FIG. 11-6 show two different perspective views of another embodiment for the stripper element 1491 of the cap stripper 149. The stripper element 1491 in the embodiment shown in FIG. 13 uses fork-shaped elements 60 arranged to engage with a cap 31 of a solution line 30. In the embodiment shown in FIG. 11-5, the stripper element 1491 not only includes the fork-shaped elements 60, but may also include a plurality of sensing elements 1112, and a plurality of rocker arms 1114. The sensing elements 1112 and rocker arms 1114 may be arranged in two parallel columns that run vertically along the stripper element 1491. In an embodiment, each vertical column may contain five individual sensing elements 1112 and rocker arms 1114, each being positioned to generally align in a row corresponding with each of the fork-shaped elements 60. Each sensing element 1112 may be mechanically connected or linked to one of the corresponding rocker arms 1114. In addition, the assembly comprising each sensing element 1112 and rocker arm 1114 may include a biasing spring (not shown) that keeps each rocker arm 1114 biased toward a non-engagement position and sensing element 1112 in a position to be contacted and moved by the presence of a solution line cap 31 in fork-shaped element 60. Each sensing element 1112 can be displaced and tilted toward the back of the stripper element 1491 by contact with a corresponding solution line cap 31 in forked-shaped element 60. Through the mechanical connection between sensing element 1112 and rocker arm 1114, rocker arm 1114 can pivotally rotate or tilt laterally toward spike cap 63 upon contact between solution line cap 31 and sensing element 1112. As rocker arm 1114 rotates or tilts toward spike cap 63, it can engage second flange 63a on spike cap 63, allowing the stripper assembly to remove spike cap 63 from its corresponding spike.

Figures 1, 11:
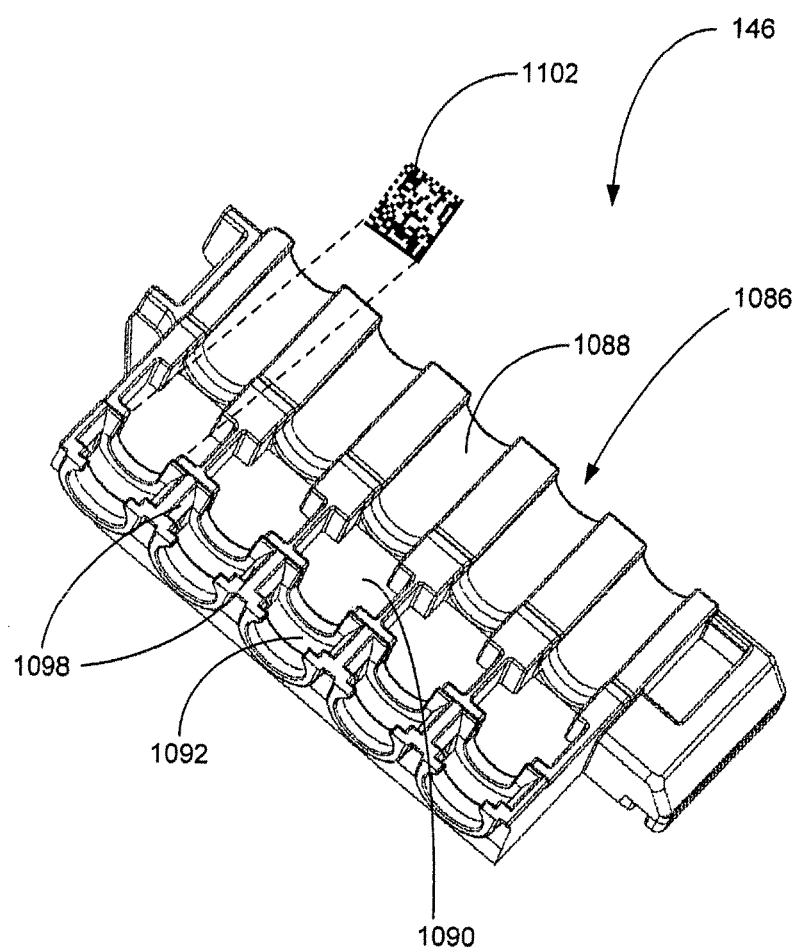
Figures 2, 11:
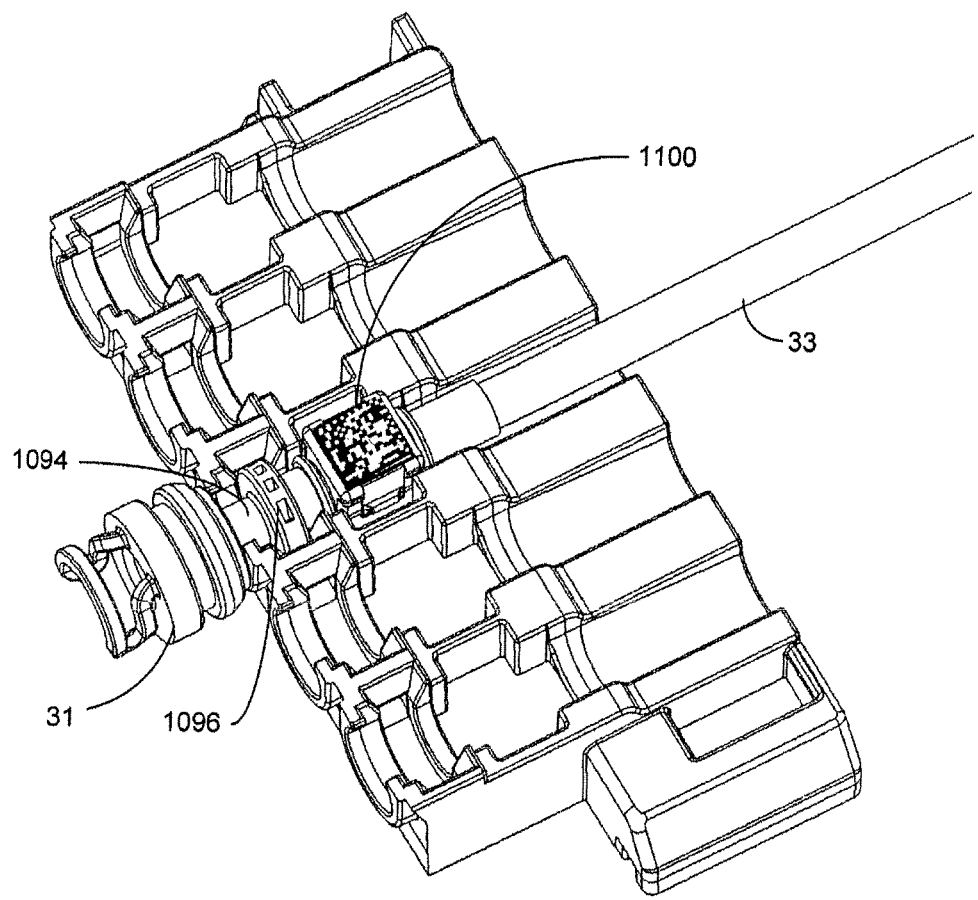
Figures 3, 11:
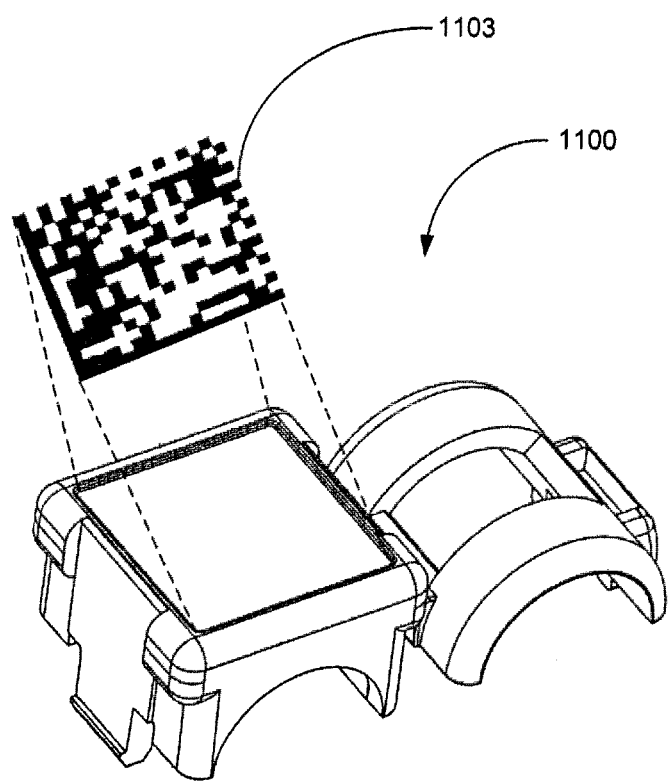
Figures 4, 11:
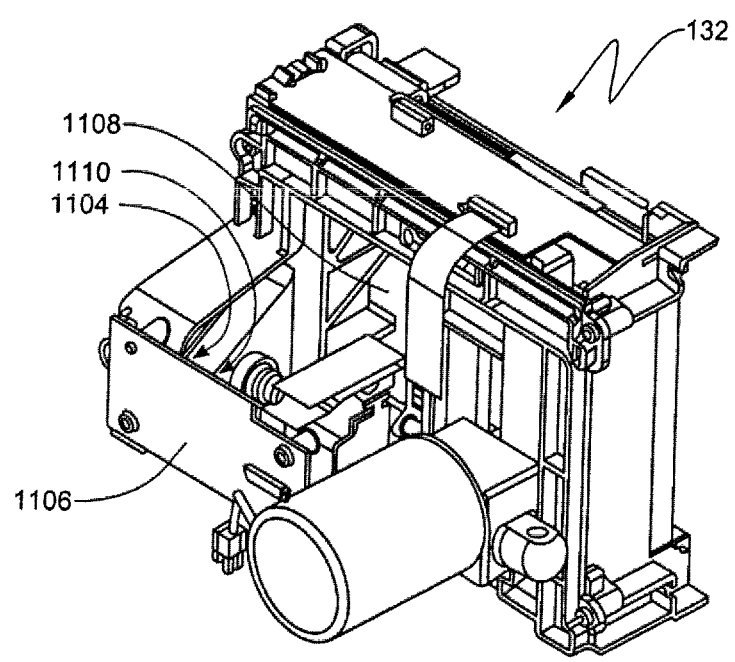
Figures 5, 11:
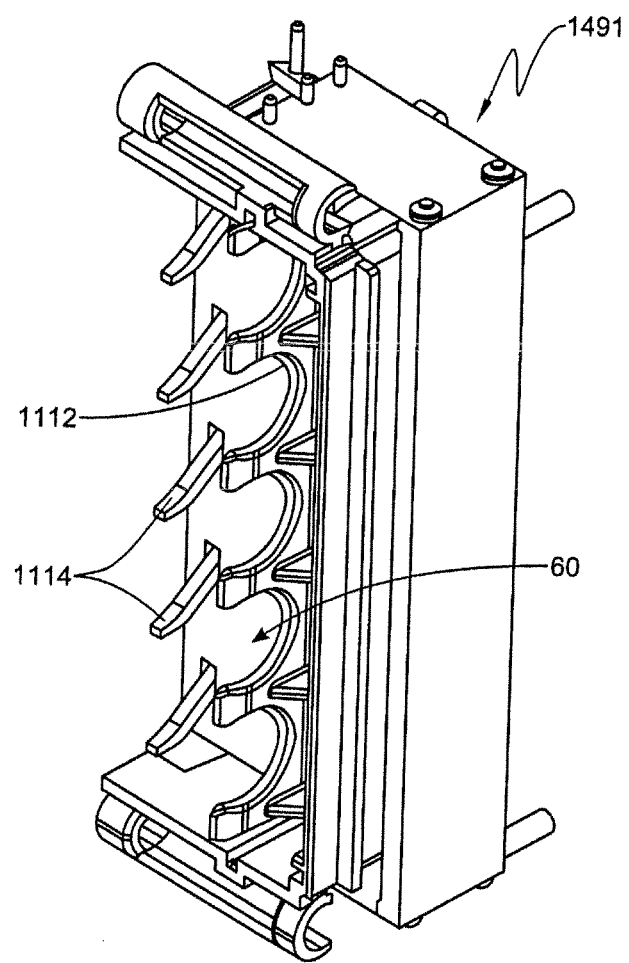
Figures 6, 11:
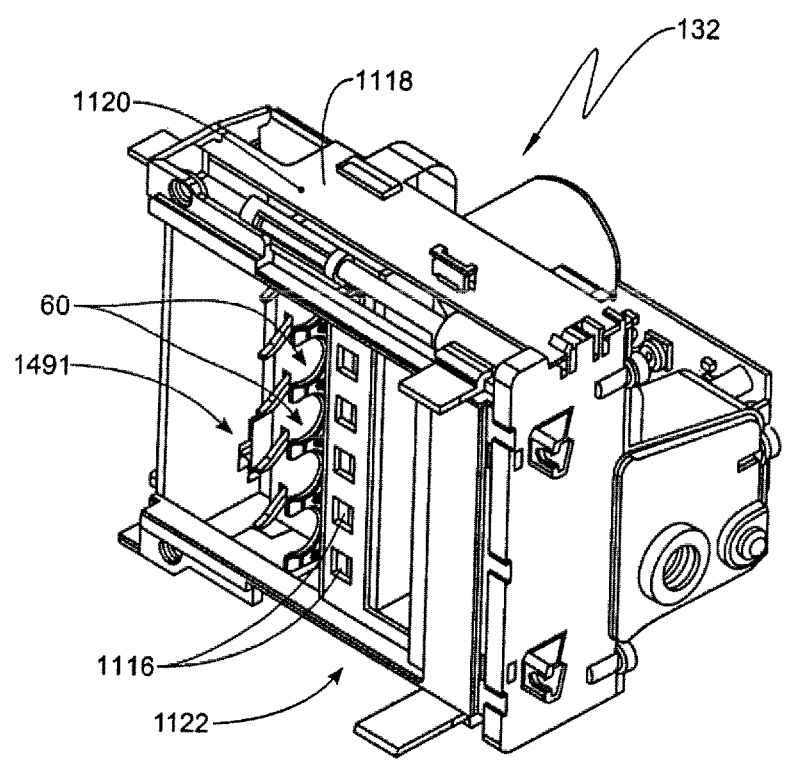
Figures 7A, 7B, 7C, 11:
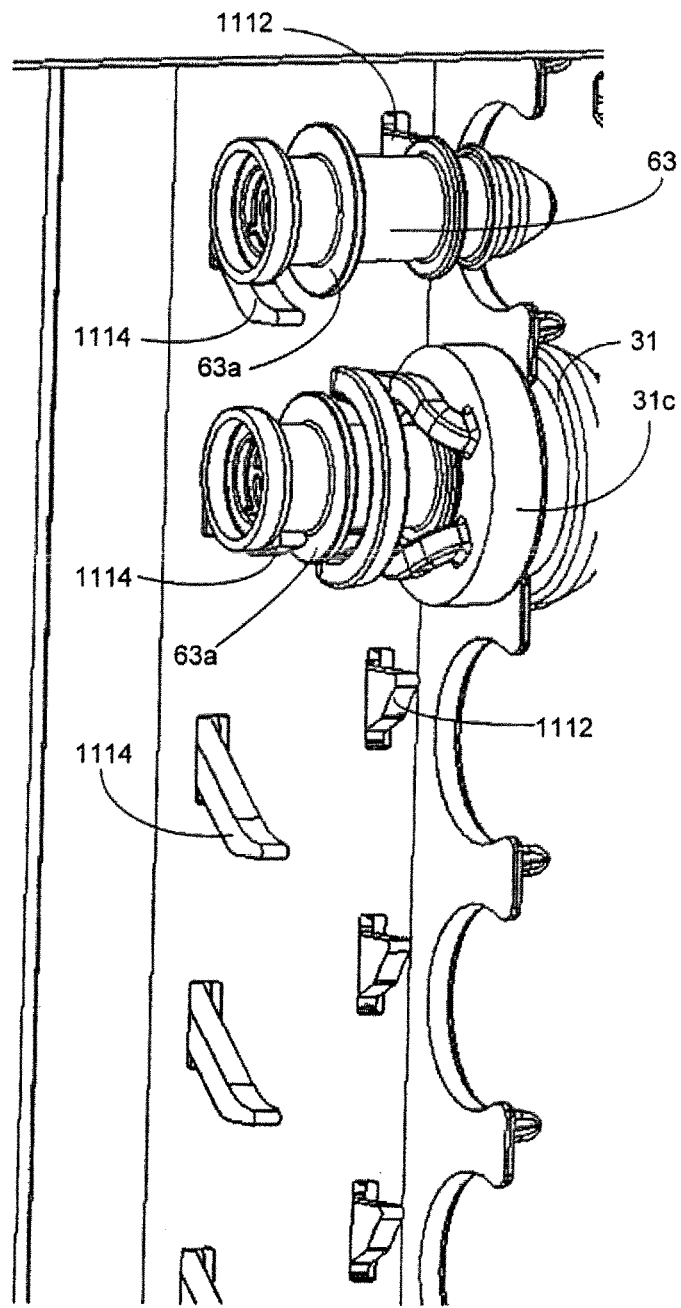
Figure 12:
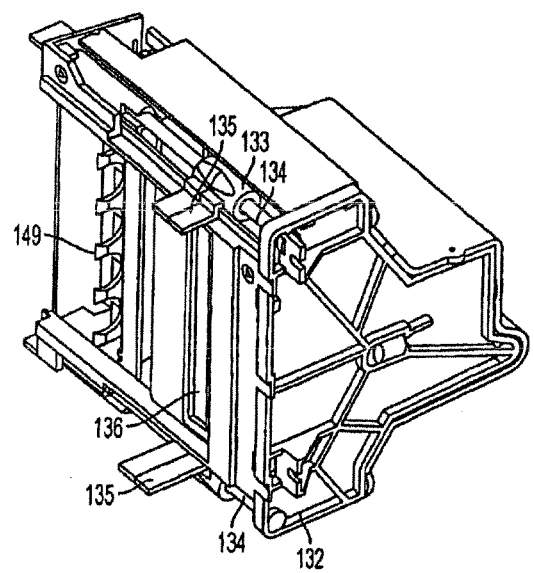
Figure 14:
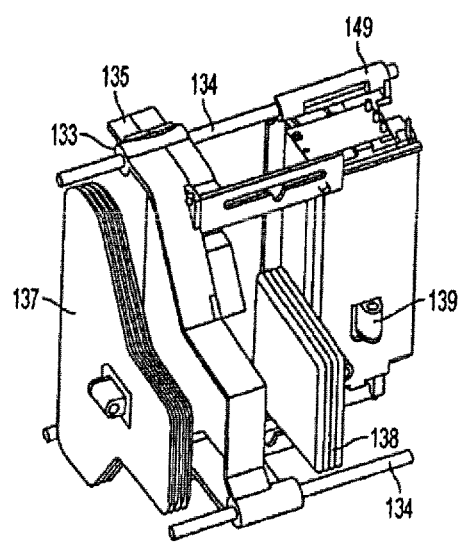

FIGS. 11-7a-c illustrate the relationship between sensing element 1112 and a solution line cap 31, and between rocker arm 1114 and spike cap 63. FIG. 11-7c shows the sensing element 1112 and rocker arm 1114 in the absence of a spike cap 63 and solution line cap 31. As shown in FIG. 11-7b, an outer flange 31c of solution line cap 31 has a diameter sufficiently large to make contact with sensing element 1112. As shown in FIG. 11-7a, in the absence of a solution line cap 31, the mere presence of spike cap 63 alone does not contact sensing element 1112 sufficiently enough to displace it and cause it to rotate away from spike cap 63. As shown in FIG. 11-7b, the displacement of sensing element 1112 causes rotation or tilting of rocker arm 1114 toward spike cap 63, ultimately to the point of being positioned adjacent flange 63a of spike cap 63. As shown in FIG. 11-7a, when rocker arm 1114 is in a non-deployed position, it can clear the outer circumference of second flange 63a of spike cap 63 by a pre-determined amount (e.g., 0.040 inch). Upon movement of rocker arm 1114 into a deployed position, its range of travel may be configured so as to provide a slight compression force against its corresponding spike cap 63 to ensure a secure engagement.

Once a rocker arm 1114 is positioned adjacent flange 63a of a spike cap 63, movement of stripper element 1491 to the right will engage spike cap 63 via flange 63a and help to pull spike cap 63 from its corresponding spike 160. In the absence of a solution line and its associated solution line cap 31, stripper element 1491 will not remove the corresponding spike cap 63, keeping its associated spike 160 sealed. Thus, fewer than the maximum number of cassette spikes 161 may be accessed when fewer than the maximum number of solution lines need to be used.

Figure 23:
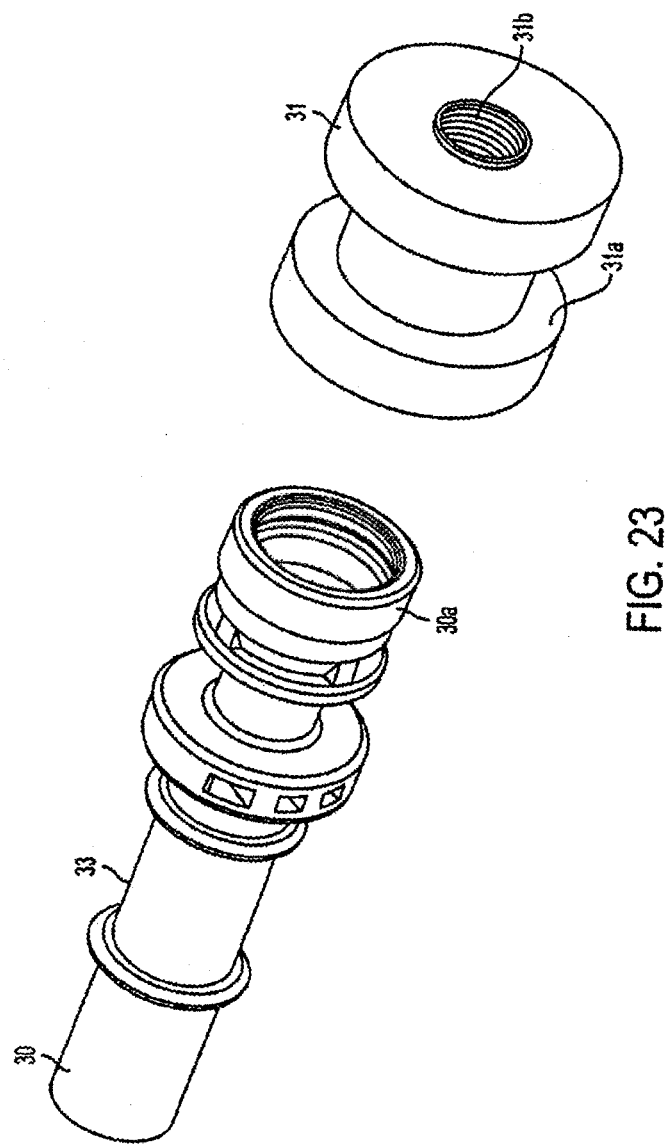
FIG. 23 is a close-up exploded view of the connector end of a solution line in an illustrative embodiment.

FIG. 23 shows a close-up exploded view of the connector end 30a of a solution line 30 with the cap 31 removed. (In FIG. 23, the caps 31 are shown without a finger pull ring like that shown in FIG. 24 for clarity. A pull ring need not be present for operation of the cap 31 with the cycler 14. It may be useful, however, in allowing an operator to manually remove the cap 31 from the terminal end of solution line 30, if necessary). In this illustrative embodiment, the indicator at indicator region 33 has an annular shape that is sized and configured to fit within a corresponding slot of the carriage 146 when mounted as shown in FIGS. 10 and 11. Of course, the indicator may take any suitable form. The cap 31 is arranged to fit over the extreme distal end of the connector end 30a, which has an internal bore, seals, and/or other features to enable a leak-free connection with a spike 160 on a cassette 24. The connector end 30a may include a pierceable wall or septum (not shown—see FIG. 33 item 30b) that prevents leakage of solution in the line 30 from the connector end 30a, even if the cap 31 is removed. The wall or septum may be pierced by the spike 160 when the connector end 30a is attached to the cassette 24, allowing flow from the line 30 to the cassette 24. As discussed above, the cap 31 may include a groove 31a that is engaged by a fork-shaped element 60 of the cap stripper 149. The cap 31 may also include a hole 31b that is arranged to receive a spike cap 63. The hole 31b and the cap 31 may be arranged so that, with the cap stripper 149 engaged with the groove 31a and the spike cap 63 of a spike 160 received in the hole 31b, the cap 31 may grip the spike cap 63 suitably so that when the carriage 146/cap stripper 149 pulls the cap 31 away from the cassette 24, the spike cap 63 is removed from the spike 160 and is carried by the cap 31. This removal may be assisted by the rocker arm 61 engaging with the second flange 63a or other feature on the spike cap 63, as described above. Thereafter, the cap 31 and spike cap 63 may be removed from the connector end 30a and the line 30 attached to the spike 160 by the carriage 146.

Solution Line Connector Heater

In one embodiment, a connector heater may be provided near the indicator region 33 of the solution lines 30. The connector heater may control the temperature of the connector end 30a and in particular the pierceable wall or septum 30b in order to limit the carriage force required attach the solution lines to the spikes 160 on the cassette 24. There may be enough variation in ambient (room) temperature to affect the hardness of the pierceable wall or septum 30b of the connector end 30a of the solution line, which may in turn affect the performance of the carriage 146 in joining the spike 160 to the connector end 30a of the solution line 30. For example, at lower ambient temperatures, the increased hardness of the pierceable wall or septum 30b may require a greater force for spike 160 to penetrate it. On the other hand, at higher ambient temperatures, the pierceable wall or septum may be so soft as to deform rather than separate when contacted by the spike 160.

The temperature of the connector ends 30a may be controlled in a number of ways, which may include placing a heating element in an appropriate location (e.g., at or near location 2807 on the door 141), installing a temperature sensor to monitor the temperature of connector ends 30a, and using a controller to receive temperature data and modulate the operation of the heating element. The temperature may be measured by a temperature sensor element mounted on the stripper element 1491 or on the carriage 146. Alternatively, the temperature of the connector end 30a may be determined using an infra-red (IR) sensor tuned to measure surface temperature of the connector end 30a.

The controller may be a software process in the automation computer 300. Alternatively, the controller may be implemented in the hardware interface 310. The controller may modulate the power sent to a resistance heater, for example, in one of a number of ways. For example, the controller may send a PWM signal to a MOSFET that can modulate the flow of electrical power to the resistance heater. The controller may control the measured temperature to the desired temperature through a number of algorithms. One exemplary algorithm includes a proportional-integral (PI) feedback loop on the measured temperature to set the heater power. Alternatively, the heater power can be modulated in an open loop algorithm that sets the heater power based on the measured ambient temperature.

In another embodiment, the temperature of the connector end 30a may be controlled by mounting a radiant heater in the door 141 at location 2807, for example, and aimed at the connector ends. Alternatively, the temperature of the connector ends may be controlled by mounting a thermo-electric element at location 2807, for example, on the door 141. The thermo-electric element may provide either heating or cooling to the area surrounding the connector ends when mounted on the carriage 146. The radiant heater or thermo-electric element may be modulated by a controller to maintain the temperature within a given range. The preferred temperature range for the connector end 30a depends on the material comprising the pierceable wall or septum, and may be determined empirically. In one embodiment, the piercable wall is PVC and the preferred temperature range is set at about 10° C. to 30° C., or more preferably to a temperature range of about 20° C. to 30° C.

In an embodiment, the connector heater near the indicator region 33 may be used after the door is closed and before the solution lines 30 are attached to the cassette 24. The automation computer 300 or a controller enables the connector heater if the measured temperature near the connector 30a is outside a preferred range. The automation computer 300 or a controller may delay the auto-connection process until the measured temperature is within the preferred range. The connector heater may be disabled after the auto-connection process is completed.

Once treatment is complete, or the line 30 and/or the cassette 24 are ready for removal from cycler 14, the cap 31 and attached spike cap 63 may be re-mounted on the spike 160 and the line 30 before the door 141 is permitted to be opened and the cassette 24 and line 30 removed from the cycler 14. Alternatively, the cassette 24 and solution containers with lines 30 can be removed en bloc from cycler 14 without re-mounting cap 31 and the attached spike cap 63. An advantage of this approach includes a simplified removal process, and avoidance of any possible fluid leaks onto the cycler or surrounding area from improperly re-mounted or inadequately sealing caps.

Figure 24:
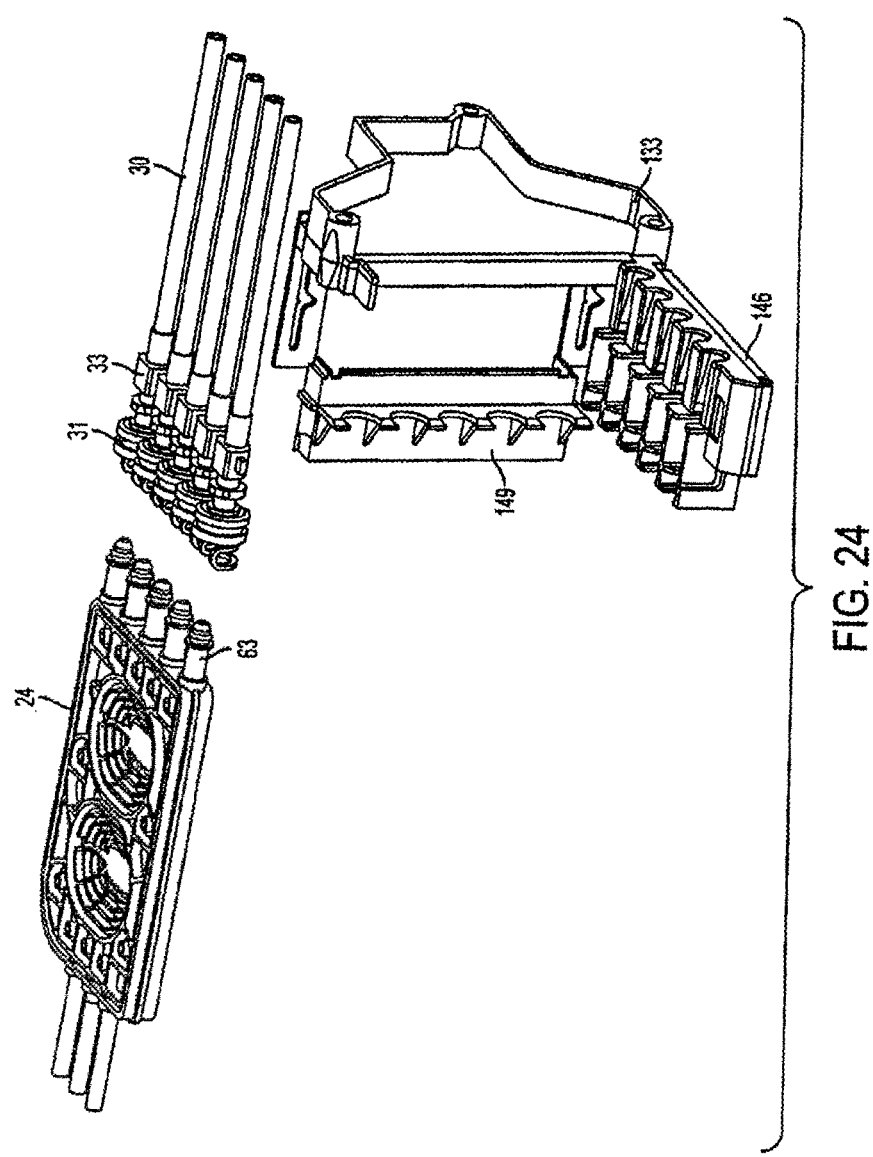
FIG. 24 is a schematic view of a cassette and solution lines being loaded into the cycler of FIG. 10.
Figure 25:
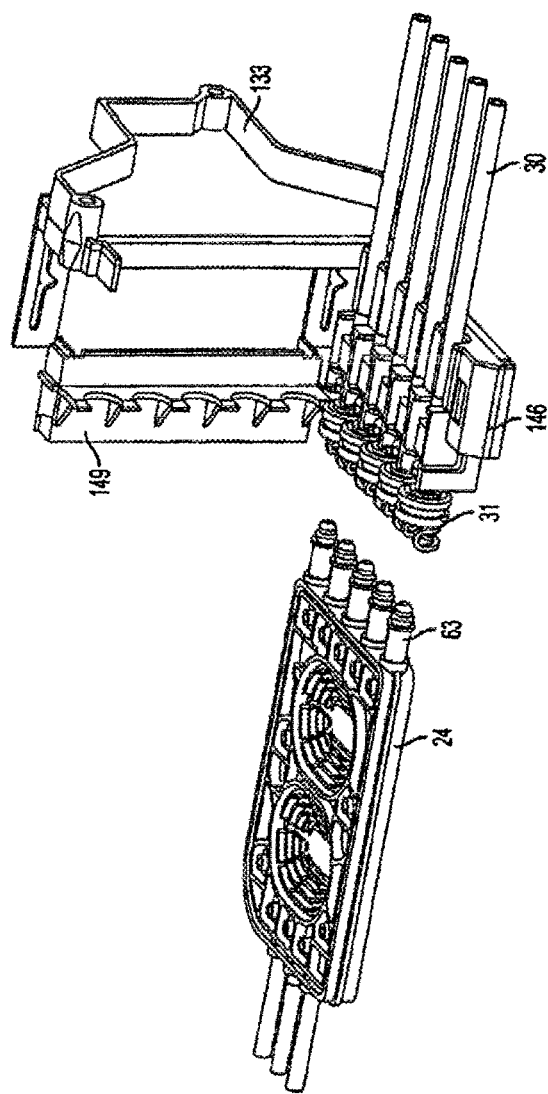
FIG. 25 is a schematic view of the cassette and solution lines after placement in respective locations of the door of the cycler of FIG. 10.
Figure 26:
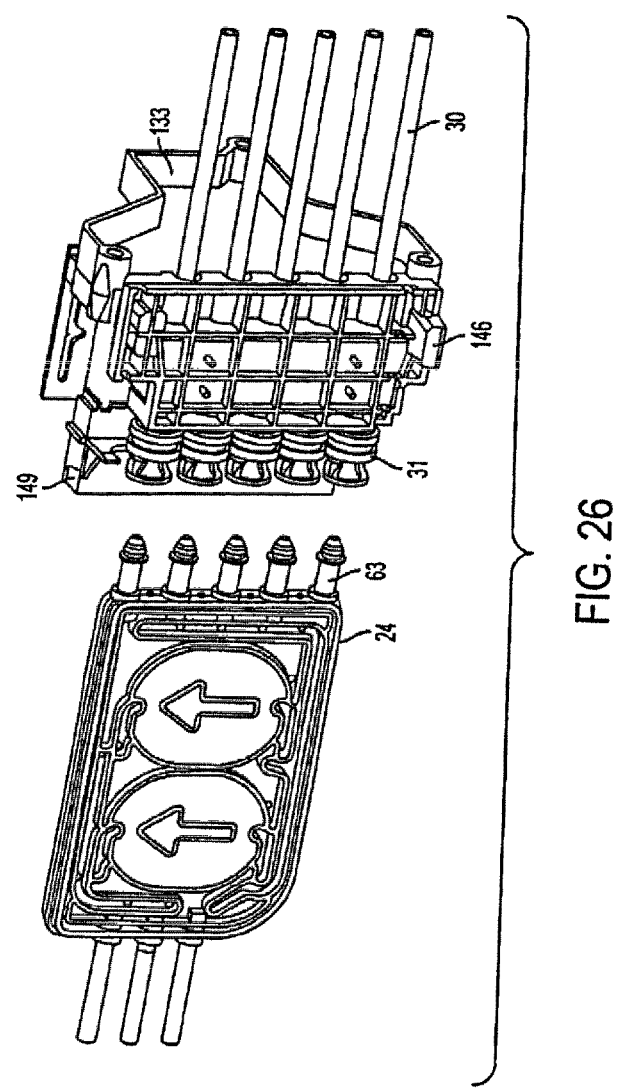
FIG. 26 is a schematic view of the cassette and solution lines after the door of the cycler is closed.
Figure 27:
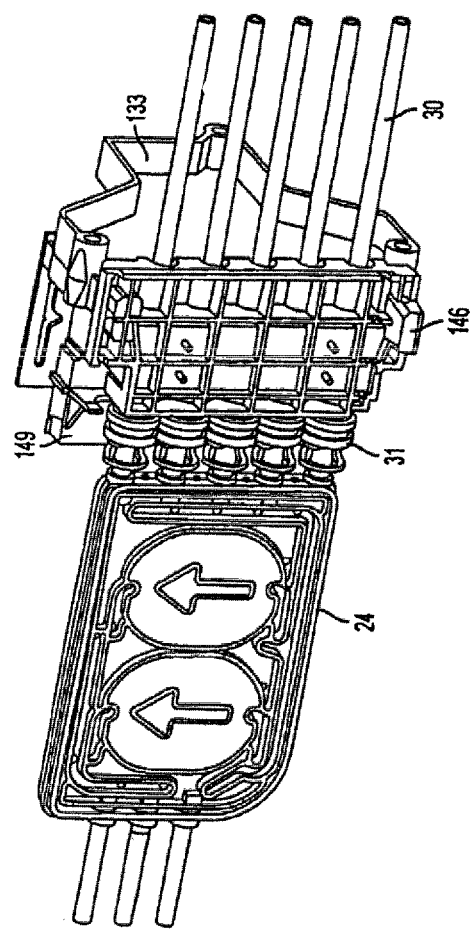
FIG. 27 is a schematic view of the solution lines being engaged with spike caps.
Figure 28:
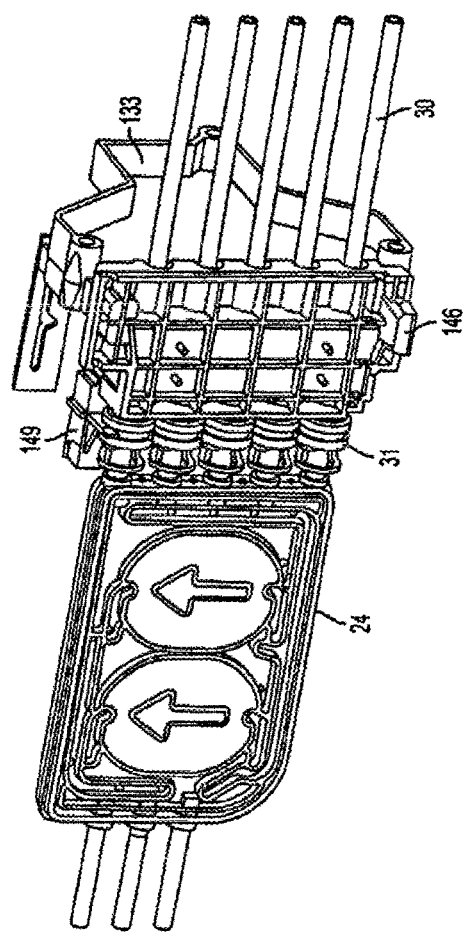
FIG. 28 is a schematic view of the cap stripper engaging with spike caps and solution line caps.
Figure 29:
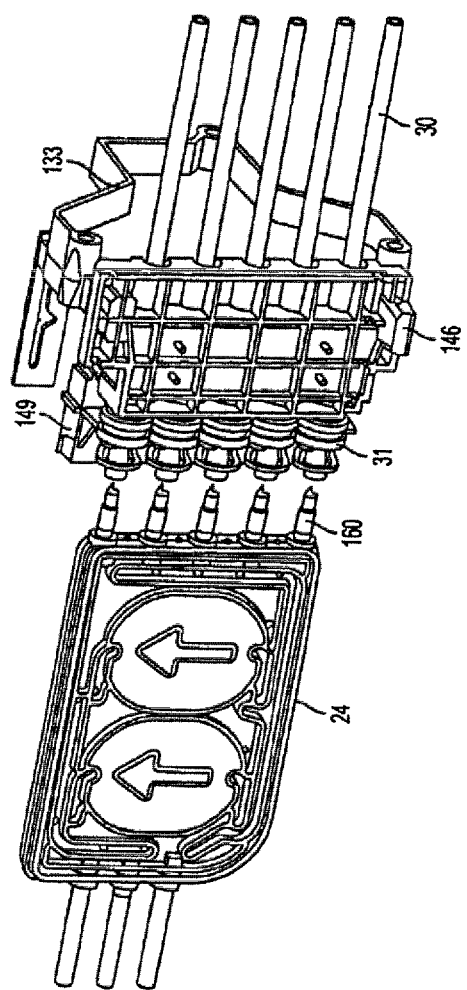
FIG. 29 is a schematic view of the solution lines with attached caps and spike caps after movement away from the cassette.
Figure 30:
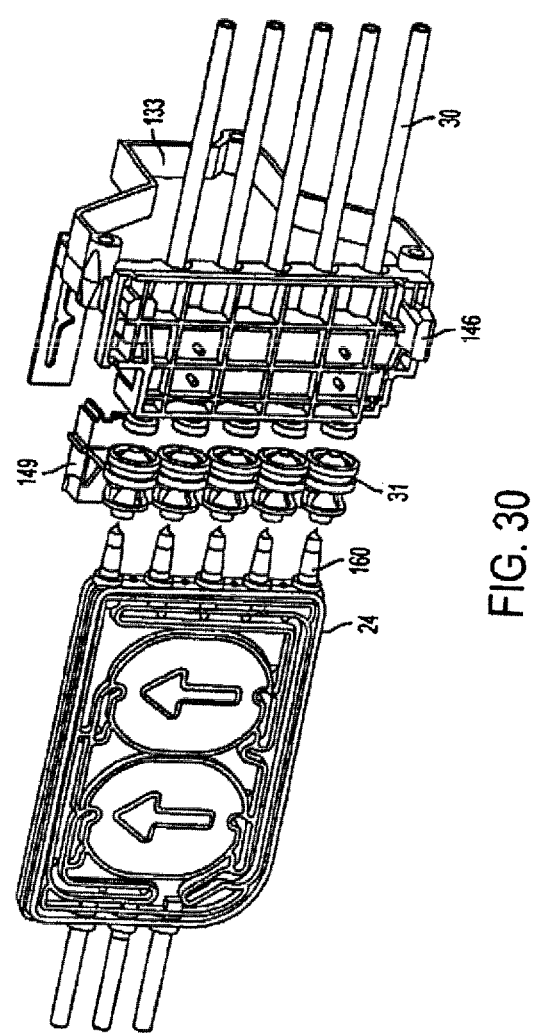
FIG. 30 is a schematic view of the solution lines after movement away from the solution line caps and spike caps.
Figure 31:
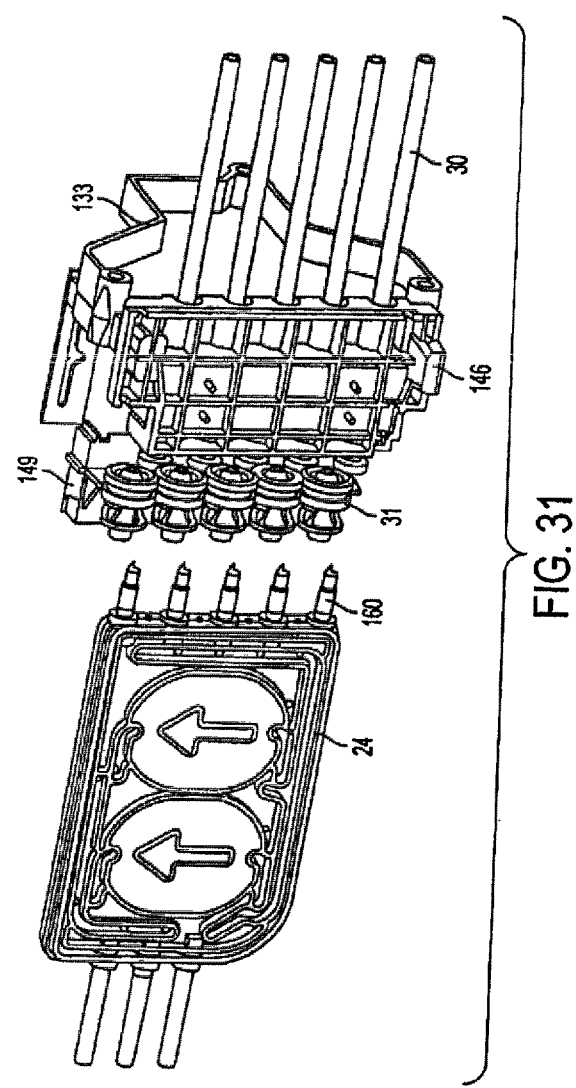
FIG. 31 is a schematic view of the cap stripper retracting with the solution line caps and spike caps.
Figure 32:
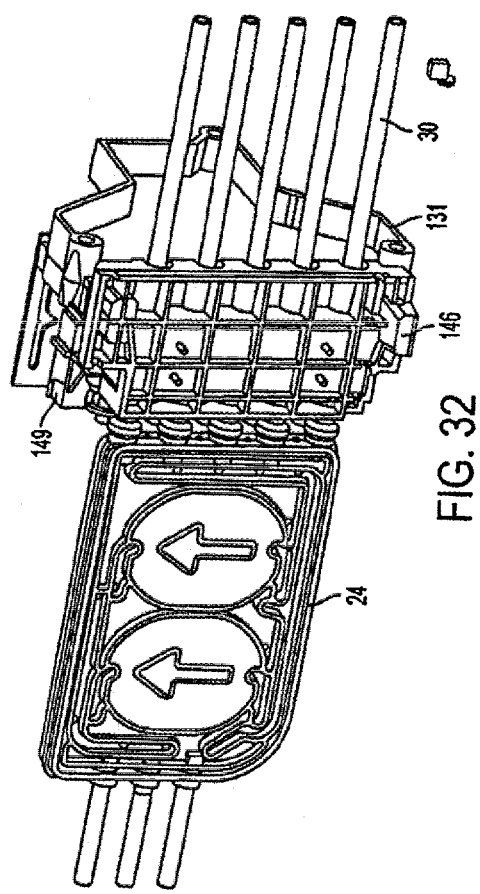
FIG. 32 is a schematic view of the solution lines being engaged with the spikes of the cassette.

FIGS. 24-32 show a perspective view of the carriage 146, cap stripper 149 and cassette 24 during a line mounting and automatic connection operation. The door 141 and other cycler components are not shown for clarity. In FIG. 24, the carriage 146 is shown in a folded down position, as if the door 141 is open in the position shown in FIG. 0.8. The lines 30 and cassette 24 are positioned to be lowered onto the door 141. In FIG. 25, the lines 30 are loaded into the carriage 146 and the cassette 24 is loaded into the mounting location 145. At this point the door 141 can be closed to ready the cycler for operation. In FIG. 26, the door 141 is closed. Identifiers or indicators located at indicator region 33 on the lines 30 may be read to identify various line characteristics so that the cycler 14 can determine what solutions, how much solution, etc., are loaded. In FIG. 27, the carriage 146 has moved to the left, engaging the caps 31 on the lines 30 with corresponding spike caps 63 on the cassette 24. During the motion, the drive element 133 engages the cap tripper 149 and moves the cap stripper 149 to the left as well. However, the cap stripper 149 remains in a retracted position. In FIG. 28, the cap stripper 149 moves forward to engage the fork-shaped elements 60 with the caps 31, thereby engaging the caps 31 that have been coupled to the spike caps 63. If present, the rocker arms 61 may move to an engagement position with respect to the spike caps 63. Next, as shown in FIG. 29, the carriage 146 and the cap stripper 149 move to the right, away from the cassette 24 so as to pull the caps 31 and spike caps 63 from the corresponding spikes 160 on the cassette 24. It is during this motion that the rocker arms 61, if present, may assist in pulling spike caps 63 from the cassette 24. In FIG. 30, the cap stripper 149 has stopped its movement to the right, while the carriage 146 continues to move away from the cassette 24. This causes the connector ends 30a of the lines 30 to be pulled from the caps 31, leaving the caps 31 and spike caps 63 mounted on the cap stripper 149 by way of the fork-shaped elements 60. In FIG. 31, the cap stripper 149 retracts, clearing a path for the carriage 146 to move again toward the cassette 24. In FIG. 32, the carriage 146 moves toward the cassette 24 to engage the connector ends 30a of the lines 30 with the corresponding spikes 160 of the cassette 24. The carriage 146 may remain in this position during cycler operation. Once treatment is complete, the movements shown in FIGS. 24-32 may be reversed to recap the spikes 160 and the solution lines 30 and remove the cassette 24 and/or lines 30 from the cycler 14.

Figure 33:
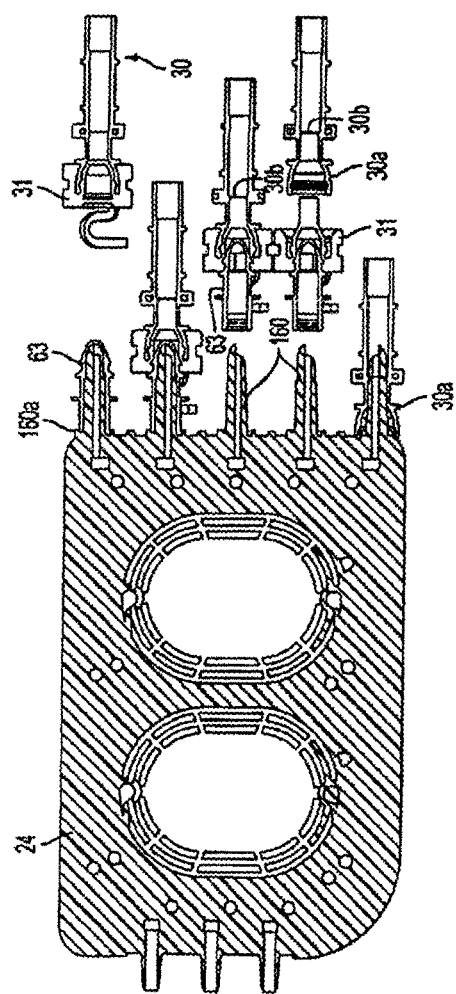
FIG. 33 is a cross sectional view of a cassette with five stages of a solution line connection operation shown with respect to corresponding spikes of the cassette.

To further illustrate the removal of caps 31 and spike caps 63, FIG. 33 shows a cross-sectional view of the cassette 24 at five different stages of line 30 connection. At the top spike 160, the spike cap 63 is still in place on the spike 160 and the solution line 30 is positioned away from the cassette 24, as in FIG. 26. At the second spike 160 down from the top, the solution line 30 and cap 31 are engaged over the spike cap 63, as in FIGS. 27 and 28. At this point, the cap stripper 149 may engage the cap 31 and spike cap 63. At the third spike 160 from the top, the solution line 30, cap 31 and spike cap 63 have moved away from the cassette 24, as in FIG. 29. At this point, the cap stripper 149 may stop movement to the right. At the fourth spike 160 from the top, the solution line 30 continues movement to the right, removing the cap 31 from the line 30, as in FIG. 30. Once the caps 31 and 63 are retracted, the solution line 30 moves to the left to fluidly connect the connector end 30a of the line 30 to the spike 160, as in FIG. 32.

Various sensors can be used to help verify that the carriage 146 and cap stripper 149 move fully to their expected positions. In an embodiment, the carriage drive assembly 132 can be equipped with six Hall effect sensors (not shown): four for the carriage 146 and two for the cap stripper 149. A first cap stripper sensor may be located to detect when the cap stripper 149 is fully retracted. A second cap stripper sensor may be located to detect when the cap stripper 149 is fully extended. A first carriage sensor may be located to detect when the carriage 146 is in the "home" position, i.e. in position to permit loading the cassette 24 and lines 30. A second carriage sensor may be located to detect when the carriage 146 is in position to have engaged the spike caps 63. A third carriage sensor may be located to detect when the carriage 146 has reached a position to have removed the caps 31 from the lines 30. A fourth carriage sensor may be located to detect when the carriage 146 has moved to a position to have engaged the connector ends 30a of the lines 30 with the corresponding spikes 160 of the cassette 24. In other embodiments, a single sensor can be used to detect more than one of the carriage positions described above. The cap stripper and carriage sensors can provide input signals to an electronic control board ("autoconnect board"), which in turn can communicate specific confirmation or error codes to the user via the user interface 144.

FIG. 11-6 shows a perspective view of an alternative embodiment of the carriage drive assembly 132. The carriage drive assembly 132 in the embodiment shown in FIG. 12 included only the drive element 133, the rods 134, the tabs 136, and the window 136. In the FIG. 11-6 embodiment, the carriage drive assembly 132 not only includes the drive element 133, the rods 134, the tabs 136, and the window 136, but may also include a vertical column of AutoID view boxes 1116. The view boxes 1116 may be positioned directly adjacent to the window 136. Also, the view boxes 1116 may be positioned and shaped so that the horizontal axis of each of the five slots 1086 located on the carriage 146 run through the center of a corresponding view box 1116, when the carriage 146 moves either right or left along the guides 130. The view boxes 1116 may allow for the AutoID camera 1104, which is attached to the camera board 1106, to detect if the solution line caps 31 are positioned on the lines 30 prior to the engaging of the solution lines with the spike cap 63. This may allow for confirmation that the user hasn't removed the caps 31 prematurely. Once the presence or absence of the caps 31 is determined, the camera 1104 can provide a corresponding input signal to an electronic control board (referred to as the autoconnect board later in the specification), which in turn can communicate specific confirmation or error codes, relating to the presence of the caps 31 on the lines 30, to the user via the user interface 144.

In accordance with another aspect of the disclosure, the carriage drive assembly 132 may include an autoconnect board 1118. The autoconnect board 1118 may be attached to the top of the carriage drive assembly 132, and may extend the entire length of the assembly 132. In this illustrative embodiment, there may also be an LED 1120 mounted to the autoconnect board 1118. The LED 1120 may be located in a fixed position directly above the fork-shaped elements 60. Also, the LED 1120 may be directed is a fashion so that the light being emitted from the LED 1120 travels downward across the stripper element 1491. In accordance with another aspect of the present disclosure, the carriage drive assembly 132 may also include a fluid board 1122. The fluid board 1122 may be attached to the bottom of the carriage drive assembly 132, and may also extent the length of the assembly 132. In this illustrative embodiment, there may be a receiver 1124 (not pictured) mounted to the fluid board 1122 at a location directly below the LED 1120, which is mounted to the autoconnect board 1118. Therefore, the LED 1120 can emit light across the fork-shaped elements 60, and if the light it detected by the receiver 1124 then there are no solution line caps 31 left in the stripper element 1491, however, if the light is interrupted on its way towards the receiver 1124 then there may be a cap 31 left in the stripper element 1491. This LED 1120 and receiver 1124 combination allows for the detection of caps 31 that may have been inadvertently left in the stripper element 1491 either by the user or by the cycler 14. In accordance with an aspect of the disclosure, the fluid board 1122 may also have the ability to detect humidity, moisture, or any other liquid that may be present inside of the carriage drive assembly 132, which could potentially cause the cycler 14 to fail.

There may be an advantage in adjusting the force with which the carriage 146 engages the spike caps 63, depending on how many lines 30 are being installed. The force required to complete a connection to the cassette 24 increases with the number of caps 31 that must be coupled to spike caps 63. The sensing device for detecting and reading information from the line indicators at indicator regions 33 can also be used to provide the data required to adjust the force applied to drive element 133. The force can be generated by a number of devices, including, for example, the first air bladder 137, or a linear actuator such as a motor/ball screw. An electronic control board (such as, for example, the autoconnect board) can be programmed to receive input from the line detection sensor(s), and send an appropriate control signal either to the motor of a linear actuator, or to the pneumatic valve that controls inflation of air bladder 137. The controller 16 can control the degree or rate of movement of drive element 133, for example by modulating the voltage applied to the motor of a linear actuator, or by modulating the pneumatic valve controlling the inflation of bladder 137.

In accordance with an aspect of the present disclosure, it may be necessary for the carriage drive assembly 132 to be capable of generating a force of at least 550 N (124 lbf) on carriage 146, in order to engage the membrane ports with spikes 160. This force is to be measured in the carriage direction of the membrane port spiking onto the cassette 24. The maximum force required to spike a sterilized PVC membrane port onto the spike 160 may be 110 N. Additionally, the maximum force required to spike a sterilized JPOC membrane port onto the spike 160 may be 110 N. These force requirements ensure carriage drive assembly 132 is able to spike five JPOC ports. In an alternative embodiment, the PVC port force requirement may be lowered further based on current insertion forces.

The aspect of the invention by which caps 31 on lines 30 are removed together with caps 63 on spikes 160 of the cassette 24 may provide other advantages aside from simplicity of operation. For example, since spike caps 63 are removed by way of their engagement with a cap 31 on a line 30, if there is no line 30 mounted at a particular slot on the carriage 146, the spike cap 63 at that position will not be removed. For example, although the cassette 24 includes five spikes 160 and corresponding spike caps 63, the cycler 14 can operate with four or less (even no) lines 30 associated with the cycler 14. For those slots on the carriage 146 where no line 30 is present, there will be no cap 31, and thus no mechanism by which a spike cap 63 at that position can be removed. Thus, if no line 30 will be connected to a particular spike 160, the cap 63 on that spike 160 may remain in place during use of the cassette 24. This may help prevent leakage at the spike 160 and/or contamination at the spike 160.

Figure 34:
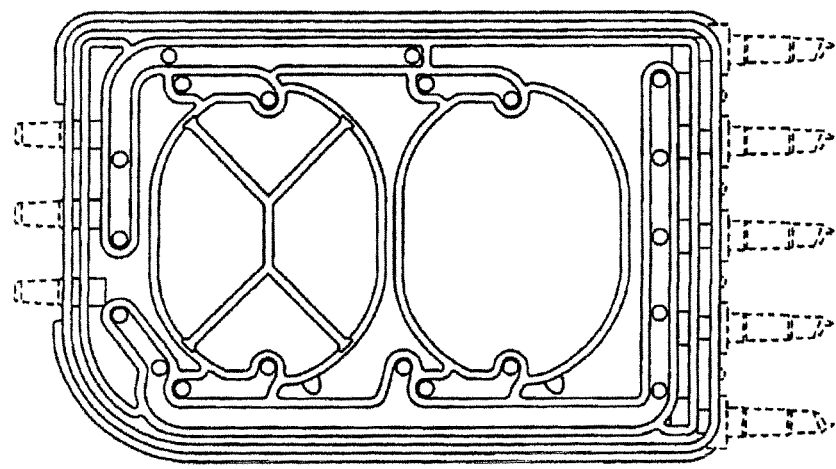
FIG. 34 shows a rear view of a cassette in another illustrative embodiment including different arrangements for a rear side of the cassette adjacent the pump chambers.

The cassette 24 in FIG. 33 includes a few features that are different from those shown, for example, in the embodiment shown in FIGS. 3, 4 and 6. In the FIGS. 3, 4 and 6 embodiment, the heater bag port 150, drain line port 152 and patient line port 154 are arranged to have a central tube 156 and a skirt 158. However, as mentioned above and shown in FIG. 33, the ports 150, 152, 154 may include only the central tube 156 and no skirt 158. This is also shown in FIG. 34. The embodiment depicted in FIG. 34 includes raised ribs formed on the outside surface of the left-side pump chamber 181. The raised ribs may also be provided on the right-side pump chamber 181, and may provide additional contact points of the outside walls of pump chambers 181 with the mechanism in the door 141 at the cassette mounting location 145, which presses the cassette against the control surface 148 when the door 141 is closed. The raised ribs are not required, and instead the pump chambers 181 may have no rib or other features, as shown for the right-side pump chamber 181 in FIG. 34. Similarly, the spikes 160 in the FIGS. 3, 4 and 6 embodiment include no skirt or similar feature at the base of the spike 160, whereas the embodiment in FIG. 33 includes a skirt 160*a*. This is also shown in FIG. 34. The skirt 160*a* may be arranged to receive the end of the spike cap 63 in a recess between the skirt 160*a* and the spike 160, helping to form a seal between the spike 160 and the spike cap 63.

Figure 35:
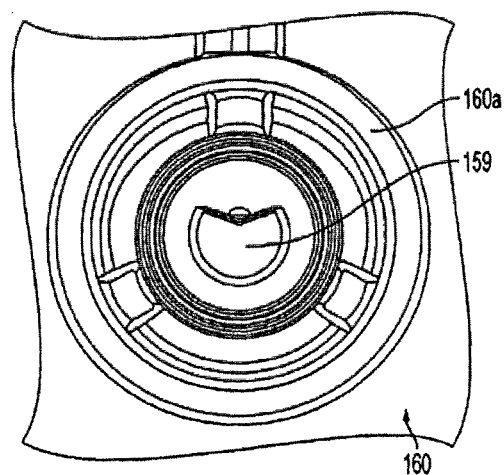
FIG. 35 shows an end view of a spike of a cassette in an illustrative embodiment.

Another inventive feature shown in FIG. 33 relates to the arrangement of the distal tip of the spike 163 and the lumen 159 through the spike 160. In this aspect, the distal tip of the spike 160 is positioned at or near the longitudinal axis of the spike 160, which runs generally along the geometric center of the spike 160. Positioning the distal tip of the spike 160 at or near the longitudinal axis may help ease alignment tolerances when engaging the spike 160 with a corresponding solution line 30 and help the spike 160 puncture a septum or membrane 30*b* in the connector end 30*a* of the line 30. As a result, the lumen 159 of the spike 160 is located generally off of the longitudinal axis of the spike 160, e.g., near a bottom of the spike 160 as shown in FIG. 33 and as shown in an end view of a spike 160 in FIG. 35. Also, the distal end of the spike 160 has a somewhat reduced diameter as compared to more proximal portions of the spike 160 (in this embodiment, the spike 160 actually has a step change in diameter at about ⅔ of the length of the spike 160 from the body 18). The reduced diameter of the spike 160 at the distal end may provide clearance between the spike 160 and the inner wall of the line 30, thus allowing the septum 30*b* a space to fold back to be positioned between the spike 160 and the line 30 when pierced by the spike 160. The stepped feature 160*b* on the spike 160 (shown, e.g., in FIG. 35A) may also be arranged to engage the line 30 at the location where the septum 30*b* is connected to the inner wall of the line 30, thus enhancing a seal formed between the line 30 and the spike 160.

Figure 35A:
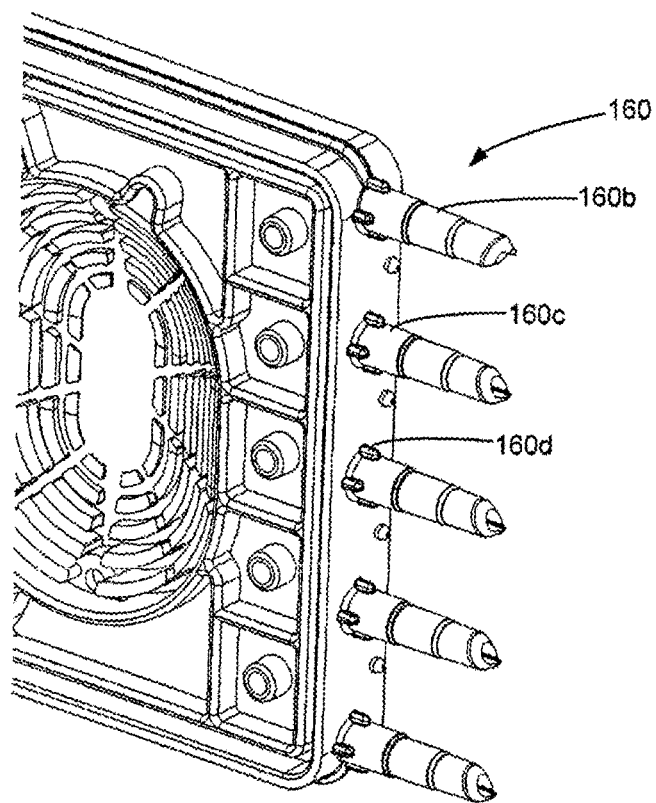
FIG. 35A shows a perspective view of an alternative embodiment of the spikes of a cassette.

In another embodiment, as shown in FIG. 35A, the length of the base 160*c* of spike 160 may be shortened to reduce the force required to remove the spike cap 63 from spike 160, or to reduce the force required to spike the connector end 30*a* of solution line 30. Shortening the base 160*c* reduces the area of frictional contact between spike 160 and its cap 63, or between spike 160 and the internal surface of connector end 30*a*. In addition, the skirt 160*a* at the base of spike 160 may be replaced by individual posts 160*d*. The posts 160*d* allow the spike cap 63 to be properly seated onto spike 160 while also allowing for more thorough circulation of sterilization fluid or gas around spike 160 during the sterilization process prior to or after packaging of the dialysate delivery set 12.

Figure 35B:
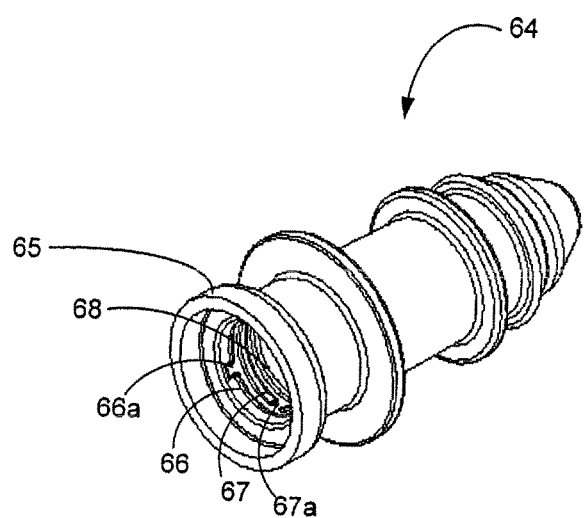
FIG. 35B shows an embodiment of a spike cap configured to fit over the spikes shown in FIG. 35A.
Figure 35C:
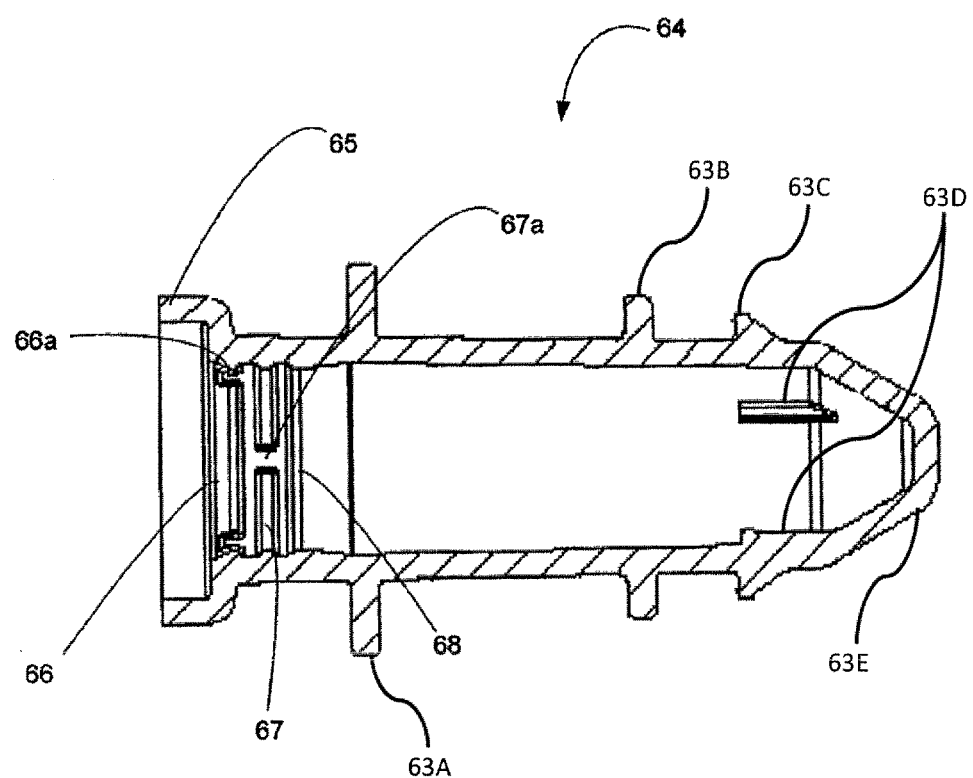
FIG. 35C shows a cross-sectional view of a spike cap shown in FIG. 35B.

To more fully take advantage of the embodiment shown in FIG. 35A, a spike cap 64, as shown in FIG. 35B may be used. A skirt 65 on the base of spike cap 64 is constructed to fit snugly over the posts 160*d* of the base of spike 160 shown in FIG. 35A. In addition, interrupted ribs 66, 67 within the inner circumference of the base of spike 160 may provide a snug fit between spike cap 64 and the base 160*c* of spike 160, while also permitting sterilizing gas or fluid to penetrate more distally over the base of a capped spike 160. As shown in FIG. 35C, in a cross-sectional view of spike cap 64, a set of three inner ribs 66, 67, 68 may be used to provide a snug fit between spike cap 64 and the base 160*c* of spike 160. In an embodiment, rib 66 and rib 67 have interruptions or gaps 66*a* and 67*a* along their circumference to permit gas or fluid external to the cassette to flow over the base 160*c* of spike 160. A third rib 68 may be circumferentially intact in order to make a sealing engagement between spike cap 64 and the base 160*c* of spike 160, sealing off the base 160*c* from rest of the external surface of spike 160. In other embodiments, ribs within spike cap 64 may be oriented longitudinally rather than circumferentially, or in any other orientation to provide a snug fit between spike cap 64 and spike 160, while also permitting an external gas or fluid to make contact with the outside of the base 160*c* of spike 160. In the embodiment shown, for example, the outer surface of the cassette, spike cap and most of the base 160*c* of spike 160 can be sterilized by exposing the cassette externally to ethylene oxide gas. Because the diameter of the stepped feature 160*b* and the distal end of spike 160 are smaller than the inner diameter of the overlying portion of spike cap 64, any gas or fluid entering the spike lumen from within the cassette can reach the outer surface of spike 160 up to the sealing rib 68. Thus any sterilizing gas such as ethylene oxide entering the fluid passages of the cassette may reach the remainder of the external surface of spike 160. In an embodiment, the gas may enter the cassette through a vented cap, for example, on the end of patient line 34 or drain line 28.

The spike cap 34 may include 3 or more centering ribs 64D that contact the end of the spike 160. The ribs 64D are oriented along the major access of spike cap 34 and located near the closed end of the spike cap 34. Preferably there are at least three ribs 63D to center the closed end of the cap on the spike without over constraining the cap/spike orientation. The spike cap 64 includes a tapered end with a blunt tip to facilitate the penetration of the spike cap 34 into the hole 31*b* of the solution cap 31. The tapered end will guide the spike cap 34 if it misaligned with the hole 31*b*. The blunt tip avoids snagging the solution cap 31 unlike a sharp tip that might catch the inside edge of the hole 31*b* and dig into the solution cap material. In contrast a blunt tip can slide past the edges of the hole 31*b*.

Figure 36:
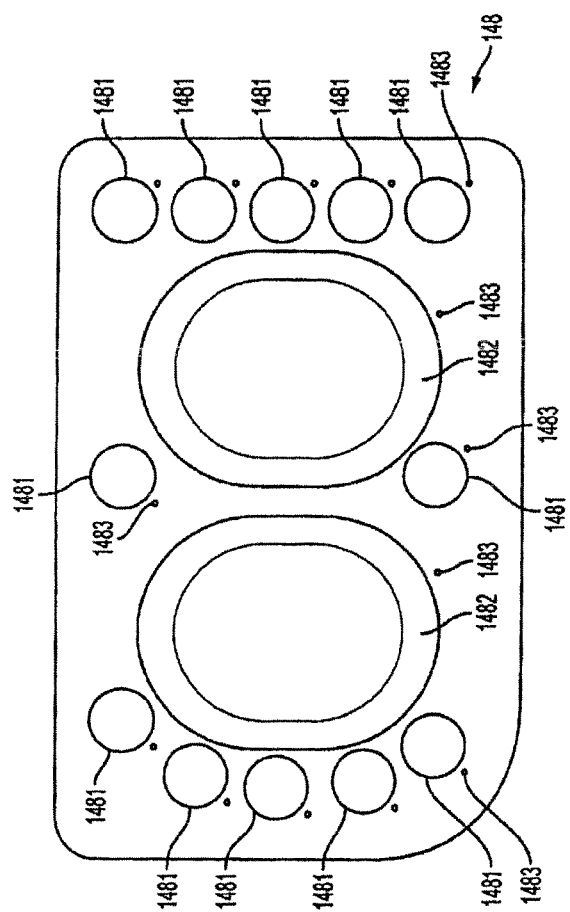
FIG. 36 shows a front view of a control surface of the cycler for interaction with a cassette in the FIG. 10 embodiment.

Once the cassette 24 and lines 30 are loaded into the cycler 14, the cycler 14 must control the operation of the cassette 24 to move fluid from the solution lines 30 to the heater bag 22 and to the patient. FIG. 36 shows a plan view of the control surface 148 of the cycler 14 that interacts with the pump chamber side of the cassette 24 (e.g., shown in FIG. 6) to cause fluid pumping and flowpath control in the cassette 24. When at rest, the control surface 148, which may be described as a type of gasket, and comprise a sheet of silicone rubber, may be generally flat. Valve control regions 1481 may (or may not) be defined in the control surface 148, e.g., by a scoring, groove, rib or other feature in or on the sheet surface, and be arranged to be movable in a direction generally transverse to the plane of the sheet. By moving inwardly/outwardly, the valve control regions 1481 can move associated portions of the membrane 15 on the cassette 24 so as to open and close respective valve ports 184, 186, 190 and 192 of the cassette 24, and thus control flow in the cassette 24. Two larger regions, pump control regions 1482, may likewise be movable so as to move associated shaped portions 151 of the membrane 15 that cooperate with the pump chambers 181. Like the shaped portions 151 of the membrane 15, the pump control regions 1482 may be shaped in a way to correspond to the shape of the pump chambers 181 when the control regions 1482 are extended into the pump chambers 181. In this way, the portion of the control sheet 148 at the pump control regions 1482 need not necessarily be stretched or otherwise resiliently deformed during pumping operation.

Each of the regions 1481 and 1482 may have an associated vacuum or evacuation port 1483 that may be used to remove all or substantially all of any air or other fluid that may be present between the membrane 15 of cassette 24, and the control surface 148 of cycler 14, e.g., after the cassette 24 is loaded into the cycler 14 and the door 141 closed. This may help ensure close contact of the membrane 15 with the control regions 1481 and 1482, and help control the delivery of desired volumes with pump operation and/or the open/closed state of the various valve ports. Note that the vacuum ports 1482 are formed in locations where the control surface 148 will not be pressed into contact with a wall or other relatively rigid feature of the cassette 24. For example, in accordance with one aspect of the invention, one or both of the pump chambers of the cassette may include a vacuum vent clearance region formed adjacent the pump chamber. In this illustrative embodiment as shown in FIGS. 3 and 6, the base member 18 may include vacuum vent port clearance or extension features 182 (e.g., recessed areas that are fluidly connected to the pump chambers) adjacent and outside the oval-shaped depressions forming the pump chambers 181 to allow the vacuum vent port 1483 for the pump control region 1482 to remove any air or fluid from between membrane 15 and control surface 148 (e.g., due to rupture of the membrane 15) without obstruction. The extension feature may also be located within the perimeter of pump chamber 181. However, locating vent port feature 182 outside the perimeter of pump chamber 181 may preserve more of the pumping chamber volume for pumping liquids, e.g., allows for the full footprint of pump chamber 181 to be used for pumping dialysate. Preferably, extension feature 182 is located in a vertically lower position in relation to pump chamber 181, so that any liquid that leaks between membrane 15 and control surface 148 is drawn out through vacuum port 1483 at the earliest opportunity. Similarly, vacuum ports 1483 associated with valves 1481 are preferably located in a vertically inferior position with respect to valves 1481.

FIG. 36A shows that control surface 148 may be constructed or molded to have a rounded transition between the base element 1480 of control surface 148 and its valve and pump control regions 1481, 1482. The junctions 1491 and 1492 may be molded with a small radius to transition from base element 1480 to valve control region 1481 and pump control region 1482, respectively. A rounded or smooth transition helps to prevent premature fatigue and fracture of the material comprising control surface 148, and may improve its longevity. In this embodiment, channels 1484 leading from vacuum ports 1483 to the pump control regions 1482 and valve control regions 1481 may need to be lengthened somewhat to accommodate the transition feature.

Figure 37:
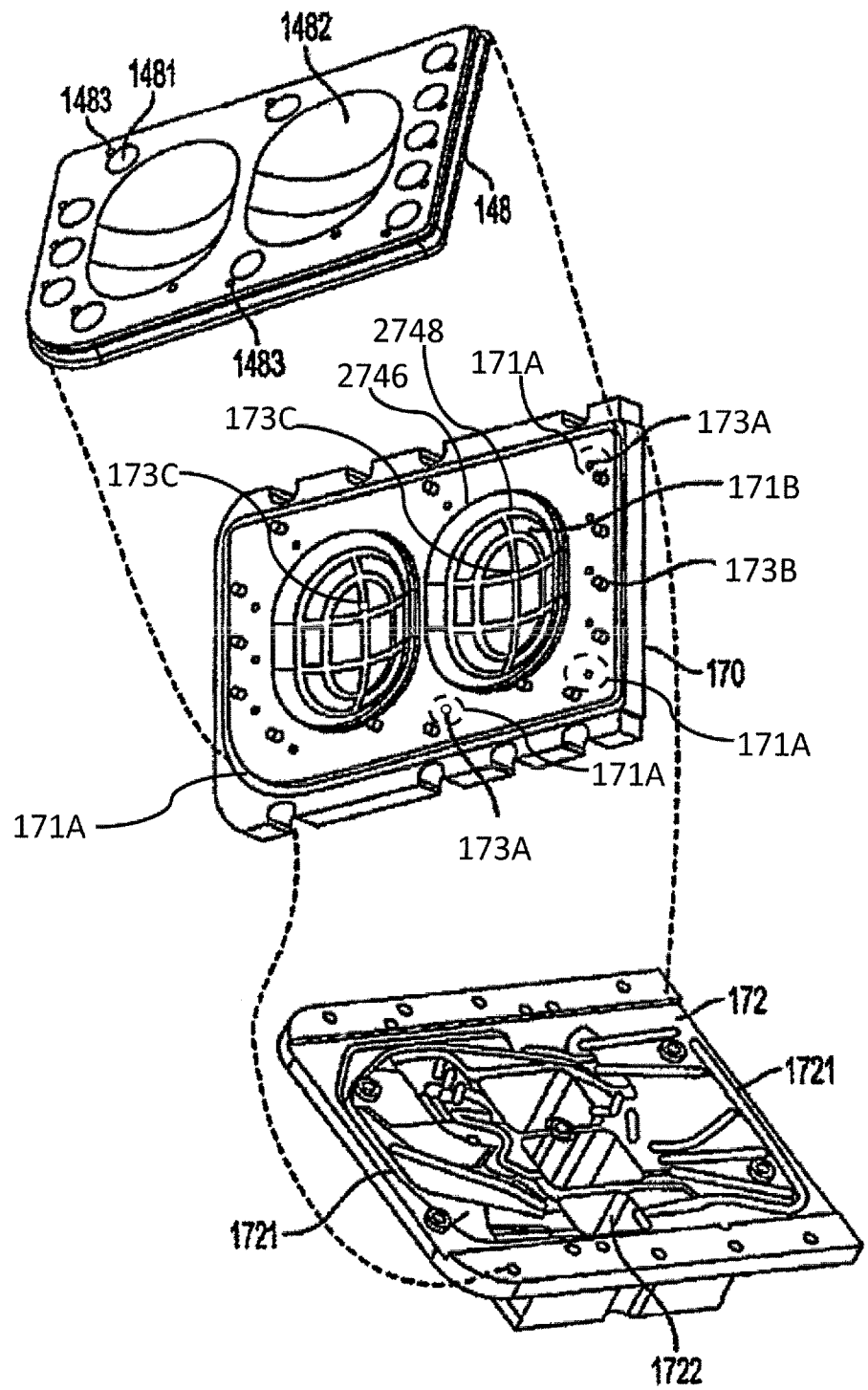
FIG. 37 shows an exploded view of an assembly for the interface surface of FIG. 36, with the mating pressure delivery block and pressure distribution module.

The control regions 1481 and 1482 may be moved by controlling a pneumatic pressure and/or volume on a side of the control surface 148 opposite the cassette 24, e.g., on a back side of the rubber sheet that forms the control surface 148. For example, as shown in FIG. 37, the control surface 148 may be backed by a mating or pressure delivery block 170 that includes control chambers or depressions 171A located in association with each control region 1481, and control chambers or depressions 171B, located in association with each control region 1482, and that are isolated from each other (or at least can be controlled independently of each other if desired). The surface of mating or pressure delivery block 170 forms a mating interface with cassette 24 when cassette 24 is pressed into operative association with control surface 148 backed by mating block 170. The control chambers or depressions of mating block 170 are thus coupled to complementary valve or pumping chambers of cassette 24, sandwiching control regions 1481 and 1482 of control surface 148 adjacent to mating block 170, and the associated regions of membrane 15 (such as shaped portion 151) adjacent to cassette 24. Air or other control fluid may be moved into or out of the control chambers or depressions 171A, 171B of mating block 170 for the regions 1481, 1482, thereby moving the control regions 1481, 1482 as desired to open/close valve ports of the cassette 24 and/or effect pumping action at the pump chambers 181. In one illustrative embodiment shown in FIG. 37, the control chambers 171A may be arranged as cylindrically-shaped regions backing each of the valve control regions 1481. The control chambers or depressions 171B may comprise ellipsoid, ovoid or hemi-spheroid voids or depressions backing the pump control regions 1482. Fluid control ports 173A may be provided for each control chamber 171A so that the cycler 14 can control the volume of fluid and/or the pressure of fluid in each of the valve control chambers 1481. Fluid control ports 173C may be provided for each control chamber 171B so that the cycler 14 can control the volume of fluid and/or the pressure of fluid in each of the volume control chambers 1482. For example, the mating block 170 may be mated with a manifold 172 that includes various ports, channels, openings, voids and/or other features that communicate with the control chambers 171 and allow suitable pneumatic pressure/vacuum to be applied to the control chambers 171. Although not shown, control of the pneumatic pressure/vacuum may be performed in any suitable way, such as through the use of controllable valves, pumps, pressure sensors, accumulators, and so on. Of course, it should be understood that the control regions 1481, 1482 may be moved in other ways, such as by gravity-based systems, hydraulic systems, and/or mechanical systems (such as by linear motors, etc.), or by a combination of systems including pneumatic, hydraulic, gravity-based and mechanical systems.

Figure 37A:
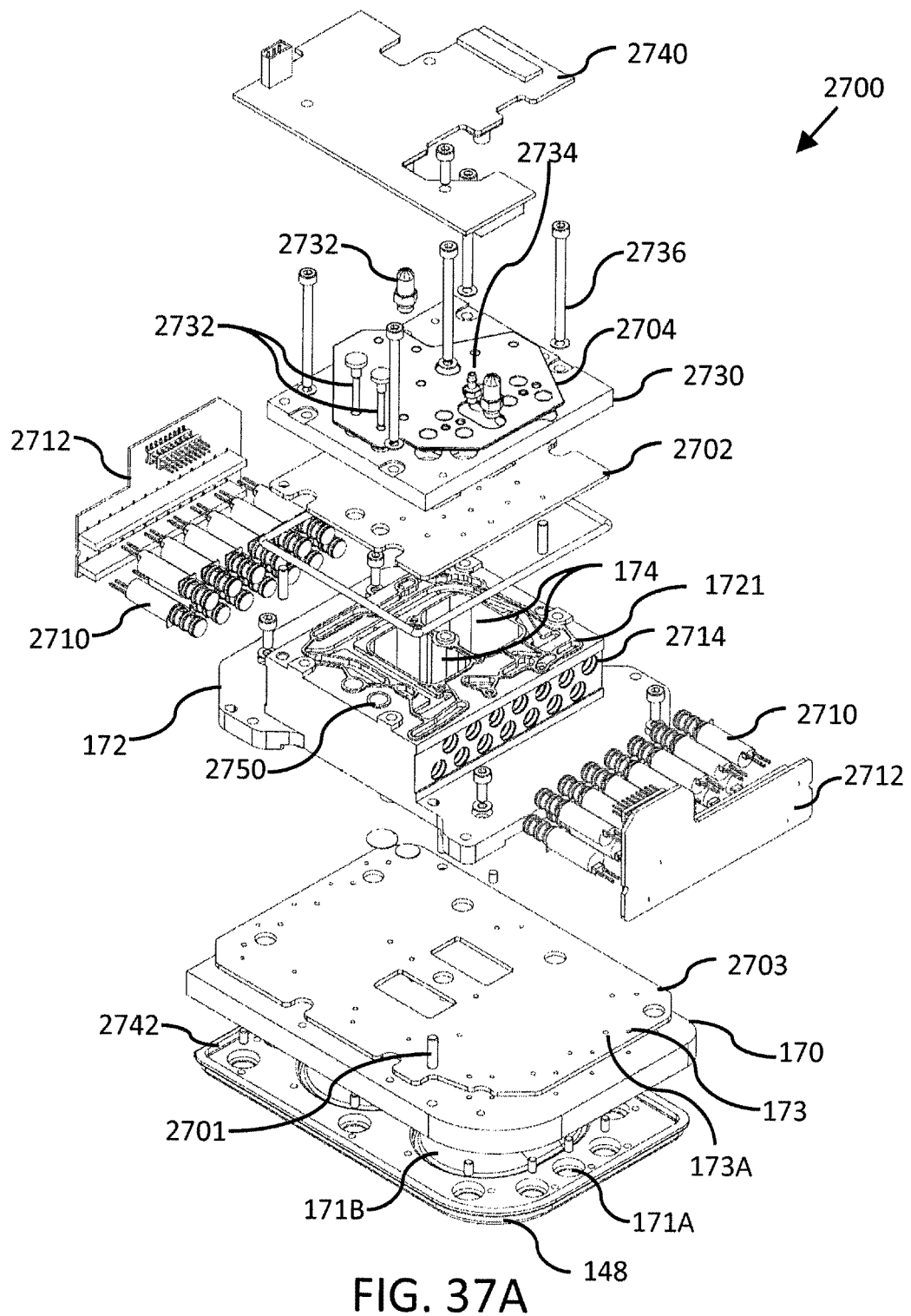
FIG. 37A shows an exploded view of the integrated manifold.
Figure 37B:
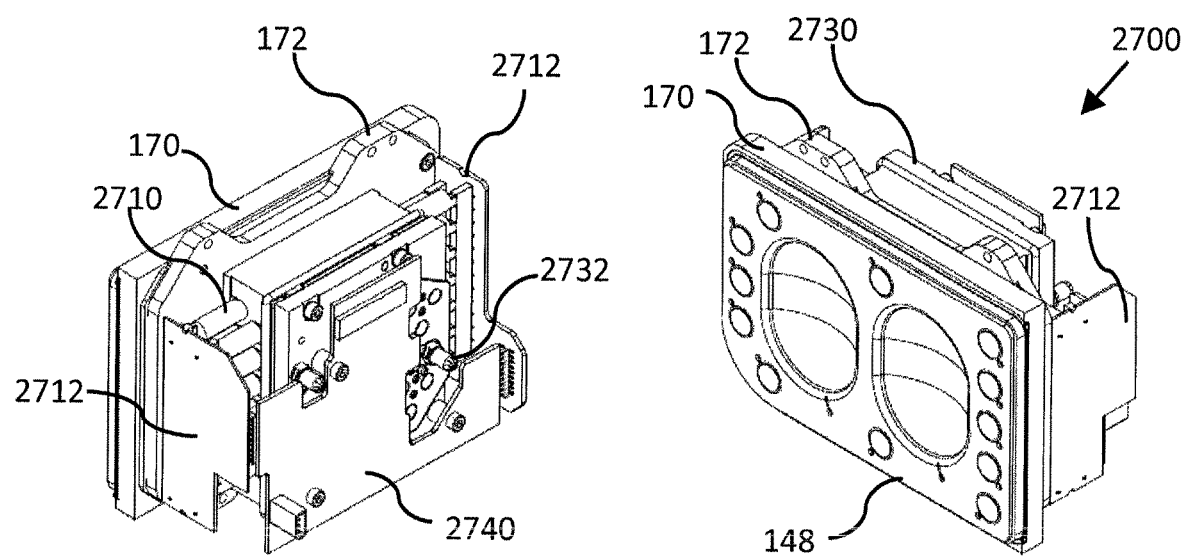
FIG. 37B shows two isometric views of the integrated manifold.

FIG. 37A shows an exploded view of an integrated pressure distribution module or assembly 2700 for use in a fluid flow control apparatus for operating a pumping cassette, and suitable for use as pressure distribution manifold 172 and mating block 170 of cycler 14. FIG. 37B shows a view of an integrated module 2700 comprising a pneumatic manifold or block, ports for supply pressures, pneumatic control valves, pressure sensors, a pressure delivery or mating block and a control surface or actuator that includes regions comprising flexible membranes for actuating pumps and valves on a pumping cassette. The integrated module 2700 may also include reference chambers within the pneumatic manifold for an FMS volume measurement process for determining the volume of fluid present in a pumping chamber of a pumping cassette. The integrated module may also comprise a vacuum port, and a set of pathways or channels from interfaces between the actuator and flexible pump and valve membranes of a pumping cassette to a fluid trap and liquid detection system. In some embodiments, the pneumatic manifold may be formed as a single block. In other embodiments, the pneumatic manifold may be formed from two or more manifold blocks mated together with gaskets positioned between the manifold blocks. The integrated module 2700 occupies a relatively small space in a fluid flow control apparatus, and eliminates the use of tubes or flexible conduits connecting the manifold ports with corresponding ports of a pressure delivery module or block mated to a pumping cassette. Among other possible advantages, the integrated module 2700 reduces the size and assembly cost of the pneumatic actuation assembly of a peritoneal dialysis cycler, which may result in a smaller and less expensive cycler. Additionally, the short distances between pressure or vacuum distribution ports on the pressure distribution manifold block and corresponding pressure or vacuum delivery ports on a mating pressure delivery block, together with the rigidity of the conduits connecting the ports, may improve the responsiveness of an attached pumping cassette and the accuracy of cassette pump volume measurement processes. When used in a peritoneal dialysis cycler 14, in an embodiment, an integrated module comprising a metallic pressure distribution manifold mated directly to a metallic pressure delivery block may also reduce any temperature differences between the control volume 171B and the reference chamber 174 of the cycler 14, which may improve the accuracy of the pump volume measurement process.

An exploded view of the integrated module 2700 is presented in FIG. 37A. The actuator surface, mounted on a mating block or pressure delivery block, is analogous or equivalent to the gasket or control surface 148, that includes flexible regions arranged to move back and forth to pump fluid and/or open and close valves by pushing or pulling on a membrane 15 of a pump cassette 24. With respect to cycler 14, the control surface 148 is actuated by the positive and negative pneumatic pressure supplied to the control volumes 171A, 171B behind the control regions 1481, 1482. The control surface 148 attaches to the pressure delivery block or mating block 170 by fitting tightly on a raised surface 2744 on the front surface of the mating block 170 with a lip 2742. The mating block 170 may include one or more surface depressions 2746 to align with and support the oval curved shape of one or more corresponding pump control surfaces 1482, forming a pump control chamber. A similar arrangement, with or without a surface depression, may be included in forming a valve control region 171A to align with a corresponding control surface 1481 for controlling one or more valves of a pumping cassette. The mating block 170 may further include grooves 2748 on the surface of depression 2746 of mating block 170 behind the pump control surface 1482 to facilitate the flow of control fluid or gas from the port 173C to the entire back surface the pump control surface 1482. Alternatively, rather than having grooves 2748, the depression 2746 may be formed with a roughened surface or a tangentially porous surface.

The mating block 170 connects the pressure distribution manifold 172 to the control surface 148, and delivers pressure or vacuum to various control regions on control surface 148. The mating block 170 may also be referred to as a pressure delivery block in that it provides pneumatic conduits to supply pressure and vacuum to the valve control regions 1481 and the pump control regions 1482, vacuum to the vacuum ports 1483 and connections from the pump control volumes 171B to the pressure sensors. The ports 173A connect the valve control volumes 171A to the pressure distribution manifold 172. The ports 173C connect the pump control volume 171B to the pressure distribution manifold 172. The vacuum ports 1483 are connected to the pressure distribution manifold 172 via ports 173B. In one embodiment, the ports 173B extend above the surface of the pressure delivery block 170 to pass through the control surface 148 to provide vacuum at port 1483 without pulling the control surface 148 onto the port 173B and blocking flow.

The pressure delivery block 170 is attached to the front face of the pressure distribution manifold 172. The ports 173A, 173B, 173C line up with pneumatic circuits on the pressure distribution manifold 172 that connect to valve ports 2714. In one example, the pressure delivery block 170 is mated to the pressure distribution manifold 172 with a front flat gasket 2703 clamped between them. The block 170 and manifold 172 are held together mechanically, which in an embodiment is through the use of bolts 2736 or other types of fasteners. In another example, rather than a flat gasket 2703, compliant elements are placed in or molded in either the pressure delivery block 170 or the pressure distribution manifold 172. Alternatively, the pressure delivery block 170 may be bonded to the pressure distribution manifold 172 by an adhesive, double sided tape, friction welding, laser welding, or other bonding method. The block 170 and manifold 172 may be formed of metal or plastic and the bonding methods will vary depending on the material.

The pressure distribution manifold 172 contains ports for the pneumatic valves 2710, reference chambers 174, a fluid trap 1722 and pneumatic circuitry or of the integrated module 2700. connections provides pneumatic connections between the pressure reservoirs, valves, and contains ports 2714 that receive multiple cartridge valves 2710. The cartridge valves 2710 includes but is not limited to the binary valves 2660 controlling flow to valve control volumes 171A, the binary valves X1A, X1B, X2, X3 controlling flow to pump control volumes 171B, and the binary valves 2661-2667 controlling flow to the bladders 2630, 2640, 2650 and pressure reservoirs 2610, 2620. The cartridge valves 2710 are pressed into the valve ports 2714 and electrically connected to the hardware interface 310 via circuit board 2712.

The pneumatic circuitry in the pressure distribution manifold 172 may be formed with a combination of grooves or slots 1721 on the front and back faces and approximately perpendicular holes that connect the grooves 1721 on one face to valve ports 2714, the fluid trap 1722 and to grooves and ports on the opposite face. Some grooves 1721 may connect directly to the reference chambers 174. A single perpendicular hole may connect a groove 1721 to multiple valve ports 174 that are closely spaced and staggered. Sealed pneumatic conduits are formed when the grooves 1721 are isolated from one another by in one example the front flat gasket 2703 as shown in FIG. 37A.

The presence of liquid in the fluid trap 1722 may be detected by a pair of conductivity probes 2732. The conductivity probes 2732 slide through a back gasket 2704, a back plate 2730 and holes 2750 before entering the fluid trap 1722 in the pressure distribution manifold 172.

The back plate 2730 seals the reference volumes 174, the grooves 1721 on the back face of the pressure distribution manifold 172 and provides ports for the pressure sensors 2740 and ports for pressure and vacuum lines 2734 and vents to the atmosphere 2732. In one example, the pressure sensors may be IC chips soldered to a single board 2740 and pressed as a group against the back gasket 2704 on the back plate 2730. In one example, bolts 2736 clamp the back plate 2730, pressure distribution manifold 172 and pressure delivery block 170 together with gaskets 2703, 2702 between them. In another example, the back plate 2730 may be bonded to the pressure delivery manifold 172 as described above. The assembled integrated module 2700 is presented in FIG. 37C.

Figure 37C:
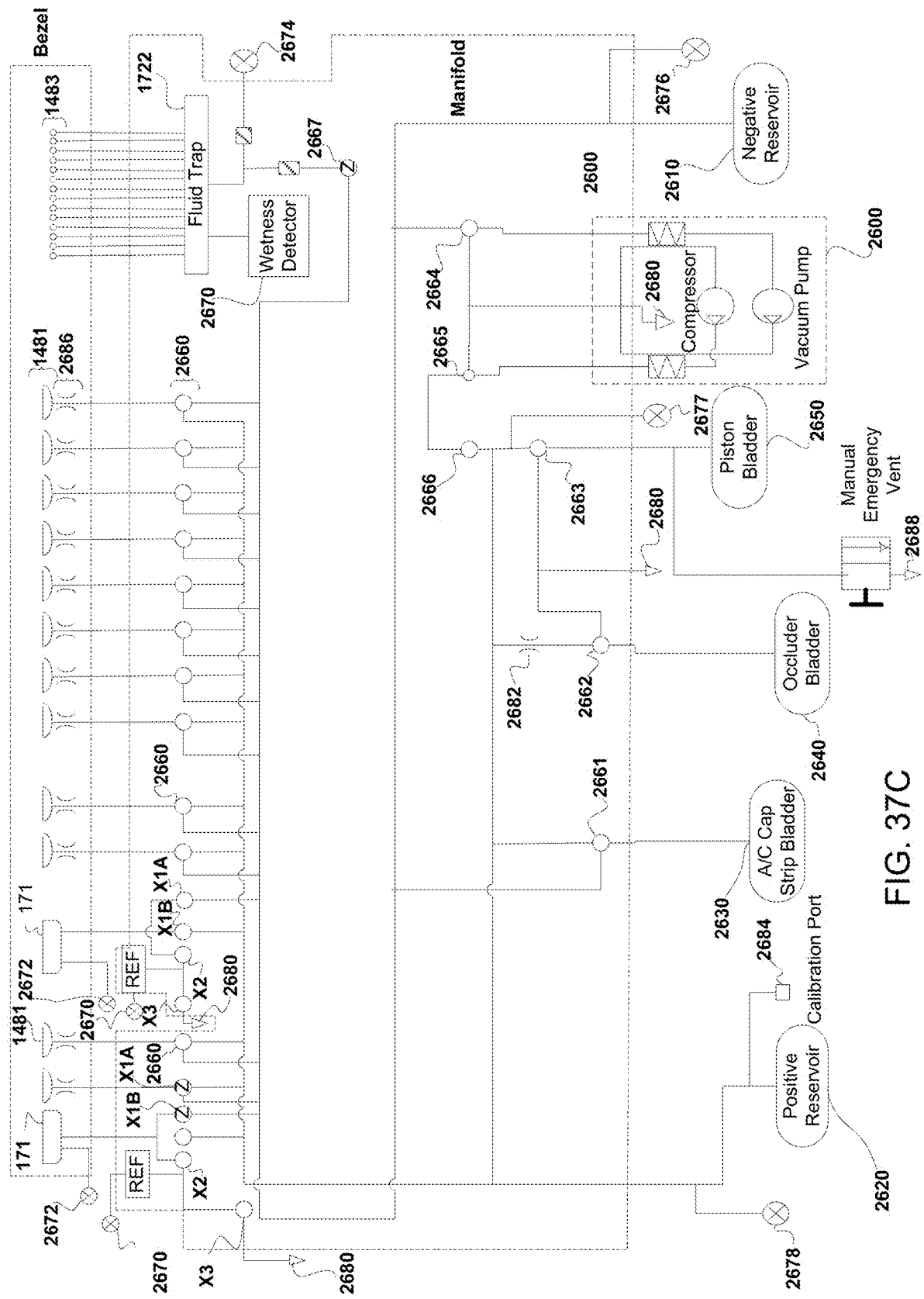
FIG. 37C shows an schematic of the pneumatic system that controls fluid flow through the cycler.

FIG. 37C presents a schematic of the pneumatic circuit in the integrated manifold 2700 and pneumatic elements outside the manifold. The pump 2600 produces vacuum and pressure. The pump 2600 is connected via 3 way valves 2664 and 2665 to a vent 2680 and the negative or vacuum reservoir 2610 and the positive reservoir 2620. The pressure in the positive and negative reservoirs 2620, 2610 are measure respectively by pressure sensors 2678, 2676. The hardware interface 310 controls the speed of the pump 2600 and the position of 3-way valves 2664, 2665, 2666 to control the pressure in each reservoir. The autoconnect stripper element bladder 2630 is connected via 3-way valve 2661 to either the positive pressure line 2622 or the negative or vacuum line 2612. The automation computer 300 commands the position of valve 2661 to control the location of the stripper element 1461. The occluder bladder 2640 and piston bladder 2650 are connected via 3-way valves 2662 and 2663 to either the pressure line 2622 or vent 2680. The automation computer 300 commands valve 2663 to connect the piston bladder to the pressure line 2622 after the door 141 is closed to securely engage the cassette 24 against the control surface 148. The occluder bladder 2640 is connected to the pressure line 2622 via valve 2662 and restriction 2682. The occluder bladder 2640 is connected to the vent 2680 via valve 2662. The orifice 2682 advantageously slows the filling of the occluder bladder 2640 that retracts the occluder 147 in order to maintain the pressure in the pressure line 2622. The high pressure in the pressure line 2622 keeps the various valve control surfaces 171A and the piston bladder actuated against the cassette 24, which prevents flow to or from the patient as the occluder 147 opens. Conversely the connection from the occluder bladder 2640 to the vent 2680 is unrestricted, so that occluder 147 can quickly close.

The valve control surfaces 1481 are controlled by the pressure in the valve control volume 171A, which in turn is controlled by the position of the 3-way valves 2660. The valves 2660 can be controlled individually via commands from the automation computer 300 passed to the hardware interface 310. The valves controlling the pumping pressures in the pump control volumes 171B are controlled with 2-way valves X1A, X1B. The valves X1A, X1B in one example may be controlled by the hardware interface 310 to achieve a pressure commanded by the automation computer 300. The pressure in each pump control chamber 171B is measured by sensors 2672. The pressure in the reference chambers is measured by sensors 2670. The 2-way valves X2, X3 respectively connect the reference chamber 174 to the pump control chamber 171B and the vent 2680.

The fluid trap 2622 is to the vacuum line 2612 during operation as explained elsewhere in this application. The fluid trap is connected by several lines to the ports 173B in the pressure delivery block 170. The pressure in the fluid trap is monitored by pressure sensor 2674 that is mounted on the back plate 2730.

The vacuum ports 1483 may be employed to separate the membrane 15 from the control surface 148 at the end of therapy before or during the opening the door. The vacuum provided by the negative pressure source to the vacuum ports 1483 sealingly engages the membrane 15 to the control surface 148 during therapy. In some instances a substantial amount of force may be needed to separate the control surface from the cassette membrane 15, preventing the door 141 from freely rotating into the open position, even when the application of vacuum is discontinued. Thus, in an embodiment, the pressure distribution module 2700 is configured to provide a valved channel between the positive pressure source and the vacuum ports 1483. Supplying positive pressure at the vacuum ports may aid in separating the membrane 15 from the control surface 148, thereby allowing the cassette 24 to separate more easily from the control surface 148 and allow the door 141 to open freely. The pneumatic valves in the cycler may be controlled by the automation computer 300 to provide a positive pressure to the vacuum ports 1483. The manifold 172 may include a separately valved channel dedicated for this purpose, or alternatively it may employ the existing channel configurations and valves, operated in a particular sequence.

In one example the vacuum ports 1483 may be supplied with positive pressure by temporarily connecting the vacuum ports 1483 to the positive pressure reservoir 2620. The vacuum ports 1483 are normally connected to the vacuum reservoir 2610 via a common fluid collection chamber or Fluid Trap 1722 in the manifold 172 during therapy. In one example, the controller or automation computer may open valve X1B between the positive pressure reservoir and the volume control chamber 171B and the valve X1A between the negative pressure reservoir and the same volume control chamber 171B simultaneously, which will pressurize the air in the Fluid Trap 1722 and the vacuum ports 1483. The pressurized air will flow through the vacuum ports 1483 and between the membrane 15 and the control surface 148, breaking any vacuum bond between the membrane and control surface. However, in the illustrated manifold, the stripper element 1491 of the cap stripper 149 may extend while the positive pressure is supplied to common fluid collection chamber 1722 fluid, because the stripper bladder 2630 is connected to a the vacuum supply line 2612. In this example, in a subsequent step, the fluid trap 1722 may be valved off from the now-pressurized vacuum line and the two valves X1A, X1B connecting the positive and vacuum reservoirs to the volume control chamber 171B may be closed. The vacuum pump 2600 is then operated to reduce the pressure in the vacuum reservoir 2610 and the vacuum supply line 2612, which in turn allows the stripper element 1491 to be withdrawn. The door 141 may then be opened after detaching the cassette 24 from the control surface 148 and retracting the stripper element 1491.

In accordance with an aspect of the invention, the vacuum ports 1483 may be used to detect leaks in the membrane 15, e.g., a liquid sensor in a conduit or chamber connected to a vacuum port 1483 may detect liquid if the membrane 15 is perforated or liquid otherwise is introduced between the membrane 15 and the control surface 148. For example, vacuum ports 1483 may align with and be sealingly associated with complementary vacuum ports 173B in mating block 170, which in turn may be sealingly associated with fluid passages 1721 leading to a common fluid collection chamber 1722 in manifold 172. The fluid collection chamber 1722 may contain an inlet through which vacuum can be applied and distributed to all vacuum ports 1483 of control surface 148. By applying vacuum to the fluid collection chamber 1722, fluid may be drawn from each of the vacuum ports 173B and 1483, thus removing fluid from any space between the membrane 15 and the control surface 148 at the various control regions. However, if there is liquid present at one or more of the regions, the associated vacuum port 1483 may draw the liquid into the vacuum ports 173B and into the lines 1721 leading to the fluid collection chamber 1722. Any such liquid may collect in the fluid collection chamber 1722, and be detected by one or more suitable sensors, e.g., a pair of conductivity sensors that detect a change in conductivity in the chamber 1722 indicating the presence of liquid. In this embodiment, the sensors may be located at a bottom side of the fluid collection chamber 1722, while a vacuum source connects to the chamber 1722 at an upper end of the chamber 1722. Therefore, if liquid is drawn into the fluid collection chamber 1722, the liquid may be detected before the liquid level reaches the vacuum source. Optionally, a hydrophobic filter, valve or other component may be place at the vacuum source connection point into the chamber 1722 to help further resist the entry of liquid into the vacuum source. In this way, a liquid leak may be detected and acted upon by controller 16 (e.g., generating an alert, closing liquid inlet valves and ceasing pumping operations) before the vacuum source valve is placed at risk of being contaminated by the liquid.

In one embodiment, the inner wall of the control chambers 171B can include raised elements somewhat analogous to the spacer elements 50 of the pump chamber, e.g., as shown in FIG. 37 for the control chambers 171B associated with the pump control regions 1482. These raised elements can take the form of plateau features, ribs, or other protrusions that keep the control ports recessed away from the fully retracted control regions 1482. This arrangement may allow for a more uniform distribution of pressure or vacuum in the control chamber 171B, and prevent premature blocking of any control port by the control surface 148. A pre-formed control surface 148 (at least in the pump control regions) may not be under a significant stretching force when fully extended against either the inner wall of the pump chamber of the cassette 24 during a delivery stroke, or the inner wall of the control chamber 171 during a fill stroke. It may therefore be possible for the control region 1482 to extend asymmetrically into the control chamber 171B, causing the control region 1482 to prematurely close off one or more ports of the control chamber before the chamber is fully evacuated. Having features on the inner surface of the control chamber 171B that prevent contact between the control region 1482 and the control ports may help to assure that the control region 1482 can make uniform contact with the control chamber inner wall during a fill stroke.

As suggested above, the cycler 14 may include a control system 16 with a data processor in electrical communication with the various valves, pressure sensors, motors, etc., of the system and is preferably configured to control such components according to a desired operating sequence or protocol. The control system 16 may include appropriate circuitry, programming, computer memory, electrical connections, and/or other components to perform a specified task. The system may include pumps, tanks, manifolds, valves or other components to generate desired air or other fluid pressure (whether positive pressure—above atmospheric pressure or some other reference—or negative pressure or vacuum—below atmospheric pressure or some other reference) to control operation of the regions of the control surface 148, and other pneumatically-operated components. Further details regarding the control system 16 (or at least portions of it) are provided below.

In one illustrative embodiment, the pressure in the pump control chambers 171B may be controlled by a binary valve, e.g., which opens to expose the control chamber 171 to a suitable pressure/vacuum and closes to cut off the pressure/vacuum source. The binary valve may be controlled using a saw tooth-shaped control signal which may be modulated to control pressure in the pump control chamber 171B. For example, during a pump delivery stroke (i.e., in which positive pressure is introduced into the pump control chamber 171B to move the membrane 15/control surface 148 and force liquid out of the pump chamber 181), the binary valve may be driven by the saw tooth signal so as to open and close at a relatively rapid rate to establish a suitable pressure in the control chamber 171B (e.g., a pressure between about 70-90 mmHg). If the pressure in the control chamber 171B rises above about 90 mmHg, the saw tooth signal may be adjusted to close the binary valve for a more extended period. If the pressure drops below about 70 mmHg in the control chamber 171B, the saw tooth control signal may again be applied to the binary valve to raise the pressure in the control chamber 171. Thus, during a typical pump operation, the binary valve will be opened and closed multiple times, and may be closed for one or more extended periods, so that the pressure at which the liquid is forced from the pump chamber 181 is maintained at a desired level or range (e.g., about 70-90 mmHg).

In some embodiments and in accordance with an aspect of the invention, it may be useful to detect an "end of stroke" of the membrane 15/pump control region 1482, e.g., when the membrane 15 contacts the spacers 50 in the pump chamber 181 or the pump control region 1482 contacts the wall of the pump control chamber 171B. For example, during a pumping operation, detection of the "end of stroke" may indicate that the membrane 15/pump control region 1482 movement should be reversed to initiate a new pump cycle (to fill the pump chamber 181 or drive fluid from the pump chamber 181). In one illustrative embodiment in which the pressure in the control chamber 171B for a pump is controlled by a binary valve driven by a saw tooth control signal, the pressure in the pump chamber 181 will fluctuate at a relatively high frequency, e.g., a frequency at or near the frequency at which the binary valve is opened and closed. A pressure sensor in the control chamber 171B may detect this fluctuation, which generally has a higher amplitude when the membrane 15/pump control region 1482 are not in contact with the inner wall of the pump chamber 181 or the wall of the pump control chamber 171B. However, once the membrane 15/pump control region 1482 contacts the inner wall of the pump chamber 181 or the wall of the pump control chamber 171B (i.e., the "end of stroke"), the pressure fluctuation is generally damped or otherwise changes in a way that is detectable by the pressure sensor in the pump control chamber 171B. This change in pressure fluctuation can be used to identify the end of stroke, and the pump and other components of the cassette 24 and/or cycler 14 may be controlled accordingly.

Figure 66:
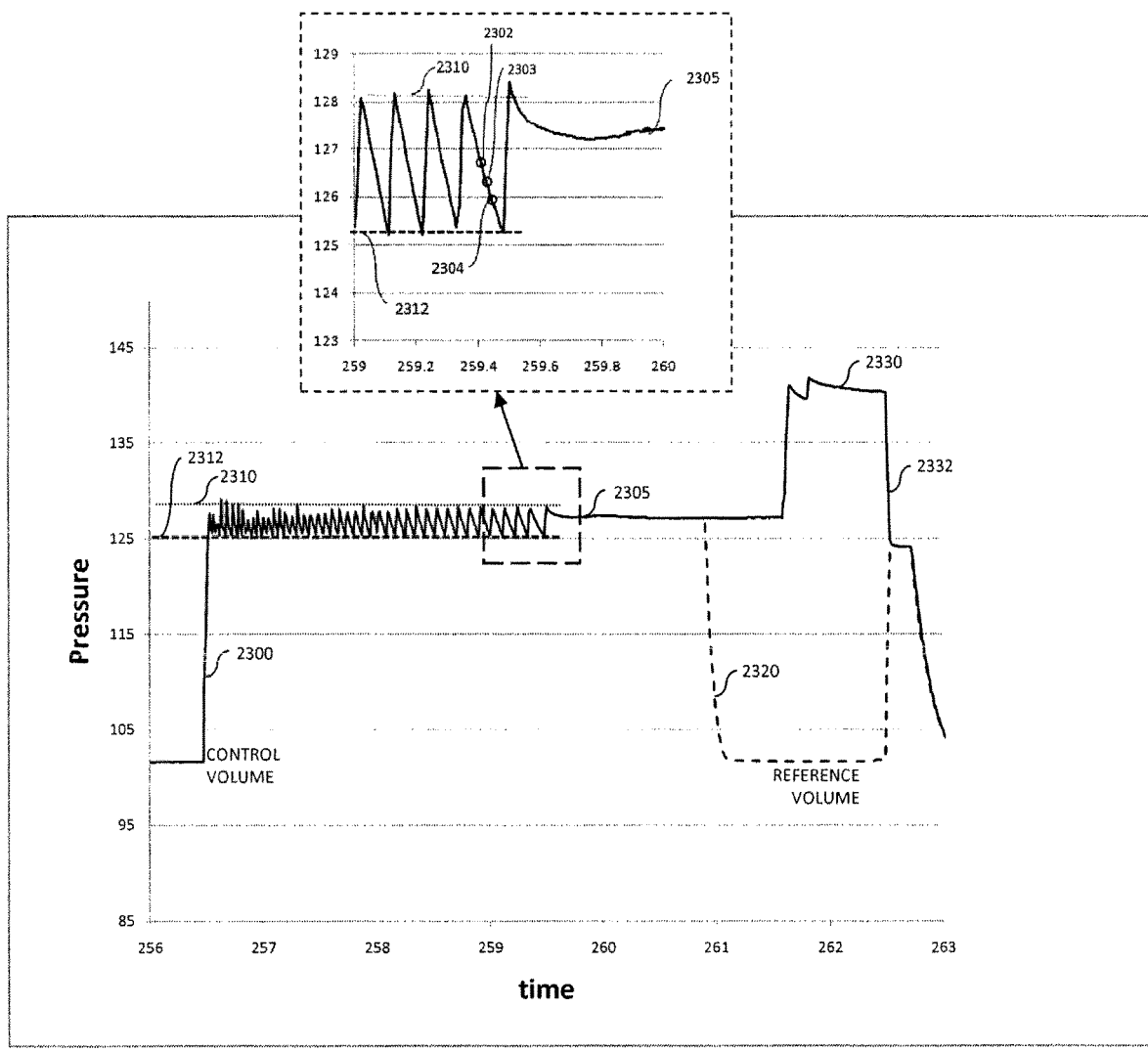
FIG. 66 shows an exemplary pressure tracing from a control or actuation chamber of a pumping cassette during a liquid delivery stroke.

In one embodiment, the pneumatic pressure applied to the control chamber 171B is actively controlled by a processor receiving a signal from a pressure transducer 2672 (FIG. 37C) connected to the control chamber 171B and a fast acting binary valve X1A, X1B between a pressure reservoir 2620, 2610 and the control chamber 171B. The processor may control the pressure with a variety of control algorithms including closed loop proportional or proportional-integrator feedback control that varies the valve duty cycle to achieve the desired pressure in the control volume 171B. In a one embodiment, the processor controls the pressure in the control chamber with an on-off controller often called a bang-bang controller. The on-off controller monitors the pressure in the control volume 171B during a deliver stroke and open the binary valve X1B (connecting the control volume 171B to the positive reservoir 2620) when the pressure is less than a lower first limit and closes the binary valve X1B when the pressure is above a higher second limit. During a fill stroke, the on-off controller opens the binary valve X1A (connecting the control volume 171B to the negative reservoir 2610) when the pressure is greater than a third limit and closes the binary valve X1A when the pressure is less than a forth limit, where the forth limit is lower than the third limit and both the third and forth limits are less than the first limit. A plot of the pressure over time as during a deliver stroke and the subsequent FMS measurement is shown in FIG. 66. The control chamber pressure 2300 oscillates between the lower first limit 2312 and the higher second limit 2310 as the membrane 15 moves across the control chamber 171B. The pressure stops oscillating between the limits when the membrane 15 stops moving. The membrane 15 typically stops moving when it contacts either the stadium steps 50 of the cassette or it contacts the control chamber surface 171B. The membrane 15 may also stop moving if the outlet fluid line is occluded.

The automation computer 300 detects the end of stroke by evaluating the pressure signals. There are many possible algorithms to detect the end of pressure oscillation that indicate the end-of-stroke (EOS). The algorithms and methods to detect EOS in the section labeled "Detailed Description of the system and Method of Measuring Change Fluid Flow Rate" in U.S. Pat. No. 6,520,747 and the section describing the filtering to detect end of stroke in U.S. Pat. No. 8,292,594 are herein incorporated by reference.

One example of an algorithm to detect EOS, the AC 300 evaluates the time between the pressure crossing the first and second limits during a deliver stroke or third and fourth limits during a fill stroke. The on-off controller opens and closes the valves X1A, X1B in response to the pressure oscillating between the two limits as the control chamber volume changes during the fill or deliver stroke. When the membrane 15 stops moving at the end-of-stroke, the pressure changes will significantly diminish so that the pressure no longer exceeds one or both limits. The AC 300 may detect EOS by measuring the time between the pressure exceeding alternating limits. If the time since pressure cross the last limit exceeds a predefined threshold, then the AC 300 may declare an EOS. The algorithm may further include an initial period during which the AC 300 does not measure the time between limit crossings.

In another example algorithm, the AC 300 evaluates the derivative of the pressure signal with respect to time. The AC 300 may declare an EOS, if the derivative remains below a minimum threshold for a minimum length of time. In a further example, the minimum threshold is the average of the absolute value of the average pressure derivative during the stroke. The algorithm calculates the slope (derivative wrt time) of a curve fit to a set of data points, where the data points are taken from a moving window. The absolute value of each slope is then averaged over the stroke to calculate the absolute a value of the average pressure derivative. In another example of an EOS algorithm, the AC 300 may not include the pressure data until after an initial delay. The AC 300 ignores the initial pressure data to avoid false EOS detections due to irregular pressure traces that occasionally occur during the early part of the stroke. In another example, the AC 300 declares an EOS only after the second derivative of the pressure in the later part of the stroke has remained below a threshold for a minimum time and a wait period of time has past.

The criteria to declare an EOS may be optimized for different pumping conditions. The optimized EOS detection conditions include the second pressure derivative threshold, the minimum time to remain below the second derivative threshold, the duration of the initial delay and a length of the wait period. These EOS detection criteria may be optimized differently, for example, the fill stroke from the bags 20, 22, the deliver stroke to the patient, the fill stroke from the patient, and the deliver stroke to the bags 20, 22. Alternatively each EOS detection criteria may be a function of the pumping pressure in the control chamber 171B.

Occluder

In one aspect of the invention, an occluder for opening/closing one or more flexible lines may include a pair of opposed occluding members, which may be configured as resilient elements, such as flat plates made of a spring steel (e.g., leaf springs), having a force actuator configured to apply a force to one or both of the occluding members to operate the occluder. In certain embodiments, the force actuator may comprise an expandable or enlargable member positioned between the resilient elements. With the expandable member in a reduced size condition, the resilient elements may be in a flat or nearly flat condition and urge a pinch head to engage with one or more lines so as to pinch the lines closed. However, when the expandable member urges the resilient elements apart, the resilient elements may bend and withdraw the pinch head, releasing the lines and allowing flow through the lines. In other embodiments, the occluding members could be essentially rigid with respect to the levels of force applied by the force actuator. In certain embodiments, the force actuator may apply a force to one or both opposed occluding members to increase the distance between the occluding members in at least a portion of the region where they are opposed to effect opening or closing of the flexible tubing.

Figure 38:
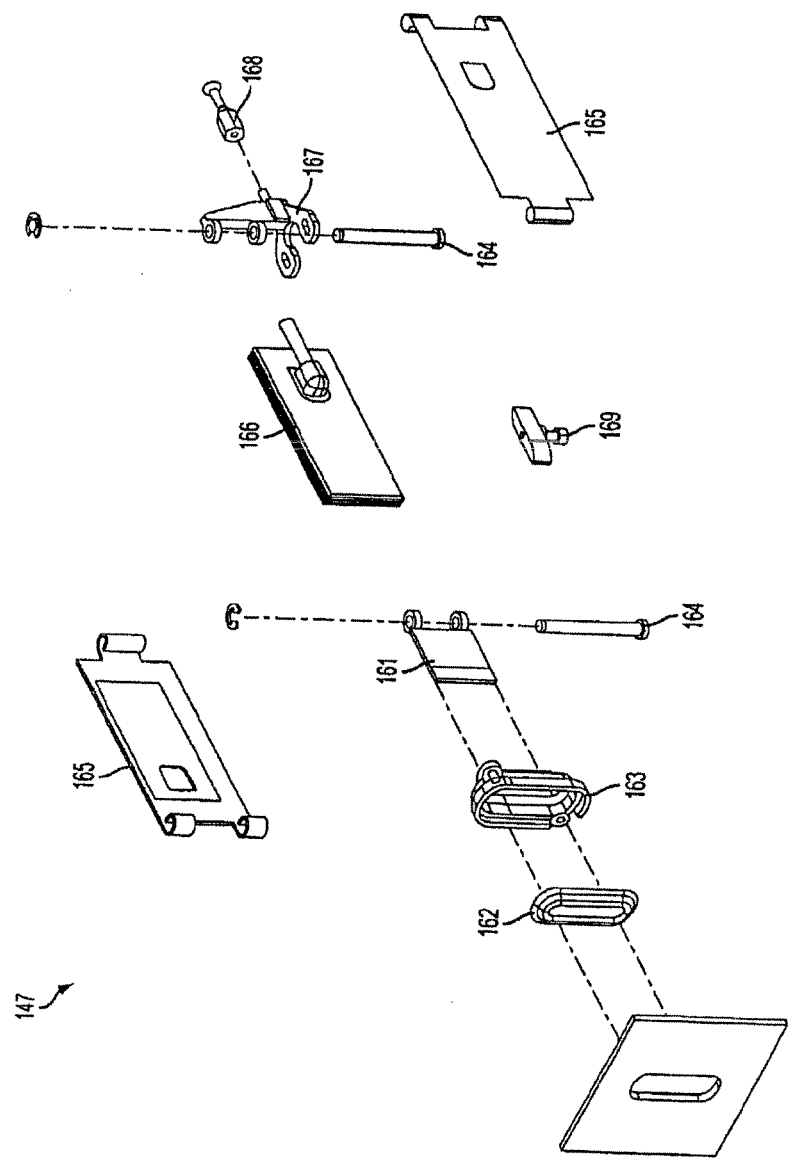
FIG. 38 shows an exploded perspective view of an occluder in an illustrative embodiment.
Figure 39:
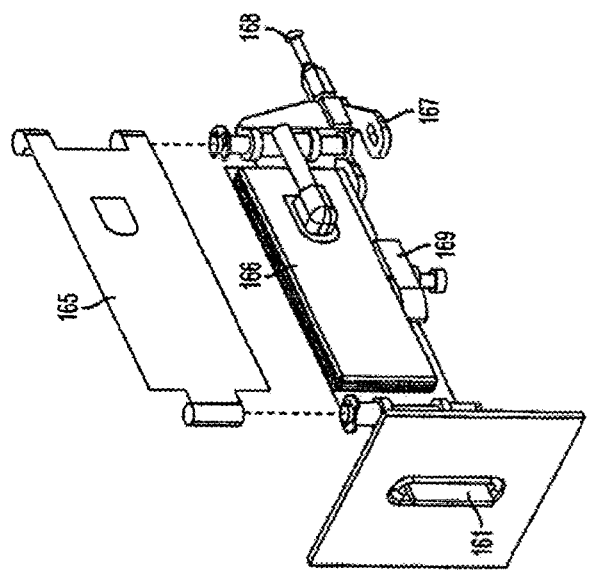
FIG. 39 shows a partially exploded perspective view of the occluder of FIG. 38.

FIG. 38 shows an exploded view and FIG. 39 shows a partially assembled view of an illustrative embodiment of an occluder 147 that may be used to close, or occlude, the patient and drain lines 34 and 28, and/or other lines in the cycler 14 or the set 12 (such as, for example, the heater bag line 26). The occluder 147 includes an optional pinch head 161, e.g., a generally flat blade-like element that contacts the tubes to press the tubes against the door 141 and pinch the tubes closed. In other embodiments, the function of the pinch head could be replaced by an extending edge of one or both of occluding members 165. The pinch head 161 includes a gasket 162, such as an O-ring or other member, that cooperates with the pinch head 161 to help resist entry of fluid (air or liquid for example) into the cycler 14 housing, e.g., in case of leakage in one of the occluded lines. The bellows gasket 162 is mounted to, and pinch head 161 passes through, a pinch head guide 163 that is mounted to the front panel of the cycler housing, i.e., the panel exposed by opening the door 141. The pinch head guide 163 allows the pinch head 161 to move in and out of the pinch head guide 163 without binding and/or substantial resistance to sliding motion of the pinch head 161. A pivot shaft 164 attaches a pair of opposed occluder members, comprising in the illustrated embodiment spring plates 165, that each include a hook-shaped pivot shaft bearing, e.g., like that found on standard door hinges, to the pinch head 161. That is, the openings of shaft guides on the pinch head 161, and the openings formed by the hook-shaped bearings on the spring plates 165 are aligned with each other and the pivot shaft 164 is inserted through the openings so the pinch head 161 and the spring plates 165 are pivotally connected together. The spring plates 165 may be made of any suitable material, such as steel, and may be arranged to be generally flat when unstressed. The opposite end of the spring plates 165 includes similar hook-shaped bearings, which are pivotally connected to a linear adjustor 167 by a second pivot shaft 164. In this embodiment, the force actuator comprises a bladder 166 is positioned between the spring plates 165 and arranged so that when fluid (e.g., air under pressure) is introduced into the bladder, the bladder may expand and push the spring plates 165 away from each other in a region between the pivot shafts 164. The bladder 166 may be attached to one or both spring plates 165 by pressure sensitive adhesive (PSA) tape. A linear adjustor 167 is fixed to the cycler housing 82 while the pinch head 161 is allowed to float, although its movement is guided by the pinch head guide 163. The linear adjustor 167 includes slot holes at its lower end, allowing the entire assembly to be adjusted in position and thus permitting the pinch head to be appropriately positioned when the occluder 147 is installed in the cycler 14. A turnbuckle 168 or other arrangement may be used to help adjust the position of the linear adjustor 167 relative to the housing 82. That is, the pinch head 161 generally needs to be properly positioned so that with the spring plates 165 located near each other and the bladder 166 substantially emptied or at ambient pressure, the pinch head 161 suitably presses on the patient and drain lines so as to pinch the tubes closed to flow without cutting, kinking or otherwise damaging the tubes. The slot openings in the linear adjustor 167 allows for this fine positioning and fixing of the occluder 147 in place. An override release device, such as provided by release blade 169 is optionally positioned between the spring plates 165, and as is discussed in more detail below, may be rotated so as to push the spring plates 165 apart, thereby withdrawing the pinch head 161 into the pinch head guide 163. The release blade 169 may be manually operated, e.g., to disable the occluder 147 in case of power loss, bladder 166 failure or other circumstance.

Additional configurations and descriptions of certain components that may be instructive in constructing certain embodiments of the occluder are provided in U.S. Pat. No. 6,302,653. The spring plates 165 may be constructed from any material that is elastically resistant to bending forces and which has sufficient longitudinal stiffness (resistance to bending) to provide sufficient restoring force, in response to a bending displacement, to occlude a desired number of collapsible tubes. In the illustrated embodiment, each spring plate is essentially flat when unstressed and in the shape of a sheet or plate. In alternative embodiments utilizing one or more resilient occluding members (spring members), any occluding member(s) that is elastically resistant to bending forces and which has sufficient longitudinal stiffness (resistance to bending) to provide sufficient restoring force, in response to a bending displacement to occlude a desired number of collapsible tubes may be utilized. Potentially suitable spring members can have a wide variety of shapes as apparent to those of ordinary skill in the art, including, but not limited to cylindrical, prism-shaped, trapezoidal, square, or rectangular bars or beams, I-beams, elliptical beams, bowl-shaped surfaces, and others. Those of ordinary skill in the art can readily select proper materials and dimensions for spring plates 165 based on the present teachings and the requirements of a particular application.

Figure 40:
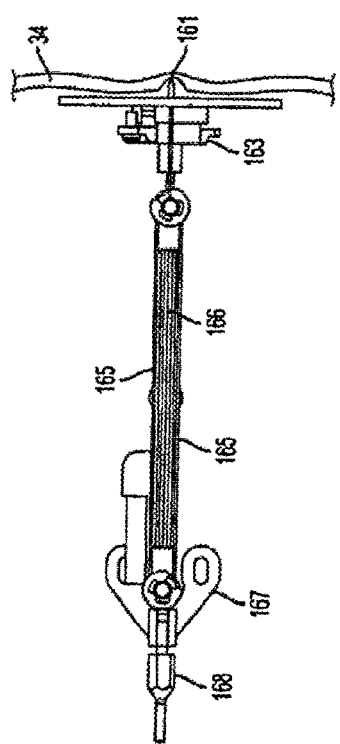
FIG. 40 shows a top view of the occluder of FIG. 38 with the bladder in a deflated state.
Figure 41:
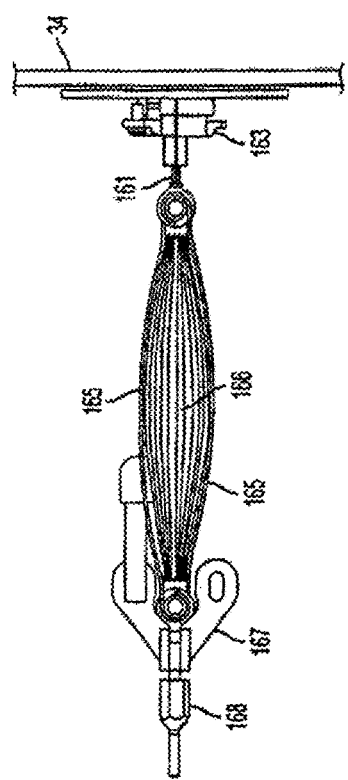
FIG. 41 shows a top view of the occluder of FIG. 38 with the bladder in an inflated state.

FIG. 40 shows a top view of the occluder 147 with the bladder 166 deflated and the spring plates 165 located near each other and in a flat or nearly flat condition. In this position, the pinch head 161 is fully extended from the pinch head guide and the front panel of the cycler 14 (i.e., the panel inside of the door 141) and enabled to occlude the patient and drain lines. FIG. 41, on the other hand, shows the bladder 166 in an inflated state in which the spring plates 165 are pushed apart, thereby retracting the pinch head 161 into the pinch head guide 163. (Note that the linear adjustor 167 is fixed in place relative to the cycler housing 82 and thus fixed relative to the front panel of the housing 82. As the spring plates 165 are moved apart, the pinch head 161 moves rearwardly relative to the front panel since the pinch head 161 is arranged to move freely in and out of the pinch head guide 163.) This condition prevents the pinch head 161 from occluding the patient and drain lines and is the condition in which the occluder 147 remains during normal operation of the cycler 14. That is, as discussed above, various components of the cycler 14 may operate using air pressure/vacuum, e.g., the control surface 148 may operate under the drive of suitable air pressure/vacuum to cause fluid pumping and valve operation for the cassette 24. Thus, when the cycler 14 is operating normally, the cycler 14 may produce sufficient air pressure to not only control system operation, but also to inflate the bladder 166 to retract the pinch head 161 and prevent occlusion of the patient and drain lines. However, in the case of system shut down, failure, fault or other condition, air pressure to the bladder 166 may be terminated, causing the bladder 166 to deflate and the spring plates 165 to straighten and extend the pinch head 161 to occlude the lines. One possible advantage of the arrangement shown is that the return force of the spring plates 165 is balanced such that the pinch head 161 generally will not bind in the pinch head guide 163 when moving relative to the pinch head guide 163. In addition, the opposing forces of the spring plates 165 will tend to reduce the amount of asymmetrical frictional wear of the pivot shafts and bushings of the assembly. Also, once the spring plates 165 are in an approximately straight position, the spring plates 165 can exert a force in a direction generally along the length of the pinch head 161 that is several times larger than the force exerted by the bladder 166 on the spring plates 165 to separate the spring plates 165 from each other and retract the pinch head 161. Further, with the spring plates 165 in a flat or nearly flat condition, the force needed to be exerted by fluid in the collapsed tubing to overcome the pinching force exerted by the pinch head 161 approaches a relatively high force required, when applied to the spring plates at their ends and essentially parallel to the plane of the flattened spring plates, to buckle the spring plates by breaking the column stability of the flattened spring plates. As a result, the occluder 147 can be very effective in occluding the lines with a reduced chance of failure while also requiring a relatively small force be applied by the bladder 166 to retract the pinch head 161. The dual spring plate arrangement of the illustrative embodiment may have the additional advantage of significantly increasing the pinching force provided by the pinch head, for any given force needed to bend the spring plate, and/or for any given size and thickness of spring plate.

In some circumstances, the force of the occluder 147 on the lines may be relatively large and may cause the door 141 to be difficult to open. That is, the door 141 must oppose the force of the occluder 147 when the pinch head 161 is in contact with and occluding lines, and in some cases this may cause the latch that maintains the door 141 in a closed state to be difficult or impossible to operate by hand. Of course, if the cycler 14 is started and produces air pressure to operate, the occluder bladder 166 can be inflated and the occluder pinch head 161 retracted. However, in some cases, such as with a pump failure in the cycler 14, inflation of the bladder 166 may be impossible or difficult. To allow opening of the door, the occluder 147 may include a manual release. In this illustrative embodiment, the occluder 147 may include a release blade 169 as shown in FIGS. 38 and 39 which includes a pair of wings pivotally mounted for rotary movement between the spring plates 165. When at rest, the release blade wings may be aligned with the springs as shown in FIG. 39, allowing the occluder to operate normally. However, if the spring plates 165 are in a flat condition and the pinch head 161 needs to be retracted manually, the release blade 169 may be rotated, e.g., by engaging a hex key or other tool with the release blade 169 and turning the release blade 169, so that the wings push the spring plates 165 apart. The hex key or other tool may be inserted through an opening in the housing 82 of the cycler 14, e.g., an opening near the left side handle depression in the cycler housing 82, and operated to disengage the occluder 147 and allow the door 141 to be opened.

Pump Volume Delivery Measurement

In another aspect of the invention, the cycler 14 may determine a volume of fluid delivered in various lines of the system 10 without the use of a flowmeter, weight scale or other direct measurement of fluid volume or weight. For example, in one embodiment, a volume of fluid moved by a pump, such as a pump in the cassette 24, may be determined based on pressure measurements of a gas used to drive the pump. In one embodiment, a volume determination can be made by isolating two chambers from each other, measuring the respective pressures in the isolated chambers, allowing the pressures in the chambers to partially or substantially equalize (by fluidly connecting the two chambers) and measuring the pressures. Using the measured pressures, the known volume of one of the chambers, and an assumption that the equalization occurs in an adiabatic way, the volume of the other chamber (e.g., a pump chamber) can be calculated. In one embodiment, the pressures measured after the chambers are fluidly connected may be substantially unequal to each other, i.e., the pressures in the chambers may not have yet completely equalized. However, these substantially unequal pressures may be used to determine a volume of the pump control chamber, as explained below.

Figure 42:
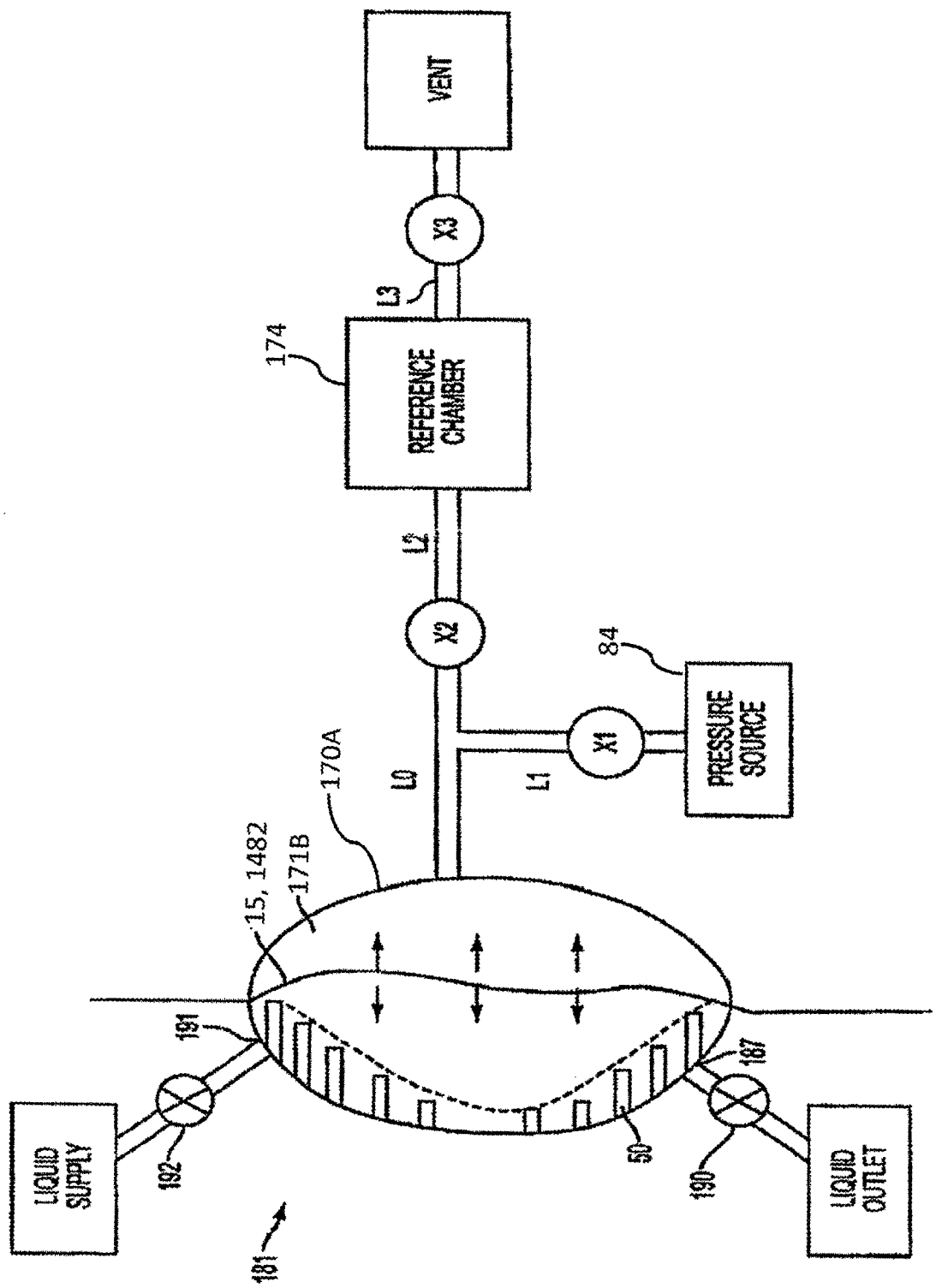
FIG. 42 is a schematic view of a pump chamber of a cassette and associated control components and inflow/outflow paths in an illustrative embodiment.

For example, FIG. 42 shows a schematic view of a pump chamber 181 of the cassette 24 and associated control components and inflow/outflow paths. In this illustrative example, a liquid supply, which may include the heater bag 22, heater bag line 26 and a flow path through the cassette 24, is shown providing a liquid input at the upper opening 191 of the pump chamber. The liquid outlet is shown in this example as receiving liquid from the lower opening 187 of the pump chamber 181, and may include a flow path of the cassette 24 and the patient line 34, for example. The liquid supply may include a valve, e.g., including the valve port 192, that can be opened and closed to permit/impede flow to or from the pump chamber 181. Similarly, the liquid outlet may include a valve, e.g., including the valve port 190, that can be opened and closed to permit/impede flow to or from the pump chamber 181. Of course, the liquid supply could include any suitable arrangement, such as one or more solution containers, the patient line, one or more flow paths in the cassette 24 or other liquid source, and the liquid outlet could likewise include any suitable arrangement, such as the drain line, the heater bag and heater bag line, one or more flow paths in the cassette 24 or other liquid outlet. Generally speaking, the pump chamber 181 (i.e., on the left side of the membrane 14 in FIG. 42) will be filled with an incompressible liquid, such as water or dialysate, during operation. However, air or other gas may be present in the pump chamber 181 in some circumstances, such as during initial operation, priming, or other situations as discussed below. Also, it should be understood that although aspects of the invention relating to volume and/or pressure detection for a pump are described with reference to the pump arrangement of the cassette 24, aspects of the invention may be used with any suitable pump or fluid movement system.

FIG. 42 also shows schematically to the right of the membrane 15 and the control surface 1482 (which are adjacent each other) a control chamber 171B, which may be formed as a void or other space in the mating block 170A associated with the pump control region 1482 of the control surface 1482 for the pump chamber 181, as discussed above. It is in the control chamber 171B that suitable air pressure is introduced to cause the membrane 15/control region 1482 to move and effect pumping of liquid in the pump chamber 181. The control chamber 171B may communicate with a line L0 that branches to another line L1 and a first valve X1 that communicates with a pressure source 84 (e.g., a source of air pressure or vacuum). The pressure source 84 may include a piston pump in which the piston is moved in a chamber to control a pressure delivered to the control chamber 171B, or may include a different type of pressure pump and/or tank(s) to deliver suitable gas pressure to move the membrane 15/control region 1482 and perform pumping action. The line L0 also leads to a second valve X2 that communicates with another line L2 and a reference chamber 174 (e.g., a space suitably configured for performing the measurements described below). The reference chamber 174 also communicates with a line L3 having a valve X3 that leads to a vent or other reference pressure (e.g., a source of atmospheric pressure or other reference). Each of the valves X1, X2 and X3 may be independently controlled.

Pressure sensors may be arranged, e.g., one sensor at the control chamber 171B and another sensor at the reference chamber 174, to measure pressure associated with the control chamber and the reference chamber. These pressure sensors may be positioned and may operate to detect pressure in any suitable way. The pressure sensors may communicate with the control system 16 for the cycler 14 or other suitable processor for determining a volume delivered by the pump or other features.

As mentioned above, the valves and other components of the pump system shown in FIG. 42 can be controlled so as to measure pressures in the pump chamber 181, the liquid supply and/or liquid outlet, and/or to measure a volume of fluid delivered from the pump chamber 181 to the liquid supply or liquid outlet. Regarding volume measurement, one technique used to determine a volume of fluid delivered from the pump chamber 181 is to compare the relative pressures at the control chamber 171B to that of the reference chamber 174 in two different pump states. By comparing the relative pressures, a change in volume at the control chamber 171B can be determined, which corresponds to a change in volume in the pump chamber 181 and reflects a volume delivered from/received into the pump chamber 181. For example, after the pressure is reduced in the control chamber 171B during a pump chamber fill cycle (e.g., by applying negative pressure from the pressure source through open valve X1) so as to draw the membrane 15 and pump control region 1482 into contact with at least a portion of the control chamber wall (or to another suitable position for the membrane 15/region 1482), valve X1 may be closed to isolate the control chamber from the pressure source, and valve X2 may be closed, thereby isolating the reference chamber 174 from the control chamber 171B. Valve X3 may be opened to vent the reference chamber to ambient pressure, then closed to isolate the reference chamber. With valve X1 closed and the pressures in the control chamber and reference chamber measured, valve X2 is then opened to allow the pressure in the control chamber and the reference chamber to start to equalize. The initial pressures of the reference chamber and the control chamber, together with the known volume of the reference chamber and pressures measured after equalization has been initiated (but not yet necessarily completed) can be used to determine a volume for the control chamber. This process may be repeated at the end of the pump delivery cycle when the sheet 15/control region 1482 are pushed into contact with the spacer elements 50 of the pump chamber 181. By comparing the control chamber volume at the end of the fill cycle to the volume at the end of the delivery cycle, a volume of liquid delivered from the pump can be determined.

Conceptually, the pressure equalization process (e.g., at opening of the valve X2) is viewed as happening in an adiabatic way, i.e., without heat transfer occurring between air in the control and reference chambers and its environment. The conceptual notion is that there is an imaginary piston located initially at the valve X2 when the valve X2 is closed, and that the imaginary piston moves in the line L0 or L2 when the valve X2 is opened to equalize the pressure in the control and reference chambers. Since (a) the pressure equalization process happens relatively quickly, (b) the air in the control chamber and the reference chamber has approximately the same concentrations of elements, and (c) the temperatures are similar, the assumption that the pressure equalization happens in an adiabatic way may introduce only small error into the volume measurements. Also, in one embodiment, the pressures taken after equalization has been initiated may be measured before substantial equalization has occurred—further reducing the time between measuring the initial pressures and the final pressures used to determine the pump chamber volume. Error can be further reduced, for example, by using low thermal conductivity materials for the membrane 15/control surface 1482, the cassette 24, the control chamber 171B, the lines, the reference chamber 174, etc., so as to reduce heat transfer.

Given the assumption that an adiabatic system exists between the state when the valve X2 is closed until after the valve X2 is opened and the pressures equalize, the following applies:

$$PV^\gamma = \text{Constant} \quad (1)$$

where P is pressure, V is volume and $\gamma$ is equal to a constant (e.g., about 1.4 where the gas is diatomic, such as air). Thus, the following equation can be written to relate the pressures and volumes in the control chamber and the reference chamber before and after the opening of valve X2 and pressure equalization occurs:

$$Pr Vr^\gamma + Pd Vd^\gamma = \text{Constant} = Pf Vf^\gamma \quad (2)$$

where Pr is the pressure in the reference chamber and lines L2 and L3 prior to the valve X2 opening, Vr is the volume of the reference chamber and lines L2 and L3 prior to the valve X2 opening, Pd is the pressure in the control chamber and the lines L0 and L1 prior to the valve X2 opening, Vd is the volume of the control chamber and the lines L0 and L1 prior to the valve X2 opening, Pf is the equalized pressure in the reference chamber and the control chamber after opening of the valve X2, and Vf is the volume of the entire system including the control chamber, the reference chamber and the lines L0, L1, L2, and L3, i.e., Vf=Vd+Vr. Since Pr, Vr, Pd, Pf and $\gamma$ are known, and Vf=Vr+Vd, this equation can be used to solve for Vd. (Although reference is made herein, including in the claims, to use of a "measured pressure" in determining volume values, etc., it should be understood that such a measured pressure value need not necessarily be any particular form, such as in psi units. Instead, a "measured pressure" or "determined pressure" may include any value that is representative of a pressure, such as a voltage level, a resistance value, a multibit digital number, etc. For example, a pressure transducer used to measure pressure in the pump control chamber may output an analog voltage level, resistance or other indication that is representative of the pressure in the pump control chamber. The raw output from the transducer may be used as a measured pressure, and/or some modified form of the output, such as a digital number generated using an analog output from the transducer, a psi or other value that is generated based on the transducer output, and so on. The same is true of other values, such as a determined volume, which need not necessarily be in a particular form such as cubic centimeters. Instead, a determined volume may include any value that is representative of the volume, e.g., could be used to generate an actual volume in, say, cubic centimeters.)

In an embodiment of a fluid management system ("FMS") technique to determine a volume delivered by the pump, it is assumed that pressure equalization upon opening of the valve X2 occurs in an adiabatic system. Thus, Equation 3 below gives the relationship of the volume of the reference chamber system before and after pressure equalization:

$$Vrf = Vri(Pf/Patm)^{-(1/\gamma)} \quad (3)$$

where Vrf is the final (post-equalization) volume of the reference chamber system including the volume of the reference chamber, the volume of the lines L2 and L3 and the volume adjustment resulting from movement of the "piston", which may move to the left or right of the valve X2 after opening, Vri is the initial (pre-equalization) volume of the reference chamber and the lines L2 and L3 with the "piston" located at the valve X2, Pf is the final equalized pressure after the valve X2 is opened, and Patm is the initial pressure of the reference chamber before valve X2 opening (in this example, atmospheric pressure). Similarly, Equation 4 gives the relationship of the volume of the control chamber system before and after pressure equalization:

$$Vdf = Vdi(Pf/Pdi)^{-(1/\gamma)} \quad (4)$$

where Vdf is the final volume of the control chamber system including the volume of the control chamber, the volume of the lines L0 and L1, and the volume adjustment resulting from movement of the "piston", which may move to the left or right of the valve X2 after opening, Vdi is the initial volume of the control chamber and the lines L0 and L1 with the "piston" located at the valve X2, Pf is the final pressure after the valve X2 is opened, and Pdi is the initial pressure of the control chamber before valve X2 opening.

The volumes of the reference chamber system and the control chamber system will change by the same absolute amount after the valve X2 is opened and the pressure equalizes, but will differ in sign (e.g., because the change in volume is caused by movement of the "piston" left or right when the valve X2 opens), as shown in Equation 5:

$$\Delta Vr = (-1)\Delta Vd \quad (5)$$

(Note that this change in volume for the reference chamber and the control chamber is due only to movement of the imaginary piston. The reference chamber and control chamber will not actually change in volume during the equalization process under normal conditions.) Also, using the relationship from Equation 3, the change in volume of the reference chamber system is given by:

$$\Delta Vr = Vrf - Vri = Vri(-1+(Pf/Patm)^{-(1/\gamma)}) \quad (6)$$

Similarly, using Equation 4, the change in volume of the control chamber system is given by:

$$\Delta Vd = Vdf - Vdi = Vdi(-1+(Pf/Pdi)^{-(1/\gamma)}) \quad (7)$$

Because Vri is known, and Pf and Patm are measured or known, $\Delta Vr$ can be calculated, which according to Equation 5 is assumed to be equal to $(-)\Delta Vd$. Therefore, Vdi (the volume of the control chamber system before pressure equalization with the reference chamber) can be calculated using Equation 7. In this embodiment, Vdi represents the volume of the control chamber plus lines L0 and L1, of which L0 and L1 are fixed and known quantities. Subtracting L0 and L1 from Vdi yields the volume of the control chamber alone. By using Equation 7 above, for example, both before (Vdi1) and after (Vdi2) a pump operation (e.g., at the end of a fill cycle and at the end of a discharge cycle), the change in volume of the control chamber can be determined, thus providing a measurement of the volume of fluid delivered by (or taken in by) the pump. For example, if Vdi1 is the volume of the control chamber at the end of a fill stroke, and Vdi2 is the volume of the control chamber at the end of the subsequent delivery stroke, the volume of fluid delivered by the pump may be estimated by subtracting Vdi1 from Vdi2. Since this measurement is made based on pressure, the volume determination can be made for nearly any position of the membrane 15/pump control region 1482 in the pump chamber 181, whether for a full or partial pump stroke. However, measurement made at the ends of fill and delivery strokes can be accomplished with little or no impact on pump operation and/or flow rate.

One aspect of the invention involves a technique for identifying pressure measurement values that are to be used in determining a volume for the control chamber and/or other purposes. For example, although pressure sensors may be used to detect a pressure in the control chamber and a pressure in the reference chamber, the sensed pressure values may vary with opening/closing of valves, introduction of pressure to the control chamber, venting of the reference chamber to atmospheric pressure or other reference pressure, etc. Also, since in one embodiment, an adiabatic system is assumed to exist from a time before pressure equalization between the control chamber and the reference chamber until after equalization, identifying appropriate pressure values that were measured as close together in time may help to reduce error (e.g., because a shorter time elapsed between pressure measurements may reduce the amount of heat that is exchanged in the system). Thus, the measured pressure values may need to be chosen carefully to help ensure appropriate pressures are used for determining a volume delivered by the pump, etc.

Figure 43:
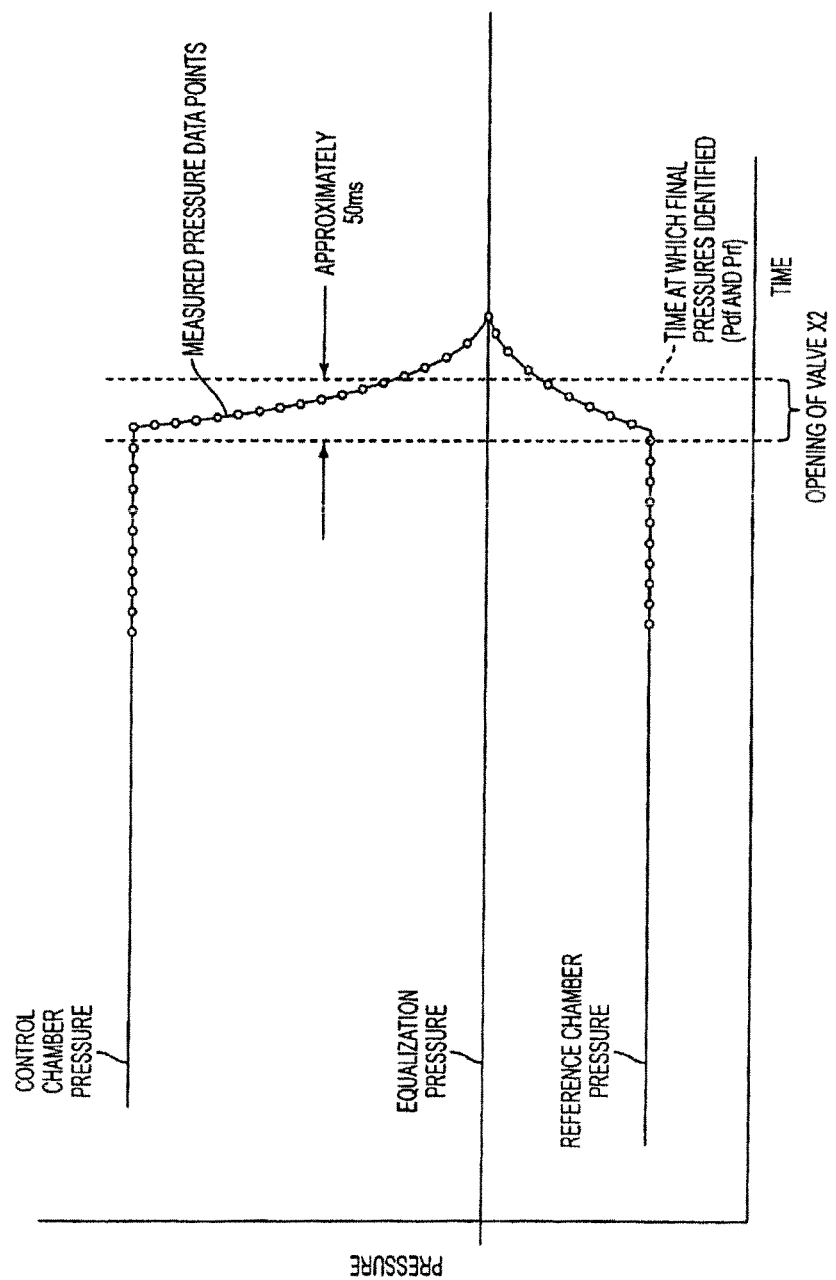
FIG. 43 is a plot of illustrative pressure values for the control chamber and the reference chamber from a point in time before opening of the valve X2 until some time after the valve X2 is opened for the embodiment of FIG. 42.

For purposes of explanation, FIG. 43 shows a plot of illustrative pressure values for the control chamber and the reference chamber from a point in time before opening of the valve X2 until some time after the valve X2 is opened to allow the pressure in the chambers to equalize. In this illustrative embodiment, the pressure in the control chamber is higher than the pressure in the reference chamber before equalization, but it should be understood that the control chamber pressure may be lower than the reference chamber pressure before equalization in some arrangements, such as during and/or at the end of a fill stroke. Also, the plot in FIG. 43 shows a horizontal line marking the equalization pressure, but it should be understood that this line is shown for clarity only. The equalization pressure in general will not be known prior to opening of the valve X2. In this embodiment, the pressure sensors sense pressure at a rate of about 2000 Hz for both the control chamber and the reference chamber, although other suitable sampling rates could be used. Before opening of the valve X2, the pressures in the control chamber and the reference chamber are approximately constant, there being no air or other fluid being introduced into the chambers. Thus, the valves X1 and X3 will generally be closed at a time before opening of the valve X2. Also, valves leading into the pump chamber, such as the valve ports 190 and 192, may be closed to prevent influence of pressure variations in the pump chamber, the liquid supply or liquid outlet.

At first, the measured pressure data is processed to identify the initial pressures for the control chamber and reference chambers, i.e., Pd and Pr. In one illustrative embodiment, the initial pressures are identified based on analysis of a 10-point sliding window used on the measured pressure data. This analysis involves generating a best fit line for the data in each window (or set), e.g., using a least squares technique, and determining a slope for the best fit line. For example, each time a new pressure is measured for the control chamber or the reference chamber, a least squares fit line may be determined for a data set including the latest measurement and the 9 prior pressure measurements. This process may be repeated for several sets of pressure data, and a determination may be made as to when the slope of the least squares fit lines first becomes negative (or otherwise non-zero) and continues to grow more negative for subsequent data sets (or otherwise deviates from a zero slope). The point at which the least squares fit lines begin to have a suitable, and increasing, non-zero slope may be used to identify the initial pressure of the chambers, i.e., at a time before the valve X2 is opened.

In one embodiment, the initial pressure value for the reference chamber and the control chamber may be determined to be in the last of 5 consecutive data sets, where the slope of the best fit line for the data sets increases from the first data set to the fifth data set, and the slope of the best fit line for the first data set first becomes non-zero (i.e., the slope of best fit lines for data sets preceding the first data set is zero or otherwise not sufficiently non-zero). For example, the pressure sensor may take samples every ½ millisecond (or other sampling rate) starting at a time before the valve X2 opens. Every time a pressure measurement is made, the cycler 14 may take the most recent measurement together with the prior 9 measurements, and generate a best fit line to the 10 data points in the set. Upon taking the next pressure measurement (e.g., ½ millisecond later), the cycler 14 may take the measurement together with the 9 prior measurements, and again generate a best fit line to the 10 points in the set. This process may be repeated, and the cycler 14 may determine when the slope of the best fit line for a set of 10 data points first turns non-zero (or otherwise suitably sloped) and, for example, that the slope of the best fit line for 5 subsequent sets of 10 data points increases with each later data set. To identify the specific pressure measurement to use, one technique is to select the third measurement in the $5^{th}$ data set (i.e., the $5^{th}$ data set with which it was found that the best fit line has been consistently increasing in slope and the $1^{st}$ measurement is the pressure measurement that was taken earliest in time) as the measurement to be used as the initial pressure for the control chamber or the reference chamber, i.e., Pd or Pr. This selection was chosen using empirical methods, e.g., plotting the pressure measurement values and then selecting which point best represents the time when the pressure began the equalization process. Of course, other techniques could be used to select the appropriate initial pressure.

In one illustrative embodiment, a check may be made that the times at which the selected Pd and Pr measurements occurred were within a desired time threshold, e.g., within 1-2 milliseconds of each other. For example, if the technique described above is used to analyze the control chamber pressure and the reference chamber pressure and identify a pressure measurement (and thus a point in time) just before pressure equalization began, the times at which the pressures were measured should be relatively close to each other. Otherwise, there may have been an error or other fault condition that invalidates one or both of the pressure measurements. By confirming that the time at which Pd and Pr occurred are suitably close together, the cycler 14 may confirm that the initial pressures were properly identified.

To identify when the pressures in the control chamber and the reference chamber have equalized such that measured pressures for the chamber can be used to reliably determine pump chamber volume, the cycler 14 may analyze data sets including a series of data points from pressure measurements for both the control chamber and the reference chamber, determine a best fit line for each of the data sets (e.g., using a least squares method), and identify when the slopes of the best fit lines for a data set for the control chamber and a data set for the reference chamber are first suitably similar to each other, e.g., the slopes are both close to zero or have values that are within a threshold of each other. When the slopes of the best fit lines are similar or close to zero, the pressure may be determined to be equalized. The first pressure measurement value for either data set may be used as the final equalized pressure, i.e., Pf. In one illustrative embodiment, it was found that pressure equalization occurred generally within about 200-400 milliseconds after valve X2 is opened, with the bulk of equalization occurring within about 50 milliseconds. Accordingly, the pressure in the control and reference chambers may be sampled approximately 400-800 times or more during the entire equalization process from a time before the valve X2 is opened until a time when equalization has been achieved.

In some cases, it may be desirable to increase the accuracy of the control chamber volume measurement using an alternate FMS technique. Substantial differences in temperature between the liquid being pumped, the control chamber gas, and the reference chamber gas may introduce significant errors in calculations based on the assumption that pressure equalization occurs adiabatically. Waiting to make pressure measurements until full equalization of pressure between the control chamber and the reference chamber may allow an excessive amount of heat transfer to occur. In one aspect of the invention, pressure values for the pump chamber and reference chamber that are substantially unequal to each other, i.e., that are measured before complete equalization has occurred, may be used to determine pump chamber volume.

In one embodiment, heat transfer may be minimized, and adiabatic calculation error reduced, by measuring the chamber pressures throughout the equalization period from the opening of valve X2 through full pressure equalization, and selecting a sampling point during the equalization period for the adiabatic calculations. In one embodiment of an APD system, measured chamber pressures that are taken prior to complete pressure equalization between the control chamber and the reference chamber can be used to determine pump chamber volume. In one embodiment, these pressure values may be measured about 50 ms after the chambers are first fluidly connected and equalization is initiated. As mentioned above, in one embodiment, complete equalization may occur about 200-400 ms after the valve X2 is opened. Thus, the measured pressures may be taken at a point in time after the valve X2 is opened (or equalization is initiated) that is about 10% to 50% or less of the total equalization time period. Said another way, the measured pressures may be taken at a point in time at which 50-70% of pressure equalization has occurred (i.e., the reference and pump chamber pressures have changed by about 50-70% of the difference between the initial chamber pressure and the final equalized pressure. Using a computer-enabled controller, a substantial number of pressure measurements in the control and reference chambers can be made, stored and analyzed during the equalization period (for example, 40-100 individual pressure measurements). Among the time points sampled during the first 50 ms of the equalization period, there is a theoretically optimized sampling point for conducting the adiabatic calculations (e.g., see FIG. 43 in which the optimized sampling point occurs at about 50 ms after opening of the valve X2). The optimized sampling point may occur at a time early enough after valve X2 opening to minimize thermal transfer between the gas volumes of the two chambers, but not so early as to introduce significant errors in pressure measurements due to the properties of the pressure sensors and delays in valve actuation. However, as can be seen in FIG. 43, the pressures for the pump chamber and reference chambers may be substantially unequal to each other at this point, and thus equalization may not be complete. (Note that in some cases, it may be technically difficult to take reliable pressure measurements immediately after the opening of valve X2, for example, because of the inherent inaccuracies of the pressure sensors, the time required for valve X2 to fully open, and the rapid initial change in the pressure of either the control chamber or the reference chamber immediately after the opening of valve X2.)

During pressure equalization, when the final pressure for the control chamber and reference chambers are not the same, Equation 2 becomes:

$$Pri Vri^\gamma + Pdi Vdi^\gamma = \text{Constant} = Prf Vrf^\gamma + Pdf Vd^\gamma \tag{8}$$

where: Pri=pressure in the reference chamber prior to opening valve X2, Pdi=pressure in the control chamber prior to opening valve X2, Prf=final reference chamber pressure, Pdf=final control chamber pressure.

An optimization algorithm can be used to select a point in time during the pressure equalization period at which the difference between the absolute values of ΔVd and ΔVr is minimized (or below a desired threshold) over the equalization period. (In an adiabatic process, this difference should ideally be zero, as indicated by Equation 5. In FIG. 43 the point in time at which the difference between the absolute values of ΔVd and ΔVr is minimized occurs at the 50 ms line, marked "time at which final pressures identified.") First, pressure data can be collected from the control and reference chambers at multiple points j=1 through n between the opening of valve X2 and final pressure equalization. Since Vri, the fixed volume of the reference chamber system before pressure equalization, is known, a subsequent value for Vrj (reference chamber system volume at sampling point j after valve X2 has opened) can be calculated using Equation 3 at each sampling point Prj along the equalization curve. For each such value of Vrj, a value for ΔVd can be calculated using Equations 5 and 7, each value of Vrj thus yielding Vdij, a putative value for Vdi, the volume of the control chamber system prior to pressure equalization. Using each value of Vrj and its corresponding value of Vdij, and using Equations 3 and 4, the difference in the absolute values of ΔVd and ΔVr can be calculated at each pressure measurement point along the equalization curve. The sum of these differences squared provides a measure of the error in the calculated value of Vdi during pressure equalization for each value of Vrj and its corresponding Vdij. Denoting the reference chamber pressure that yields the least sum of the squared differences of |ΔVd| and |ΔVr| as Prf, and its associated reference chamber volume as Vrf, the data points Prf and Pdf corresponding to Vrf can then be used to calculate an optimized estimate of Vdi, the initial volume of the control chamber system.

One method for determining where on the equalization curve to capture an optimized value for Pdf and Prf is as follows:

1) Acquire a series of pressure data sets from the control and reference chambers starting just before the opening of valve X2 and ending with Pr and Pd becoming close to equal. If Pri is the first reference chamber pressure captured, then the subsequent sampling points in FIG. 32 will be referred to as Prj=Pr1, Pr2, . . . , Prn.
2) Using Equation 6, for each Prj after Pri, calculate the corresponding ΔVrj where j represents the jth pressure data point after Pri.

$$\Delta Vrj = Vrj - Vri = Vri(-1 + (Prj/Pri)^{-(1/\gamma)})$$

3) For each such $\Delta Vrj$ calculate the corresponding Vdij using Equation 7. For example:

$$\Delta Vr1 = Vri*\left(-1 + (Pr1/Pri)^{-(1/\gamma)}\right)$$

$$\Delta Vd1 = -\Delta Vr1$$

Therefore, $$Vdi1 = \Delta Vd1/\left(-1 + (Pd1/Pdi)^{-(1/\gamma)}\right)$$

$$\vdots$$

$$Vdin = \Delta Vdn/\left(-1 + (Pdn/Pdi)^{-(1/\gamma)}\right)$$

Having calculated a set of n control chamber system initial volumes (Vdi1 to Vdin) based on the set of reference chamber pressure data points Pr1 to Prn during pressure equalization, it is now possible to select the point in time (f) that yields an optimized measure of the control chamber system initial volume (Vdi) over the entire pressure equalization period.

4) Using Equation 7, for each Vdi1 through Vdin, calculate all $\Delta Vdj,k$ using control chamber pressure measurements Pd for time points k=1 to n.

For the Vdi corresponding to Pr1:

$$\Delta Vd1, 1 = Vdi1*\left(-1 + (Pd1/Pdi)^{-1(1/\gamma)}\right)$$

$$\Delta Vd1, 2 = Vdi1*\left(-1 + (Pd2/Pdi)^{-1(1/\gamma)}\right)$$

$$\vdots$$

$$\Delta Vd1, n = Vd1*(-1 + Pdn/Pdi)^{-(1/\gamma)}$$

$$\vdots$$

For the Vdi corresponding to Prn:

$$\Delta Vdn, 1 = Vdin*\left(-1 + (Pd1/Pdi)^{-(1/\gamma)}\right)$$

$$\Delta Vdn, 2 = Vdin*\left(-1 + (Pd2/Pdi)^{-(1/\gamma)}\right)$$

$$\vdots$$

$$\Delta Vdn, n = Vdin*\left(-1 + (Pdn/Pdi)^{(1/\gamma)}\right)$$

5) Take the sum-square error between the absolute values of the $\Delta Vr$'s and $\Delta Vdj,k$'s $$S_1 \sum_{k=1}^{n} (|\Delta V_{d1,k}| - |\Delta V_{rk}|)^2$$

[S1 represents the sum-square error of $|\Delta Vd|$ minus $|\Delta Vr|$ over all data points during the equalization period when using the first data point Pr1 to determine Vdi, the control chamber system initial volume, from Vr1 and $\Delta Vr$.]

$$S_2 \sum_{k=1}^{n} (|\Delta V_{d2,k}| - |\Delta V_{rk}|)^2$$

[S2 represents the sum-square error of $|\Delta Vr|$ minus $|\Delta Vd|$ over all data points during the equalization period when using the second data point Pr2 to determine Vdi, the control chamber system initial volume, from Vr2 and $\Delta Vr$.]

$$\vdots$$

$$S_n \sum_{k=1}^{n} (|\Delta V_{dn,k}| - |\Delta V_{rk}|)^2$$

6) The Pr data point between Pr1 and Prn that generates the minimum sum-square error S from step 5 (or a value that is below a desired threshold) then becomes the chosen Prf, from which Pdf and an optimized estimate of Vdi, the control chamber initial volume, can then be determined. In this example, Pdf occurs at, or about, the same time as Prf.

7) The above procedure can be applied any time that an estimate of the control chamber volume is desired, but can preferably be applied at the end of each fill stroke and each delivery stroke. The difference between the optimized Vdi at the end of a fill stroke and the optimized Vdi at the end of a corresponding delivery stroke can be used to estimate the volume of liquid delivered by the pump.

Air Detection

Another aspect of the invention involves the determination of a presence of air in the pump chamber 181, and if present, a volume of air present. Such a determination can be important, e.g., to help ensure that a priming sequence is adequately performed to remove air from the cassette 24 and/or to help ensure that air is not delivered to the patient. In certain embodiments, for example, when delivering fluid to the patient through the lower opening 187 at the bottom of the pump chamber 181, air or other gas that is trapped in the pump chamber may tend to remain in the pump chamber 181 and will be inhibited from being pumped to the patient unless the volume of the gas is larger than the volume of the effective dead space of pump chamber 181. As discussed below, the volume of the air or other gas contained in pump chambers 181 can be determined in accordance with aspects of the present invention and the gas can be purged from pump chamber 181 before the volume of the gas is larger than the volume of the effective dead space of pump chamber 181.

A determination of an amount of air in the pump chamber 181 may be made at the end of a fill stroke, and thus, may be performed without interrupting a pumping process. For example, at the end of a fill stroke during which the membrane 15 and the pump control region 1482 are drawn away from the cassette 24 such that the membrane 15/region 1482 are brought into contact with the wall of the control chamber 171, the valve X2 may be closed, and the reference chamber vented to atmospheric pressure, e.g., by opening the valve X3. Thereafter, the valves X1 and X3 may be closed, fixing the imaginary "piston" at the valve X2. The valve X2 may then be opened, allowing the pressure in the control chamber and the reference chamber to equalize, as was described above when performing pressure measurements to determine a volume for the control chamber.

If there is no air bubble in the pump chamber 181, the change in volume of the reference chamber, i.e., due to the movement of the imaginary "piston," determined using the known initial volume of the reference chamber system and the initial pressure in the reference chamber, will be equal to the change in volume of the control chamber determined using the known initial volume of the control chamber system and the initial pressure in the control chamber. (The initial volume of the control chamber may be known in conditions where the membrane 15/control region 1482 are in contact with the wall of the control chamber or in contact with the spacer elements 50 of the pump chamber 181.) However, if air is present in the pump chamber 181, the change in volume of the control chamber will actually be distributed between the control chamber volume and the air bubble(s) in the pump chamber 181. As a result, the calculated change in volume for the control chamber using the known initial volume of the control chamber system will not be equal to the calculated change in volume for the reference chamber, thus signaling the presence of air in the pump chamber.

If there is air in the pump chamber 181, the initial volume of the control chamber system Vdi is actually equal to the sum of the volume of the control chamber and lines L0 and L1 (referred to as Vdfix) plus the initial volume of the air bubble in the pump chamber 181, (referred to as Vbi), as shown in Equation 9:

$$Vdi = Vbi + Vdfix \quad (9)$$

With the membrane 15/control region 1482 pressed against the wall of the control chamber at the end of a fill stroke, the volume of any air space in the control chamber, e.g., due to the presence of grooves or other features in the control chamber wall, and the volume of the lines L0 and L1—together Vdfix—can be known quite accurately. (Similarly, with the membrane 15/control region 1482 pressed against the spacer elements 50 of the pump chamber 181, the volume of the control chamber and the lines L0 and L1 can be known accurately.) After a fill stroke, the volume of the control chamber system is tested using a positive control chamber pre-charge. Any discrepancy between this tested volume and the tested volume at the end of the fill stroke may indicate a volume of air present in the pump chamber. Substituting from Equation 9 into Equation 7, the change in volume of the control chamber $\Delta Vd$ is given by:

$$\Delta Vd = (Vbi + Vdfix)(-1 + (Pdf/Pdi)^{-(1/\gamma)}) \quad (10)$$

Since $\Delta Vr$ can be calculated from Equation 6, and we know from Equation 5 that $\Delta Vr = (-1) \Delta Vd$, Equation 10 can be re-written as:

$$(-1)\Delta Vr = (Vbi + Vdfix)(-1 + (Pdf/Pdi)^{-(1/\gamma)}) \quad (11)$$

and again as:

$$Vbi = (-1)\Delta Vr/(-1 + (Pdf/Pdi)^{-(1/\gamma)}) - Vdfix \quad (12)$$

Accordingly, the cycler 14 can determine whether there is air in the pump chamber 181, and the approximate volume of the bubble using Equation 12. This calculation of the air bubble volume may be performed if it is found, for example, that the absolute values of $\Delta Vr$ (as determined from Equation 6) and $\Delta Vd$ (as determined from Equation 7 using Vdi=Vdfix) are not equal to each other. That is, Vdi should be equal to Vdfix if there is no air present in the pump chamber 181, and thus the absolute value for $\Delta Vd$ given by Equation 7 using Vdfix in place of Vdi will be equal to $\Delta Vr$.

After a fill stroke has been completed, and if air is detected according to the methods described above, it may be difficult to determine whether the air is located on the pump chamber side or the control side of the membrane 15. Air bubbles could be present in the liquid being pumped, or there could be residual air on the control (pneumatic) side of the pump membrane 15 because of a condition (such as, for example, an occlusion) during pumping that caused an incomplete pump stroke, and incomplete filling of the pump chamber. At this point, an adiabatic FMS measurement using a negative pump chamber pre-charge can be done. If this FMS volume matches the FMS volume with the positive precharge, then the membrane is free to move in both directions, which implies that the pump chamber is only partially filled (possibly, for example, due to an occlusion). If the value of the negative pump chamber pre-charge FMS volume equals the nominal control chamber air volume when the membrane 15/region 1482 is in contact with the inner wall of the control chamber, then it is possible to conclude that there is an air bubble in the liquid on the pump chamber side of the flexible membrane.

Head Height Detection

In some circumstances, it may be useful to determine the heightwise location of the patient relative to the cassette 24 or other portion of the system. For example, dialysis patients in some circumstances can sense a "tugging" or other motion due to fluid flowing into or out of the patient's peritoneal cavity during a fill or drain operation. To reduce this sensation, the cycler 14 may reduce the pressure applied to the patient line 34 during fill and/or drain operations. However, to suitably set the pressure for the patient line 34, the cycler 14 may determine the height of the patient relative to the cycler 14, the heater bag 22, drain or other portion of the system. For example, when performing a fill operation, if the patient's peritoneal cavity is located 5 feet above the heater bag 22 or the cassette 24, the cycler 14 may need to use a higher pressure in the patient line 34 to deliver dialysate than if the patient's peritoneal cavity is located 5 ft below the cycler 14. The pressure may be adjusted, for example, by alternately opening and closing a binary pneumatic source valve for variable time intervals to achieve the desired target pump chamber pressure. An average desired target pressure can be maintained, for example, by adjusting the time intervals to keep the valve open when the pump chamber pressure is below the target pressure by a specified amount, and to keep the valve closed when the pump chamber pressure is above the target pressure by a specified amount. Any adjustments to maintain the delivery of a complete stroke volume can be made by adjusting the fill and/or delivery times of the pump chamber. If a variable orifice source valve is used, the target pump chamber pressure can be reached by varying the orifice of the source valve in addition to timing the intervals during which the valve is opened and closed. To adjust for patient position, the cycler 14 may momentarily stop pumping of fluid, leaving the patient line 34 in open fluid communication with one or more pump chambers 181 in the cassette (e.g., by opening suitable valve ports in the cassette 24). However, other fluid lines may be closed, such as the upper valve ports 192 for the pump chambers 181. In this condition, the pressure in the control chamber for one of the pumps may be measured. As is well known in the art, this pressure correlates with the "head" height of the patient, and can be used by the cycler 14 to control the delivery pressure of fluid to the patient. A similar approach can be used to determine the "head" height of the heater bag 22 (which will generally be known), and/or the solution containers 20, as the head height of these components may have an effect on pressure needed for pumping fluid in a suitable way.

Noise Reduction Features of the Cycler

In accordance with aspects of the invention, the cycler 14 may include one or more features to reduce noise generated by the cycler 14 during operation and/or when idle. In one aspect of the invention, the cycler 14 may include a single pump that generates both pressure and vacuum that are used to control the various pneumatic systems of the cycler 14. In one embodiment, the pump can simultaneously generate both pressure and vacuum, thereby reducing overall run time, and allowing the pump to run more slowly (and thus more quietly). In another embodiment, the air pump start and/or stop may be ramped, e.g., slowly increases pump speed or power output at starting and/or slowly decreases pump speed or power output at shut down. This arrangement may help reduce "on/off" noise associated with start and stop of the air pump so pump noise is less noticeable. In another embodiment, the air pump may be operated at a lower duty cycle when nearing a target output pressure or volume flow rate so that the air pump can continue operating as opposed to shutting off, only to be turned on after a short time. As a result, disruption caused by repeated on and off cycles of the air pump may be avoided.

Figure 44:
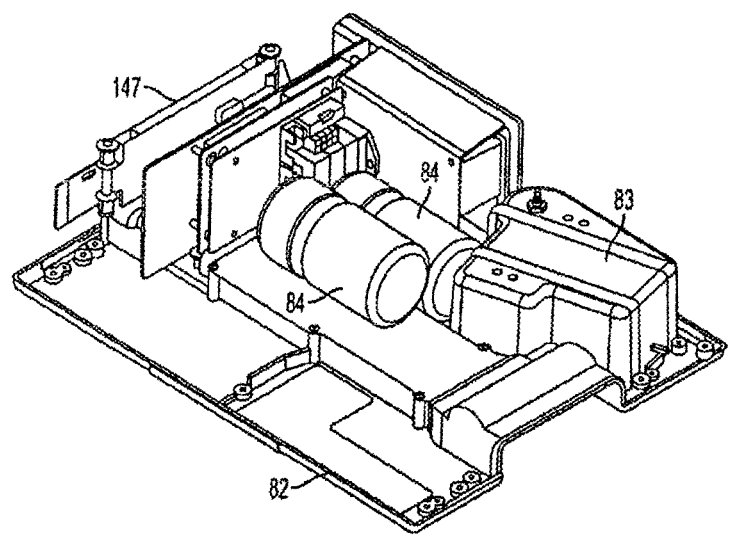
FIG. 44 is a perspective view of an interior section of the cycler of FIG. 10 with the upper portion of the housing removed.

FIG. 44 shows a perspective view of an interior section of the cycler 14 with the upper portion of the housing 82 removed. In this illustrative embodiment, the cycler 14 includes a single air pump 83, which includes the actual pump and motor drive contained within a sound barrier enclosure. The sound barrier enclosure includes an outer shield, such as a metal or plastic frame, and a sound insulation material within the outer shield and at least partially surrounding the motor and pump. This air pump 83 may simultaneously provide air pressure and vacuum, e.g., to a pair of accumulator tanks 84. One of the tanks 84 may store positive pressure air, while the other stores vacuum. A suitable manifold and valve arrangement may be coupled to the tanks 84 so as to provide and control air pressure/vacuum supplied to the components of the cycler 14.

In accordance with another aspect of the invention, components that require a relatively constant pressure or vacuum supply during cycler operation, such as an occluder, may be isolated from the source of air pressure/vacuum at least for relatively long periods of time. For example, the occluder 147 in the cycler 14 generally requires a constant air pressure in the occluder bladder 166 so that the patient and drain lines remain open for flow. If the cycler 14 continues to operate properly without power failure, etc., the bladder 166 may be inflated once at the beginning of system operation and remain inflated until shut down. The inventors have recognized that in some circumstances air powered devices that are relatively static, such as the bladder 166, may "creak" or otherwise make noise in response to slight variations in supplied air pressure. Such variations may cause the bladder 166 to change size slightly, which causes associated mechanical parts to move and potentially make noise. In accordance with an aspect of the bladder 166 and other components having similar pneumatic power requirements, may be isolated from the air pump 83 and/or the tanks 84, e.g., by the closing of a valve, so as to reduce variations of pressure in the bladder or other pneumatic component, thus reducing noise that may be generated as a result of pressure variations. Another component that may be isolated from the pneumatic supply is the bladder in the door 141 at the cassette mounting location 145 which inflates to press the cassette 24 against the control surface 148 when the door 141 is closed. Other suitable components may be isolated as desired.

In accordance with another aspect of the invention, the speed and/or force at which pneumatic components are actuated may be controlled to as to reduce noise generated by component operation. For example, movement of the valve control regions 1481 to move a corresponding portion of the cassette membrane 15 so as to open or close a valve port on the cassette 24 may cause a "popping" noise as the membrane 15 slaps against and/or pull away from the cassette 24. Such noise may be reduced by controlling the rate of operation of the valve control regions 1481, e.g., by restricting the flow rate of air used to move the control regions 1481. Air flow may be restricted by, for example, providing a suitably small sized orifice in the line leading to the associated control chamber, or in other ways.

A controller may also be programmed to apply pulse width modulation ("PWM") to the activation of one or more pneumatic source valves at a manifold of cycler 14. The pneumatic pressure delivered to various valves and pumps of cassette 24 can be controlled by causing the associated manifold source valves to open and close repeatedly during the period of actuation of a valve or pump in cassette 24. The rate of rise or fall of pressure against membrane 15/control surface 148 can then be controlled by modulating the duration of the "on" portion of the particular manifold valve during the actuation period. An additional advantage of applying PWM to the manifold source valves is that variable pneumatic pressure can be delivered to the cassette 24 components using only a binary (on-off) source valve, rather than a more expensive and potentially less reliable variable-orifice source valve.

In accordance with another aspect of the invention, the movement of one or more valve elements may be suitably damped so as to reduce noise generated by valve cycling. For example, a fluid (such as a ferro fluid) may be provided with the valve element of high frequency solenoid valves to damp the movement of the element and/or reduce noise generated by movement of the valve element between open and closed positions.

In accordance with another embodiment, pneumatic control line vents may be connected together and/or routed into a common, sound-insulated space so that noise associated with air pressure or vacuum release may be reduced. For example, when the occluder bladder 166 is vented to allow the spring plates 165 to move toward each other and occlude one or more lines, the air pressure released may be released into a sound insulated enclosure, as opposed to being released into a space where noise associated with the release may be heard more easily. In another embodiment, lines that are arranged to release air pressure may be connected together with lines that are arranged to release an air vacuum. With this connection (which may include a vent to atmosphere, an accumulator or other), noise generated by pressure/vacuum release may be further reduced.

Control System

The control system 16 described in connection with FIG. 1 has a number of functions, such as controlling dialysis therapy and communicating information related to the dialysis therapy. While these functions may be handled by a single computer or processor, it may be desirable to use different computers for different functions so that the implementations of those functions are kept physically and conceptually separate. For example, it may be desirable to use one computer to control the dialysis machinery and another computer to control the user interface.

Figure 45:
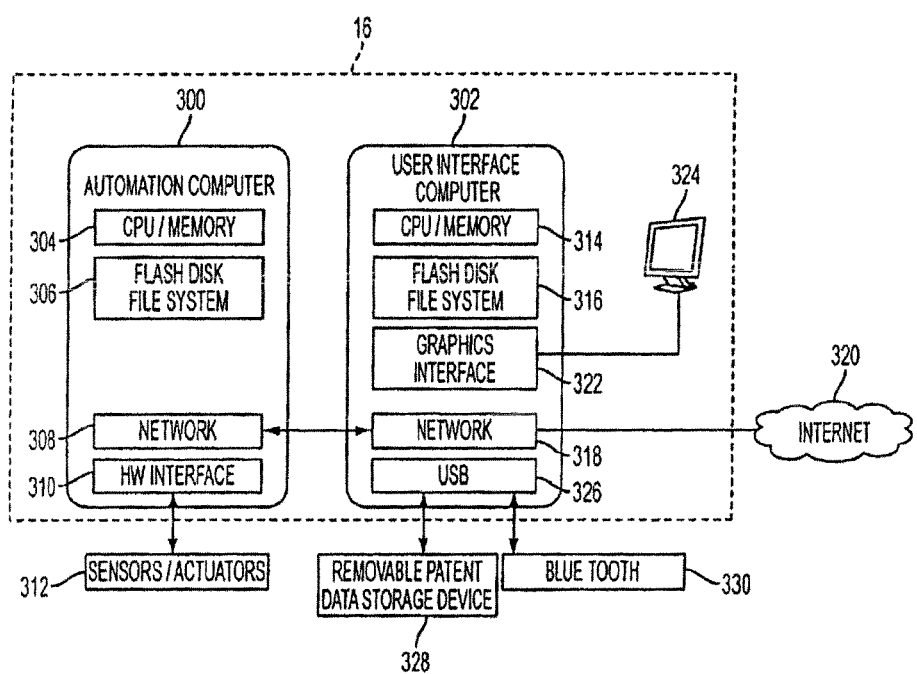
FIG. 45 is a schematic block diagram illustrating an exemplary implementation of control system for an APD system.

FIG. 45 shows a block diagram illustrating an exemplary implementation of control system 16, wherein the control system comprises a computer that controls the dialysis machinery (an "automation computer" 300) and a separate computer that controls the user interface (a "user interface computer" 302). As will be described, safety-critical system functions may be run solely on the automation computer 300, such that the user interface computer 302 is isolated from executing safety-critical functions.

The automation computer 300 controls the hardware, such as the valves, heaters and pumps, that implement the dialysis therapy. In addition, the automation computer 300 sequences the therapy and maintains a "model" of the user interface, as further described herein. As shown, the automation computer 300 comprises a computer processing unit (CPU)/memory 304, a flash disk file system 306, a network interface 308, and a hardware interface 310. The hardware interface 310 is coupled to sensors/actuators 312. This coupling allows the automation computer 300 to read the sensors and control the hardware actuators of the APD system to monitor and perform therapy operations. The network interface 308 provides an interface to couple the automation computer 300 to the user interface computer 302.

The user interface computer 302 controls the components that enable data exchange with the outside world, including the user and external devices and entities. The user interface computer 302 comprises a computer processing unit (CPU)/memory 314, a flash disk file system 316, and a network interface 318, each of which may be the same as or similar to their counterparts on the automation computer 300. The Linux operating system may run on each of the automation computer 300 and the user interface computer 302. An exemplary processor that may be suitable for use as the CPU of the automation computer 300 and/or for use as the CPU of the user interface computer 302 is Freescale's Power PC 5200B®.

Via the network interface 318, the user interface computer 302 may be connected to the automation computer 300. Both the automation computer 300 and the user interface computer 302 may be included within the same chassis of the APD system. Alternatively, one or both computers or a portion of said computers (e.g., display 324) may be located outside of the chassis. The automation computer 300 and the user interface computer 302 may be coupled by a wide area network, a local area network, a bus structure, a wireless connection, and/or some other data transfer medium.

The network interface 318 may also be used to couple the user interface computer 302 to the Internet 320 and/or other networks. Such a network connection may be used, for example, to initiate connections to a clinic or clinician, upload therapy data to a remote database server, obtain new prescriptions from a clinician, upgrade application software, obtain service support, request supplies, and/or export data for maintenance use. According to one example, call center technicians may access alarm logs and machine configuration information remotely over the Internet 320 through the network interface 318. If desired, the user interface computer 302 may be configured such that connections may only be initiated by the user or otherwise locally by the system, and not by remote initiators.

The user interface computer 302 also comprises a graphics interface 322 that is coupled to a user interface, such as the user interface 144 described in connection with FIG. 10. According to one exemplary implementation, the user interface comprises a display 324 that includes a liquid crystal display (LCD) and is associated with a touch screen. For example, a touch screen may be overlaid on the LCD so that the user can provide inputs to the user interface computer 302 by touching the display with a finger, stylus or the like. The display may also be associated with an audio system capable of playing, among other things, audio prompts and recorded speech. The user may adjust the brightness of the display 324 based on their environment and preference. Optionally, the APD system may include a light sensor, and the brightness of the display may be adjusted automatically in response to the amount of ambient light detected by the light sensor.

The brightness of the display may be set by the users for two different conditions: high ambient light and low ambient light. The light sensor will detect the ambient light level and the control system 16 will set the display brightness to the preselected levels for either high or low ambient light based on the measured ambient light. The user may select the brightness level for high and low ambient light by selection a value from 1 to 5 for each condition. The user interface may be a slider bar for each condition. In another example the user may select a number. The control system may set the button light levels to match the display light levels.

The LCD display and/or the touch screen of the display 324 may develop faults, where they do not display and/or respond correctly. One theory, but not the only theory, of the cause is an electro-static discharge from a user to the screen that changes the values in the memories of the drivers for the LCD display and touch screen. The software processes UIC executive 354 or the AC executive 354 may include a low priority sub-process or thread that checks the constant memory registers of the drivers for the touch screen and LCD display. If thread finds that any of the constant values in the memory registers are different from those stored elsewhere in the User Interface computer 302 or automation computer 300, then the thread calls for another software process to reinitialize the drivers for LCD display and/or the touch screen. In one embodiment, the LCD display is driven by a Kieko Epson S1d13513 chip and the touch screen is driven by Wolfson Microelectronics WM97156 chip. Examples of the constant register values include but are not limited to the number of pixels display on the screen, the number colors displayed.

Figure 65:
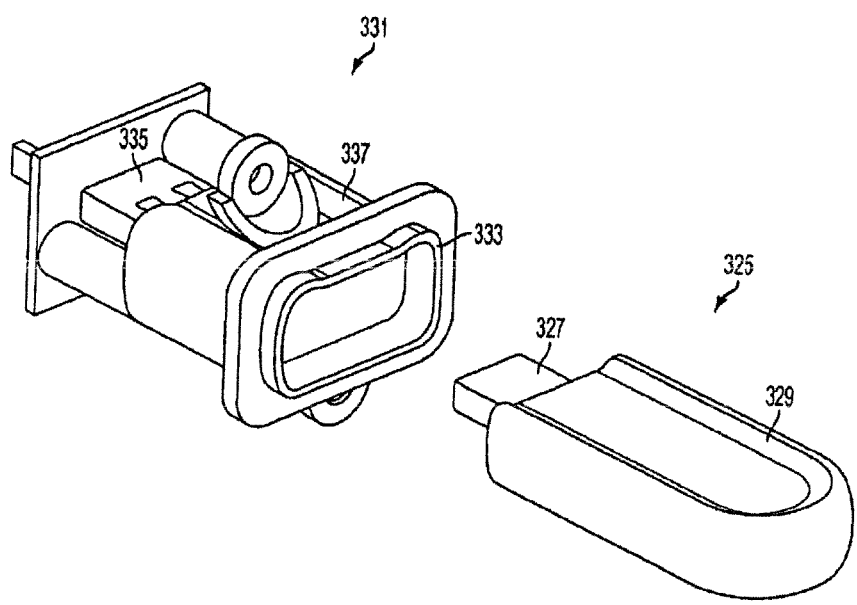
FIG. 65 shows an exemplary patient data key and associated port for transferring patient data to and from the APD system.

In addition, the user interface computer 302 comprises a USB interface 326. A data storage device 328, such as a USB flash drive, may be selectively coupled to the user interface computer 302 via the USB interface 326. The data storage device 328 may comprise a "patient data key" used to store patient-specific data. Data from dialysis therapies and/or survey questions (e.g., weight, blood pressure) may be logged to the patient data key. In this way, patient data may be accessible to the user interface computer 302 when coupled to the USB interface 326 and portable when removed from the interface. The patient data key may be used for transferring data from one system or cycler to another during a cycler swap, transferring new therapy and cycler configuration data from clinical software to the system, and transferring treatment history and device history information from the system to clinical software. An exemplary patient data key 325 is shown in FIG. 65.

As shown, the patient data key 325 comprises a connector 327 and a housing 329 coupled to the connector. The patient data key 325 may be optionally be associated with a dedicated USB port 331. The port 331 comprises a recess 333 (e.g., in the chassis of the APD system) and a connector 335 disposed within the recess. The recess may be defined, at least in part, by a housing 337 associated with the port 331. The patient data key connector 327 and the port connector 335 are adapted to be selectively electrically and mechanically coupled to each other. As may be appreciated from FIG. 65, when the patient data key connector 327 and the port connector 335 are coupled, the housing 329 of the patient data storage device 325 is received at least partially within the recess 333.

The housing 329 of the patient data key 325 may include visual cues indicative of the port with which it is associated and/or be shaped to prevent incorrect insertion. For example, the recess 333 and/or housing 337 of the port 331 may have a shape corresponding to the shape of the housing 329 of the patient data key 325. For example, each may have a non-rectangular or otherwise irregular shape, such as an oblong shape with an upper indentation as shown in FIG. 65. The recess 333 and/or housing 337 of the port 331 and the housing 329 of the patient data key 325 may include additional visual cues to indicate their association. For example, each may be formed of the same material and/or have the same or a similar color and/or pattern.

Figure 65A:
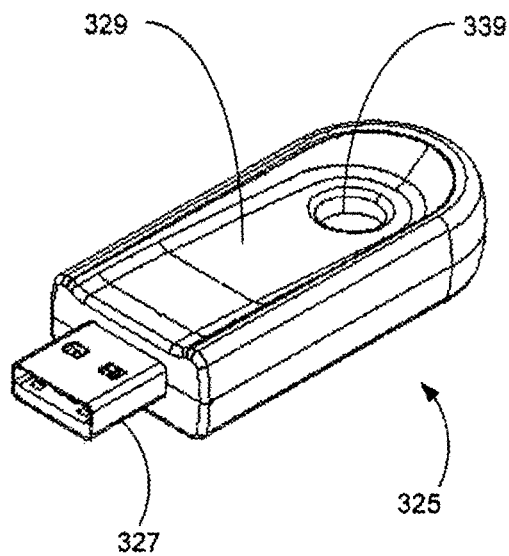
FIG. 65A shows a patient data key with an alternative housing configuration.

In a further embodiment, as shown in FIG. 65A, the housing 329 of the patient data key 325 may constructed to be sloped away from connector 327 to carry any liquids that may splash onto the key 325 away from connector 327 and toward the opposite end of the housing 329, where a hole 339 in the housing 329 may help drain the liquid off and away from the patient data key 325 and its coupling with the port connector 335.

In one embodiment, the port 331 and recess 333 are located on the front panel 1084 of cycler 14 as shown in FIG. 9-11. The patient data key 325 is inserted in the port 331 before the door 141 is closed and therapy is started. The door 141 includes a second recess 2802 to accommodate the patient data key 325, when the door 141 is closed. Locating the patient data key 325 behind the door 141 assures that all the therapy data may be recorded on to the PDK. This location prevents a user from removing the key mid-therapy.

Alternatively or additionally, the patient data key 325 may comprise a verification code that is readable by the APD system to verify that the patient data key is of an expected type and/or origin. Such a verification code may be stored in a memory of the patient data key 325, and be read from the patient data key and processed by a processor of the APD system. Alternatively or additionally, such a verification code may be included on an exterior of the patient data key 325, e.g., as a barcode or numeric code. In this case, the code may be read by a camera and associated processor, a barcode scanner, or another code reading device.

If the patient data key is not inserted when the system is powered on, an alert may be generated requesting that the key be inserted. However, the system may be able to run without the patient data key as long as it has been previously configured. Thus, a patient who has lost their patient data key may receive therapy until a replacement key can be obtained. Data may be stored directly to the patient data key or transferred to the patient data key after storage on the user interface computer 302. Data may also be transferred from the patient data key to the user interface computer 302.

In addition, a USB Bluetooth® adapter 330 may be coupled to the user interface computer 302 via the USB interface 326 to allow, for example, data to be exchanged with nearby Bluetooth®-enabled devices. For example, a Bluetooth®-enabled scale in the vicinity of the APD system may wirelessly transfer information concerning a patient's weight to the system via the USB interface 326 using the USB Bluetooth® adapter 330. Similarly, a Bluetooth®-enabled blood pressure cuff may wirelessly transfer information concerning a patient's blood pressure to the system using the USB Bluetooth® adapter 330. The Bluetooth® adapter may be built-in to the user interface computer 302 or may be external (e.g., a Bluetooth® dongle).

The USB interface 326 may comprise several ports, and these ports may have different physical locations and be used for different USB device. For example, it may be desirable to make the USB port for the patient data key accessible from the front of the machine, while another USB port may be provided at and accessible from the back of the machine. A USB port for the Bluetooth® connection may be included on the outside of the chassis, or instead be located internal to the machine or inside the battery door, for example.

As noted above, functions that could have safety-critical implications may be isolated on the automation computer. Safety-critical information relates to operations of the APD system. For example, safety-critical information may comprise a state of a APD procedure and/or the algorithms for implementing or monitoring therapies. Non safety-critical information may comprise information that relates to the visual presentation of the screen display that is not material to the operations of the APD system.

By isolating functions that could have safety-critical implications on the automation computer 300, the user interface computer 302 may be relieved of handling safety-critical operations. Thus, problems with or changes to the software that executes on the user interface computer 302 will not affect the delivery of therapy to the patient. Consider the example of graphical libraries (e.g., Trolltech's Qt® toolkit), which may be used by the user interface computer 302 to reduce the amount of time needed to develop the user interface view. Because these libraries are handled by a process and processor separate from those of the automation computer 300, the automation computer is protected from any potential flaws in the libraries that might affect the rest of the system (including safety-critical functions) were they handled by the same processor or process.

Of course, while the user interface computer 302 is responsible for the presentation of the interface to the user, data may also be input by the user using the user interface computer 302, e.g., via the display 324. To maintain the isolation between the functions of the automation computer 300 and the user interface computer 302, data received via the display 324 may be sent to the automation computer for interpretation and returned to the user interface computer for display.

Although FIG. 45 shows two separate computers, separation of the storage and/or execution of safety-critical functions from the storage and/or execution of non safety-critical functions may be provided by having a single computer including separate processors, such as CPU/memory components 304 and 314. Thus, it should be appreciated that providing separate processors or "computers" is not necessary. Further, a single processor may alternatively be used to perform the functions described above. In this case, it may be desirable to functionally isolate the execution and/or storage of the software components that control the dialysis machinery from those that control the user interface, although the invention is not limited in this respect.

Other aspects of the system architecture may also be designed to address safety concerns. For example, the automation computer 300 and user interface computer 302 may include a "safe line" that can be enabled or disabled by the CPU on each computer. The safe line may be coupled to a voltage supply that generates a voltage (e.g., 12 V) sufficient to enable at least some of the sensors/actuators 312 of the APD system. When both the CPU of the automation computer 300 and the CPU of the user interface computer 302 send an enable signal to the safe line, the voltage generated by the voltage supply may be transmitted to the sensors/actuators to activate and disable certain components. The voltage may, for example, activate the pneumatic valves and pump, disable the occluder, and activate the heater. When either CPU stops sending the enable signal to the safe line, the voltage pathway may be interrupted (e.g., by a mechanical relay) to deactivate the pneumatic valves and pump, enable the occluder, and deactivate the heater. In this way, when either the automation computer 300 or the user interface computer 302 deems it necessary, the patient may be rapidly isolated from the fluid path, and other activities such as heating and pumping may be stopped. Each CPU can disable the safe line at any time, such as when a safety-critical error is detected or a software watchdog detects an error. The system may be configured such that, once disabled, the safe line may not be re-enabled until both the automation computer 300 and user interface computer 302 have completed self-tests.

Figure 46:
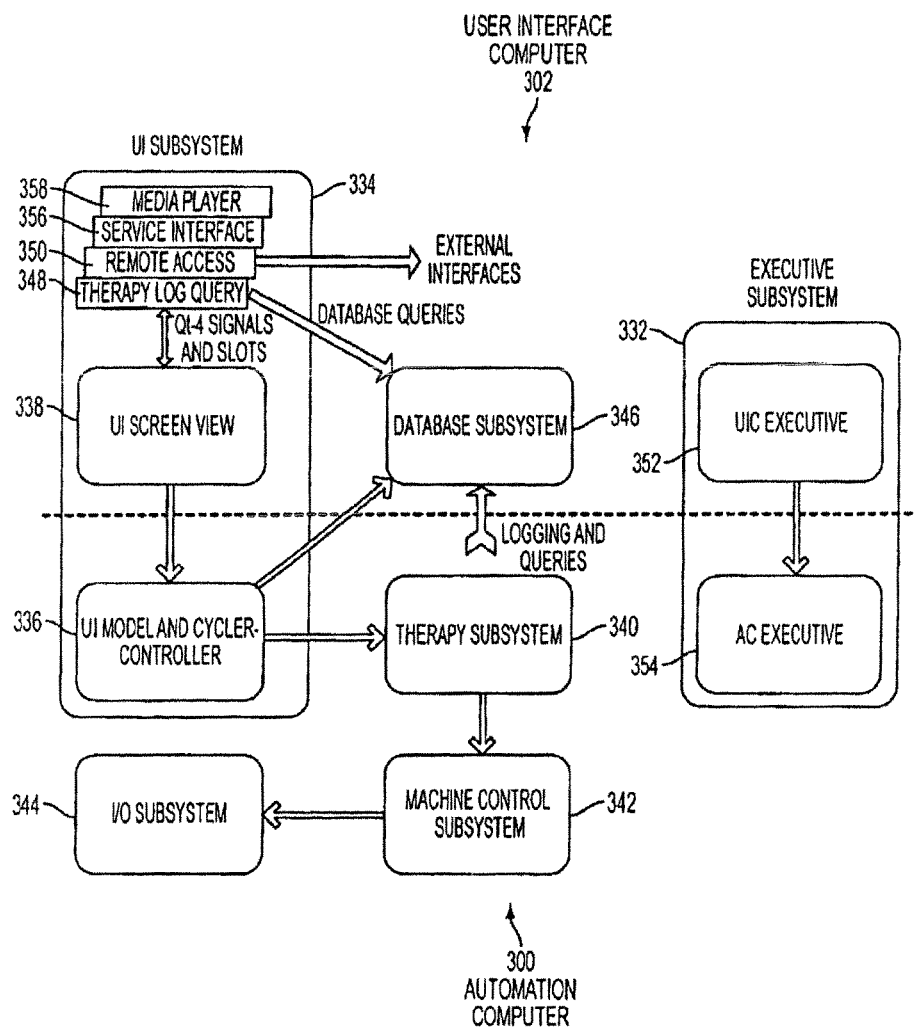
FIG. 46 is a schematic block diagram of illustrative software subsystems of a user interface computer and the automation computer for the control system of FIG. 45.

FIG. 46 shows a block diagram of the software subsystems of the user interface computer 302 and the automation computer 300. In this example, a "subsystem" is a collection of software, and perhaps hardware, assigned to a specific set of related system functionality. A "process" may be an independent executable which runs in its own virtual address space, and which passes data to other processes using inter-process communication facilities.

The executive subsystem 332 includes the software and scripts used to inventory, verify, start and monitor the execution of the software running on the CPU of the automation computer 300 and the CPU of the user interface computer 302. A custom executive process is run on each of the foregoing CPUs. Each executive process loads and monitors the software on its own processor and monitors the executive on the other processor.

The user interface (UI) subsystem 334, handles system interactions with the user and the clinic. The UI subsystem 334 is implemented according to a "model-view-controller" design pattern, separating the display of the data ("view") from the data itself ("model"). In particular, system state and data modification functions ("model") and cycler control functions ("controller") are handled by the UI model and cycler controller 336 on the automation computer 300, while the "view" portion of the subsystem is handled by the UI screen view 338 on the UI computer 302. Data display and export functionality, such as log viewing or remote access, may be handled entirely by the UI screen view 338. The UI screen view 338 monitors and controls additional applications, such as those that provide log viewing and a clinician interface. These applications are spawned in a window controlled by the UI screen view 338 so that control can be returned to the UI screen view 338 in the case of an alert, an alarm or an error.

The therapy subsystem 340 directs and times the delivery of the dialysis treatment. It may also be responsible verifying a prescription, calculating the number and duration of therapy cycles based upon the prescription, time and available fluids, controlling the therapy cycles, tracking fluid in the supply bags, tracking fluid in the heater bag, tracking the amount of fluid in the patient, tracking the amount of ultra-filtrate removed from patient, and detecting alert or alarm conditions.

The machine control subsystem 342 controls the machinery used to implement the dialysis therapy, orchestrating the high level pumping and control functionality when called upon by the therapy subsystem 340. In particular, the following control functions may be performed by the machine control subsystem 342: air compressor control; heater control; fluid delivery control (pumping); and fluid volume measurement. The machine control subsystem 342 also signals the reading of sensors by the I/O subsystem 344, described below.

The I/O subsystem 344 on the automation computer 300 controls access to the sensors and actuators used to control the therapy. In this implementation, the I/O subsystem 344 is the only application process with direct access to the hardware. Thus, the I/O subsystem 344 publishes an interface to allow other processes to obtain the state of the hardware inputs and set the state of the hardware outputs.

FPGA

In some embodiments, the Hardware Interface 310 in FIG. 45 may be a separate processor from the automation computer 300 and the User Interface 302 that may perform a defined set of machine control functions and provide an additional layer of safety to the cycler controller 16. A second processor, such as a field programmable gate array (FPGA) may increase the responsiveness and speed of the cycler 14 by moving some computing tasks from the automation computer 300 to the hardware interface 310 (e.g., an FPGA), so that the automation computer 300 can devote more resources to fluid management and therapy control, as these comprise resource-intensive calculations. The hardware interface 310 may control the pneumatic valves and record and temporarily store data from the various sensors. The real time control of the valves, pressure levels and data recording by the hardware interface 310 allows the automation computer 300 to send commands and receive data, when the software processes or functions running on the automation computer 300 are ready for them.

A hardware interface processor 310 may advantageously be implemented on any medical fluid delivery apparatus, including (but not limited to) a peritoneal dialysis cycler 14, in which fluid is pumped by one or more pumps and an arrangement of one or more valves from one or more source containers of fluid (e.g., dialysate solution bags, or a heater bag containing fluid to be infused) to a patient or user. It may also be implemented on a fluid delivery apparatus that is configured to pump fluid from a patient or user (e.g., peritoneal dialysis cycler) to a receptacle (e.g., drain bag). A main processor may be dedicated to controlling the proper sequence and timing of pumps and valves to perform specific functions (e.g., pumping from a solution bag to a heater bag, pumping from a heater bag to a user, or pumping from a user to a drain receptacle), and to monitor the volumes of fluid pumped from one location to the next. A secondary (hardware interface) processor (e.g. an FPGA) may correspondingly be dedicated to collect and store data received from various sensors (e.g., pressure sensors associated with the pumps, or temperature sensors associated with a heating system) at an uninterrupted fixed rate (e.g., about 100 Hz or 200 Hz), and to store the data until it is requested by the main processor. It may also control the pumping pressures of the pumps at a rate or on a schedule that is independent from any processes occurring in the main processor. In addition to other functions (see below) it may also open or close individual valves on command from the main processor.

In one example the Hardware Interface 310 may be a processor that performs a number of functions including but not limited to:

Acquiring pneumatic pressure sensor data on a predictable and fine resolution time base;
Storing the pressure data with a timestamp until requested by automation computer 300;
Validating the messages received from that automation computer 30;
Providing automated control of one or more pneumatic valves
Controlling some valves with a variable pulse width modulation (PWM) duty cycle to provide Pick & Hold functionality and/or control some valves with current feedback;

Provide automated and redundant safety checking of valve combinations, maximum pressures and temperatures and ability.

Independent of the other computers 300, 302 putting the cycler 14 into a failsafe mode as needed.

Monitoring status of buttons on the cycler 14 and controlling the level of button illumination;

Controlling the Auto Connect screw-drive mechanism 1321 and monitoring the Auto-Connect position sensing;

Detecting the presence of solution caps 31 and/or spike caps 63;

Control of the pneumatic pump;

Control of the prime sensor LED and detector;

Detecting over-voltages and testing hardware to detect over-voltages;

Controlling and monitoring one or more fluid detectors;

Monitoring the latch 1080 and proximity sensor 1076 on the door 141;

Monitoring critical voltages at the system level.

The Hardware Interface 310 may comprise a processor separate from the processors in the automation computer 300 and user interface 302, A to D converts and one or more IO boards. In another embodiment, the hardware interface is comprised of a FPGA (Field Programmable Gate Array). In one embodiment the FPGA is a SPARTAN® 3A in the 400K gate and 256 ball package made by Xilinx Inc. of California. The Hardware Interface 310 is an intelligent entity that is employed to operate as an independent safety monitor for many of the Control CPU functions. There are several safety critical operations where either the Hardware Interface or the Control CPU serves as a primary controller and the other serves as a monitor.

The hardware interface 310 serves to monitor the following automation computer 300 functions including but not limited to:

Monitoring the integrity of system control data being received from the automation computer 300;

Evaluating the commanded valve configurations for combination that could create a patient hazard during therapy;

Monitoring the fluid and pan temperature for excessive high or low temperatures;

Monitoring and testing the overvoltage monitor; and

Provide a means for the automation computer 300 to validate critical data returned from the hardware interface.

Figure 45A:
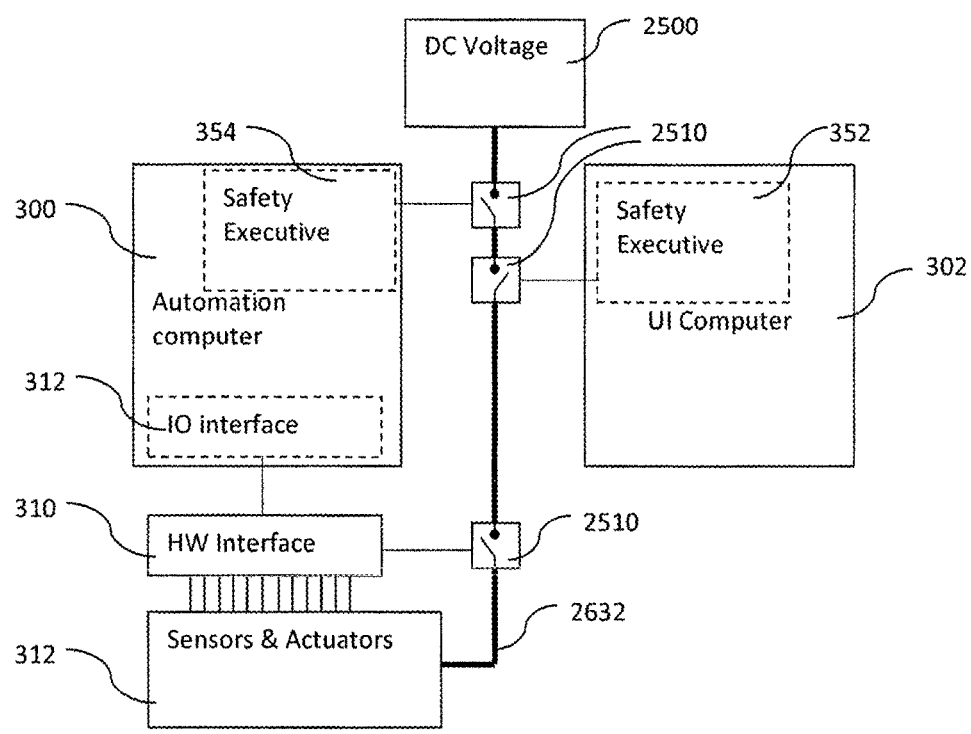
FIG. 45A is a schematic block diagram illustrating an exemplary arrangement of the multiple processors controlling the cycler and the safe line.

FIG. 45A is a schematic representation of one arrangement of the automation computer 300, the UI computer 302 and the hardware interface processor 310. The hardware interface 310 is connected via a communication line to the automation computer 300 and connects to the sensors and actuators 312 in the cycler 14. A voltage supply 2500 provides power for the safety critical actuators that can be enabled or disabled by any of the computers 300, 302, 310. The safety critical actuators include but are not limited to the pneumatic valves, the pneumatic pump and a safety relay on the heater circuit. The pneumatic system is configured to safe condition when unpowered. The pneumatic safe condition may include occluding the lines 28, 34 to the patient, isolating the control chambers 171 and/or closing all the valves 184, 186, 190, 192, on the cassette 24. The safety relay 2030 in the heater circuit 2212 is open, preventing electrical heating, when the relay is unpowered. Each computer 300, 302, 310 controls a separate electrical switch 2510 that can each interrupt power to the valves, pump and safety relay. If any of the three computers detects a fault condition, it can put the cycler 14 in a failsafe condition by opening one of the three switches 2510. The electrical switches 2510 are controlled by the safety executive process 352, 354 in the UI computer 302, and automation computer 300 respectively.

Figure 45B:
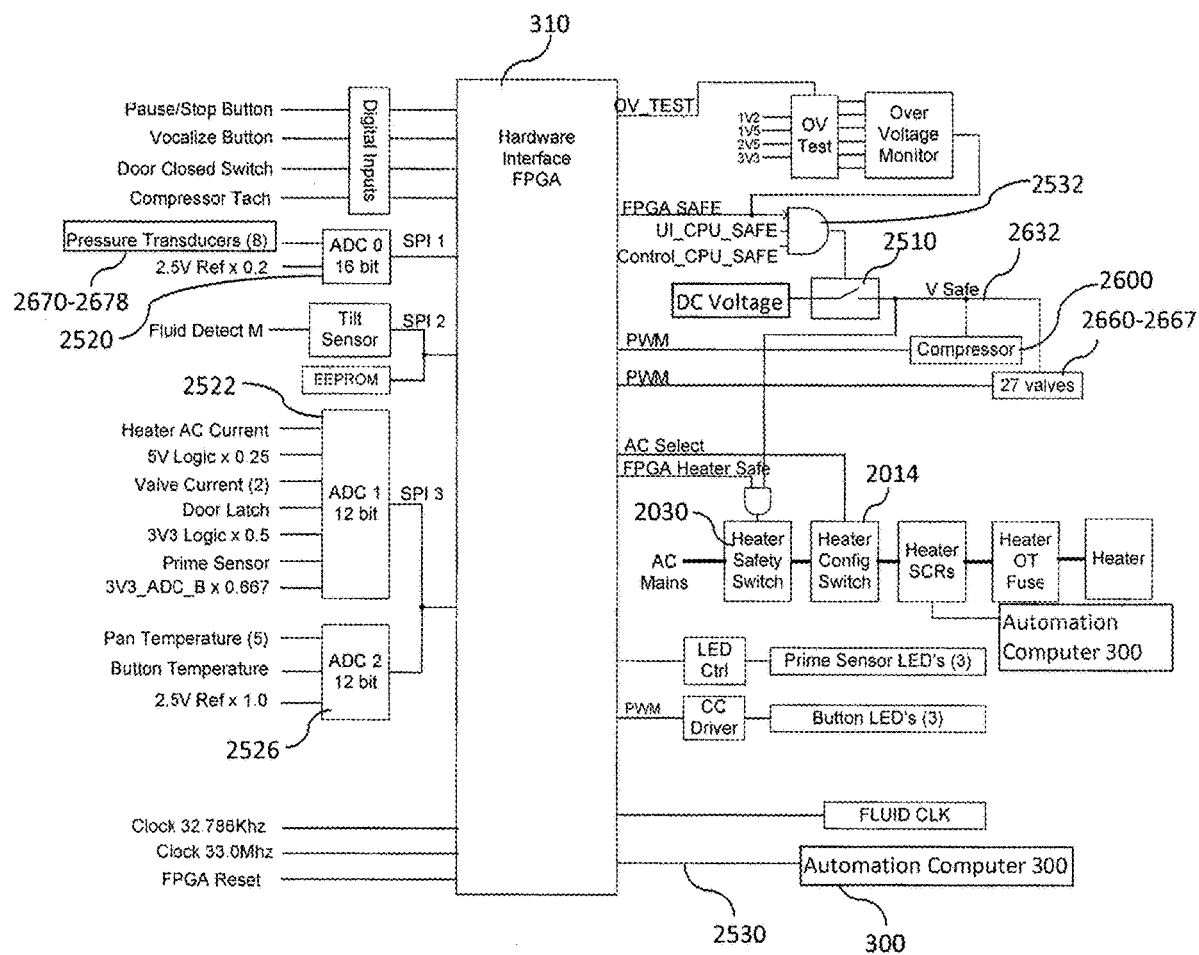
FIG. 45B is a schematic block diagram illustrating exemplary connections between the hardware interface processor and the sensors, the actuators and the automation computer.

FIG. 45B is a schematic illustration of the connections between the Hardware Interface 310, the various sensors, the pneumatic valves, the bag heater and the automation computer 300. The Hardware Interface 300 controls each of the pneumatic valves 2660-2667 and the pneumatic pump or compressor 2600 via pulse-width-modulated DC voltages. FIG. 45B presents an alternative embodiment of the safe line 2632 supplying power to the pneumatic valves 2660-2667, pump 2600 and heater safety relay 2030, in which a single switch 2510 is driven by an AND gate 2532 connected to the three computers 300, 302, 310. The prime sensor is controlled and monitored by the Hardware Interface 310. The brightness of the button LEDs is controlled by the Hardware Interface 310 via a PWM'd voltage.

The data signals from the buttons, pressure sensors, temperature sensors and other elements listed in FIG. 45B are monitored by the Hardware Interface 310, and the data is stored in a buffer memory until called for by the automation computer 300. The digital inputs are connected directly to the Hardware Interface 310. The analog signals from pressure, temperature, current sensors and others are connected to Analog-to-Digital-Converter (ADC) boards that convert the analog signals to digital values and may a scale and/or offset the digital values. The outputs of the ADCs are communicated over SPI buses to the Hardware Interface 310. The data is recorded and stored in the buffer at a fixed rate. Some of the data signals may be recorded at a relatively slow rate, including the pressure data on the pressure reservoirs and the fluid trap, temperatures, and current measurements. The low speed data may be recorded at 100 Hz. The adiabatic FMS volume measurement algorithm can be improved with high speed pressure data that is recorded at regular intervals. In a preferred embodiment, the pressure data from the sensors on the control volume 171 and the reference chamber 174 are recorded at 2000 Hz. The data may be stored in random-access-memory (RAM) along with a time stamp. The rate of data collection may preferably proceed independently of the automation computer 300 and of processes or subroutines on the hardware interface. The data is reported to the automation computer 300, when a process calls for that value.

The transfer of data between the hardware interface 310 to the automation computer 300 may occur in a two step process where a data packet transferred and stored in a buffer before being validated and then accepted for use by the receiving computer. In one example, the sending computer transmits a first data packet, followed by a second transmission of the cyclic redundancy check (CRC) value for the first data packet. The receiving computer stores the first data packet in a memory buffer and calculates a new CRC value first data packet. The receiving computer then compares the newly calculated CRC value to the CRC value received and accepts the first data packet if the two CRC values match. The cyclic redundancy check (CRC) is an error-detecting code commonly used in digital networks and storage devices to detect accidental changes to raw data. Blocks of data entering these systems get a short check value attached, based on the remainder of a polynomial division of their contents; on retrieval the calculation is repeated, and corrective action can be taken against presumed data corruption if the check values do not match. The data is not transferred between the automation computer and hardware interface if CRC values do not match. If multiple consecutive data packets fail the CRC test, the receiving computer may signal an alarm and put the machine in a fail-safe condition by de-energizing the safe line 2632. In one example, the alarm condition occurs on the third consecutive failed CRC check.

The automation computer 300 passes commands to open selected valves and set specified pressures in specified volumes to the hardware interface 300. The hardware interface 310 in turn controls the valve position by providing a PWM'd voltage to each valve. The hardware interface 310 opens valves as requested with a pick-and-hold algorithm, where the valve is initially actuated with a high voltage or current, and then held in place with a lower voltage or current. Pick-and-hold operation of valves may advantageously reduce the power draw and the level of heat dissipation inside the cycler 14.

The hardware interface 310 controls the pressure in the specified volume by opening and closing the valves between the specified volume and the appropriate pressure reservoir based on the measured pressure in the specified volume. The hardware interface 310 may also control the pressure in the pressure reservoirs by opening and closing the valves between a pneumatic pump and one of the pressure reservoirs based on the measured pressure in the reservoir. The specified volumes may include each of the control chambers 171, the reference volumes 174, the fluid trap and the positive and negative reservoirs. The hardware interface 310 may control the pressure in each of these specified volumes via a number of control schemes, including but not limited to on-off control, or proportional control of the valve with a PWM signal. In one example, as described above, the hardware interface 310 implements an on-off controller, sometimes referred to as a bang-bang controller, which sets a first and second limit and closes the valve when the pressure exceeds the upper second limit and opens the valve when the pressure is less than the first lower limit. In another example, the hardware interface 310 may operate valves between the specified volume and both pressure reservoirs to achieve a desired pressure. In other examples the automation computer 300 may specify one or more valves and command a specific valve to control the pressure as measured by a specified sensor.

The hardware interface 310 controls the position and operation of the Auto-Connect carriage. The movement and positioning of the Auto-Connect carriage 146 is controlled in real time by the hardware interface based on the measured position of the carriage 146. The automation computer 300 may command a particular function or position for the carriage. The hardware interface 310 carries out the commanded function without burdening memory or processing of the automation computer 300. The positioning of the carriage 146 is controlled with a feedback loop from a position sensor. In addition, the FPGA detects the presence of solution caps 31 and/or spike caps 63 with sensing elements 1112 as described above. Alternatively, the presence of the caps 31 and/or spike caps 63 can be detected by a range of sensing technologies, including but not limited to vision systems, optical sensors that can be blocked by a solution cap and/or spike cap, or, for example, a microswitch on the stripper element 1491.

The hardware interface 310 may implement safety functions independently of the automation computer 300 or the user interface computer 302. The independent action of the hardware interface 310 to disable the safety line 2632 and/or signal an alarm to the safety executives 352, 354 further reduces the possibility of an unsafe condition occurring. The hardware interface 310 may send an alarm and/or de-energize the safe line 2632 for defined valve combinations at any time. Shutting the cycler down based on disallowed valve positions protects the patient and preserves the ability to complete the therapy (after a reset if needed). The hardware interface 310 may also alarm and de-energize the safe line at unsafe conditions including excessive temperature on the heater pan and/or bag button, excessive pressure in control chamber or reservoir. The hardware interface may alarm and de-energize the safe line when water is detected in the fluid trap.

Heater Control System

The control systems described above may be used to ensure that the solution delivered to a patient is maintained within a pre-determined range of temperatures. During the therapy process, the cycler 14 fills the heater bag 22 with solution from the connected solution containers 20, via a heater bag line 26. The heater bag 22 rests on the heater pan 142 which may include electrical resistance heaters. The heater bag 22 may be covered with an insulated cover 143. A heater controller may function so as to control the thermal energy delivered to the heater pan 142 in order to control the temperature of the solution to a desired set point prior to delivering the solution to the patient. The solution temperature should be within a safe range prior to being delivered to the patient's abdominal cavity in order to avoid injuring or causing discomfort to the patient, or causing hypothermia or hyperthermia. The heater controller may also limit the temperature of the heater pan to touch-safe temperatures. The heater controller is constructed to heat and maintain the solution within a range of acceptable temperatures in a timely manner in order to ensure the most effective therapy.

Figure 49:
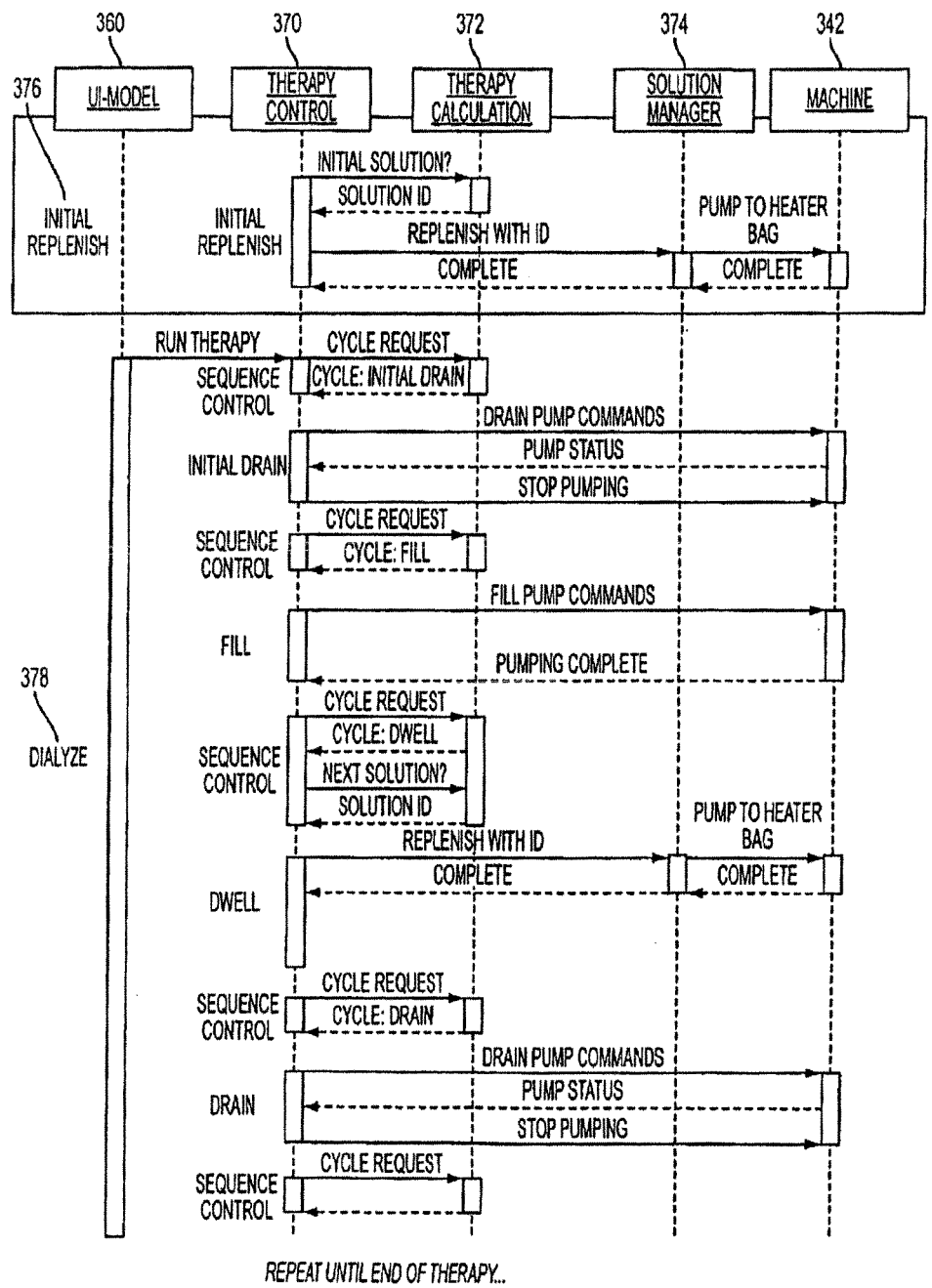
FIG. 49 shows a sequence diagram depicting exemplary interactions of therapy module processes during initial replenish and dialyze portions of the therapy.
Figures 1, 49:
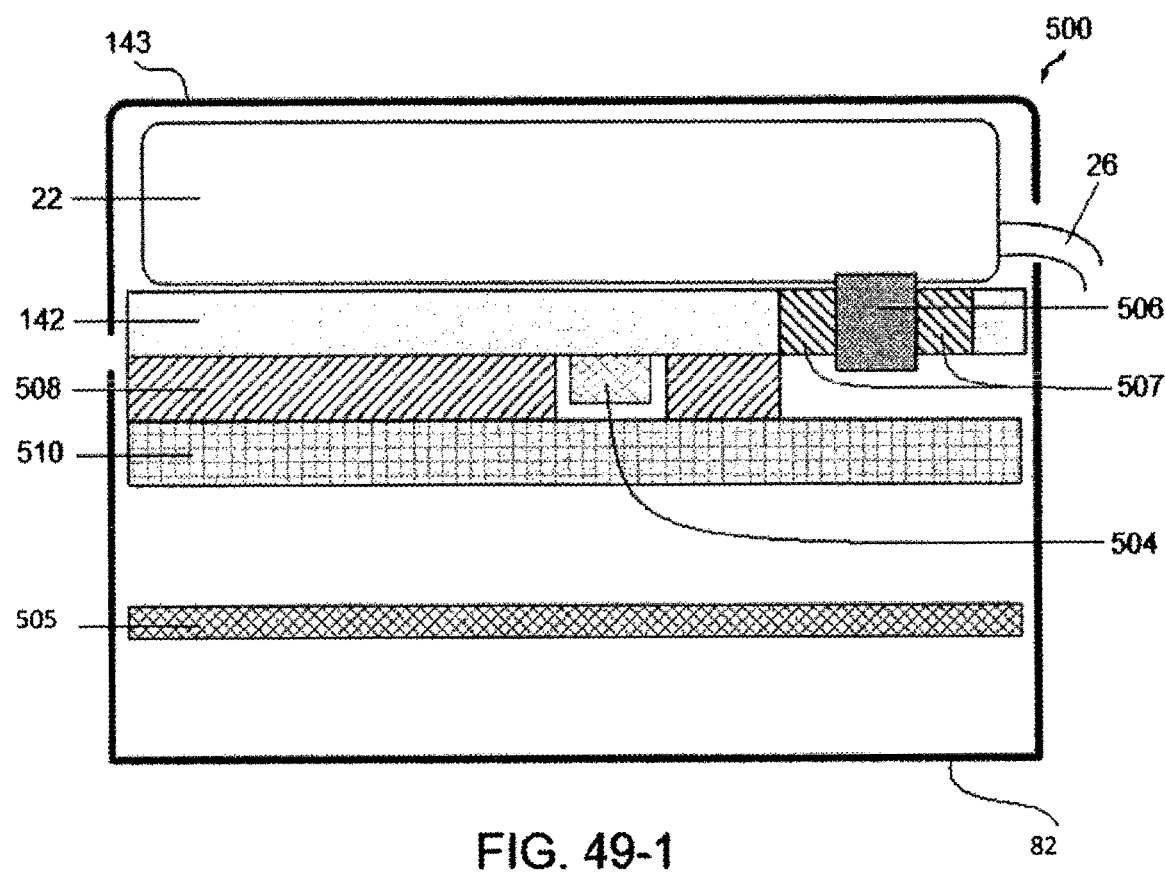
Figures 2, 49:
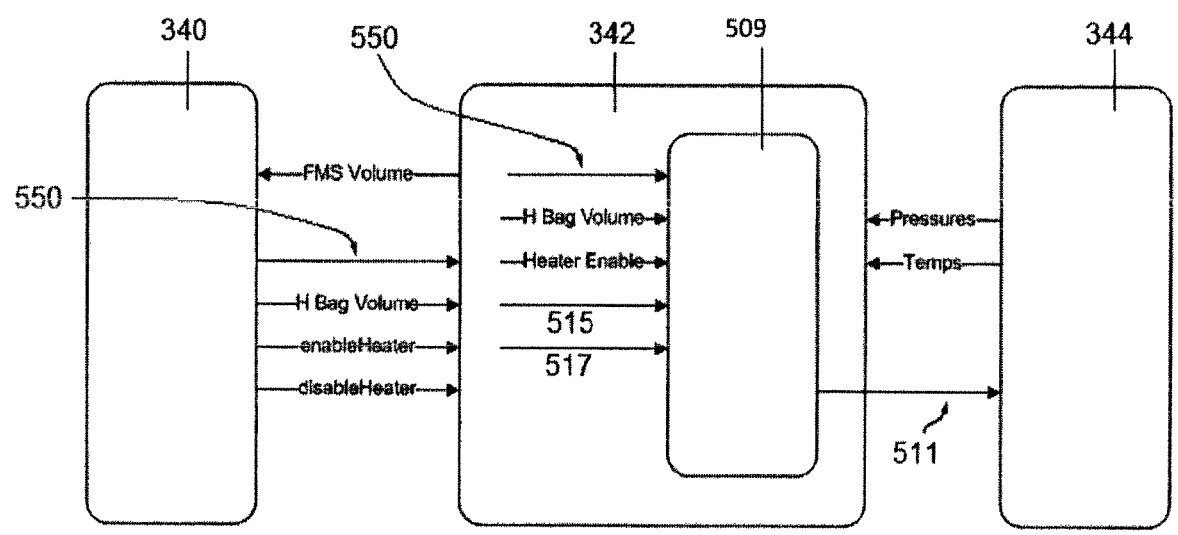
Figures 3, 49:
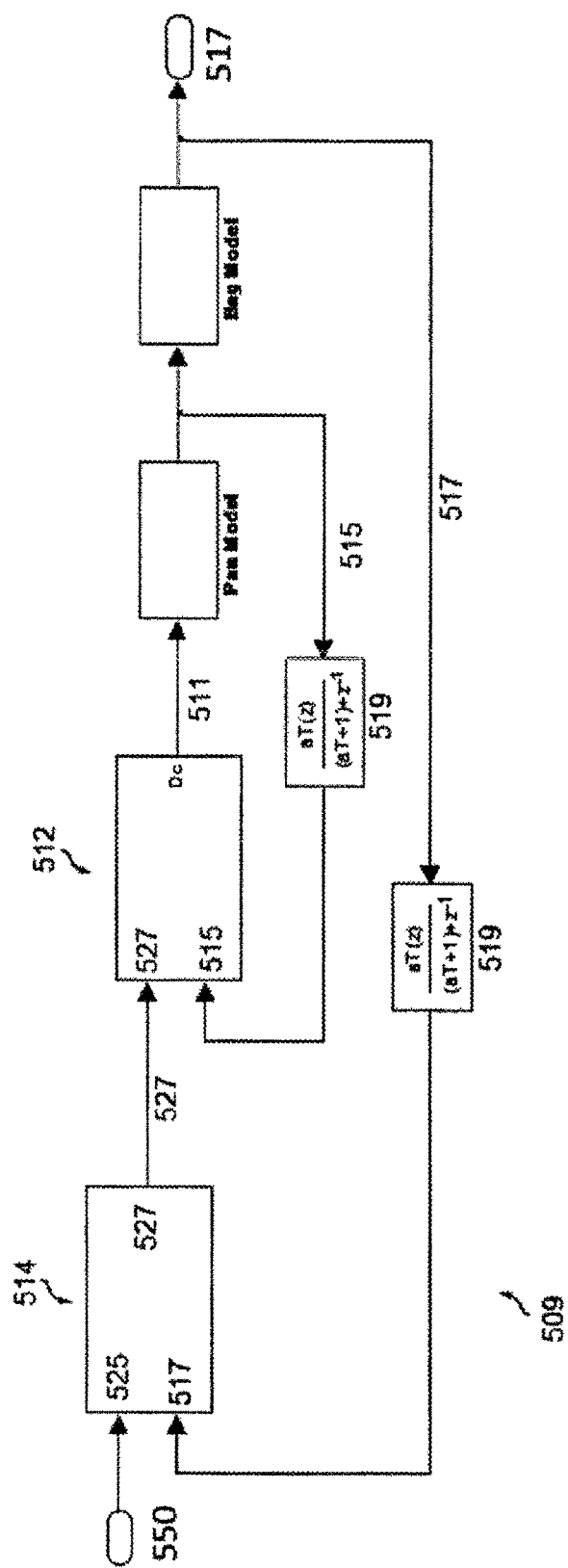
Figures 4, 49:
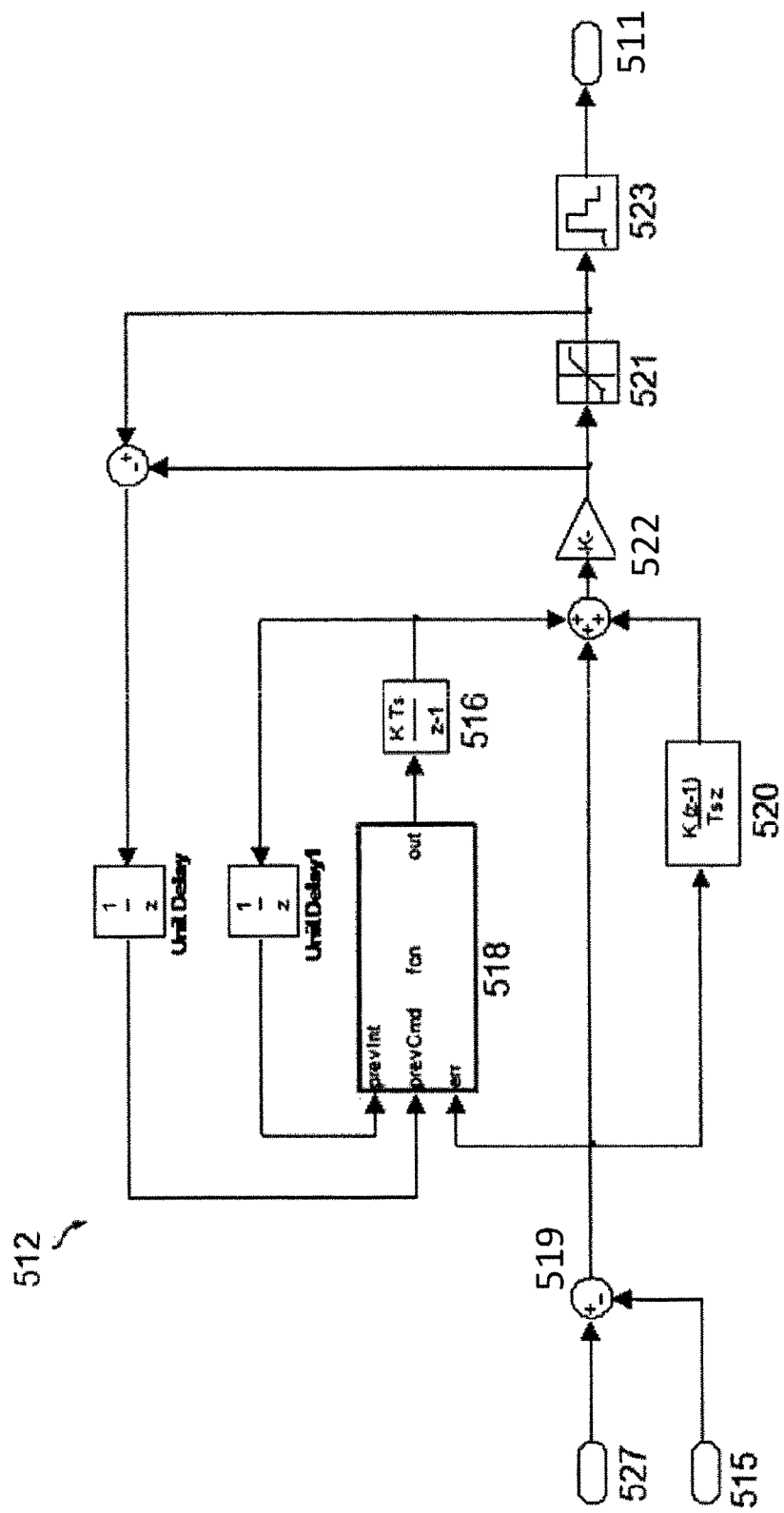
Figures 5, 49:
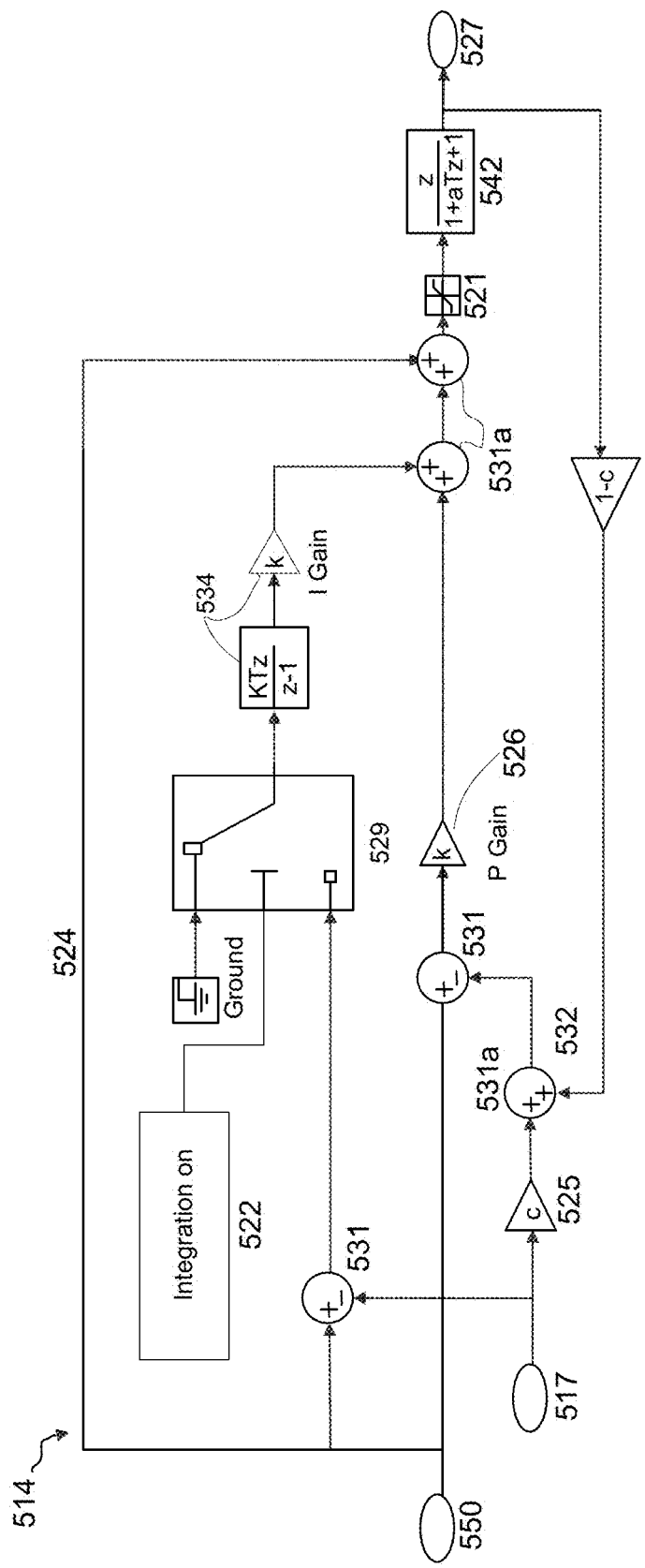
Figures 6, 49:
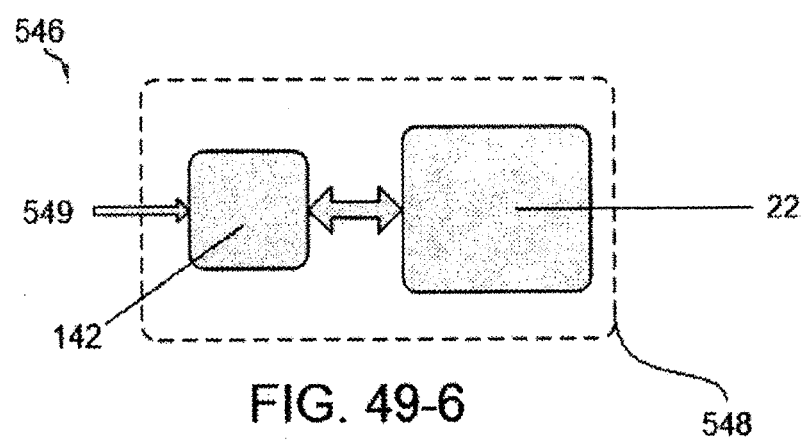
Figures 7, 49:
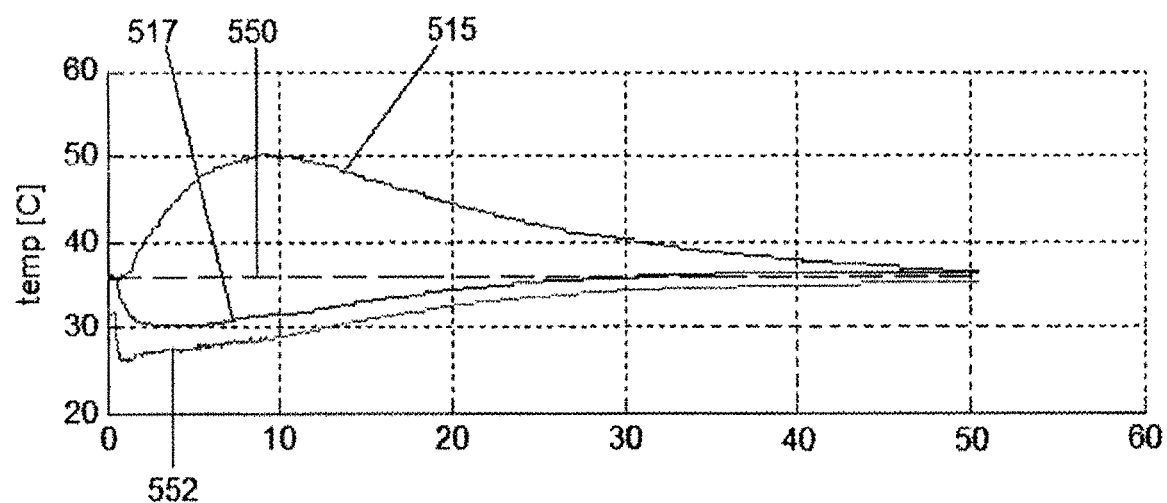
Figures 8, 49:
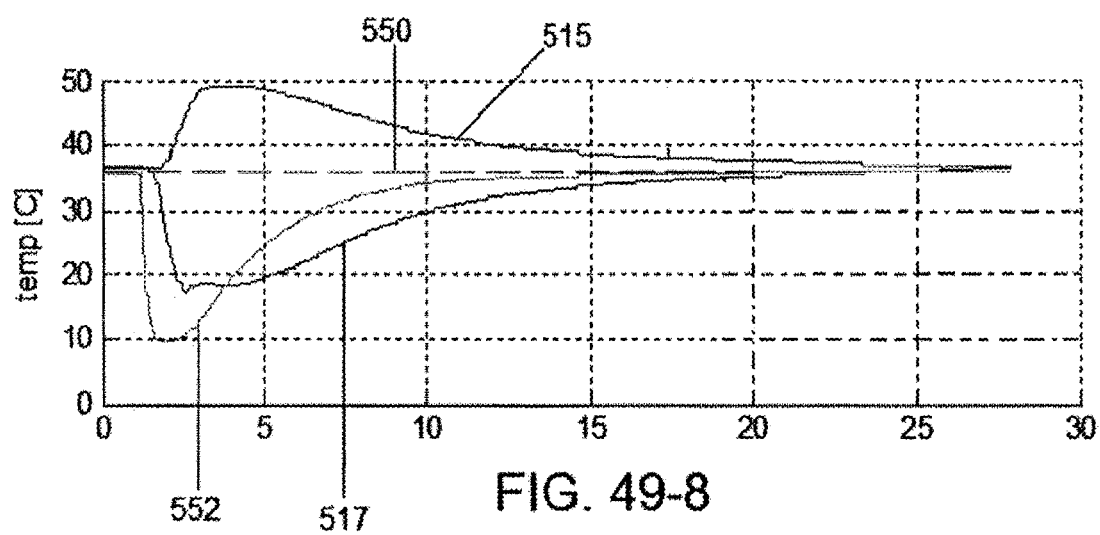
Figures 9, 49:
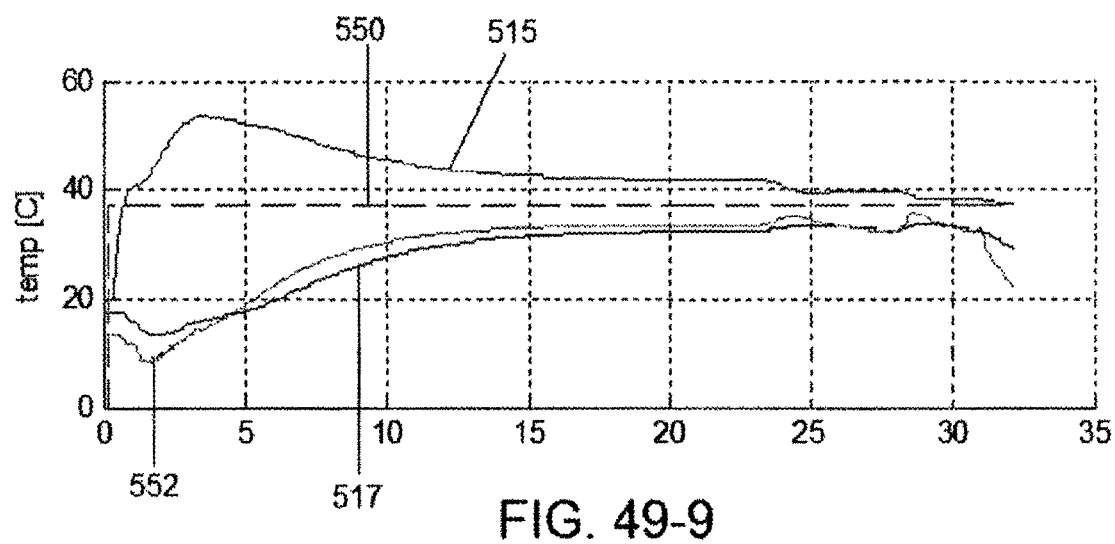
Figures 10, 49:
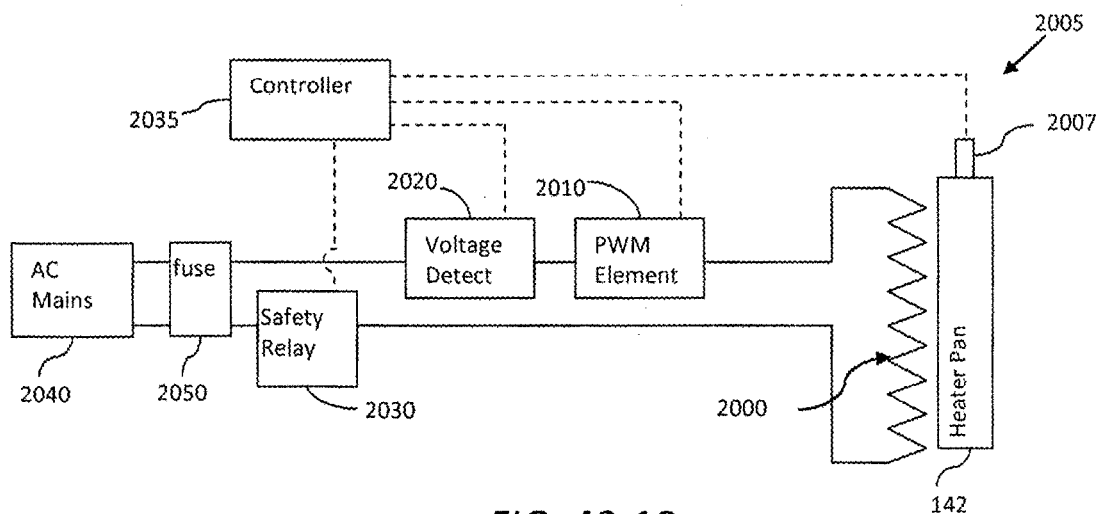
Figures 11, 49:
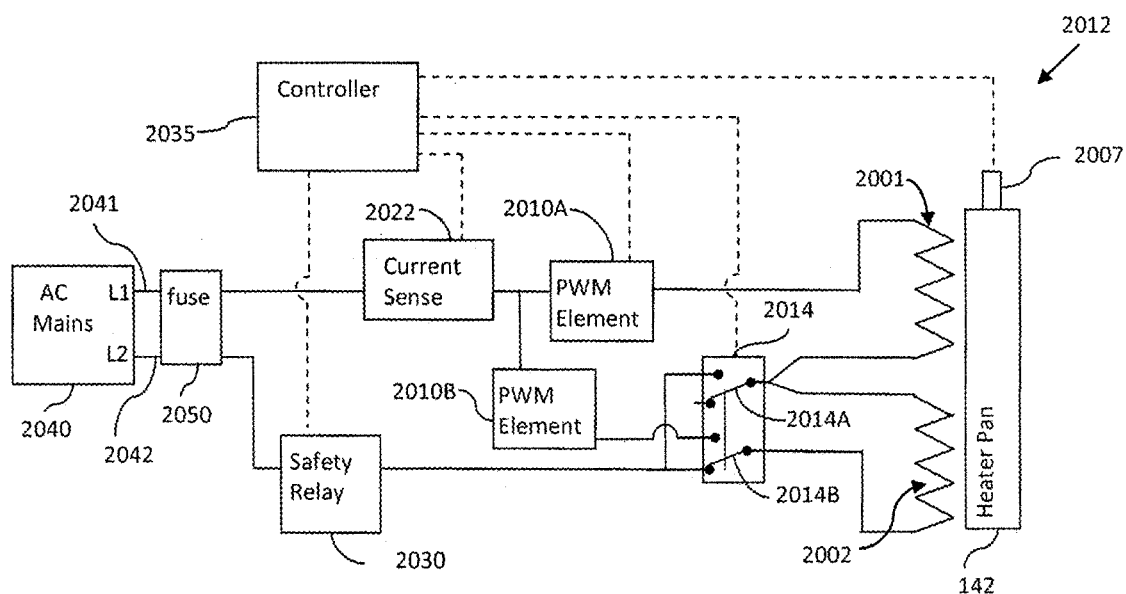
Figures 12, 49:
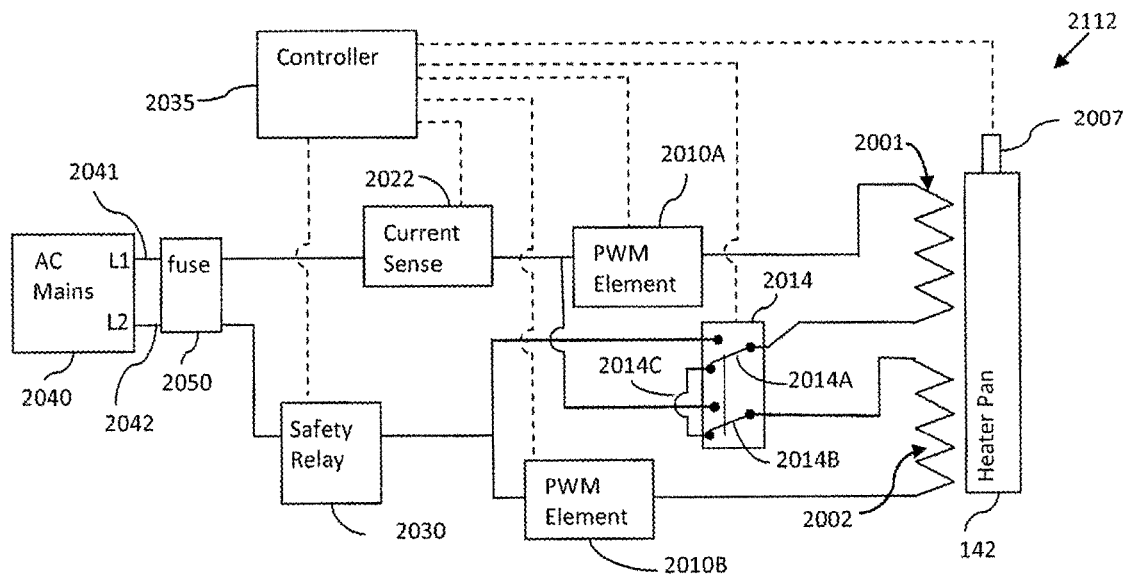
Figures 13, 49:
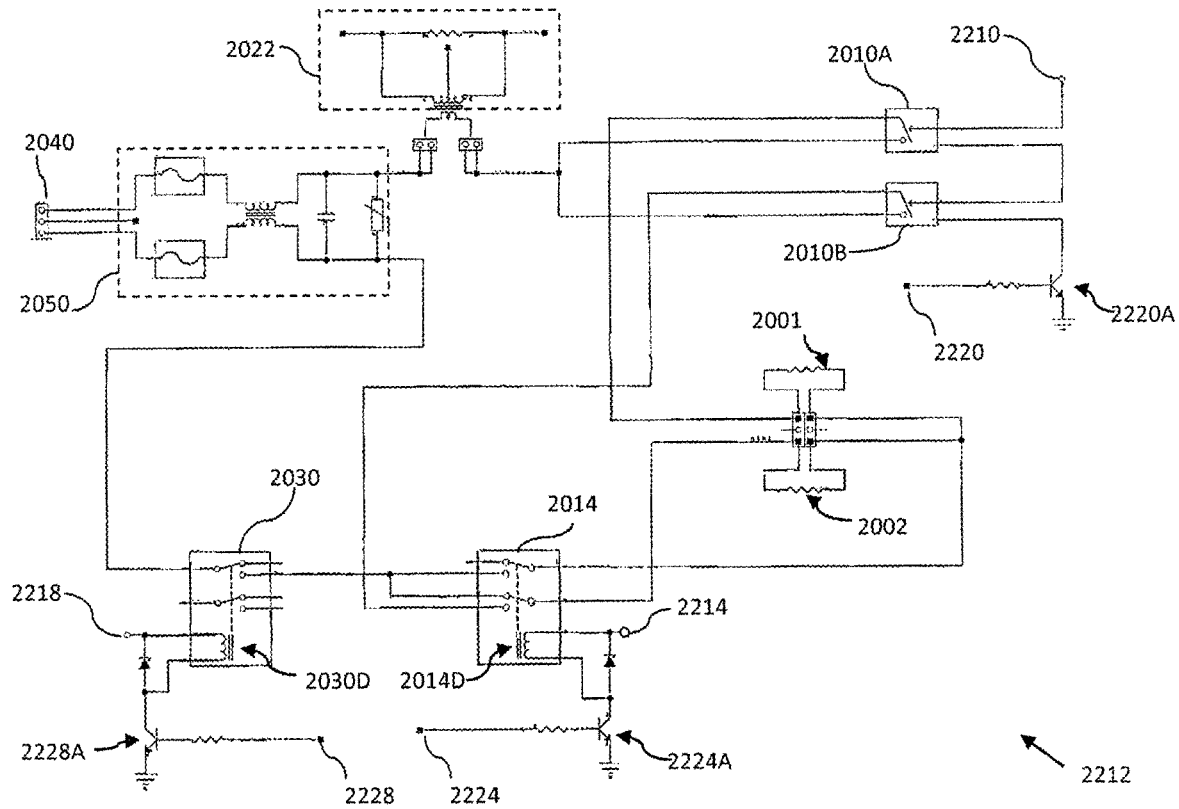
Figures 14, 49:
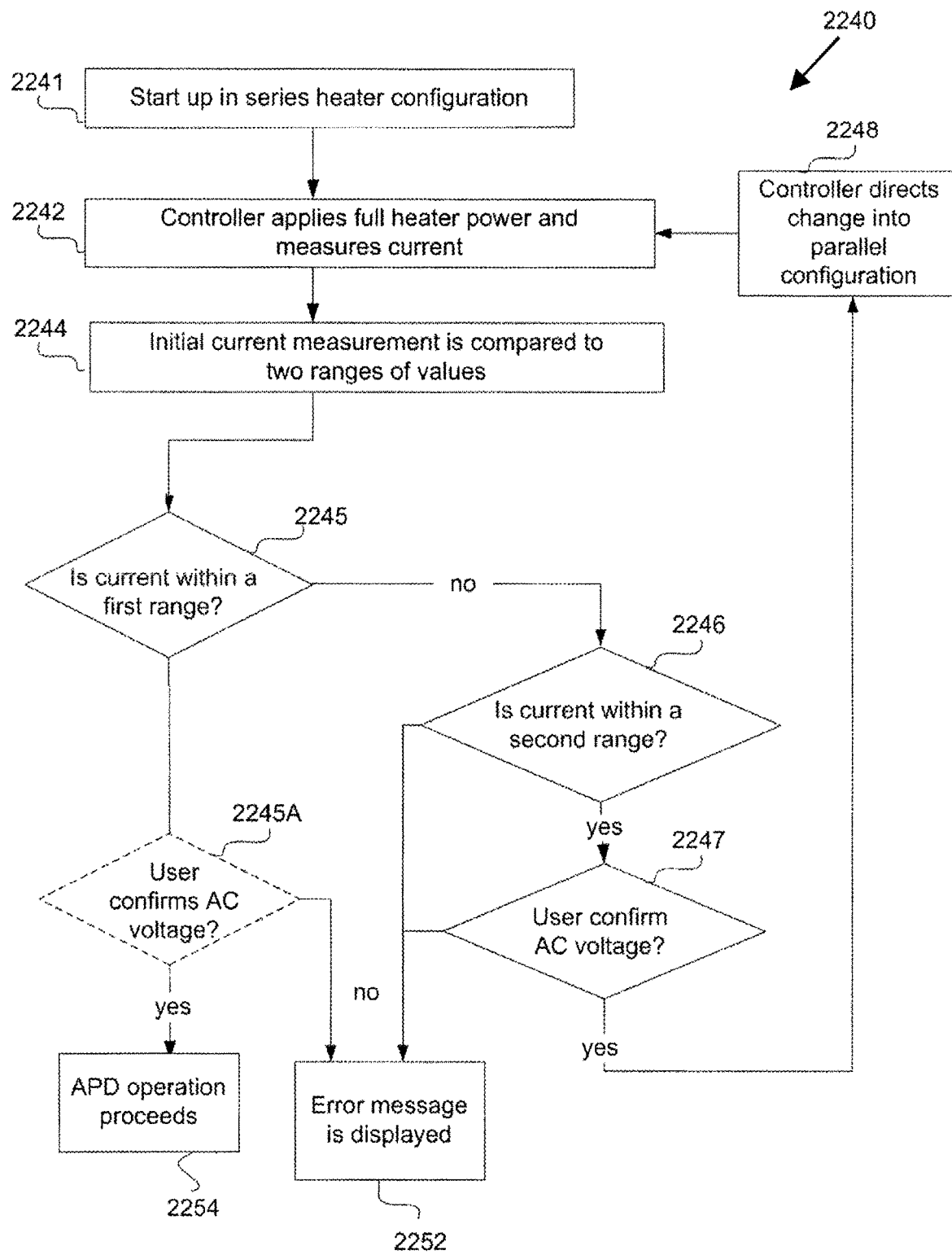
Figures 15, 49:
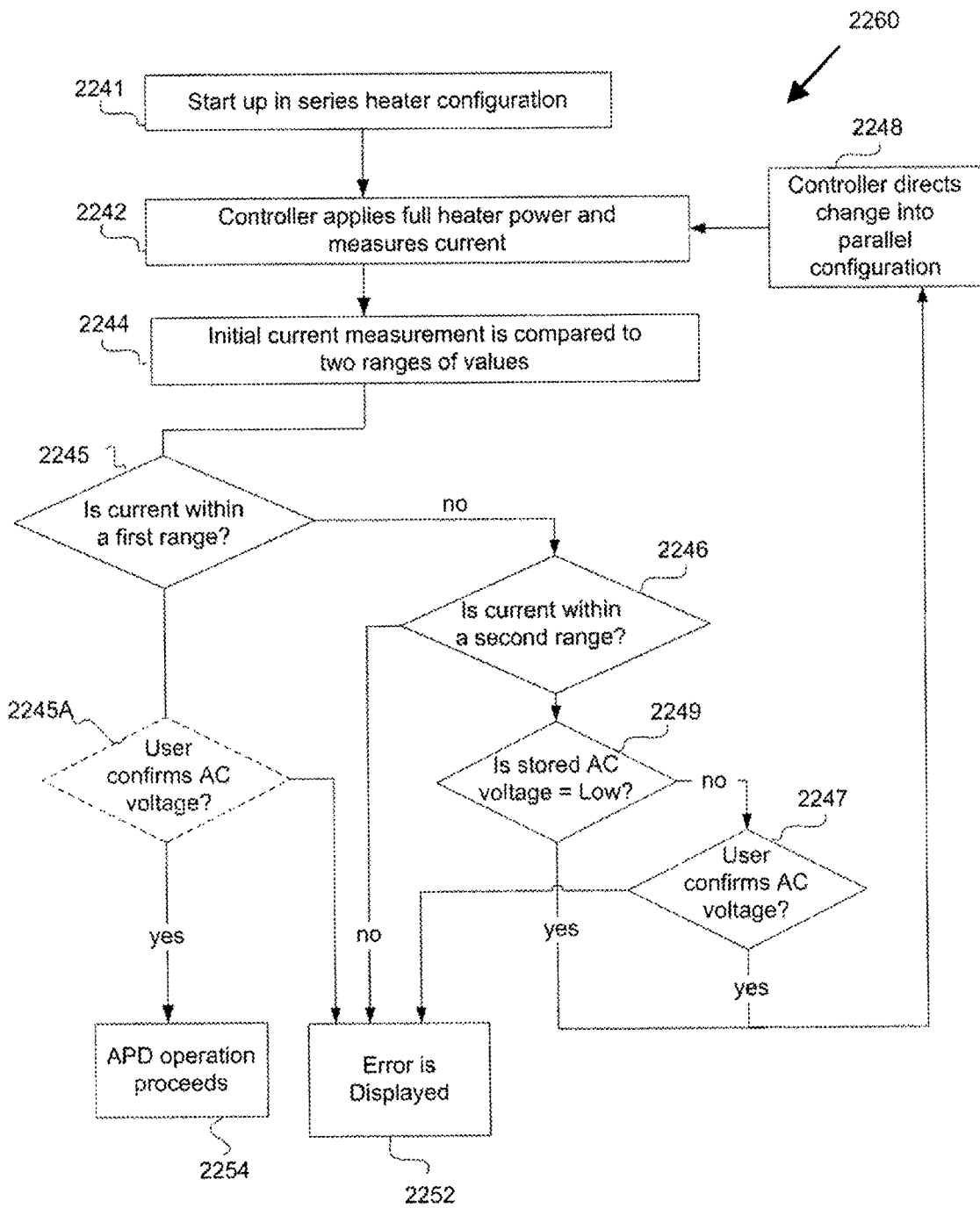

FIG. 49-1 is a schematic view of an exemplary embodiment of a solution heater system 500. In this example, the solution heater system 500 is located within the housing 82 of the cycler 14. The housing includes an insulated lid 143 that may be affixed to the top of the housing 82. The housing 82 and the heater lid 143 may therefore define a region that serves to house the components of the solution heater system 500. The solution heater system may include the following elements: housing 82, heater lid 143, heater pan 22, heater elements 508, heater pan temperature sensors 504, button temperature sensor 506, insulating ring 507 and heater control electronics 50. The heater pan 142 is positioned inside the housing 82, and may accommodate a heater bag 22 when positioned on top of the heater tray 142. Preferably, the heater pan 142 is inclined to place the inlet and/or outlet of the heater bag in a dependent position, to help ensure that fluid in the bag is always in contact with the inlet/outlet regardless of the amount of fluid in the bag. In an embodiment, there can be up to six or more heater pan temperature sensors 504 (only one exemplary heater pan temperature sensor 504 is shown in FIG. 49-1) positioned along the floor of the heater pan 142. Additionally, there may be a button temperature sensor 506 positioned within the heater pan 142. The button sensor 506 is positioned to make good thermal contact with the heater bag, while being thermally isolated from the heater pan 142 by an insulating ring 507, in order to provide an approximation of the temperature of the fluid or dialysate in the bag. In another embodiment, the button sensor 506 may comprise a pair of thermistors mounted on an aluminum button. The aluminum button is thermally isolated by an insulating ring made of, for example, LEXAN® 3412R plastic or another low thermal conductivity material. The button temperature sensor 506 may be located near the end of the tray where the fluid lines connect to the heater bag 22 in order to better measure the temperature of the fluid within the heater bag when the heater bag is less than approximately one-third full. The button sensor 506 may also be referred to as the fluid or dialysate temperature sensor. There may also be a plurality of heater elements 508 positioned under the heater pan 142, more toward the superior end of the pan, with the bag sensor located more toward the dependent portion of the pan, in order for the sensor to provide a more accurate reading of the fluid temperature within the bag, and to be relatively unaffected by the heater elements 508. The thermal output of the heater elements 508 may be controlled by the heater control electronics 505 to achieve the desired fluid temperature in the heater bag. The heater control electronics 505 may include but not be limited to a heater control module 509 that produces a Pulse Width Modulation (PWM) signal (PWM signal 511, represented in FIG. 49-2). Electrical hardware in the input-output (10) subsystem 344 connects electrical power to the heater elements 508 based on the PWM signal 511, and hardware on the IO subsystem 344 reads the output of heater pan temperature sensors 504 and button temperature sensor 506. The PWM signal 511 may control the power supplied to each of the heater elements 508, and consequently the solution heater system 500 may then heat the heater bag 22 to a user-settable comfort temperature, which may be controlled within a preferred safe temperature range. The solution heater system 500 may also limit the surface temperature of the heater pan 142 to a safe-to-touch temperature. The hardware components of the heater control circuitry 505 may be part of controller 16. There may also be insulation 510 positioned below the heater element 508 which functions to thermally isolate the heater pan 142 and heater bag 22 from the electronic and pneumatic components of the cycler 12. Additionally, the heater lid 143 may insulate the heater bag 22 from the surrounding environment. The solution heater system 500 may thus be constructed to bring the solution temperature inside the heater bag 22, as measured by the button temperature sensor 506, to the desired fluid set point temperature 550 (see FIG. 49-3) as quickly as possible, and maintaining that desired fluid set point temperature 550 through the rest of the therapy cycle. In some embodiments, the temperature sensors connect to the hardware interface 310. The same hardware interface 310 may control a safety relay that disables the heater.

In some embodiments, the heater elements may include thermal switches that open when the temperature of the switch exceeds a first pre-determined value. The switch will close again once the temperature of the switch drops below the second lower pre-determined value. The thermal switch may be incorporated directly into the heater elements or may be mounted on the outside of the heater element or on the heater pan. The thermal switches provide an additional layer of protection against unsafe pan temperatures.

In another example, the thermal switch may be a thermal fuse with a one-time fusible link. A service call will be required to replace the blown thermal fuse, which may advantageously provide an opportunity to inspect and/or test cycler 14 before restarting therapy. FIG. 49-2 shows a schematic block diagram of the software context of the heater control subsystem. In an embodiment, the logic of the heater control circuitry 505 may be implemented as a heater control module 509 in the machine control subsystem 342 in the APD System software architecture. The heater controller software may be implemented in the controller 16 (FIG. 45) as described below. Additionally, the therapy subsystem 340 may supply information to the machine control subsystem 342 such as the heater bag volume and the set point for the button temperature sensor 506. The heater elements 508 may be enabled by the therapy subsystem 340. The machine control subsystem 342 may also read temperature values from the I/O subsystem 344, which is located below the machine control subsystem 342. Furthermore, the heater controller 509 may output a PWM signal 511 which may then control the power supplied to the heater elements 508.

In an embodiment, the machine control subsystem 342 may be called periodically (e.g., approximately every 10 milliseconds) to service the I/O subsystem 344, update variables, and detect conditions. The machine control subsystem 342 may also send updated signals to the heater control module 509 periodically (e.g., approximately every 10 ms.). The updated signals may include the heater bag volume, heater pan temperatures 515, the button temperature 517, the set point temperature 550 and the heater enable function. The heater control module may average some or all of these signals continuously, but only calculate and update its output 511 at a lower frequency (e.g, every 2 seconds).

In another aspect, the solution heater system 500 may be able to control the solution temperature in the heater bag 22 within a given range of a desired fluid set point temperature 550 (see FIG. 49-2 and FIGS. 49-7-49-9). Furthermore, the solution heater system 500 has been designed to function within pre-defined specifications under a variety of different operating conditions, such as a relatively wide range of ambient temperatures (e.g., approximately 5° C. to approximately 37° C.), bag fill volumes (e.g., approximately 0 mL to approximately 3200 mL), and solution container 20 temperatures (e.g., between approximately 5° C. and approximately 37° C.). In addition, the solution heater system 500 is capable of functioning within specifications even if the solution in the heater bag 22 and the solution introduced during the replenish cycle may be at different temperatures. The solution heater system 500 has also been designed to function within specifications with heater supply voltages varying as much as +10% of nominal voltage.

The solution heater system 500 may be considered to be an asymmetrical system, in which the solution heater system 500 can increase the solution temperature with the heater elements 508, but relies on natural convection to lower the solution temperature in the heater bag 22. The heat loss may be further limited by the insulation 510 and the insulated cover 143. One possible consequence is that in the event of a temperature overshoot, the APD system 10 may delay a patient fill while the heater bag slowly cools. A possible consequence of placing the heater elements on the heater pan 142 is that the heater pan 142 may be at a substantially higher temperature than that of the heater bag 22 during the heating process. A simple feedback control on the heater bag temperature as recorded by the button temperature sensor 506, may not turn the heater off soon enough to avoid the thermal energy at a higher temperature in the heater pan from causing the heater bag 22 to overshoot the desired set point temperature 550. Alternatively controlling the heaters 508 to achieve a heater pan temperature 504 that would not cause the heater bag temperature to overshoot may result in a slow heater system and thus delay therapy.

In order to minimize the time for the solution in the heater bag to achieve the set point temperature 550 without overshoot, the heater control module may implement a control loop that varies the electrical power of the heater elements 508 to achieve a desired fluid temperature in the heater bag, in part by controlling the equilibrium temperature of the heater pan 142, the heater bag 22 and the fluid within the heater bag 22. In one embodiment, a Proportional-Integral (PI) controller controls an equilibrium temperature 532 that is a function of the temperatures of the heater bag 22 and the heater pan 142 and the volume of solution in the heater bag.

The equilibrium temperature may be understood to be the temperature that the solution in the heater bag 22 and the heater pan 142 would reach if the heater were turned off and the two components allowed to reach equilibrium. The equilibrium temperature may also be understood as the weighted average of the target temperature for the heater pan 142 and the measured temperature of the solution-filled heater bag, weighted by the thermal capacitance of each. The equilibrium temperature may also be calculated as the weighted average of the measured heater pan temperature and the solution temperature, in which the temperatures are weighted by their respective thermal capacitances. In an embodiment, the weighted average temperature of the heater pan and fluid in the heater bag may be calculated as the sum of the target heater pan temperature times the thermal capacitance of the heater pan plus the fluid temperature times the thermal capacitance of the fluid in the heater bag, where the sum is divided by the sum of the thermal capacitance of the heater pan plus the thermal capacitance of the fluid in the heater bag. The weighted averages of the heater pan and fluid may be alternatively weighted by the mass of the heater pan and fluid in the bag or the volume of the heater pan and fluid in the bag.

The control of the equilibrium temperature may be implemented using a number of control schemes, such as, for example, single feedback loops using proportional, integral and or derivative controllers and nested loops. One embodiment of a control scheme using cascaded nested control loops is shown in FIG. 49-3. The outer loop controller 514 may control the heater bag temperature as measured by the button temperature sensor 506 to the fluid set point temperature 550 by varying the heater pan set point temperature 527 supplied to the inner loop controller 512. Alternatively, the outer loop controller 514 may control the equilibrium temperature of the heater bag 22, fluid and heater pan 142 to the fluid set point temperature 550 by varying the heater pan set point temperature 527. The temperature of the heater bag 22 and fluid may be measured by the button temperature sensor 506 and the heater pan temperature may be measured by one or more of the heater pan temperature sensors 504. The outer loop controller may include one or more of the following elements: proportional controller, integral controller, derivative controller, saturation limits, anti-windup logic and zero-order hold logic elements.

The inner loop controller 512 may control the heater pan temperature to the heater pan set point temperature 527 by varying the thermal output of the heater elements 508. The temperature of the pan may be measured by one or more of the heater pan temperature sensors 504. The inner loop controller may include one or more of the following elements: proportional controller, integral controller, derivative controller, saturation limits, anti-windup logic and zero-order hold logic elements.

An exemplary implementation of the heater control module 509 utilizes a PI regulator cascade-coupled with a Proportional-Integral-Derivative (PID) controller. In the FIG. 49-3 embodiment, a PID inner loop controller 512 may control the temperature of the heater pan 142, and a PI outer loop controller 514 may control the equilibrium temperature of the heater bag, the fluid in the heater bag and the heater pan as measured by the heater pan temperature sensors 504 and button temperature sensor 506. The loop controller 514 differs from a standard PI regulator in that any overshoot of the desired fluid set point 550 by the solution heater system 500 may be minimized by a logic controllable integrator as described below. In an embodiment, the heater pan temperature signal 515 and the button temperature sensor (heater bag) signal 517 are low-pass filtered through a pair of control filters 519 at a relatively high frame rate (e.g., a full 100 Hz frame rate), while the heater control module 509 may change the output of the heaters at a lower rate (e.g., rate of ½ Hz).

FIG. 49-4 shows a schematic diagram of one embodiment of the inner loop controller 512 (heater pan controller). In this embodiment, the inner loop controller 512 uses a standard PID regulator including but not limited to a differencing element 519 to produce a temperature error and a proportional gain element 522 to create an PWM signal 511. The inner loop controller 512 may further include a discrete-time integrator 516 to reduce the offset error. The inner loop controller 512 may also include an anti-windup logic element 518 to minimize overshoot due a temperature error existing for a long period of time when the output of the inner loop controller 512 is saturated. The inner loop controller 512 may further include a discrete derivative term 520 that acts on the heater pan actual temperature 515 to improve heater responsiveness. The inner loop controller 512 may further include a saturation limit element 521 that sets a maximum and/or minimum allowed heater command or PWM signal 511. The inner loop controller 512 may further include zero-order hold logic 523 to hold the PWM signal 511 constant between controller calculations that occur approximately every 2 seconds.

FIG. 49-5 shows a schematic diagram of the outer loop controller 514 (button temperature sensor controller). In this example, the outer loop controller 514 utilizes a modified PI-type regulator, which may include differencing elements 531, an integrator 534 and a proportional gain element 526. The outer loop controller 514 may further include an integrator switching logic 522 and corresponding switch 529, to allow the integrator to be switched on or off by logic in the heater control module 509. The outer loop controller 514 may further include a command feed forward 524 to improve the responsiveness of the outer loop controller 514. The outer loop controller 514 may further include a proportional feedback term 526 to act on a weighted combination of the button temperature sensor target temperature 517 and the heater pan target temperature 527. The resulting measurement is an equilibrium temperature 532 as described above. The outer loop controller 514 may further include a saturation limit element 521 and/or a low pass filter 542. The saturation limit element 521 in the outer loop sets a maximum allowed target pan temperature 527. The low pass filter 542 may be designed to filter out transient control signals at frequencies outside the bandwidth of the solution heater system 500.

The integral elements 534 in the outer loop controller 514 may be turned on by a switch 529 when some or all of the following conditions are present: the rate of change of the button temperature 517 is below a pre-determined threshold, the button temperature 517 is within a pre-determined number of degrees of the fluid set point temperature 550, or the bag volume is greater than a pre-determined minimum and neither of the controllers 512, 514 are saturated. An equilibrium temperature feedback loop may control the transient behavior of the solution heater system 500, and may be dominant when the surrounding ambient temperature is in a normal to elevated range. The action of the integrator 516 may only be significant in colder environments, which may result in a substantial temperature difference between the button sensor actual temperature 517 and the heater pan actual temperature 515 at equilibrium. The feed-forward term 524 may pass the fluid set point temperature 550 through to the heater pan target temperature 527.

This action will start the heater pan target temperature 527 at the fluid set point temperature 550, instead of zero, which thereby improves the transient response of the solution heater system 500.

The heater module 509 may also include a check that turns off the PWM signal 511 if the heater pan actual temperature 515 crosses a pre-determined threshold (this threshold may be set to be slightly higher than the maximum allowed heater pan target temperature 527). This check may not be triggered under normal operation, but may be triggered if the heater bag 22 is removed while the temperature of the heater pan 142 is at a pre-determined maximum value.

The PI controller 514 may include a proportional term that acts on the equilibrium temperature 532. The equilibrium temperature is the heater bag temperature measured by the button sensor 506 that would result if the heater 508 was turned off and the heater pan 142 and the solution-filled heater bag 22 were allowed to come to equilibrium. The equilibrium temperature can be better understood by referring to FIG. 49-6, which shows a schematic block diagram of the heater pan 142 and heater bag 22 in a control volume analysis 546. The control volume analysis 546 depicts a model environment in which the equilibrium temperature 532 may be determined. In this illustrative embodiment, the solution heater system 500 may be modeled in as control volume 548, which may comprise at least two thermal masses: the heater pan 142 and the heater bag 22. The boundary of the control volume 548 may be assumed to function as a perfect insulator, in which the only heat transfer is between the heater pan 142 and the heater bag 22. In this model, thermal energy 549 may be added to the system via the heater elements 508, but thermal energy may not be removed from the heater pan 142 and heater bag 22. In this model, as in the solution heater system 500, it is desirable to heat the heater pan 142 just enough that the heater bag 22 reaches its target temperature as the heater pan 142 and heater bag 22 come to equilibrium. Therefore, the equilibrium temperature 532 may be calculated as a function of the initial temperature of the heater bag 22 and the initial temperature of the heater pan 142:

$$E = M_p c_p T_p + V_b \rho_b c_b T_b = (M_p c_p + V_b \rho_b c_b) T_e$$

where $M_p$, $c_p$ are the mass and specific heat of the heater pan 142, $V_p$, $\rho_b$, $c_b$ are the volume, density and specific heat of the solution in the bag, $T_p$ and $T_b$ are the temperatures of the heater pan 515 and the button 517 respectively. Solving for the equilibrium temperature yields a linear combination of pan and button temperatures:

$$T_e = c T_b + (1-c) T_p$$

where $$C = \frac{V_b}{k + V_b} \text{ and } k = \frac{M_p C_p}{\rho_b C_b}$$

The constant c is an equilibrium constant, k is the thermal capacitance ratio of the heater pan over the solution. The subscript b denotes the solution in the heater bag 22, while p denotes the heater pan 142.

In this model, allowing the heater module 509 to control the equilibrium temperature 532 during the initial transient may allow for rapid heating of the heater bag 22 while also reducing the heater pan actual temperature 515 sufficiently early to prevent thermal overshoot. The c parameter may be determined empirically. The heater module 509 may set c to a value larger than the measured value to underestimate the total energy required to reach the desired set point 550, further limiting the thermal overshoot of the solution heater system 500.

FIG. 49-7 shows graphically the performance of solution heater system 500 of the disclosed embodiment operating under normal conditions. The measured temperatures of the heater pan sensors 504, the button temperature sensor 506 and an additional temperature probe are plotted against time. The fluid temperature probe was part of the experimental setup up to verify the control scheme. The fluid probe temperature is shown as line 552. The button temperature is shown as line 517 and the heat pan temperatures are shown as line 515. Line 550 is the target temperature for the button temperature sensor 506. At the start of this trial, the heater bag is substantially empty, the heater is off and fluid is not moving, so that all the temperatures are at a nominal value. At a time T=1, the fluid at 25 C starts to flow into the heater bag 22 bringing down the probe and button temperatures 552, 517, while the heater turns on and increases the heater pan temperature 515. Under normal operation, proportional control of the equilibrium temperature 532 may be sufficient to heat the solution within the heater bag 22 to a temperature close to the desired fluid set point temperature 550. Therefore, in FIG. 49-7, the solution heater system 500 functions effectively, and the heater pan actual temperature 515, the button sensor actual temperature 517, and a probe temperature 552 all converge to the fluid set point temperature 550 within approximately 50 minutes.

FIG. 49-8 shows graphically the performance of the solution heater system 500 operated in a high temperature environment in which the ambient temperature is 35 C. As described above, the trial begins with the heater bag being substantially empty. Once the fluid starts to flow and the heater turns on, the probe and button temperatures 552, 517 decrease and the heater pan temperature 515 increases. In a high temperature environment, the solution heater system 500 functions in a manner substantially similar to normal conditions. Thus, proportional control of the equilibrium temperature 532 may again be sufficient to heat the solution within the heater bag 22 to a temperature close to the desired fluid set point temperature 550. In FIG. 49-7, the solution heater system 500 functions effectively and within desired specifications, and the heater pan actual temperature 515, the button sensor actual temperature 517, and a probe temperature 552 all converge to the desired set point temperature 550 within approximately 30 minutes.

FIG. 49-9 shows graphically the performance of the solution heater system 500 operated in a cold environment where the ambient temperature is 10 degrees C. and the source fluid is 5 degrees C. As described above, the trial begins with the heater bag being substantially empty. Once the fluid starts to flow and the heater turns on, the probe and button temperatures 552, 517 decrease and the heater pan temperature 515 increases. In a cold environment, setting the desired fluid set point temperature 550 equal to the equilibrium temperature 532 may lead to a steady-state error in the temperature of the button sensor 506. The heat loss in cold environments may necessitate a large temperature difference between the heater pan 142 and the button sensor 506 during thermal equilibrium. Since the equilibrium temperature 532 is a weighted sum of the heater pan 142 and the button sensor 506, the temperature of the button sensor 506 may be below the fluid set point temperature 550 if the temperature of the heater pan 142 is above the desired fluid set point temperature 550 at equilibrium. This may occur even if the equilibrium temperature 532 is equal to the fluid set point temperature 550. To compensate for this steady-state-error an integral term may be added to outer PI controller 514 that acts on the temperature error of the button sensor 506. The integrator 538 may be turned on when one or more of the following conditions are met: a first derivative of the temperature of the button sensor 506 is low; the button sensor 506 is close to the fluid set point temperature 550, the volume of the heater bag 22 exceeds a minimum threshold; and neither inner PID loop 512 or outer PI controller 514 are saturated. In this illustrative embodiment, the switching of the integral term may minimize the effect of the integrator 538 during normal operation and may also minimize the overshoot caused by integration during temperature transients. Therefore, in FIG. 49-9, the solution heater system 500 functions effectively and within desired specifications, and the heater pan actual temperature 515, the button sensor actual temperature 517, and a probe temperature 552 all converge to the fluid set point temperature 550 within approximately 30 minutes.

In summary, the disclosed temperature controller can achieve good thermal control of a two component system, in which the mass of the first component varies over time, and in which the second component includes a heater or cooler, and both components are in an insulated volume. This thermal control can be achieved by controlling the equilibrium temperature. The temperature controller determines the temperature of both components as well as the mass of the variable component. The temperature controller varies the heating or cooling of the second component to bring the equilibrium temperature to the desired set point temperature. The equilibrium temperature is the thermal capacitance weighted average temperature of the two components. The controller may use a proportional feedback loop to control the equilibrium temperature.

The temperature controller may also include an integral term that responds to the difference between the set point temperature and the temperature of the first component. The integral term may optionally be turned on when some or all of the following conditions are met:

the rate of temperature change of the first component is low;
the temperature of the first part is near the set point temperature;
the volume of the first part exceeds some minimum level;
the control output signal is not saturated.

The temperature controller may also include a feed-forward term that adds the set point temperature to the output of the proportional and integral terms.

Further, the temperature controller may be the outer loop controller of a cascade temperature controller in which the outer loop controller includes at least a proportional control term on the equilibrium temperature and outputs a set point temperature for the inner controller. The inner controller controls the temperature of the first component with the heater or cooler elements to the set point temperature produced by the outer controller.

Universal Power Supply

In accordance with an aspect of the disclosure, the APD system 10 may include a universal power supply that converts line voltage to one or more levels of DC voltage for some or all of the electro-mechanical elements and electronics in the cycler 14, and provides AC power to the electric heater for the heater pan 142. The electro-mechanical elements in the cycler 14 may include pneumatic valves, electric motors, and pneumatic pumps. The electronics in the cycler 14 may include the control system 16, display 324, and sensors. AC power is supplied to a heater controller to control the temperature of the solution in the heater bag 22 on the heater tray 142 to a desired set point prior to delivering the solution to the user/patient. The universal power supply changes the configuration of two (or more) heater elements to accommodate two ranges of AC line voltages: e.g., a first range of 110±10 volts rms; and a second range of 220±20 volts rms. This arrangement is intended to accommodate using the APD system 10 in a number of different countries. During the start of a therapy session, the APD cycler 14 fills the heater bag 22 with solution from the connected solution containers 20, via a heater bag line 26. In an alternative embodiment, a pre-filled bag of solution may be placed on a heater pan 142 at the start of a therapy.

PWM Heater Circuit

The heater controller in the APD cycler modulates the electrical power delivered to the heater elements attached to the heater pan 142. The APD cycler may be used in various locations around the world and may be plugged into AC mains that supply power from 100 to 230 volts rms. The heater controller and circuits may adapt to the variety of AC voltages while continuing to supply sufficient heater power and not blowing fuses or damaging heater elements in a number of ways.

One embodiment of a heater circuit is presented in FIG. 49-10, where a pulse width modulator (PWM) based circuit 2005 controls the temperature of the heater pan 142 with a pulse-width-modulated (PWM) element 2010 connected between one lead of the AC mains 2040 and the heater element 2000. The controller 2035 is operably connected to the relay 2030 and the PWM element 2010. The controller 2035 monitors the operation of the heater by interrogating the voltage detect 2020 and temperature sensor 2007. The controller 2035 may modulate the amount of power delivered to the heater 2000 via a signal to the PWM element 2010. The PWM or pulse-width-modulated element is closed for some fraction of a fixed period between 0 and 100%. When the PWM element 2010 is closed 0% of the time, no electrical energy flows to the heater 2000. The heater is continuously connected to the AC mains 2040 when the PWM element is closed 100%. The controller 2035 can modulate the amount of power dissipated by the heater 2000 by setting the PWM element 2010 to a range of values between 0 and 100%, inclusive.

The PWM elements 2010 switch large current flows on and off multiple times a second. PWM elements 2010 are typically some kind of solid state relay (SSR). SSRs for AC voltage typically include a triggering circuit that controls the power switch. The triggering circuit may be, for example, a reed relay, a transformer or an optical coupler. The power switch may be a silicon control rectifier (SCR) or a TRIAC. The SCR or TRIAC are also referred to as thyristors. One example of a SSR is the MCX240D5® by Crydom Inc.

In one example, the controller 2035 may modulate the PWM element value in order to control the temperature of the heater pan 142 as measured by temperature sensor 2007. In another example, the controller 2035 may modulate the PWM element value to control the temperature of the fluid in the heater bag 22. In another example the controller 2935 may control the PWM element 2010 to provide a fixed schedule of heater power. The controller 2035 may command a safety relay 2030 that opens the heater circuit and stops the flow of electrical power to the heater 2000. The safety relay 2030 may be controlled by a separate controller (not shown) in order to provide a safety circuit independent of the controller 2035.

The PWM based circuit 2005 may include a voltage detect element 2020 that provides a signal to the controller 2035 indicative of the voltage on the AC mains 2040. In one example, the voltage detect element 2020 may measure the AC potential across the AC mains 2040. In another example the voltage detect element 2020 may measure the current flow through the heater 2000. The controller 2035 may calculate the voltage across the AC mains from a known resistance of the heater element 2000, the PWM element 2010 signal and the measured current.

The PWM based circuit 2005 may vary the maximum allowed duty cycle of PWM element 2010 to accommodate different AC Mains voltage. The heater element 2000 may be designed to provide the maximum required power with the lowest possible AC voltage. The controller may vary the duty cycle of the PWM element 2010 to provide a constant maximum heater power for a range of voltages at the AC mains. For example, the voltage supplied to the heater 2000 from a 110 volt AC line may be supplied at a 100% duty cycle, and the same amount of electrical power may be delivered to the heater 2000 from a 220 volt AC line if the PWM element 2010 is set to 25%. The duty cycle of the PWM element 2010 may be further reduced below the maximum value to control the temperature of the heater pan 142.

The temperature of the heater element 2000 and the heater pan 142 may be controlled by the average heater power over a time constant that is a function of the thermal mass of the element and heater pan. The average heater power may be calculated from the heater resistance, which is relatively constant, and the rms voltage across the heater element 2000. In a practical sized heater, the PWM frequency is much faster than the time constant of the heater system, so the effective voltage across the heater element is simply the PWM duty cycle multiplied by the rms voltage.

One method to control the heater pan temperature of the circuit in FIG. 49-10 may direct the controller 2035 to set a maximum PWM duty cycle based on the measured voltage at 2020. The maximum duty cycle may be calculated from the desired maximum heater power, known resistance of the heater element 2000 and the measured voltage. One possible example of the calculation is:

$$PWM_{MAX}=(P_{MAX}*R_{HEATER})^{0.5}/V_{rms}$$

where $PWM_{MAX}$ is the maximum allowed PWM duty cycle, $P_{MAX}$ is the maximum heater power, $R_{HEATER}$ is the nominal resistance of the heater element 2000, and $V_{rms}$ is the supplied voltage as measured by the Voltage Detect 2020. Another example of the calculation is:

$$PWM_{MAX}=P_{MAX}(I^2*R_{HEATER})$$

where I is the current flow through heater when the voltage is applied. The controller 2035, after setting the maximum PWM duty cycle, then varies the PWM duty cycle of the PWM element 2010 to control the temperature of the heater pan 142 as measured by a temperature sensor 2007. The controller may control the PWM element to achieve a desired temperature in a number of ways, including, for example, a PID feedback loop, or a PI feedback system.

In an alternative method and configuration, the PWM circuit 2005 does not include the voltage detect 2020. In this alternative method the controller 2035 varies the PWM duty cycle of the PWM element 2010 to achieve the desired heater pan temperature as measured by temperature sensor 2007. The controller 2035 begins the heating cycle at a minimum PWM duty cycle and increases the PWM duty cycle until the temperature sensor reports the desired temperature to the controller 2035. The rate of increase of the PWM rate may be limited or controlled to avoid excessive currents that could trip and blow the fuses 2050. The controller 2035 may alternatively use small gains in a feedback calculation to limit rate of PWM duty cycle increase. Alternatively the controller may use a feed forward control to limit the rate of PWM duty cycle increase.

Dual-Voltage Heater Circuit

An example of a dual-voltage heater circuit 2012 that changes the resistance of the heater is shown as a schematic block diagram in FIG. 49-11. The block diagram in FIG. 49-11 presents one example of a dual-voltage heater circuit 2012 to provide approximately constant heater power for the two standard AC voltages of 110 and 220 volts rms. Dual-voltage heater circuit 2012 limits the maximum current flow by reconfiguring the heater and thus is less sensitive to software errors setting the duty cycle of the PWM element as in circuit 2005. Circuit 2012 lowers the maximum current flows through the PWM element 2010 which allows for smaller and less expensive SSRs. The selection of the heater configuration in circuit 2012 is separated from the heater modulation to improve control and reliability. The PWM elements 2010A, 2010B that modulate the heater power are typically SSR, which typically fail closed, thus providing maximum power. The heater select relay 2014 may be an electromechanical relay, which while less than ideal for high cycle applications, may typically be preferred for safety critical circuits, due in part to the tendency of electromechanical relays to fail open. The selection of the heater configuration by the processor allows more control of heater configuration.

In the event of the AC Mains voltage fluctuating, perhaps due to a brown-out, the controller preferably holds the heater configuration constant. In contrast, a circuit that automatically changes the heater configuration based on the instantaneous voltage could fluctuate between heater configurations. This may result in high current flows if the circuit does not respond fast enough to line voltage that returns to its original level from a temporarily lower level. In an embodiment, the processor receives input from the user or patient in selecting the heater configuration (parallel or series), and the dual-voltage heater circuit 2012 does not automatically switch between configurations in response to fluctuating line voltage. In another embodiment, the processor measures the current flow in the series configuration (i.e. the higher resistance configuration) at full power, selects a heater configuration appropriate to the AC mains voltage at the start of therapy, and does not change configuration for the duration of therapy.

The dual-voltage heater circuit 2012 may comprise two heater elements 2001, 2002 that can be connected in parallel or in series with one another to provide the same heater power for two different voltages at the AC mains 2040. Each heater element 2001, 2002 may comprise one or more heater sub-elements. The electrical resistance of heater elements 2001, 2002 is preferably approximately equal. The controller 2035 may receive a signal from the current sense 2022 and control the heater select relay 2014 to connect the heater elements 2001, 2002 in either series or parallel. The controller 2035 may change the electrical arrangement of the two heater elements to limit the current flow resulting from different AC mains voltages. One example of a current sense 2022 is a current sense transformer AC-1005 made by Acme Electric.

The power in the heater elements 2001, 2002 may be further modulated by the PWM elements 2010A, 2010B controlled by the controller 2035 to achieve a desired temperature as measured by temperature sensor 2007, or to achieve other control goals as described above. The PWM elements 2010A, 2010B may be a solid state relays such as MCX240D5® by Crydom Inc. The safety relay 2030 may be configured to disconnect the heater elements 2001, 2002 from the AC mains 2040. The safety relay 2030 may be controlled by the controller 2035 or another processor or safety circuit (not shown).

The safety relay 2030 and heater select relay 2014 may be solid state or electro-mechanical relays. In a preferred embodiment, the safety relay 2030 and/or heater select relay 2014 are electro-mechanical relays. One example of an electro-mechanical relay is a G2AL-24-DC12 relay made by OMRON ELECTRONIC COMPONENTS and other manufacturers. Electro-mechanical relays are often preferred for safety critical circuits as they are considered to be more robust and more reliable than solid state relays, and have a tendency to fail open. They may also be less susceptible to various failures in the controller software.

In one example, the heater select relay 2014 comprises a double-pole double-throw relay, in which the outputs connect to the heater elements 2001, 2002. The heater select relay 2014, in the non-energized state, connects the heater elements 2001, 2002 in series such that the current flows through one element and then the other. The series configuration may be achieved, in one example circuit, by the following: connect the first end of the heater element 2001 to L1 circuit 2041 via PWM element 2010A; connect the joined ends of heater elements 2001, 2002 to an open circuit via the first pole 2014A; connect second end of heater element 2002 to the L2 circuit 2042 via the second pole 2014B. In an energized state, the heater select relay 2014 connects the heater elements in parallel such that approximately half the current flows through each PWM and heater element. The parallel configuration may be achieved in the same example circuit by the following: connect the first end of the heater element 2001 to L1 circuit 2041 via PWM element 2010A; connect the second end of heater element 2002 to the L1 circuit 2041 via PWM element 2010B; connect the joined ends of heater elements 2001, 2002 to L2 circuit 2042 via the first pole 2014A. The preferred circuit connects the heater elements 2001, 2002 in series in the unpowered condition as it is a safer configuration because the resulting higher resistance will limit current flows and avoid overloading the fuses 2050, or overheating the heating elements 2001, 2002 if connected to a higher voltage AC main.

Another example of a heater circuit 2112 that changes the effective resistance of the heater by changing the heater configuration is shown in FIG. 49-12 as a schematic block diagram. The heater circuit 2112 is similar to heater circuit 2012 (shown in FIG. 49-11) except that heater circuit 2112 provides better leakage current protection in the event that the L1 and L2 power circuits are reversed at the wall socket. The reversal of the L1 and L2 power circuits is possible if the power was incorrectly wired in the building that supplies power to the heater circuit. Wiring in a residential building may not be as reliable as a hospital, where all the electrical system is installed and maintained by qualified personnel.

The electrical components and connections between the PWM elements 2010A, 2010B, the nominal L1 circuit 2041, heater elements 2001, 2002, heater select relay 2014 and the nominal L2 circuit 2042 in heater circuit 2112 are arranged to minimize leakage current regardless of wall socket polarity. In the non-energized state as shown in FIG. 49-12, the heater select relay 2014 connects the heater elements 2001, 2002 in series with the PWM element 2010A. One possible circuit that connects the heater elements in series includes: the first end of heater element 2001 connected to the L1 circuit 2041 via PWM element 2010A; the second end of heater element 2001 connected to the first end of heater element 2002 via the first pole 2014A, a L1 2014C and the second pole 2014B; and the second end of heater element 2002 connected to the L2 circuit 2042 via PWM element 2010B. In the energized state, the heater elements 2001, 2002 and PWM elements 2010A, 2010B are connected in parallel. In an energized state, the heater select relay 2014 connects the heater elements in circuit 2122 in parallel such that approximately half the current flows through each PWM and heater element. One possible circuit to connect the two heater and PWM elements in parallel includes: the first end of heater element 2001 connected to the L1 circuit 2041 via PWM element 2010A; the second end of heater element 2001 connected via the first pole 2014A to the L2 circuit; the first end of heater element 2002 is connected to the L1 circuit 2041 via the second pole 2014B; the second end of heater element 2002 is connected to the L2 circuit 2042 via the PWM element 2010B. The safety relay 2030 is located on the L2 circuit 2042 and creates a fail-safe condition of no current flow by opening if a fault occurs. The control of the safety relay is described below. The controller 2035 controls the heater configuration to limit the current flow as measured by the current sense 2022 to levels below the current rating for the fuses 2050, heater elements 20001, 2002, the PWM elements 2010A, 2010B and limits total heater power. The controller 2035 varies the duty cycle of the PWM elements 2010A, 2010B to control the heater pan 142 temperature as measured by the sensor 2007.

Dual-Voltage Heater Circuit Implementation

A circuit diagram 2212 of one embodiment of the present invention is shown in FIG. 49-13, which is equivalent to heater circuit 2012 in FIG. 49-11. In the circuit 2212, the heater elements 2001, 2002 are connected in series by the heater select relay 2014 when the relay coil 2014D is not energized. The controller (not shown) connects the heater elements 2001, 2002 and PWM elements 2010A, 2010B in parallel by supplying a signal at node 2224, which closes transistor switch 2224A, and energizing the relay coil using the Vs DC power 2214, The controller modulates the heater power by varying the duty cycle of the PWM elements 2010A, 2010B through a signal at node 2220 and powered with Vsupply 2210. The current flow is measured with the current sense 2022. The safety relay 2030 is normally open. The safety relay 2030 may be controlled by an FPGA board that is separate from the controller. The FPGA board monitors the operation of the APD cycler, including the heater pan temperature and the current sense and several other parameters. The FPGA board may open the relay by removing the signal at node 2228. The safety relay coil 2030D is powered by the Vsafety 2218.

In one example, the voltage supplying Vsupply 2210, Vs 2214, Vsafety 2218 may be the same voltage source. In another example each voltage source be controllable to provide additional operation control of the heater circuit for added safety. In one example the Vsafety 2218 may be controlled by multiple processors in the APD cycler 14. If any of the processors detects an error and fails, then the Vsafety circuit is opened, the Safety Relay 2030 is opened and heater power is turned off.

Dual-Voltage Heater Circuit Operation

The heater circuit is operated to provide adequate heater power without allowing damaging currents to flow through the heater elements 2001, 2002 or the fuses 2050. The heater circuit 2212 may be configured before the therapies are run on the APD cycler 14 and not changed during operation regardless of the voltage changes in the AC mains. The control system 16 (in FIG. 45) starts up the heater control circuit 2212 with the heater select relay 2014 un-energized, so the heater elements are connected in series to minimize the current. As one part of the startup processes, software in the automation computer 300 may run a current flow test of the heaters by commanding the PWM elements 2010A, 2010B to 100% duty cycle and the resulting test current is measured by the current sense 2022 and communicated to the automation computer 300. The duty cycle of the PWM elements 2010 may be reset to zero after current flow test.

In one example method, the automation computer 300 evaluates the measured test current against a predetermined value. If the measured test current is above a given value, the automation computer 300 will proceed with the ADP cycler startup procedure. If the measured test current value is below that same given value, then the automation computer 300 will energize the heater select relay to reconfigure the heater elements 2001, 2002 in parallel. The current flow test is repeated and if the new measured test current is above the predetermined value the automation computer 300 will proceed with the ADP cycler startup procedure. If the measure test current from the current flow test with parallel heater elements, is below above the predetermined value, the automation computer 300 will signal an error to the user interface computer 302.

Alternatively, the automation computer 300 may calculate a test voltage based on the measured test current and heater element configuration. If the test voltage is in the range of 180 to 250 volts rms, then the automation computer 300 will proceed with the ADP cycler startup procedure. If the test voltage is in the range of 90 to 130 V rms, then the automation computer 300 will energize the heater select relay to reconfigure the heater elements 2001, 2002 in parallel, repeat the current flow test, and recalculate the test voltage. If the test voltage is in the range of 90 to 130 V rms, the automation computer 300 will proceed with the ADP cycler startup procedure, if not automation computer 300 will signal an error to the user interface computer 302.

In another example method, the automation computer 300 compares the measured test current with the heater elements configured in series to a series-low-range and series-high-range of current values. The series-low-range is consistent with a low AC voltage flowing through the heater elements arranged in series. The series-high-range is consistent with a high AC voltage flowing through the heater elements arranged in series. In an exemplary embodiment, the low AC voltage includes rms values from 100 to 130 volts, while the high AC voltage includes rms values from 200 to 250 volts.

If the measured test current is outside of low-range and the high-range, then the automation computer 300 may determine that the heater circuit is broken and signal an error to the user interface computer 302. If the measured test current is within the high-range, the heater configuration is left unchanged and the startup of the APD cycler 14 may continue. If the measured test current is within the low-range and the heater elements are arranged in series, then the automation computer 300 may reconfigure the heater elements 2001, 2002 to a parallel arrangement by energizing the heater select relay 2014 through a signal at node 2224. The automation computer 300 may control the heater select relay 2014 via a command sent to the hardware interface 310 that in turn provides the signal to actuate the heater select relay 2014.

The automation computer 300 may repeat the current flow test after reconfiguring the heater elements into a parallel arrangement by again commanding the PWM elements 2010A, 2010B to 100% duty cycle and measuring the current flow with the current sense 2022. The measured test current may be evaluated against the parallel-low-range of current values. If the measured test current is within the parallel-low-range values proceed with the ADP cycler startup procedure. If the newly measured test current is outside the parallel-low-range values, then automation computer 300 will signal an error to the user interface computer 302.

The FPGA controller implemented in the hardware interface 310 may be programmed to command the safety relay 2030 to open through a signal at node 2228 while the heater select relay 2014 is switched. The safety relay 2030 may be opened each time the heater select relay 2014 is opened or closed to prevent a short circuit from one pole to the other within the heater select relay 2014.

Dual-Voltage Heater Circuit Operation with User Input

In an alternative embodiment, the automation computer 300 may require user intervention before reconfiguring the heater elements 2001, 2002. Requiring user input provides a valuable safety feature of one embodiment of the present invention. FIG. 49-14 shows a logic flow chart illustrating a method 2240 to include the user in configuring the heater elements appropriately for the available AC voltage. In step 2241, the control system 16 (in FIG. 45) starts up the heater control circuit 2212 (FIG. 49-13) with the heater select relay 2014 un-energized, so the heater elements are connected in series to minimize the current. In setup 2242, the automation computer 300 commands the PWM elements 2010A, 2010B to 100% duty cycle and the current is measured by the current sense 2022 and the measure test current is communicated to the processor. The duty cycle of the PWM elements 2010 may be reset to zero after the test current is measured. In step 2244, the automation computer 300 compares the measured test current to a first range. In step 2245, if the measured test current is within the first range, then the heater configuration is correct and the APD operation proceeds in step 2254. In an alternative embodiment, method 2240 includes step 2245A where the user interface computer 302 ask the user to confirm the AC mains voltage that the automation computer 300 determined from measured test current and the heater configuration before proceeding from step 2245. If the user does not confirm the AC voltage level, method 2240 will proceed to step 2252 and displays an error.

In step 2246, if the measured current is outside the second range, then method 2240 displays an error in step 2252, otherwise the method 2240 proceeds to step 2247. In step 2247, if the user confirms low AC voltage then the heater configuration will be changed in step 2248, otherwise the method 2240 displays an error in step 2252. In step 2248, the automation computer 300 reconfigures the heater elements 2001, 2002 to a parallel arrangement by energizing the heater select relay 2014 through a signal at node 2224. After reconfiguring the heater elements in step 2248, the method 2240 retests the heater in step 2242 and continues through the logic flow chart of method 2240.

Figure 15:
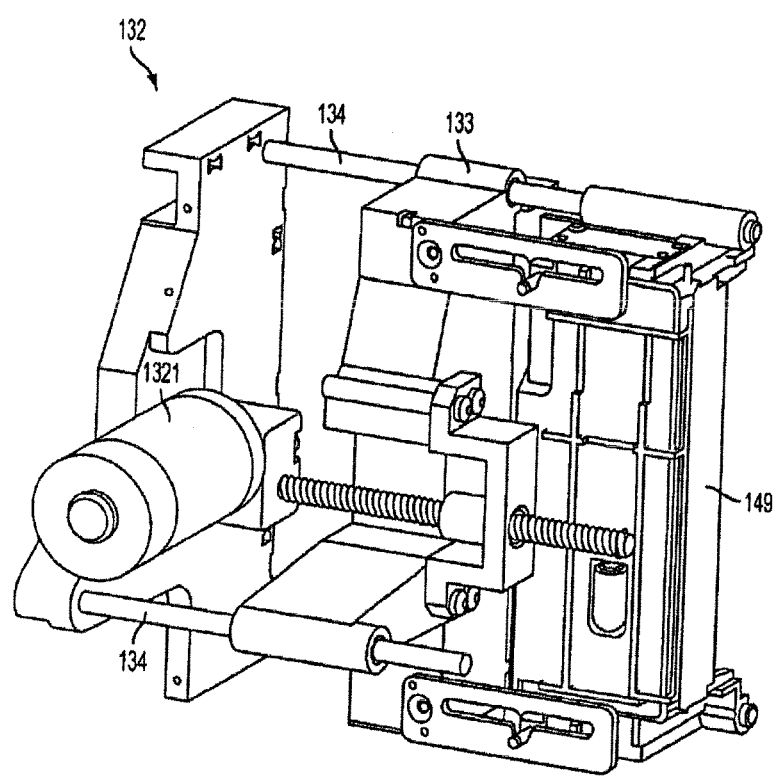
FIG. 15 is a rear perspective view of a carriage drive assembly in a second illustrative embodiment.
Figure 16:
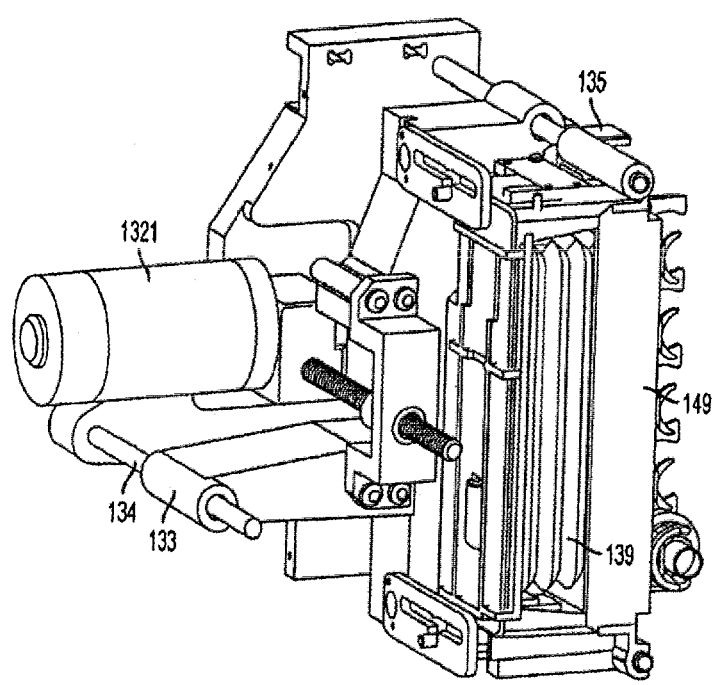
FIG. 16 is a left rear perspective view of the carriage drive assembly and cap stripper of FIG. 15.

An alternative embodiment, a user or patient may store the AC voltage as high or low in the memory of the control system 16 so that the automation computer 300 need not query the user or patient at each treatment to confirm the AC voltage. FIG. 49-15 shows a logic flow chart illustrating a method 2260 where the AC voltage value is stored in the memory of the control system 16. The steps 2241 through 2246 are the same as method 2240 described above. In step 2249, the memory is queried for the stored AC voltage value. If the stored AC voltage value is low, then the method 2260 proceeds to step 2248 and reconfigures the heater elements into a parallel arrangement. If the stored AC voltage is high nor zero, then the user interface computer 302 may query the user to confirm a low AC mains voltage. If a user confirms the low AC voltage, then the method 2260 proceeds to step 2248 and reconfigures the heater elements into a parallel arrangement. Step 2248 may also include the setting the stored AC voltage to low. After reconfiguring the heater elements in step 2248, the method 2260 retests the heater in step 2242 and continues through the logic flow chart of method 2260.

In one example, method 2260 may include a step 2245A which reads from memory or calculates the test voltage from the measured test current and heater configuration and then has the user interface computer 302 asks the user to confirm the test voltage. The method may include a step between 2245 and 2246, where if the heater has been reconfigured to a parallel arrangement and the current is not within the high range, then the method proceeds to step 2252 and shuts down the APD cycler 14.

The methods 2240 and 2260 may evaluate the measured test current by a number of different methods. A preferred method was described above and alternative examples are es are described below. The first range in step 2245 may be a range of current levels that would provide the desired amount of maximum heater power for the current heater element configuration. Alternatively step 2245 may calculate a test voltage from the measured test current and heater element configuration and evaluate if the test voltage is correct for the heater configuration: approximately 110 V rms for parallel configuration and approximately 220 V rms for series configuration. Alternatively step 2245 may test if the measured test current is above a given predetermined value. The second range in step 2246 may be a range of current values corresponding to approximately 110 V rms in a series configuration. Alternatively step 2246 may calculate a test voltage from the measured test current and heater element configuration and evaluate if the test voltage approximately 110 V rms for a series configuration. Alternatively, step 2246 may evaluate if the measure test current is below a given predetermined value.

In another embodiment, the selected AC voltage value in method 2260 may be preloaded in the factory or distribution center based on the expected location of usage. For example, the AC voltage value may be selected for low if the APD cycler will be used in the US, Canada or Japan. For another example, the AC voltage value may be selected for high if the APD cycler will be used in Europe, or Asia.

For machines expected to operate in a given region, this database may be as simple as a regional voltage being loaded on the machine at the factory, or loaded by a technician during initial set-up at a place of operation. These regional AC voltage value prescriptions may be entered manually, using a memory stick or similar device, using a personal data key (PDK), a compact disc, bar code reader over the world wide web using an Ethernet or wireless connection or by any other data transfer mechanism obvious to one skilled in the art. In other embodiments, sets of regional voltages may be accessible to control system 16 and may be used to inform a user of the typical operating voltage in his or her area. In one embodiment, prior to accepting a user input in step 2247 to change voltage from a previous setting, a user would be informed of the typical voltage of a region; thus a user unfamiliar with the value of regional voltages would only be required to know his or her current location to provide a safeguard against voltage incompatibility.

In another embodiment, APD cycler 14 would be equipped with a mechanism to determine its current location, for example a GPS tracker, an Ethernet connection and a mechanism to determine the location of the connection, or a mode where user interface 302 can be used to enter the present location, such as country or continent. In an embodiment, after starting up in a series heater configuration and running a current flow test, a user may simply be queried as to his or her present location; if the response to that query matches both the voltage associated with the measured test current and heater configuration and the typical voltage for that region, then treatment is allowed to proceed.

In one embodiment of the present invention a manual switch (not shown), or alternately a logic switch, is used to set the APD machine to the appropriate, safe voltage for use. The instantaneous voltage is measured and this measurement, either as the specific value or as a categorical descriptor, is displayed to the user. The user must respond that the measured voltage is within the safe operating range for the machine as currently configured, or alternately must respond by altering the configuration of the machine, before power is allowed to flow to the heating element. The configuration could be altered electronically, for example via the user interface computer 302, or could be performed manually by flipping a switch.

In another embodiment of the present invention, a rectifier converts any incoming alternating current (AC) into a single direct current (DC). The heater circuit would resemble heater circuit 2005 in FIG. 49-8 except the voltage detect 2020 element is replaced with a universal DC supply that rectifies the AC voltage into a selected DC voltage. The electrical power supplied to the heater elements 2001, 2002 may be modulated by a PWM element in the rectifier or by a separate PWM element 2030. The heater circuit may include a safety relay 2010. The single voltage DC power source allows the use of one heater configuration. The PWM element in this embodiment may comprise one or more IGBT or an MOSFET switches and related electrical hardware. In a preferred embodiment, the incoming alternating current would be converted to direct current in the range of 12V to 48V.

In another embodiment, the heater element 2000 may comprise a Positive Temperature Coefficient (PTC) element that self limits the power dissipated. The internal electrical resistance of a PTC element increases with temperature, so the power level is self limiting. PTC heater elements are commercially available from companies such as STEGO that are rated to run on voltages from 110 to 220 V rms. A heater circuit employing a PTC heating element would resemble heater circuit 2005 with the voltage detect element 2020 removed. The heater power would be controlled with the PWM element 2010 using a Triac.

Database and User Interface Systems

The database subsystem 346, also on the user interface computer 302, stores all data to and retrieves all data from the databases used for the onboard storage of machine, patient, prescription, user-entry and treatment history information. This provides a common access point when such information is needed by the system. The interface provided by the database subsystem 346 is used by several processes for their data storage needs. The database subsystem 346 also manages database file maintenance and back-up.

The UI screen view 338 may invoke a therapy log query application to browse the therapy history database. Using this application, which may alternatively be implemented as multiple applications, the user can graphically review their treatment history, their prescription and/or historical machine status information. The application transmits database queries to the database subsystem 346. The application can be run while the patient is dialyzing without impeding the safe operation of the machine.

The remote access application, which may be implemented as a single application or multiple applications, provides the functionality to export therapy and machine diagnostic data for analysis and/or display on remote systems. The therapy log query application may be used to retrieve information requested, and the data may be reformatted into a machine neutral format, such as XML, for transport. The formatted data may be transported off-board by a memory storage device, direct network connection or other external interface 348. Network connections may be initiated by the APD system, as requested by the user.

The service interface 356 may be selected by the user when a therapy is not in progress. The service interface 356 may comprise one or more specialized applications that log test results and optionally generate a test report which can be uploaded, for example, to a diagnostic center. The media player 358 may, for example, play audio and/or video to be presented to a user.

According to one exemplary implementation, the databases described above are implemented using SQLite®, a software library that implements a self-contained, serverless, zero-configuration, transactional SQL database engine.

The executive subsystem 332 implements two executive modules, the user interface computer (UIC) executive 352 on the user interface computer 302 and the automation computer (AC) executive 354 on the automation computer 300. Each executive is started by the startup scripts that run after the operating system is booted and includes a list of processes it starts. As the executives go through their respective process lists, each process image is checked to ensure its integrity in the file system before the process is launched. The executives monitor each child process to ensure that each starts as expected and continue monitoring the child processes while they run, e.g., using Linux parent-child process notifications. When a child process terminates or fails, the executive either restarts it (as in the case of the UI view) or places the system in fail safe mode to ensure that the machine behaves in a safe manner. The executive processes are also responsible for cleanly shutting down the operating system when the machine is powering off.

The executive processes communicate with each other allowing them to coordinate the startup and shutdown of the various application components. Status information is shared periodically between the two executives to support a watchdog function between the processors. The executive subsystem 332 is responsible for enabling or disabling the safe line. When both the UIC executive 352 and the AC executive 354 have enabled the safe line, the pump, the heater, and the valves can operate. Before enabling the lines, the executives test each line independently to ensure proper operation. In addition, each executive monitors the state of the other's safe line.

The UIC executive 352 and the AC executive 354 work together to synchronize the time between the user interface computer 302 and the automation computer 300. The time basis is configured via a battery backed real-time clock on the user interface computer 302 that is accessed upon startup. The user interface computer 302 initializes the CPU of the automation computer 300 to the real-time clock. After that, the operating system on each computer maintains its own internal time. The executives work together to ensure sufficiently timekeeping by periodically performing power on self tests. An alert may be generated if a discrepancy between the automation computer time and the user interface computer time exceeds a given threshold.

Figure 47:
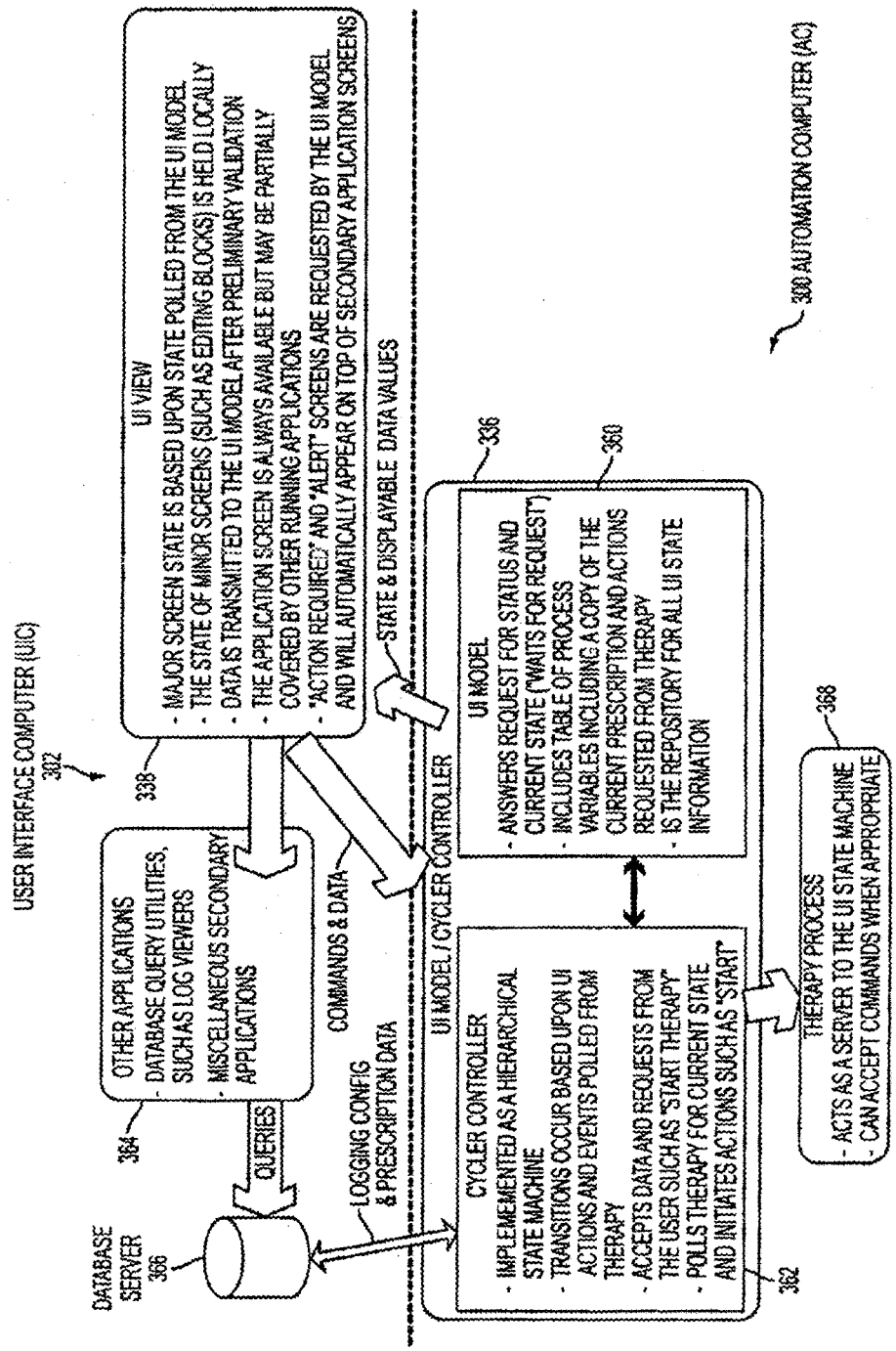
FIG. 47 shows a flow of information between various subsystems and processes of the APD system in an illustrative embodiment.

FIG. 47 shows the flow of information between various subsystems and processes of the APD system. As discussed previously, the UI model 360 and cycler controller 362 run on the automation computer. The user interface design separates the screen display, which is controlled by the UI view 338, from the screen-to-screen flow, which is controlled by the cycler controller 362, and the displayable data items, which are controlled by the UI model 360. This allows the visual representation of the screen display to be changed without affecting the underlying therapy software. All therapy values and context are stored in the UI model 360, isolating the UI view 338 from the safety-critical therapy functionality.

The UI model 360 aggregates the information describing the current state of the system and patient, and maintains the information that can be displayed via the user interface. The UI model 360 may update a state that is not currently visible or otherwise discernable to the operator. When the user navigates to a new screen, the UI model 360 provides the information relating to the new screen and its contents to the UI view 338. The UI model 360 exposes an interface allowing the UI view 338 or some other process to query for current user interface screen and contents to display. The UI model 360 thus provides a common point where interfaces such as the remote user interface and online assistance can obtain the current operational state of the system.

The cycler controller 362 handles changes to the state of the system based on operator input, time and therapy layer state. Acceptable changes are reflected in the UI model 360. The cycler controller 362 is implemented as a hierarchical state machine that coordinates therapy layer commands, therapy status, user requests and timed events, and provides view screen control via UI model 360 updates. The cycler controller 362 also validates user inputs. If the user inputs are allowed, new values relating to the user inputs are reflected back to the UI view 338 via the UI model 360. The therapy process 368 acts as a server to the cycler controller 362. Therapy commands from the cycler controller 362 are received by the therapy process 368.

The UI view 338, which runs on the UI computer 302, controls the user interface screen display and responds to user input from the touch screen. The UI view 338 keeps track of local screen state, but does not maintain machine state information. Machine state and displayed data values, unless they are in the midst of being changed by the user, are sourced from the UI model 360. If the UI view 338 terminates and is restarted, it displays the base screen for the current state with current data. The UI view 338 determines which class of screens to display from the UI model 360, which leaves the presentation of the screen to the UI view. All safety-critical aspects of the user interface are handled by the UI model 360 and cycler controller 362.

The UI view 338 may load and execute other applications 364 on the user interface computer 302. These applications may perform non-therapy controlling tasks. Exemplary applications include the log viewer, the service interface, and the remote access applications. The UI view 338 places these applications within a window controlled by the UI view, which allows the UI view to display status, error, and alert screens as appropriate. Certain applications may be run during active therapy. For example, the log viewer may be run during active therapy, while the service interface and the remote access application generally may not. When an application subservient to the UI view 338 is running and the user's attention is required by the ongoing therapy, the UI view 338 may suspend the application and regain control of the screen and input functions. The suspended application can be resumed or aborted by the UI view 338.

Figure 48:
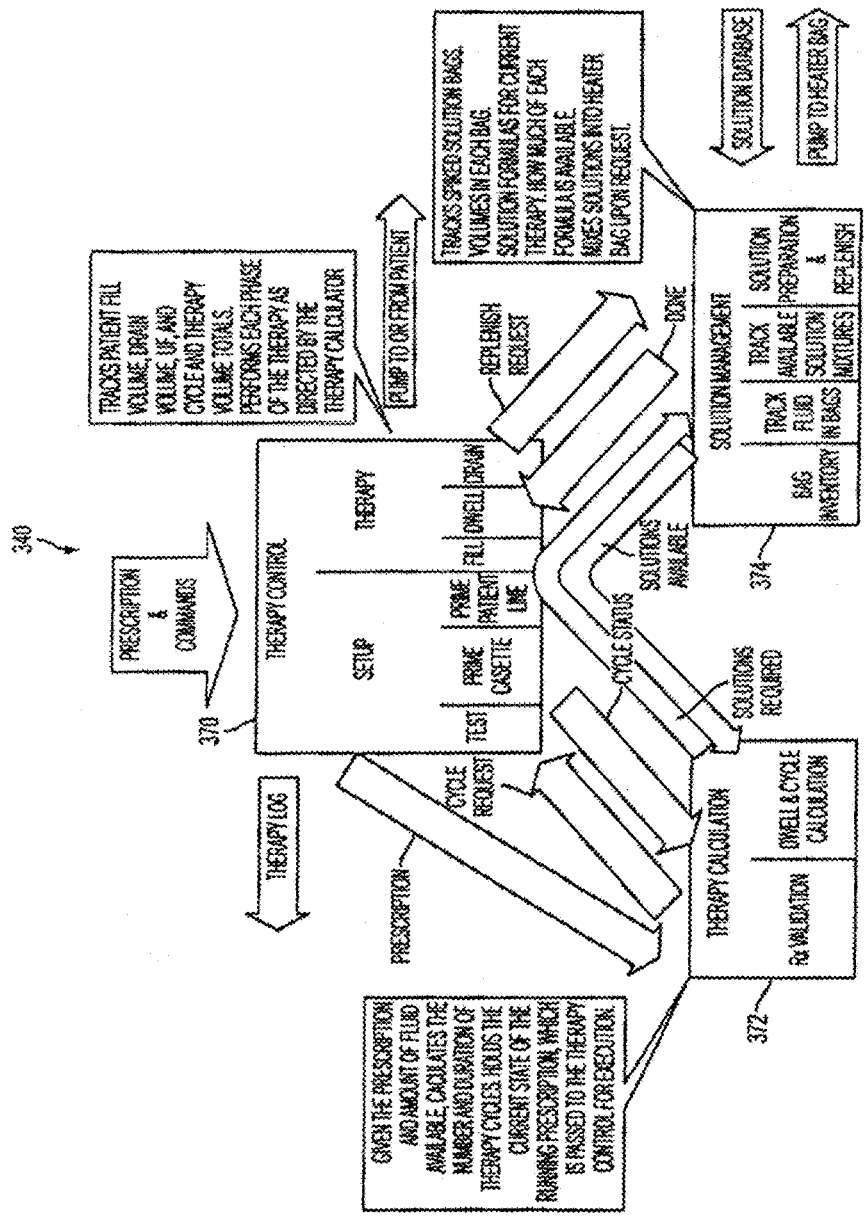
FIG. 48 illustrates an operation of the therapy subsystem of FIG. 46.

FIG. 48 illustrates the operation of the therapy subsystem 340 described in connection with FIG. 46. The therapy subsystem 340 functionality is divided across three processes: therapy control; therapy calculation; and solution management. This allows for functional decomposition, ease of testing, and ease of updates.

The therapy control module 370 uses the services of the therapy calculation module 372, solution management module 374 and machine control subsystem 342 (FIG. 46) to accomplish its tasks. Responsibilities of the therapy control module 370 include tracking fluid volume in the heater bag, tracking fluid volume in the patient, tracking patient drain volumes and ultra filtrate, tracking and logging cycle volumes, tracking and logging therapy volumes, orchestrating the execution of the dialysis therapy (drain-fill-dwell), and controlling therapy setup operations. The therapy control module 370 performs each phase of the therapy as directed by the therapy calculation module 370.

The therapy calculation module 370 tracks and recalculates the drain-fill-dwell cycles that comprise a peritoneal dialysis therapy. Using the patient's prescription, the therapy calculation module 372 calculates the number of cycles, the dwell time, and the amount of solution needed (total therapy volume). As the therapy proceeds, a subset of these values is recalculated, accounting for the actual elapsed time. The therapy calculation module 372 tracks the therapy sequence, passing the therapy phases and parameters to the therapy control module 370 when requested.

The solution management module 374 maps the placement of solution supply bags, tracks the volume in each supply bag, commands the mixing of solutions based upon recipes in the solution database, commands the transfer of the requested volume of mixed or unmixed solution into the heater bag, and tracks the volume of mixed solutions available using the solution recipe and available bag volume.

FIG. 49 shows a sequence diagram depicting exemplary interactions of the therapy module processes described above during the initial 'replenish' and 'dialyze' portions of the therapy. During the exemplary initial replenish process 376, the therapy control module 370 fetches the solution ID and volume for the first fill from the therapy calculation module 372. The solution ID is passed to the solution management module 374 with a request to fill the heater bag with solution, in preparation for priming the patient line and the first patient fill. The solution management module 374 passes the request to the machine control subsystem 342 to begin pumping the solution to the heater bag.

During the exemplary dialyze process 378, the therapy control module 370 executes one cycle (initial drain, fill, dwell-replenish, and drain) at a time, sequencing these cycles under the control of the therapy calculation module 372. During the therapy, the therapy calculation module 372 is updated with the actual cycle timing, so that it can recalculate the remainder of the therapy if needed.

In this example, the therapy calculation module 372 specifies the phase as "initial drain," and the therapy control module makes the request to the machine control subsystem 342. The next phase specified by the therapy calculation module 372 is "fill." The instruction is sent to the machine control subsystem 342. The therapy calculation module 372 is called again by the therapy control module 370, which requests that fluid be replenished to the heater bag during the "dwell" phase. The solution management module 374 is called by the therapy control module 370 to replenish fluid in the heater bag by calling the machine control subsystem 342. Processing continues with therapy control module 370 calling the therapy calculation module 372 to get the next phase. This is repeated until there are no more phases, and the therapy is complete.

Pump Monitor/Math Repeater

The Pump Monitor/Math Repeater process is a software process or function that runs on the automation computer 300 separate from the safety executive 354. The Pump Monitor/Math Repeater process is implemented in as two separate threads or sub-functions that run independently. The math repeater thread, herein referred to as the MR thread, confirms the FMS calculation result. The Pump Monitor thread, referred to as the PM thread, monitors the net fluid and air flow across relevant endpoints from information provided in the routine status messages from the Machine process 342. The relevant endpoints may include but not be limited to 5 potential bag spikes, the heater bag, patient port and drain port. The PM thread will also monitor the heater pan temperature via information from the IO Server process. The PM thread will signal an alarm to the safety executive 354, if predefined limits for fluid flow, air flow or temperature are exceeded.

The MR thread accepts the high speed pressure data and repeats the FMS calculation described above to recalculate the fluid volume displaced. The MR thread compares its recalculated fluid volume to the volume calculated by the Machine process 342 and sends a message to the safety executive. In another example, the MR thread declares and error condition if the two fluid volume values do not match.

The PM thread monitors several aspects of the pumping process as a safety check on the functioning of the cycler 14. The PM thread will declare an invalid pump operation error condition if the Hardware Interface 310 reports valves open that do not correspond to the commanded pump action by the Machine subsystem 342. An example of an invalid valve condition would be if any port valve 186, 184 (FIG. 6) are open, while the pump was in an idle mode. The state of valves in the cassette is mapped to the state of the corresponding pneumatic valves 2710, which are energized by the hardware interface 310. Another example of an invalid valve condition would be a port valve 184, 186 that is open that does not correspond to the specified source of sink of fluid.

The PM thread will declare an error condition if excess fluid is pumped to the patient while the heater button temperature sensor 506 reports less than a given temperature. In a preferred embodiment, the PM thread will declare a error condition more than 50 ml of fluid is pumped to the patient while the button temperature is less than 32° C.

The PM thread will maintain a numerical accumulator on the amount of fluid pumped to the patient. If total volume of fluid pumped to the patient exceeds a specified amount, the PM thread will declare an error. The specified amount may be defined in the prescription information and may include an additional volume equal to one chamber volume or approximately 23 ml.

The PM thread will maintain a numerical accumulator on the amount of air measured in the pumping chamber by the FMS method for air taken from each bag. If the total amount of air from any bag exceeds the maximum allowed volume of air for that bag, then the PM thread will declare an error. In a preferred embodiment, the maximum allowed air volume for the heater bag is 350 ml and the maximum allowed air volume for a supply bag is 200 ml. A large air volume from a bag indicates that it may contain a leak to the atmosphere. The maximum allowed air volume for the heater bag may be larger to account for out-gassing when the fluid is heated.

Alert/Alarm Functions

Conditions or events in the APD system may trigger alerts and/or alarms that are logged, displayed to a user, or both. These alerts and alarms are a user interface construct that reside in the user interface subsystem, and may be triggered by conditions that occur in any part of the system. These conditions may be grouped into three categories: (1) system error conditions, (2) therapy conditions, and (3) system operation conditions.

"System error conditions" relate to errors detected in software, memory, or other aspects of the processors of the APD system. These errors call the reliability of the system into question, and may be considered "unrecoverable." System error conditions cause an alarm that is displayed or otherwise made known to the user. The alarm may also be logged. Since system integrity cannot be guaranteed in the instance of a system error condition, the system may enter a fail safe mode in which the safe line described herein is disabled.

Each subsystem described in connection with FIG. 46 is responsible for detecting its own set of system errors. System errors between subsystems are monitored by the user interface computer executive 352 and automation computer executives 354. When a system error originates from a process running on the user interface computer 302, the process reporting the system error terminates. If the UI screen view subsystem 338 is terminated, the user interface computer executive 352 attempts to restart it, e.g., up to a maximum of three times. If it fails to restart the UI screen view 338 and a therapy is in progress, the user interface computer executive 352 transitions the machine to a fail safe mode.

When a system error originates from a process running on the automation computer 300, the process terminates. The automation computer executive 354 detects that the process has terminated and transitions to a safe state if a therapy is in progress.

When a system error is reported, an attempt is made to inform the user, e.g., with visual and/or audio feedback, as well as to log the error to a database. System error handling is encapsulated in the executive subsystem 332 to assure uniform handling of unrecoverable events. The executive processes of the UIC executive 352 and AC executive 354 monitor each other such that if one executive process fails during therapy, the other executive transitions the machine to a safe state.

"Therapy conditions" are caused by a status or variable associated with the therapy going outside of allowable bounds. For example, a therapy condition may be caused by an out-of-bounds sensor reading. These conditions may be associated with an alert or an alarm, and then logged. Alarms are critical events, generally requiring immediate action. Alarms may be prioritized, for example as low, medium or high, based on the severity of the condition. Alerts are less critical than alarms, and generally do not have any associated risk other than loss of therapy or discomfort. Alerts may fall into one of three categories: message alerts, escalating alerts, and user alerts.

The responsibility for detecting therapy conditions that may cause an alarm or alert condition is shared between the UI model and therapy subsystems. The UI model subsystem 360 (FIG. 47) is responsible for detecting alarm and alert conditions pre-therapy and post-therapy. The therapy subsystem 340 (FIG. 46) is responsible for detecting alarm and alert conditions during therapy.

The responsibility for handling alerts or alarms associated with therapy conditions is also shared between the UI model and therapy subsystems. Pre-therapy and post-therapy, the UI model subsystem 360 is responsible for handling the alarm or alert condition. During a therapy session, the therapy subsystem 340 is responsible for handling the alarm or alert condition and notifying the UI Model Subsystem an alarm or alert condition exists. The UI model subsystem 360 is responsible for escalating alerts, and for coordinating with the UI view subsystem 338 to provide the user with visual and/or audio feedback when an alarm or alert condition is detected.

"System operation conditions" do not have an alert or alarm associated with them. These conditions are simply logged to provide a record of system operations. Auditory or visual feedback need not be provided.

Actions that may be taken in response to the system error conditions, therapy conditions, or system operation conditions described above are implemented by the subsystem (or layer) that detected the condition, which sends the status up to the higher subsystems. The subsystem that detected the condition may log the condition and take care of any safety considerations associated with the condition. These safety considerations may comprise any one or combination of the following: pausing the therapy and engaging the occluder; clearing states and timers as needed; disabling the heater; ending the therapy entirely; deactivating the safe line to close the occluder, shut off the heater, and removing power from the valves; and preventing the cycler from running therapies even after a power cycle to require the system to be sent back to service. The UI subsystem 334 may be responsible for conditions that can be cleared automatically (i.e., non-latching conditions) and for user recoverable conditions that are latched and can only be cleared by user interaction.

Each condition may be defined such that it contains certain information to allow the software to act according to the severity of the condition. This information may comprise a numeric identifier, which may be used in combination with a lookup table to define priority; a descriptive name of the error (i.e., a condition name); the subsystem that detected the condition; a description of what status or error triggers the condition; and flags for whether the condition implements one or more actions defined above.

Conditions may be ranked in priority such that when multiple conditions occur, the higher priority condition may be handled first. This priority ranking may be based on whether the condition stops the administration of therapy. When a condition occurs that stops therapy, this condition takes precedence when relaying status to the next higher subsystem. As discussed above, the subsystem that detects a condition handles the condition and sends status information up to the subsystem above. Based on the received status information, the upper subsystem may trigger a different condition that may have different actions and a different alert/alarm associated with it. Each subsystem implements any additional actions associated with the new condition and passes status information up to the subsystem above. According to one exemplary implementation, the UI subsystem only displays one alert/alarm at a given time. In this case, the UI model sorts all active events by their priority and displays the alert/alarm that is associated with the highest priority event.

A priority may be assigned to an alarm based on the severity the potential harm and the onset of that harm. Table 1, below, shows an example of how priorities may be assigned in this manner

TABLE 1

| POTENTIAL RESULT OF FAILURE TO RESPOND TO THE CAUSE OF ALARM CONDITION | ONSET OF POTENTIAL HARM | | |
|---|---|---|---|
| | IMMEDIATE | PROMPT | DELAYED |
| death or irreversible injury | high priority | high priority | medium priority |
| reversible injury | high priority | medium priority | low priority |
| minor discomfort or injury | medium priority | low priority | low priority or no alarm signal |

In the context of Table 1, the onset of potential harm refers to when an injury occurs and not to when it is manifested. A potential harm having an onset designated as "immediate" denotes a harm having the potential to develop within a period of time not usually sufficient for manual corrective action. A potential harm having an onset designated as "prompt" denotes a harm having the potential to develop within a period of time usually sufficient for manual corrective action. A potential harm having an onset designated as "delayed" denotes a harm having the potential to develop within an unspecified time greater than that given under "prompt."

Figure 50:
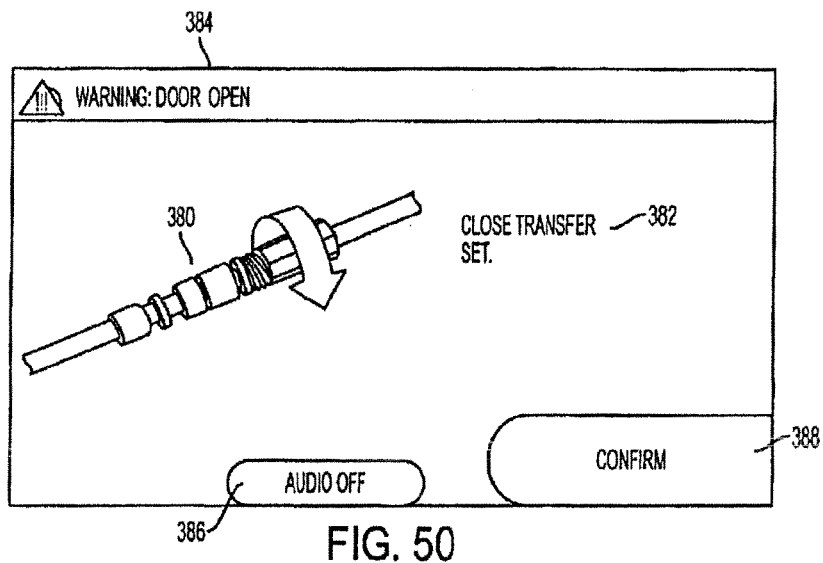
FIGS. 50-55 show exemplary screen views relating to alerts and alarms that may be displayed on a touch screen user interface for the APD system.
Figure 51:
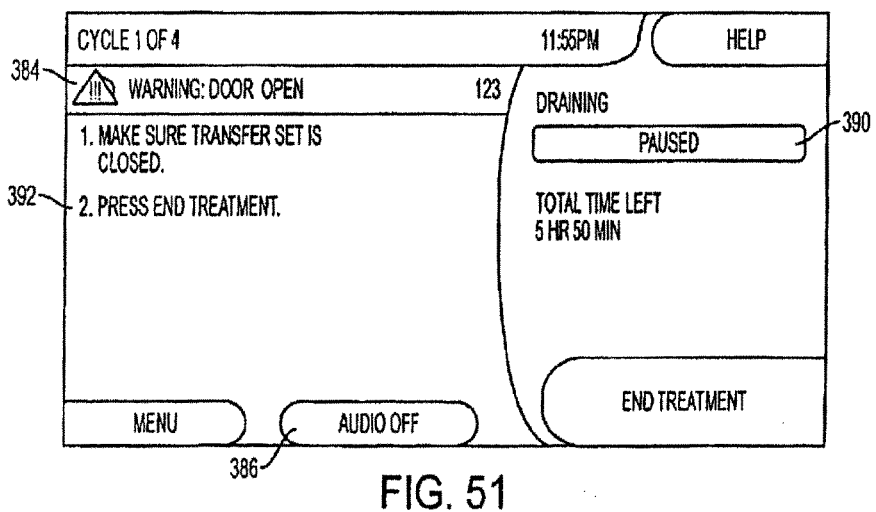

FIGS. 50-55 show exemplary screen views relating to alerts and alarms that may be displayed on a touch screen user interface. FIG. 50 shows the first screen of an alarm, which includes a diagram 380 and text 382 instructing a user to close their transfer set. The screen includes a visual warning 384, and is also associated with an audio warning. The audio warning may be turned off my selecting the "audio off" option 386 on the touch screen. When the user has closed the transfer set, the user selects the "confirm" option 388 on the touch screen. FIG. 51 shows a similar alarm screen instructing a user to close their transfer set. In this case, an indication that draining is paused 390 and an instruction to select "end treatment" are provided 392.

As previously discussed, alerts generally do not have associated risk other than loss of therapy or discomfort. Thus, an alert may or may not cause the therapy to pause. Alerts can be either "auto recoverable," such that if the event clears the alert automatically clears, or "user recoverable," such that user interaction with the user interface is needed to clear the alert. An audible alert prompt, which may have a volume that may be varied within certain limits, may be used to bring an alert to the attention of a user. In addition, information or an instruction may be displayed to the user. So that such information or instruction may be viewed by the user, an auto-dim feature of the user interface may be disabled during alerts.

In order to reduce the amount of disturbance the user, alerts may be categorized into different types based on how important an alert is and how quick a user response is required. Three exemplary types of alerts are a "message alert," an "escalating alert," and a "user alert." These alerts have different characteristics based on how information is visually presented to the user and how the audible prompt is used.

Figure 52:
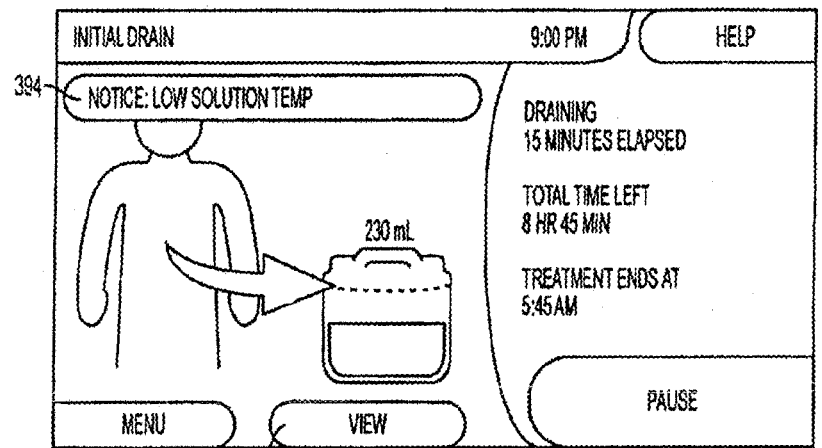
Figure 53:
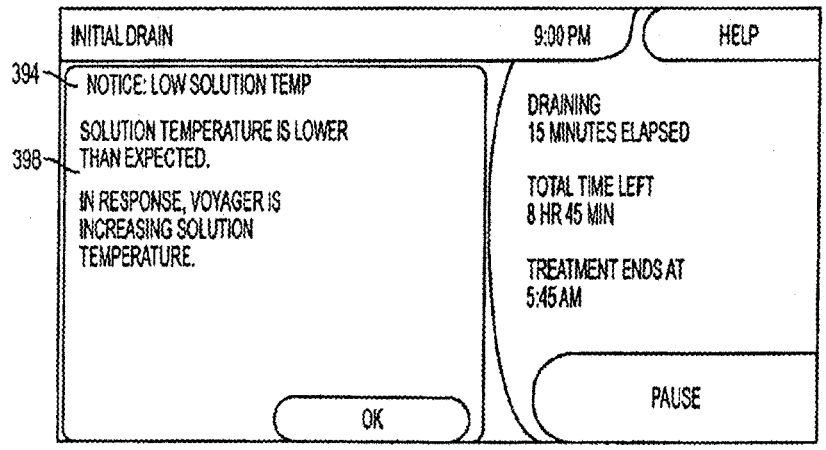

A "message alert" may appear at the top of a status screen and is used for informational purposes when a user interaction is not required. Because no action needs to be taken to clear the alert, an audible prompt is generally not used to avoid disturbing, and possibly waking, the patient. However, an audible alert may be optionally presented. FIG. 52 shows an exemplary message alert. In particular, FIG. 52 shows an under-temperature message alert 394 that may be used to inform a user when the dialysate is below a desired temperature or range. In this case, a user does not need to take any action, but is informed that therapy will be delayed while the dialysate is heated. If the patient desires more information, the "view" option 396 may be selected on the touch screen. This causes additional information 398 concerning the alert to appear on the screen, as shown in FIG. 53. A message alert may also be used when there is a low flow event that the user is trying to correct. In this case, a message alert may be displayed until the low flow event is cleared to provide feedback to the user on whether the user fixed the problem.

Figure 54:
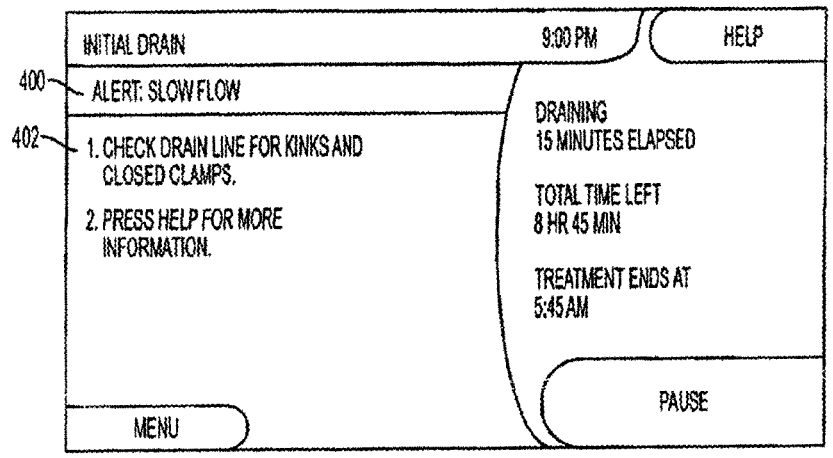
Figure 55:
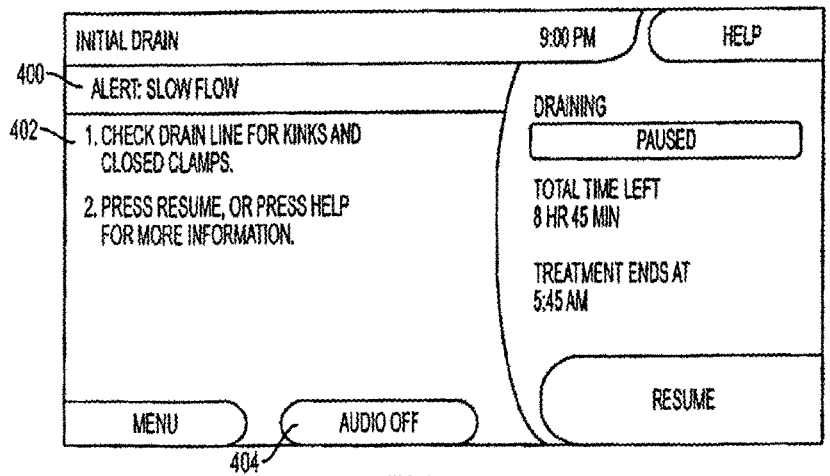

An "escalating alert" is intended to prompt the user to take action in a non-jarring manner During an escalating alert, a visual prompt may displayed on the touch screen and an audible prompt may be presented (e.g., once). After a given period of time, if the event that caused the alert is not cleared, a more emphatic audible prompt may be presented. If the event causing the alert is not cleared after an additional period of time, the alert is escalated to a "user alert." According to one exemplary implementation of a user alert, a visual prompt is displayed until the alert is cleared and an audible prompt, which can be silenced, is presented. The UI subsystem does not handle the transition to from escalating alert to user alert. Rather, the subsystem that triggered the original event will trigger a new event associated with the user alert. FIG. 54 shows a screen view displaying information concerning an escalating alert. This exemplary alert includes an on-screen alert message 400 and a prompt 402 instructing the user to check the drain line for kinks and closed clamps, as well as and an audible prompt. The audible prompt may be continuous until it is silenced by the user. FIG. 55 shows a screen view including an "audio off" option 404 that may be selected to silence the audible prompt. This alert can be used directly, or as part of the escalating alert scheme.

Each alert/alarm is specified by: an alert/alarm code, which is a unique identifier for the alert/alarm; an alert/alarm name, which is a descriptive name of the alert/alarm; an alert/alarm type, which comprises the type of alert or level of alarm; an indication of whether an audible prompt is associated with the alert/alarm; an indication of whether the alert and associated event can be bypassed (or ignored) by the user; and the event code of the event or events that trigger the alert/alarm.

During alarms, escalating alerts and user alerts, the event code (which may be different from the alert or alarm code, as described above) may be displayed on the screen so that the user can read the code to service personnel if needed. Alternatively or additionally, a voice guidance system may be used so that, once connected to a remote call center, the system can vocalize pertinent information about the system configuration, state, and error code. The system may be connected to the remote call center via a network, telephonic connection, or some other means.

Figure 56:
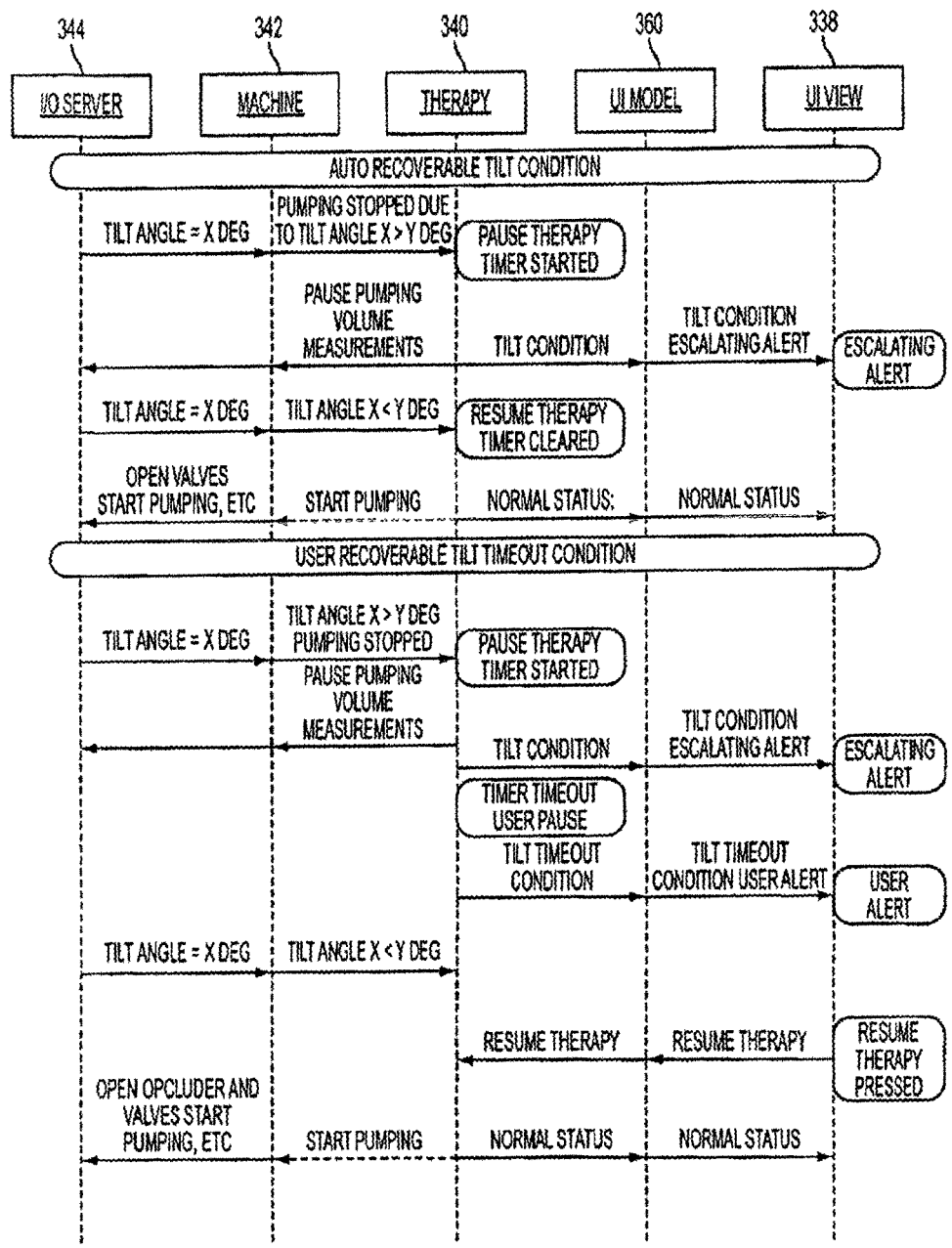
FIG. 56 illustrates component states and operations for error condition detection and recovery in an illustrative embodiment.

An example of a condition detected by the therapy subsystem is described below in connection with FIG. 56. The condition results when the APD system is not positioned on a level surface, which is important for air management. More particularly, the condition results when a tilt sensor detects that APD system is tilted beyond a predetermined threshold, such as 35°, with respect to a horizontal plane. As described below, a recoverable user alert may be generated by the therapy subsystem if the tilt sensor senses an angle with an absolute value greater than the predetermined threshold. To avoid nuisance alarms, the user may be directed to level the APD system before therapy begins. The tilt threshold may be lower during this pre-therapy period (e.g., 35°). The user may also be given feedback concerning whether the problem is corrected.

When the tilt sensor detects an angle of tilt exceeding a threshold value during therapy, the machine subsystem 342 responds by stopping the pump in a manner similar to detecting air in the pump chamber. The therapy subsystem 340 asks for status and determines that the machine layer 342 has paused pumping due to tilt. It also receives status information concerning the angle of the machine. At this point, the therapy subsystem 340 generates a tilt condition, pauses therapy, and sends a command to the machine subsystem 342 to pause pumping. This command triggers clean-up, such as taking fluid measurement system (FMS) measurements and closing the patient valve. The therapy subsystem 340 also starts a timer and sends an auto recoverable tilt condition up to the UI model 360, which sends the condition to the UI view 338. The UI view 338 maps the condition to an escalating alert. The therapy subsystem 340 continues to monitor the tilt sensor reading and, if it drops below the threshold, clears the condition and restarts therapy. If the condition does not clear before the timer expires, the therapy subsystem 340 triggers a user recoverable "tilt timeout" condition that supersedes the auto-recoverable tilt condition. It sends this condition to the UI model 360, which sends the condition to the UI view 338. The UI view 338 maps the condition to a user alert. This condition cannot be cleared until a restart therapy command is received from the UI subsystem (e.g., the user pressing the resume button). If the tilt sensor reading is below the threshold, the therapy resumes. If it is not below the threshold, the therapy layer triggers an auto recoverable tilt condition and starts the timer.

Prioritized Audible Signals

The cycler may provide audible signals and voice guidance to the user to communicate a range of information including but not limited to number selection, sound effects (button selection, action selection), machine condition, operational directions, alerts, and alarms. The cycler controller 16 may cause a speaker to annunciate audible signals and vocalizations from stored sound files stored in memory on one or both of the computers 300, 302 in the control system 16. Alternatively, vocalizations may be stored and produced by a specialized voice chip.

In some instances, the cycler may have multiple audible signals to annunciate at the same time or sequentially in a very short time. The annunciation of several signals in a short period of time may overwhelm the user resulting in annoyance or the loss of critical safety information. The cycler controller 16 may assign priorities to each audible signal and suppress the lower priority signals to allow the clear communication of higher priority audible signals. In one instance, the audible signals are prioritized from the highest priority alarm signals to the lowest priority annunciation of a sequence of numbers:

1. Alarms
2. Alerts
3. Sound Effects
4. Voice Guidance
5. Annunciation for a sequence of numbers.

Alarms and alerts are described above. Sound effects may confirm sounds to indicate that a button, or choice has been selected. Sound effects may also announce or confirm a particular action is being taken by the cycler. Voice guidance may include voiced instructions to execute a particular procedure, access help, contact a call center and other directing instructions. Annunciation for a sequence of numbers may include reading back to the user or the call center the number that the user had just keyed in or it may read the user allowable values for requested input.

Audible Sleep Aid

The cycler 14 may include an option to play soothing sounds at night to aid sleeping. The playing of sounds such as rain, ocean waves, etc are referred to as sound therapy. Sound therapy for sleep can provide some users with a higher tolerance for nighttime noises and the masking or replacing of nighttime noise with more rhythmic, soothing sounds that minimize sleep disturbance. Sound therapy may help individuals suffering from hearing conditions such as hyperacusis and tinnitus. The user interface 324 may provide the user with a menu to select types of sound, volume levels and duration so that the sound therapy can play before during the initial period of sleep. The sound files may be stored in the memories of the computers 300, 302 and played by the speaker in the cycler 14. In another example, the cycler may include an output jack to drive external speakers. In another example, the sound files and/or the speaker driver electronics may be separate from either the automation computer 300 or the user interface computer 302. The sound files may include the but be limited to rain sounds, thunder storms, ocean waves, thunder, forest sounds, crickets, white noise, and pink noise (varying amplitude and more bass).

Battery Operation

The cycler may include a rechargeable lithium ion battery for use as a backup power source. At a minimum this battery helps to ensure that the cycler does not turn off without alerting the user and saving the current state of the treatment. A power management system may be implemented by the cycler when on battery power that is contingent on the amount of charge remaining in the battery. If the battery is sufficiently charged, the cycler can prevent brownouts or short power outages from interfering with the completion of a therapy. The cycler control circuitry can measure the state of charge of the battery, and can correlate the battery charge level with operable states. This information may be obtained empirically through testing, and the correlations between battery charge level and the ability to operate the various subsystems may be stored in memory. The following functions may be associated with the battery charge level:

Level 4: Enough power to perform one cycle of therapy. Implemented if, for example, the charge level of the battery is equal to or greater than approximately 1100 milliamp-hours.

Level 3: Enough power to perform a user drain. Implemented if, for example, the charge level of the battery is equal to or greater than approximately 500 milliamp-hours.

Level 2: Enough power to end therapy, display alert, and guide user through post-therapy breakdown. Implemented if, for example, the charge level of the battery is equal to or greater than approximately 300 milliamp-hours.

Level 1: Enough power to end therapy and display an alert. Implemented if, for example, the charge level of the battery is equal to or greater than approximately 200 milliamp-hours.

Level 0: Not enough power to operate.

If there is enough charge in the battery (Level 4), the cycler will continue with the therapy until the current cycle is finished. This may not include replenishing the heater bag or heating the solution. Therefore, if already in a fill phase, the cycler may continue the therapy if the solution in the heater bag is in the proper temperature range and there is enough solution in the heater bag. If the battery only has enough capacity to perform a 20 minute drain (Level 3), the cycler will alert the user, and give the user the option to either drain or end treatment without draining. If the battery only has enough power to alert the user (Level 2) it will not give the user the option to drain and the user will be guided through the post-therapy breakdown. If there is not enough power to guide the user through breakdown (Level 1), the user will be prompted to disconnect and then the cycler will power down. At this battery level the cycler may not have enough power to release the door, so the user may not be able to breakdown the therapy. During start up, the cycler can assess the state of the batter, and alert the user if the battery has a fault or if the battery does not have a sufficient charge to at least alert the patient if main power is lost. The cycler may be programmed to not allow the user to start a treatment without the battery having enough capacity to provide and alert and guide the user through post-therapy breakdown (Battery Level 2).

Another example of battery charge levels and available therapy choices or machine actions sets 4 battery charge levels and the available therapy choices or machine actions:

Level 4:
  If the fill process has not started, then suspend operation until the AC power is restored. The suspend is limited to 30 mins.
  If the fill process has started, then complete cycle including the fill, dwell and drain processes.
  The heater bag will not be refilled as there is no heating during battery operation.
  End therapy, and guide user through post-therapy breakdown including removal of the of the dialysate delivery set 12*a* from the cycler 14.

Level 3:
  If in the fill or drain process, then suspend operation until the AC power is restored. The suspend is limited to 30 mins.
  If the drain process has started, then complete the cycle.
  The heater bag will not be refilled as there is no heating during battery operation.
  End therapy, and guide user through post-therapy breakdown including removal of the of the dialysate delivery set 12*a* from the cycler 14.

Level 2:
  End therapy, and guide user through post-therapy breakdown including removal of the of the dialysate delivery set 12*a* from the cycler 14.

Level 1:
  End therapy.

Level 0:
  Not enough power to operate.

An alert will be displayed to the user or patient at levels 1-4. The control system 16 may extend the cycler operation on battery power by dimming the display screen 324 after a given time period from the last screen touch. In another example the display screen 324 may dim after a given period from the appearance of the most recent message, alert or warning. In one example, the display screen 324 will dim 2 minutes after the more recent screen touch or last. The display screen 324 may include a message or symbol indicating operation on battery power.

The electrical circuitry connecting the battery to the pneumatic valves may include a regulated voltage boost converter that steps-up the supplied variable battery voltage to a consistent voltage. The supplied battery voltage may drop as the battery is discharged, In one example, an Li-Ion battery at full charge may supply 12.3 volts. The supplied voltage may drop as the battery is depleted to as low as 9 volts when the battery is fully discharged. The pneumatic valves may require a minimum voltage to reliably open fully. In one example, the minimum voltage to reliably open the valve may be 12 volts.

A regulated voltage boost converter may be placed between the supply batter and the valves to assure sufficient voltage to reliably open the valves as battery discharges. The regulated voltage boost converter will output a regulated voltage at a higher value than the variable battery voltage input. In one example, the regulated voltage boost converter may be an integrated chip such as the TPS61175 made by Texas Instruments. A regulated voltage buck/boost converter may also be used between the battery and the valves. The buck/boost converter is able to supply a regulated voltage output from supplied voltages that are higher, equal to, or lower than the input voltage.

In one embodiment, the PWM duty cycle of the valve drivers may vary with the measured battery voltage. The valves may be operated in a pick-and-hold manner, where an initially higher voltage is applied to open the valve and then a lower voltage is applied to hold the valve in desired condition. The PWM duty cycle for the hold function may be scaled inversely with the measure battery voltage to provide a consistent averaged voltage or current to the valves. The PWM duty cycle may be scaled inversely with measured battery voltage for the higher voltage open or pick operation.

Screen Display

As discussed previously, the UI view subsystem 338 (FIG. 47) is responsible for the presentation of the interface to the user. The UI view subsystem is a client of and interfaces with the UI model subsystem 360 (FIG. 47) running on the automation computer. For example, the UI view subsystem communicates with the UI model subsystem to determine which screen should be displayed to the user at a given time. The UI view may include templates for the screen views, and may handle locale-specific settings such as display language, skin, audio language, and culturally sensitive animations.

Figure 57:
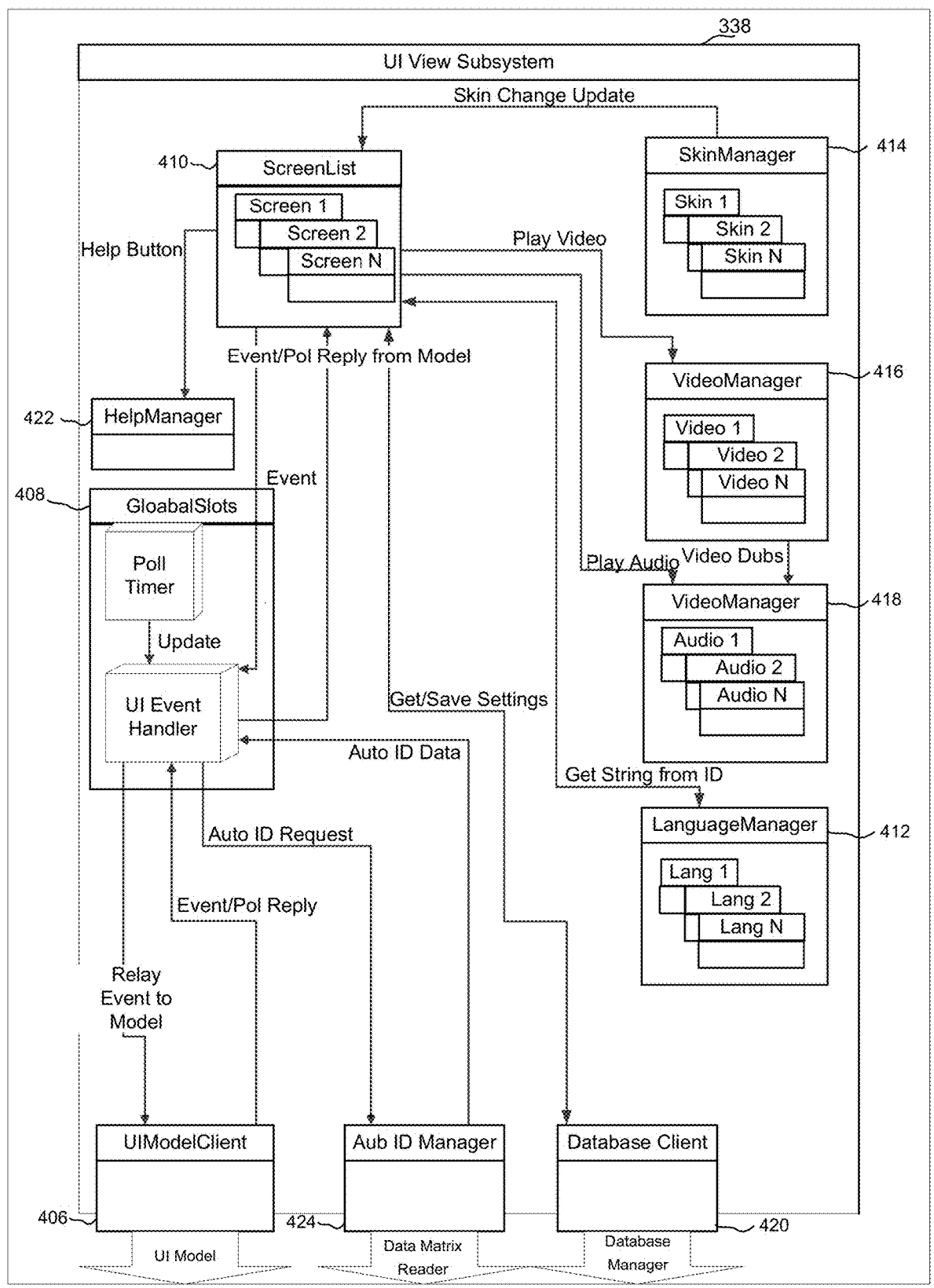
FIG. 57 shows exemplary modules of a UI view subsystem for the APD system.

There are three basic types of events that occur in the UI view subsystem. These are local screen events that are handled by the individual screens, model events in which a screen event must propagate down to the UI model subsystem, and polling events that occur on a timer and query the UI model subsystem for status. A local screen event only affects the UI view level. These events can be local screen transitions (e.g., in the case of multiple screens for a single model state), updates to view settings (e.g., locality and language options), and requests to play media clips from a given screen (e.g., instructional animations or voice prompts). Model events occur when the UI view subsystem must consult with the UI model subsystem to determine how to handle the event. Examples that fall into this category are the confirmation of therapy parameters or the pressing of the "start therapy" button. These events are initiated by the UI view subsystem, but are handled in the UI model subsystem. The UI model subsystem processes the event and returns a result to the UI view subsystem. This result drives the internal state of the UI view subsystem. Polling events occur when a timer generates a timing signal and the UI model subsystem is polled. In the case of a polling event, the current state of the UI view subsystem is sent to the UI model subsystem for evaluation. The UI model subsystem evaluates the state information and replies with the desired state of the UI view subsystem. This may constitute: (1) a state change, e.g., if the major states of the UI model subsystem and the UI view subsystem are different, (2) a screen update, e.g., if values from the UI model subsystem change values displayed on-screen, or (3) no change in state, e.g., if the state of the UI model subsystem and the UI view subsystem are identical. FIG. 57 shows the exemplary modules of the UI view subsystem 338 that perform the functions described above.

As shown in FIG. 57, the UI model client module 406 is used to communicate events to the UI model. This module 406 is also used to poll the UI model for the current status. Within a responsive status message, the UI model subsystem may embed a time to be used to synchronize the clocks of the automation computer and the user interface computer.

The global slots module 408 provides a mechanism by which multiple callback routines (slots) can subscribe to be notified when given events (signals) occur. This is a "many-to-many" relationship, as a slot can be bound to many signals, and likewise a signal can be bound to many slots to be called upon its activation. The global slots module 408 handles non-screen specific slots, such as application level timers for UI model polling or button presses that occur outside of the screen (e.g., the voice prompt button).

The screen list class 410 contains a listing of all screens in the form of templates and data tables. A screen is made up of a template and an associated data table that will be used to populate that screen. The template is a window with widgets laid out on it in a generic manner and with no content assigned to the widgets. The data table includes records that describe the content used to populate the widgets and the state of the widgets. A widget state can be checked or unchecked (in the case of a checkbox style widget), visible or hidden, or enabled or disabled. The data table can also describe the action that occurs as a result of a button press. For example, a button on window 'A' derived from template '1' could send an event down to the UI model, whereas that same button on window 'B' also derived from template '1' could simply cause a local screen transition without propagating the event down to the UI model. The data tables may also contain an index into the context-sensitive help system.

The screen list class 410 forwards data from the UI model to the intended screen, selects the proper screen-based data from the UI model, and displays the screen. The screen list class 410 selects which screen to display based on two factors: the state reported by the UI model and the internal state of the UI view. In some cases, the UI model may only inform the UI view that it is allowed to display any screen within a category. For example, the model may report that the machine is idle (e.g., no therapy has been started or the setup phase has not yet occurred). In this case, it is not necessary to confer with the UI model when the user progresses from a menu into its sub-menu. To track the change, the UI view will store the current screen locally. This local sequencing of screens is handled by the table entries described above. The table entry lists the actions that respective buttons will initiate when pressed.

The language manager class 412 is responsible for performing inventory on and managing translations. A checksum may be performed on the list of installed languages to alert the UI view if any of the translations are corrupted and or missing. Any class that wants a string translated asks the language manager class 412 to perform it. Translations may be handled by a library (e.g., Qt®). Preferably, translations are requested as close as possible to the time of rendering. To this end, most screen template member access methods request a translation right before handing it to the widget for rendering.

A skin comprises a style-sheet and images that determine the "look and feel" of the user interface. The style-sheet controls things such as fonts, colors, and which images a widget will use to display its various states (normal, pressed, disabled, etc.). Any displayed widget can have its appearance altered by a skin change. The skin manager module 414 is responsible for informing the screen list and, by extension, the screen widgets, which style-sheet and skin graphics should be displayed. The skin manager module 414 also includes any animated files the application may want to display. On a skin change event, the skin manager will update the images and style-sheet in the working set directory with the proper set, which is retrieved from an archive.

The video manager module 416 is responsible for playing locale-appropriate video given a request to display a particular video. On a locale change event, the video manager will update the videos and animations in the working set directory with the proper set from an archive. The video manager will also play videos that have accompanying audio in the audio manager module 418. Upon playback of these videos, the video manager module 416 will make the appropriate request to the audio manager module 418 to play the recording that belongs to the originally requested video clip.

Similarly, the audio manager module 418 is responsible for playing locale-appropriate audio given a request to play a particular audio clip. On a locale change event, the audio manager will update the audio clips in the working set directory with the proper set from an archive. The audio manager module 418 handles all audio initiated by the UI view. This includes dubbing for animations and sound clips for voice prompts.

The database client module 420 is used to communicate with the database manager process, which handles the interface between the UI view subsystem and the database server 366 (FIG. 47). The UI view uses this interface to store and retrieve settings, and to supplement therapy logs with user-provided answers to questions about variables (e.g., weight and blood pressure).

The help manager module 422 is used to manage the context-sensitive help system. Each page in a screen list that presents a help button may include an index into the context-sensitive help system. This index is used so that the help manager can display the help screen associated with a page. The help screen may include text, pictures, audio, and video.

The auto ID manager 424 is called upon during pre-therapy setup. This module is responsible for capturing an image (e.g., a photographic image) of a solution bag code (e.g., a datamatrix code). The data extracted from the image is then sent to the machine control subsystem to be used by the therapy subsystem to identify the contents of a solution bag, along with any other information (e.g., origin) included in the code.

Using the modules described above, the UI view subsystem 338 renders the screen views that are displayed to the user via the user interface (e.g., display 324 of FIG. 45). FIGS. 58-64 show exemplary screen views that may be rendered by the UI view subsystem. These screen views illustrate, for example, exemplary input mechanisms, display formats, screen transitions, icons and layouts. Although the screens shown are generally displayed during or before therapy, aspects of the screen views may be used for different input and output functions than those shown.

Figure 58:
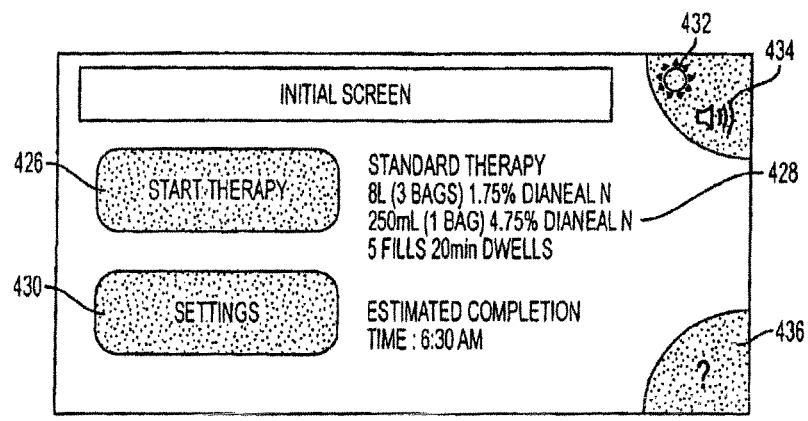
FIGS. 58-64 shows illustrative user interface screens for providing user information and receiving user input in illustrative embodiments regarding system setup, therapy status, display settings, remote assistance, and parameter settings.

The screen shown in FIG. 58 is an initial screen that provides the user the option of selecting between "start therapy" 426 to initiate the specified therapy 428 or "settings" 430 to change settings. Icons 432 and 434 are respectively provided to adjust brightness and audio levels, and an information icon 436 is provided to allow the user to solicit more information. These icons may appear on other screens in a similar manner.

Figure 59:
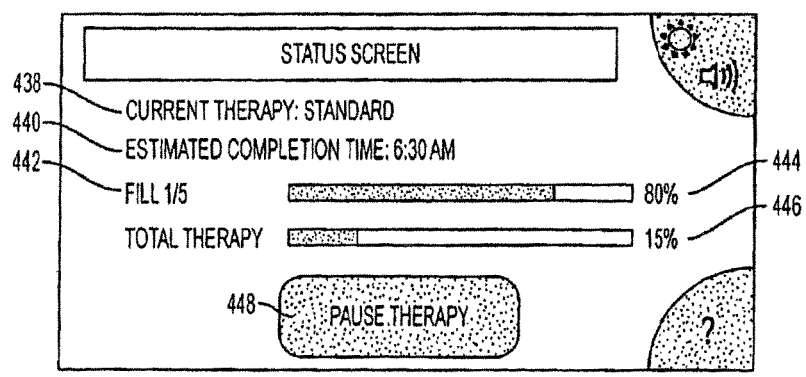

FIG. 59 shows a status screen that provides information the status of the therapy. In particular, the screen indicates the type of therapy being performed 438, the estimated completion time 440, and the current fill cycle number and total number of fill cycles 442. The completion percentage of the current fill cycle 444 and the completion percentage of the total therapy 446 are both numerically and graphically displayed. The user may select a "pause" option 448 to pause therapy.

Figure 60:
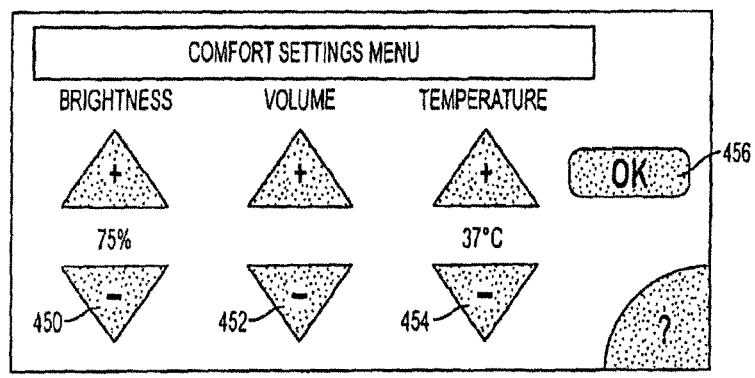

FIG. 60 shows a menu screen with various comfort settings. The menu includes brightness arrows 450, volume arrows 452 and temperature arrows 454. By selecting either the up or down arrow in each respective pair, a user can increase or decrease screen brightness, audio volume, and fluid temperature. The current brightness percentage, volume percentage and temperature are also displayed. When the settings are as desired, a user may select the "OK" button 456.

Figure 61:
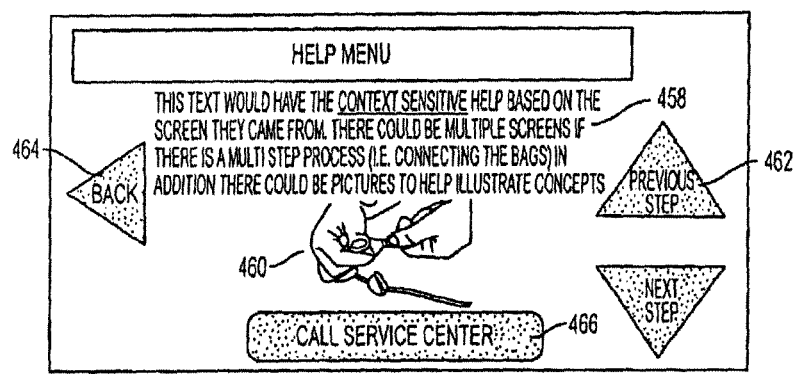

FIG. 61 shows a help menu, which may be reached, for example, by pressing a help or information button on a prior screen. The help menu may include text 458 and/or an illustration 460 to assist the user. The text and/or illustration may be "context sensitive," or based on the context of the prior screen. If the information provided to the user cannot conveniently be provided in one screen, for example in the case of a multi-step process, arrows 462 may be provided to allow the user to navigate backward and forward between a series of screens. When the user has obtained the desired information. he or she may select the "back" button 464. If additional assistance is required, a user may select the "call service center" option 466 to have the system contact the call service center.

Figure 62:
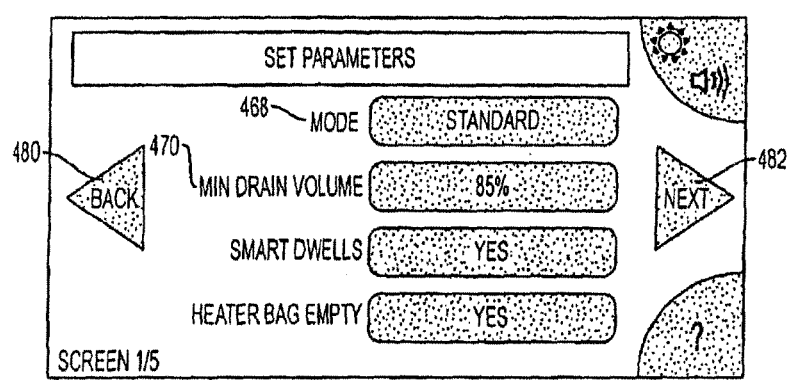
Figure 63:
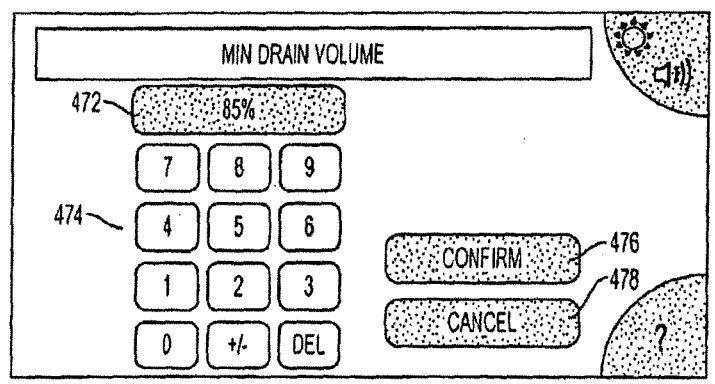

FIG. 62 illustrates a screen that allows a user to set a set of parameters. For example, the screen displays the current therapy mode 468 and minimum drain volume 470, and allows a user to select these parameters to be changed. Parameters may be changed in a number of ways, such as by selecting a desired option from a round robin style menu on the current screen. Alternatively, when the user selects a parameter to be changed, a new screen may appear, such as that shown in FIG. 63. The screen of FIG. 63 allows a user to adjust the minimum drain volume by inputting a numeric value 472 using a keypad 474. Once entered, the user may confirm or cancel the value using buttons 476 and 478. Referring again to FIG. 62, a user may then use the "back" and "next" arrows 480, 482 to navigate through a series of parameters screens, each including a different set of parameters.

Figure 64:
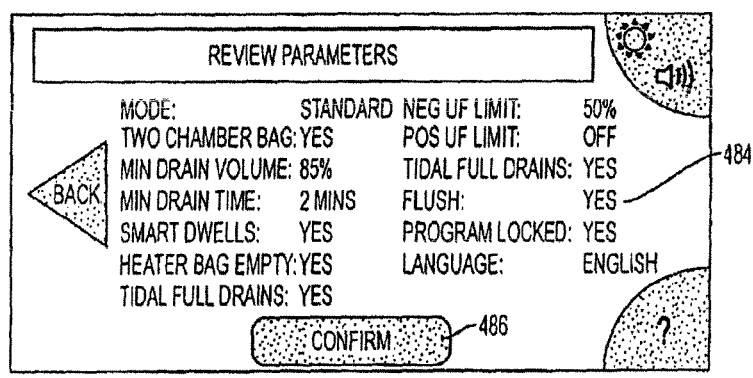

Once all desired parameters have been set or changed (e.g., when the user has navigated through the series of parameters screens), a screen such as that shown in FIG. 64 may be presented to allow a user to review and confirm the settings. Parameters that have changed may optionally be highlighted in some fashion to draw the attention of the user. When the settings are as desired, a user may select the "confirm" button 486.

Automated Peritoneal Dialysis Therapy Control

Continuous ambulatory peritoneal dialysis ("CAPD") is traditionally performed manually, with a patient or user transferring dialysis solution from a bag into his or her peritoneal cavity, having the fluid dwell in the abdomen for three to six hours, and then allowing the fluid to empty into a collection or drain bag. This is typically done three or four times a day. Automated peritoneal dialysis ("APD") differs from CAPD in that APD is achieved with the aid of a peritoneal dialysis machine ("cycler") that performs a series of fill-dwell-drain cycles during a period of several hours (e.g. when asleep or at night). In APD, the fluid introduced during a fill phase of a cycle, plus any ultrafiltration fluid, may not drain completely during the following drain phase of the cycle. This may be a result of the user's position in bed, leading to sequestration of fluid, for example, in a recess in the peritoneal cavity, and preventing an indwelling catheter from accessing all of the fluid present. In continuous cycling peritoneal dialysis ("CCPD"), the cycler attempts to perform a full drain after a fill and dwell phase in order to prevent accumulation of retained fluid (a residual intraperitoneal volume) with each succeeding cycle. APD generally comprises a plurality of short nighttime exchanges of dialysate while the user is connected to the cycler and asleep. At the end of a nighttime therapy, a volume of dialysis fluid—possibly of different composition—may be left in the peritoneal cavity during the day for continued exchange of solutes, transfer of waste compounds, and ultrafiltration. In intermittent peritoneal dialysis ("IPD"), multiple exchanges of dialysate are performed over a period of time (e.g., at night), without having a prolonged residual (or daytime) dwell cycle.

Therapy with a cycler generally begins with an initial drain phase to attempt to ensure that the peritoneal cavity is empty of fluid. The characteristics of the dialysate solution usually cause some transfer of fluid from the patient's tissues to the intraperitoneal space—ultrafiltration. As therapy proceeds through a series of cycles, fluid may accumulate in the intraperitoneal cavity if the drain phase does not yield the volume of fluid infused during the fill phase, plus the volume of ultrafiltered fluid produced during the time that dialysate solution is in the peritoneal cavity. In some modes, the cycler may be programmed to issue an alarm to the user when the drain volume has not matched the volume of fluid infused plus the expected ultrafiltration ("UF") volume. (The expected UF volume is a function of—among other things—the individual patient's physiology, the chemical composition of the dialysate solution, and the time during which the dialysate solution is expected to be present in the peritoneal cavity).

In other modes, the cycler may proceed to the next fill-dwell-drain cycle if a pre-determined amount of drain time has passed and a pre-determined minimum percentage (e.g. 85%) of the preceding fill volume has been drained. In this case, the cycler may be programmed to alarm if the drain flow decreases below a pre-determined rate after the minimum drain time and before the minimum drain percentage has been reached. The cycler may be programmed to alert the user after several minutes (e.g., two minutes) of attempting but failing to maintain a pre-determined flow rate when pumping fluid from the peritoneal cavity. A low-flow condition may be detectable by the cycler because of the increased amount of time required to fill a pump chamber before end-of-stroke is detected by the controller. A zero-flow or no-flow condition may be detectable by the cycler because of the detection by the controller of a premature end-of-stroke state. The duration of the time delay before alerting the user or initiating a new fill-dwell-drain cycle may be programmed to be a few minutes in a low-flow condition (e.g., 2 minutes), and may be shorter (e.g., 30 seconds) in a no-flow condition. A shorter wait-time during a no-flow condition may be preferable, for example, because it may be associated with a greater degree of patient discomfort, or may be the result of a quickly correctable problem, such as a bend in the patient line or catheter. This time delay may be programmed at the cycler manufacturing stage or may be selectable by a clinician as a prescription parameter. The extent of the delay may be governed, among other things, by the countervailing desire of the user or clinician to stay within the targeted total therapy time (keeping in mind that little dialysis is likely to occur when the intraperitoneal volume ("IPV") is low or close to zero). If a full drain is not achieved, the cycler may also track the amount of fluid estimated to be accumulating with each cycle, and issue a warning or alarm if the cumulative IPV exceeds a pre-determined amount. This maximum IPV may be a parameter of the therapy prescription programmed into the cycler by the clinician, taking account of the particular physiological characteristics of the individual patient/user.

One method of dealing with the cumulative retention of fluid during a series of CCPD cycles is to convert the CCPD therapy to a tidal peritoneal dialysis ("TPD") therapy. TPD generally comprises a fill-dwell-drain cycle in which a drain volume is intentionally made a prescribed fraction of the initial fill volume (which may also be initially be entered by the clinician as a prescription parameter). A pre-determined percentage of the infused fluid, or a pre-determined amount of fluid is arranged to remain in the peritoneal cavity during the subsequent fill-dwell-drain cycles during a therapy. Preferably, the subsequent fill volumes are also reduced to match the drain volume (minus the expected UF) in order to maintain a relatively constant residual intraperitoneal volume. For example, an initial fill volume of 3000 ml may be introduced at the beginning of therapy, followed by subsequent drain and [fill plus expected UF] volumes amounting to only 1500 ml, i.e. 50% of the initial fill volume. The reserve or residual fluid in the peritoneal cavity is then drained completely at the end of therapy. In an alternative mode, a complete drain may be attempted after a pre-determined or prescribed number of fill-dwell-drain cycles (e.g., a complete drain may be attempted after three cycles of tidal therapy, this grouping comprising a therapy "cluster"). TPD may be beneficial in that users may experience less discomfort associated with repeated large fill volumes or repeated attempts to fully empty the peritoneal cavity. Low-flow conditions associated with small intraperitoneal fluid volumes may also be reduced, thus helping to avoid extending the total therapy time. To reduce the discomfort associated with attempting to drain small residual volumes, for example, the tidal drain volume may be set at 75% of the initial fill volume (plus-or-minus expected UF volume), for example, leaving approximately 25% as a reserve or residual volume in the peritoneal cavity for the duration of therapy, or for the duration of a cluster of cycles.

A cycler may also be programmed to convert a CCPD mode of therapy to a TPD mode of therapy during the course of therapy if the user chooses to keep a residual volume of fluid in the peritoneal cavity at the end of the subsequent drain phases (e.g., for comfort reasons). In this case, the cycler is programmed to calculate a choice of residual volumes (or volumes as a percent of initial fill volume) based on the number of extra cycles to be added to the therapy and the volume of remaining dialysate to be infused. For example, the cycler controller can calculate the remaining fill volumes based on the remaining cycles that include an additional one, two or more cycles. Having determined the fill volumes for each of these possibilities, the cycler controller can calculate how much residual volume can be left at the end of each remaining drain phase while ensuring that the IPV remains under a maximum prescribed IPV (Max IPV). The cycler may then present the user with a range of possible residual volumes (as a percentage of the initial fill volume or in volumetric terms) available for each remaining cycle in a therapy extended by one, two or more cycles. The user may make the selection based on the number of extra cycles chosen and the desired amount of post-drain residual volume. Switching to tidal therapy may help to reduce the number of low-drain-flow alerts to the user, which can be particularly advantageous during nighttime therapy.

In switching to tidal mode, the cycler may be programmed to select a reserve or residual volume percentage (volume remaining in the peritoneal cavity as a percent of the fill volume plus expected UF). Alternatively, the reserve volume may be user-selectable or clinician-selectable from a range of values, optionally with the clinician having the ability to select a wider range of possible values than the user. In an embodiment, the cycler may calculate the effects of adding one, two or three additional cycles on the remaining fill volumes and the expected residual IP volume percentage, and give the user or clinician the option of selecting among those calculated values. Optionally, the cycler may be constrained to keep the residual IP volume percentage below a pre-determined maximum value (e.g., a percentage of the initial fill volume plus expected UF, or a percentage of the maximum permissible IPV).

If CCPD is converted to TPD, one or more therapy cycles (fill-dwell-drain cycles) may need to be added to a therapy to use all of the prescribed volume of dialysate for the therapy session. The remaining volume to be infused going forward would then be divided by the remaining number of cycles. Furthermore, the cycler may be programmed to allow the clinician or user to select between extending the targeted total therapy time to accommodate the additional cycles (cycle-based therapy), or to attempt to maintain the targeted therapy time by adjusting the dwell times (i.e., shortening them) if necessary to reduce the fill-dwell-drain cycle durations going forward (time-based therapy).

In an alternative embodiment, the cycler may allow the residual IP volume to fluctuate (optionally within pre-determined limits) from one cycle to the next, depending on how much fluid can be drained within a specified drain time interval. The time available for the drain phase may be limited if the cycler has been programmed to complete the therapy within the previously scheduled time, or the drain phase may be terminated to prevent the cycler from attempting to pull fluid at a slow rate for a prolonged period of time. In switching from CCPD to TPD, if the cycler adds one or more additional cycles to perform a complete therapy with the available dialysate solution, then meeting the scheduled therapy end-time may require shortening the dwell times, or reducing each drain phase, which could cause the residual volume for the tidal mode to vary, depending on the drain flow conditions. As the cycler estimates and tracks the amount of residual volume, it may be programmed to calculate whether the subsequent fill volume plus expected UF volume will reach or exceed a prescribed maximum IPV. If so, the cycler can alert and provide the user with two or more options: the user may terminate treatment, repeat or extend a drain phase in an attempt to lower the residual intraperitoneal volume, or add a cycle to reduce the subsequent fill volumes. After calculating the effect on treatment time of adding an additional one or more cycles (increased number of cycles vs. reduced fill and drain times at lower volumes) the cycler may optionally reduce subsequent dwell times by an amount of time necessary to offset the additional therapy time generated by an additional one or more cycles. The cycler may be programmed to deliver an optional last-fill phase that delivers fresh dialysate of the same or a different composition to the user's peritoneal cavity for an extended dwell time while not connected to the cycler (e.g., a prolonged dwell phase for a "day therapy," i.e., during the day following a nighttime therapy). At the user's option, the last fill volume may be selected to be less than the fill volumes used during nighttime therapy. The cycler may also optionally prompt the user to select an optional extra last drain to give the user the chance to completely empty the peritoneal cavity prior to the infusion of a last fill volume (which may be carried by the user for a relatively prolonged period of time after the end of nighttime therapy). If this function is enabled, the cycler may prompt the user to sit up or stand, or otherwise move about to mobilize any trapped fluid in the peritoneal cavity during this last drain phase.

The cycler may also be programmed to account for an expected amount of ultrafiltration ("UF") fluid produced during a dwell phase on or off the machine, and to alert the user if a minimum drain volume that includes the volume infused plus this expected UF is not drained either initially at the beginning of therapy, or during a fill-dwell-drain cycle during therapy. In an embodiment, the cycler may be programmed for a minimum initial drain volume and a minimum initial drain time, and to pause or terminate the drain phase if the measured drain flow rate has decreased below a pre-determined threshold value for a pre-determined number of minutes. The minimum initial drain volume may comprise the volume of the last fill phase in the preceding nighttime therapy, plus an expected UF volume from the day therapy dwell phase. If the minimum (or more) initial drain volume is achieved, the minimum initial drain time is reached, and/or the drain flow rate has decreased, the IPV tracked by the cycler controller may be set to zero at the end of the initial drain phase. If not, the cycler may alert the user. The cycler may allow the user to bypass the minimum initial drain volume requirement. For example, the user may have manually drained at some time before initiating APD. If the user elects to forego adherence to the minimum initial drain volume, the cycler may be programmed to perform a full drain at the end of the first cycle regardless of the type of therapy selected by the user. If enabled, this feature helps to ensure that the second fill-dwell-drain cycle begins at an IPV that is as close to zero as possible, helping to ensure that a prescribed maximum IPV should not be exceeded during subsequent cycles of the therapy.

The cycler may also be programmed to allow the user to pause therapy. During a pause, the user may have the option to alter the therapy by reducing the fill volume, reducing therapy time, terminating a planned "day therapy," or ending therapy altogether. In addition, the user may have the option to perform an immediate drain at any time during therapy. The volume of an unscheduled drain may be selected by the user, whereupon the cycler may resume the cycle at the stage at which it was interrupted.

The cycler may be programmed to have a prescriber or "clinician" mode. A software application may be enabled to allow a clinician to create or modify a set of parameters forming the therapy prescription for a particular patient or user, as well as setting the limits within which a user may adjust user-accessible parameters. The clinician mode may also allow a clinician to fix one or more treatment parameters that would otherwise be accessible to a user, as well as lock a parameter to prevent a user from changing it. A clinician mode may be password-protected to prevent unauthorized access. The clinician mode application may be constructed to interface with a database to read and write the parameters comprising a prescription. Preferably, a "user mode" permits a user to access and adjust user-accessible parameters during a pre-therapy startup phase of a therapy.

In addition, an "active therapy mode" may optionally be available to a user during therapy, but with access to only a subset of the parameters or parameter ranges available in the user mode. In an embodiment, the cycler controller may be programmed to allow parameter changes during active therapy mode to affect only the current therapy, the parameter settings being reset to previously prescribed values before subsequent therapies. Certain parameters preferably are not user-adjustable at all, user-adjustable with concurrence of a clinician through a prescription setting, or user-adjustable only within a range of values set by a clinician in programming a prescription. Examples of parameters that may not be adjustable solely by the user include, for example, the minimum initial drain volume or time, maximum initial fill volume, and maximum IPV. User-adjustable parameters may include, for example, the tidal drain frequency in a cluster (e.g., adjustable between 1 and 5 cycles), and the percentage of a tidal therapy fill volume to be drained (e.g., adjustable up or down by a pre-determined amount from a default value of, for example, 85%). In an alternative embodiment, the clinician mode may allow a clinician to prevent a user from programming a maximum IPV to be greater than a pre-determined multiple (e.g., 200%) of the initial fill volume assigned to a nighttime fill-dwell-drain cycle.

The cycler may also be programmed to routinely alert the user and to request confirmation when a user-adjustable parameter is entered that is outside of pre-determined ranges. For example, if the maximum IPV has been made user-adjustable in the clinician mode, the cycler may alert the user if he or she attempts to select a Max IPV value outside of a fractional range (e.g., 130-160%) of the programmed fill volume for nighttime therapy.

The cycler may also be programmed to alert the user (and possibly seek confirmation) if the initial drain volume has been made user-adjustable in the clinician mode, and the user selects an initial drain volume below a pre-determined percentage of the fill volume of the last therapy (e.g., if it is adjusted to be less than 70% of the last fill volume). In another example, the cycler may be programmed to alert the user (and possibly seek confirmation) if the total expected UF volume has been made user-adjustable by the clinician mode, and the user selects a total expected UF volume to be below a certain percentage of the total volume processed for a nighttime therapy (e.g., if the total expected UF volume is set at less than 7% of the total nighttime therapy volume). Generally the expected UF volume may be determined empirically by a clinician based on a user's prior experience with peritoneal dialysis. In a further embodiment, the cycler may be programmed to adjust the expected UF volume value according to the actual UF volume in one or more preceding cycles of a therapy. This volume may be calculated in a CCPD mode by calculating the difference between a measured full drain volume and the measured fill volume that preceded it. In some cases, it may be difficult to determine when the peritoneal cavity is fully drained of fluid, and it may be preferable to take an average value of the difference between a full drain volume and a preceding fill volume over a number of cycles.

Some of the programmable treatment settings may include:
- the number of daytime exchanges using the cycler;
- the volume of solution to be used for each daytime exchange;
- the total time for a nighttime therapy;
- the total volume of dialysis solution to be used for nighttime therapy (not including a last fill volume if a daytime dwell phase is used);

the volume of dialysis solution to be infused per cycle;

in a Tidal therapy, the volume of fluid to be drained and refilled during each cycle (a percentage of the initial fill volume in a nighttime therapy);

the estimated ultrafiltration volume to be produced during a nighttime therapy;

the volume of solution to be delivered at the end of a therapy and to be left in the peritoneal cavity for an extended period (e.g, daytime dwell);

the minimum initial drain volume required to proceed with a therapy;

the maximum intraperitoneal volume known or estimated to be present that the cycler will allow to reside in the patient's peritoneal cavity (which may be based on the measured volumes introduced into the peritoneal cavity, the measured volume removed from the peritoneal cavity, and the estimated volume of ultrafiltration produced during therapy).

Some of the more advanced programmable treatment settings for the cycler may include:

the frequency of full drains to be conducted during tidal peritoneal dialysis;

the minimum percentage of the volume delivered to the peritoneum during a day therapy that must be drained before a subsequent fill is allowed;

prompting the user to perform an extra drain phase at the end of therapy if a pre-determined percentage of the estimated total UF is not collected;

a minimum length of time required to perform an initial drain before therapy begins;

a minimum length of time required to perform subsequent drains, either in day-therapy mode or night-therapy mode;

variable dwell times, adjusted by the cycler controller to maintain a fixed total therapy time when either the fill times or drain times have been changed (thus helping to avoid disruptions of the user's schedule;

The cycler can provide the user with alerts or warnings about parameters that have been entered outside a recommended range of values. For example, a warning may be issued if:

the minimum initial drain volume before a therapy is less than a pre-determined percentage of the currently prescribed last-fill volume at the end of the previous therapy (e.g., <70%);

the maximum IPV is outside a pre-determined percentage range of the fill volume per cycle (e.g., <130% or >160%);

the UF volume threshold to trigger an alert to perform an extra drain at the end of therapy is less than a pre-determined percentage of the estimated UF volume per therapy (e.g. <60%);

the calculated or entered dwell time is less than a pre-determined number of minutes (e.g., <30 minutes);

the estimated UF volume per therapy is more than a pre-determined percentage of the total dialysis solution volume per therapy (e.g., >25%);

the sum of all the solution bag volumes for a therapy should be somewhat greater than the volume of solution used during a CCPD therapy session, in order to account for priming of fluid lines and for loss of fluid to drain during air mitigation procedures.

In the clinician mode, in addition to having a selectable maximum IPV, the cycler may be programmed to accept separate minimum drain times for initial drains, day-therapy drains, and night-therapy drains. In the user mode or in the active-therapy mode, the cycler may be programmed to prevent a user from skipping or shortening the initial drain phase at the start of a therapy. In addition, the cycler may permit early termination of the initial drain phase only after a series of escalating low-drain-flow alerts have been issued. (An initial alert may instruct the user to change positions or re-position the peritoneal dialysis catheter, which may then be followed by additional alternative instructions if low flow conditions persist, up to a maximum number of alerts). The cycler may also require the user to confirm any change the user makes to the planned therapy, including bypassing a phase. The clinician may specify in a prescription setting to prevent the user from bypassing a drain phase during nighttime therapy. During therapy, the cycler controller may be programmed to not reset the IPV to zero unless the drain volume exceeds the preceding fill volume (to account for the additional IPV produced by ultrafiltration). The cycler may also be programmed to display to the user the estimated IPV during fills, and may notify the user if any drain volume exceeds the fill volume by a pre-determined amount (e.g. drain volume greater than fill volume plus expected UF volume). The cycler may also be programmed to identify errors in user input and to notify the user of apparent input errors. For example, the number of cycles during a therapy calculated by the cycler, based on the prescription parameters entered by the clinician or user, should be within a pre-determined range (e.g. 1-10). Similarly, the dwell time calculated by the cycler should be greater than zero. In addition, the maximum IPV entered by the user or clinician should be greater than or equal to the fill volume per cycle, plus the expected UF volume. Furthermore, the cycler may be programmed to reject an entered value for maximum IPV that is greater than a pre-determined amount over the fill volume per cycle (e.g., maximum IPV≤200% of initial fill volume). In some cases, it may be desirable for the cycler to be programmed to set the maximum IPV to no greater than the last fill volume if the solution is to remain in the peritoneal cavity for a prolonged period of time, such as during a daytime therapy. In this case, the cycler may be programmed to alert the user if the cycler controller calculates that the last drain volume amounts to less than a complete drain, whereupon the cycler may provide the user with a choice to terminate therapy or undertake another drain phase.

Managing Increasing IPV while Minimizing Alarms

In an embodiment, the cycler may be programmed to track and manage an increasing IPV during a therapy without converting the therapy from continuous cycling peritoneal dialysis ("CCPD") therapy to a standard tidal peritoneal dialysis ("TPD") therapy, which would fix the residual volume to a percentage of the initial fill volume. Rather, an adaptive tidal therapy mode may be initiated, in which the residual volume is allowed to fluctuate or 'float' in response to any slow-drain conditions that may be encountered during any drain phase. The cycler may be programmed to permit this mode to operate as long as any subsequent fill volume plus expected UF does not exceed a prescribed maximum IPV ("Max IPV"). Thus the dwell-phase IPV may be permitted to increase or decrease during a therapy up to a maximum IPV, preferably set by a clinician in the clinician mode. In this adaptive tidal therapy mode, at each drain phase during a therapy, the cycler continues to attempt a complete drain within the allotted time, or as long as a low-flow or no-flow condition has not been detected for a prescribed or pre-set number of minutes. The residual volume at the end of the drain phase is allowed to vary or 'float' as long as it does not exceed an amount that would lead to exceeding the maximum IPV in the next fill phase or during the next dwell phase. In a preferred embodiment, the cycler may be programmed to not issue an alert or alarm to the user as long as it calculates that the subsequent fill phase or dwell phase will not reach or exceed maximum IPV.

The cycler may be programmed to deliver full fill volumes during each cycle of a therapy until the cycler controller calculates that the next fill volume will likely cause the IPV to exceed the maximum IPV. At a convenient time (such as, e.g., the end of a drain phase), the cycler controller may be programmed to calculate a maximum residual IP volume, which represents the maximum permissible residual IP volume at the end of a drain to allow the next cycle to proceed with the previously programmed fill volume. Partial drains will be permitted by the cycler without alarming or issuing an alert as long as the amount of fluid drained brings the residual IPV below the maximum residual IPV. If the estimated or predicted IPV at the end of a drain phase is less than the maximum residual IPV, the cycler can proceed with a full fill phase in the next cycle without risking exceeding the Max IPV. If the estimated IPV at the end of a drain is greater than the maximum residual IPV, the cycler controller may trigger an alert to the user that the subsequent fill plus UF may exceed the maximum IPV. In an embodiment, the cycler may display several options for the user to respond to this alert: it may allow the user to terminate therapy, to attempt another drain phase, or to proceed to enter a revised-cycle therapy mode, in which each subsequent fill volume is reduced and one or more cycles are added to the therapy (thereby ensuring that the remaining volume of fresh dialysate is used during that therapy). In an embodiment, a clinician or user may enable the cycler at the beginning of therapy to automatically enter this revised-cycle therapy mode without having to alert the user during therapy.

In some circumstances, the number of additional cycles may be limited by the planned total therapy time. For example, the duration of night time therapy may be limited by the time at which the user is scheduled to wake up or to get up to go to work. For nighttime therapy, the cycler controller may be programmed, for example, to prioritize the use of all dialysate solution that was planned for therapy in favor of ending therapy at the scheduled time. If the clinician or user has selected the dwell time to be adjustable, then the cycler controller will (1) add one or more cycles to ensure that the fill volume plus expected UF does not exceed maximum IPV; (2) ensure that all of the dialysis solution is used for therapy; and (3) attempt to reach the targeted end-of-therapy time by shortening the dwell times of the remaining cycles. An alternative option available to the user is to extend the end-of-therapy time. In a preferred embodiment, the cycler is programmed to add one or two additional cycles to the therapy to permit a reduced fill volume in order to prevent exceeding the maximum IPV. The cycler controller is programmed to recalculate the maximum residual IPV using the reduced fill volume occasioned by the increased number of cycles. Thus, if a low flow condition during drain occurs at the same IPV, the new higher maximum residual IPV may permit dialysis to proceed without exceeding maximum IPV. If the fill volume cannot be reduced enough by adding a maximum allowable number of extra cycles (e.g., 2 cycles in an exemplary night time therapy scenario), then the cycler may present the user with two options: re-attempt a drain phase, or end therapy. The cycler may be programmed to reset the fill volume again after an adjustment of the fill volume, possibly adding an additional cycle, if a low flow condition at the end of drain is again encountered at an IPV above the newly recalculated and reset maximum residual IPV. Thus the cycler may be programmed to repeatedly adjust the subsequent fill volumes to prevent exceeding maximum IPV if a premature low flow condition is repeatedly encountered.

Replenishment Limitation on Dwell Time Reductions

In an embodiment, if the cycler reduces fill volumes by adding one or more cycles, then it may also reduce the dwell time in order to attempt to keep the therapy session within the total scheduled therapy time. This mode may be useful for nighttime therapy, so that the patient may be reasonably assured that therapy will have ended before a planned time of awakening in the morning. However, the cycler will continue to replenish the heater bag as needed during therapy, the replenishment generally occurring during dwell phases (when the PD cassette is not otherwise pumping to or from the patient). Therefore, in some circumstances, total therapy time may need to be extended when the required reduction in remaining dwell times leads to a total remaining dwell time that is less than the total estimated time needed to replenish the heater bag with the remaining fresh dialysate. The cycler controller may therefore calculate a maximum dwell time reduction available for the remaining therapy cycles, and extend total therapy time to ensure that the remaining fresh dialysate is properly heated. Because the cycler controller keeps track of the volume of dialysate in the heater bag, the temperature of the dialysate in the heater bag, and the volume of remaining fresh dialysate that is scheduled to be infused, it can calculate an estimate of the amount of time needed to replenish the heater bag to a pre-determined volume (given its intrinsic pumping capacity), and the time needed to bring the dialysate in the heater bag up to the prescribed temperature before it is infused into the user. In an alternative embodiment, the cycler controller may interrupt pumping operations to or from the user at any time in order to engage the pumps for replenishment of the heater bag. The cycler controller may be programmed, for example, to prevent the volume of fluid in the heater bag from dropping below a pre-determined volume at any time during therapy, other than during the last cycle.

In an embodiment, the cycler may be programmed to deliver fluid to the heater bag at a greater flow rate than when it is transferring fluid to or from the user. If binary valves are used to regulate the flow of control fluid or gas between the positive/negative pressure reservoirs and the control or actuation chambers of the cassette pumps, the controller may issue on-off commands to the valves at different pressure levels measured in the control or actuation chambers of the pumps. Thus the pressure threshold in the pump control or actuation chamber at which the controller triggers an 'off' command to the binary valve may have an absolute value that is greater during delivery to or from the heater bag than the corresponding pressure threshold when the cycler is delivering or pulling fluid to or from the user's peritoneal cavity. A higher average pressure applied to the pump membrane may be expected to result in a greater flow rate of the liquid being pumped. A similar approach may be used if variable orifice valves are used to regulate the flow of control fluid or gas between the pressure reservoirs and the control or actuation chambers of the cassette pumps. In this case, the controller may modulate the flow resistance offered by the variable orifice valves to maintain a desired pressure in the pump control chamber within pre-determined limits as the pump membrane is moving through its stroke.

Exemplary Modes of Therapy

Figure 67:
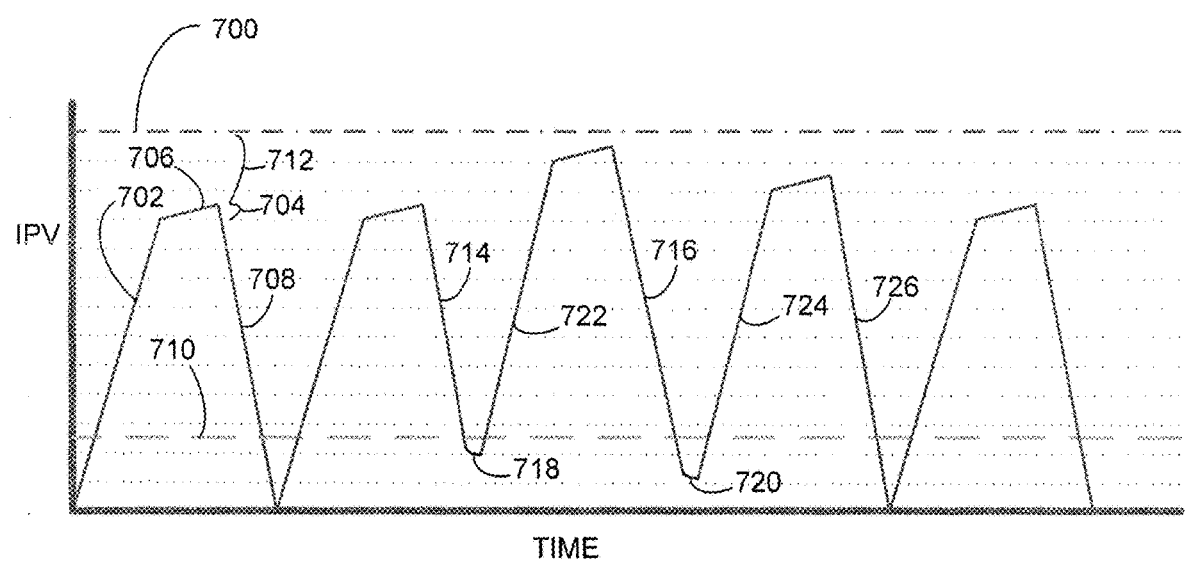
FIG. 67 shows an illustration of an adaptive tidal therapy mode during CCPD.

FIG. 67 is a graphical illustration (not to scale in either volumes or time) of an adaptive tidal mode of the cycler when in a CCPD mode. The initial drain at the beginning of therapy is omitted for clarity. The maximum IPV (Max IPV)

700 is a prescription parameter preferably set by the clinician. The initial fill volume 702 is also preferably set by the clinician as a prescription parameter. The expected UF volume is represented by the additional IPV increase 704 during the dwell phase 706. The expected UF volume for an entire therapy may be entered by a clinician into the prescription, and the cycler may then calculate the dwell time per cycle based on the number of cycles during the therapy, and thus the expected UF volume per cycle. It should be noted that ultrafiltration is expected to occur throughout the fill-dwell-drain cycle, and the expected UF volume may include the volume of fluid ultrafiltered throughout the cycle period. In most cases, the dwell time is much larger than the fill or drain times, rendering the ultrafiltration volumes during fill or drain relatively insignificant. (The fill and drain times may be adjustable by altering the pressure set points used by the controller to regulate the control valves between the pressure reservoirs and the pumps. However, the adjustability of liquid delivery flow rates and pressures to the user is preferably limited in order to ensure user comfort). Thus the expected UF volume per cycle 704 may be reasonably representative of ultrafiltration during the cycle. The drain phase 708 of the cycle in this example is a full drain, as would occur in a CCPD mode of therapy.

The maximum residual volume 710 can be calculated by the cycler controller once the Max IPV 700, the initial fill volume 702, and the expected UF volume are entered by the clinician. The maximum residual volume 710 is an indication of the 'headroom' 712 available in the peritoneal cavity to accommodate more fluid before reaching Max IPV 700. In an adaptive tidal mode within a CCPD mode of therapy, as long as a drain volume 714, 716 leaves an estimated residual volume 718, 720 less than the maximum residual volume 710, the subsequent fill volume 722, 724 can remain unchanged, because Max IPV 700 is not expected to be breached. As shown in FIG. 67, the occurrence of a low flow condition at the residual volumes 718 and 720 triggers the cycler to initiate the next fill phase 722 and 724. During this form of therapy, the cycler will continue to attempt to perform a full drain 726 within an allotted time assuming a low-flow or no-flow condition is not encountered before the estimated zero IPV is reached. Thus, even if a full drain is not performed (because of a low-flow or no-flow condition), in this case, full fill volumes will continue to be infused, the residual IPV will be allowed to float within a pre-determined range, and the user preferably will not be disturbed by any alarms or alert notifications.

Figure 68:
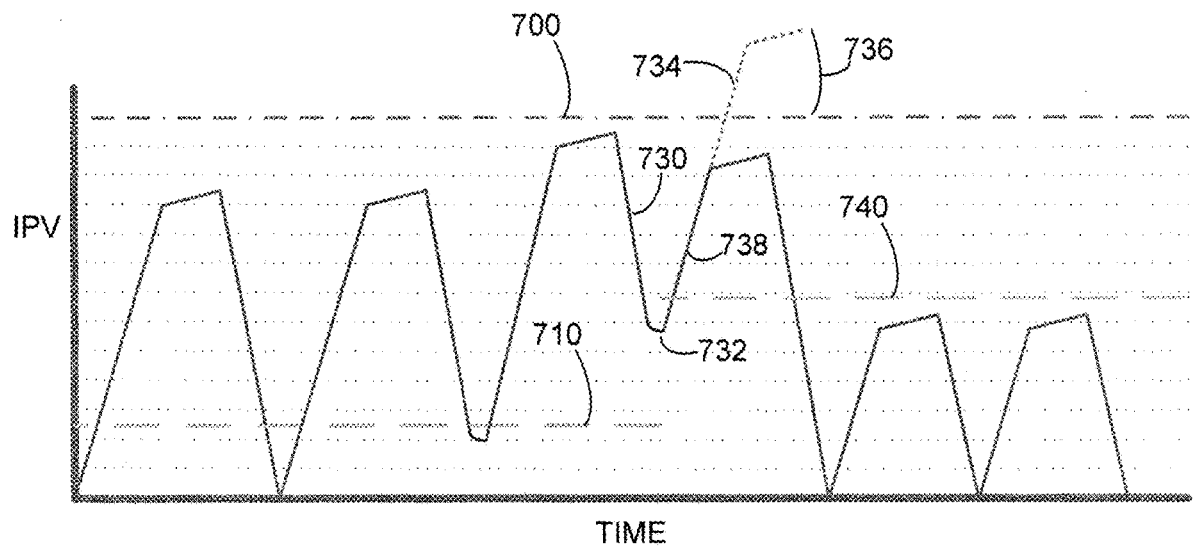
FIG. 68 shows an illustration of the implementation of a revised-cycle mode during CCPD.

FIG. 68 is a graphical illustration of how the cycler may handle incomplete drains that fail to reach the maximum residual IPV 710. In this case, the drain phase 730 of the third cycle encounters a low-flow or no-flow condition that prevents the cycler from draining the peritoneal cavity below the maximum residual IPV 710. Given the estimated residual volume 732 (the estimated residual volume after a pre-determined duration of a low-flow condition), the cycler calculates that a subsequent fill phase volume 734 will likely cause the prescribed Max IPV 700 to be reached or exceeded 736. Therefore, at the end of drain phase 730, the cycler may alert the user to this issue. The user may then have the option to terminate therapy, instruct the cycler to re-attempt a drain phase (after possibly changing positions or repositioning the PD catheter), or instruct the cycler to enter into a revised-cycle therapy mode in which the subsequent fill volumes are reduced and one or more cycles added to complete the therapy with the planned total volume of dialysate. To keep within the allotted or prescribed total therapy time, the cycler can calculate the duration of the modified cycles by reducing the fill and drain times to account for the reduced fill and drain volumes, and then determining whether and how much the dwell times need to be reduced to meet the designated ending time of the therapy session.

A user may optionally enable a revised-cycle mode of CCPD at the beginning of a therapy, so that the occurrence of a low-flow condition during therapy can trigger the revised-cycle mode without disturbing the user with an alert or alarm. Otherwise, the user may select the revised-cycle mode upon the occurrence of a low-flow condition above the maximum residual IPV. If the user elects to enter a revised-cycle mode, the cycler controller may calculate the required fill volumes for each of an additional one, two or more cycles (remaining fill volume divided by the remaining planned cycles plus the additional one or more cycles). If one additional cycle yields a fill volume (plus expected UF) low enough to avoid reaching or exceeding Max IPV, the cycler (either automatically or at the user's option) will resume CCPD at that new fill volume 738. Otherwise, the cycler controller will calculate a new fill volume based on an additional two cycles of therapy. (Rarely, more than two additional cycles may be required to ensure that Max IPV is not breached during the remaining therapy. If the additional cycles require a substantial reduction in the remaining dwell times, the cycler may alert the user, particularly if a minimum dwell time has been prescribed, or heater bag replenishment limitations will require a lengthening of the total therapy time). The now-reduced fill volume 738 allows the cycler controller to re-calculate a revised maximum residual IPV 740, which is a function of the sum of the new fill volume plus the expected UF volume per cycle. Any subsequent drain phases that leave an estimated residual IP volume less than the revised maximum residual volume 740 will preferably not trigger any further alerts or alarms to the user, allowing for the adaptive mode of tidal therapy to remain enabled. In an embodiment, the cycler may re-calculate the expected UF volume if it has reduced the duration of the remaining dwell phases in order to stay within the planned total therapy time. Any re-calculated reduction in the expected UF volume may further increase the revised maximum residual IPV. In the example shown in FIG. 68, the cycler continues to perform CCPD mode therapy, and happens to be able to drain fully in the remaining cycles. In order not to further inconvenience the user, the cycler may optionally refrain from making any further adjustments to the therapy (particularly if the total volume of dialysate and the total therapy time have been kept within the prescribed parameters).

Figure 69:
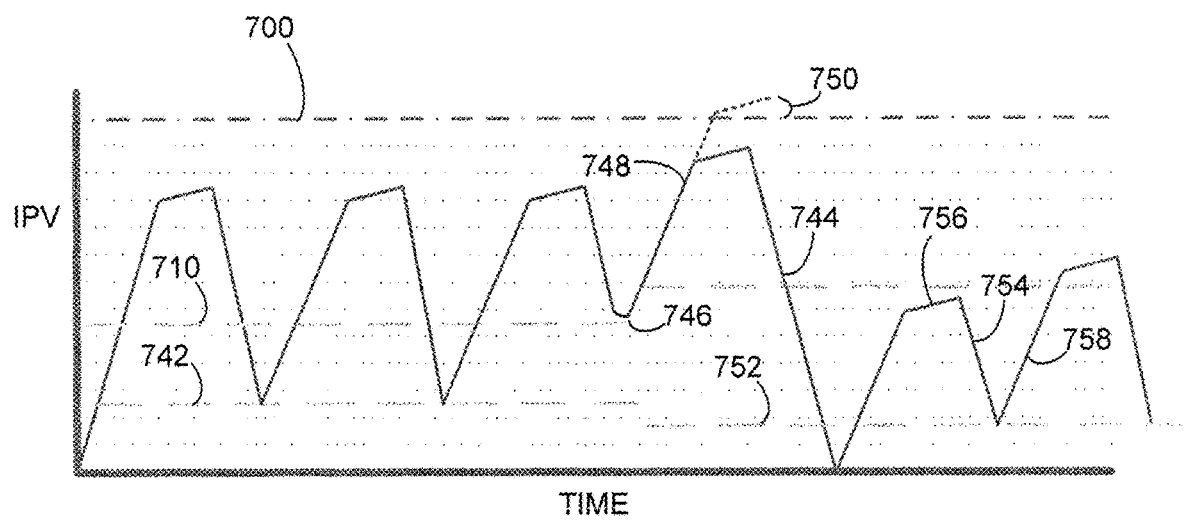
FIG. 69 shows an illustration of the implementation of a revised-cycle mode during a tidal therapy.

FIG. 69 illustrates that a planned standard tidal peritoneal dialysis (TPD) therapy may also be subject to a revised-cycle mode of TPD therapy if the cycler controller calculates that the user's Max IPV 700 is likely to be reached or exceeded during therapy. In this example, a user or clinician has selected a standard tidal therapy, in which a planned residual IP volume 742 (in actual volumetric terms or as a percentage of the initial fill volume) has been selected. As an optional feature of the cycler, the user or clinician has also chosen to perform a complete drain 744 after every three tidal fill-dwell-drain cycles, comprising a cycle cluster during a therapy session. In this example, a low-flow condition preventing draining below the maximum residual volume 710 occurs at the end of the third cycle 746. At the option of the user or clinician, the cycler either alerts the user to choose to end therapy, repeat a drain phase, or initiate a revised-cycle TPD therapy, or the cycler is allowed to automatically initiate a revised-cycle TPD therapy. In this case, the addition of a sixth cycle with a consequent reduction of the fill volume to a revised fill volume 748, is sufficient to avoid exceeding the Max IPV 700, which otherwise would have occurred 750. In this example, the cycler proceeds to perform a complete drain 744 at the end of a cluster, but resumes a standard TPD therapy thereafter. If the planned residual volume has been specified to be a percentage of the initial fill volume of the cluster, then that percentage may be applied to a revised residual IPV 752. The cycler may then calculate the subsequent drain volumes 754 by calculating the appropriate fraction of the revised fill volume 748 plus expected UF volume in order to drain to the revised residual IPV 752. Any subsequent fill volumes 758 may remain similar to the revised fill volume 748, as long as the cycler calculates that the Max IPV 700 will not be breached. Alternatively, the subsequent fill volumes may be reduced in a manner designed to maintain a relatively constant revised dwell-phase IPV 756. In this case, the cycler controller may be programmed to make the additional calculations necessary to ensure that the entire remaining dialysate solution will be properly divided among a revised fill volume 748 and later fill volumes reduced to maintain a revised dwell-phase IPV 756. In an alternative embodiment, the clinician or user may select the prescribed residual IP volume 742 to be relatively fixed volumetrically throughout therapy. In this case, the cycler controller may convert the percentage value of the residual IP volume 742 into a volumetric value (e.g. in milliliters), and continue to use that targeted residual volume after the revised-cycle mode has been instituted. In any event, the cycler controller may continue to apply the Max IPV 700 limitation in calculating any revised fill volumes.

Figure 70:
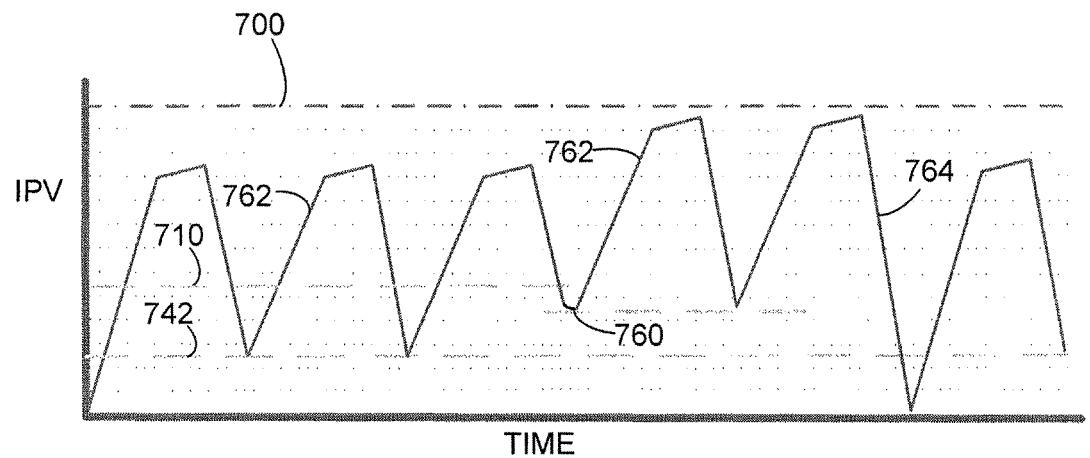
FIG. 70 shows an illustration of the implementation of an adaptive tidal mode during a tidal therapy.

FIG. 70 illustrates how an adaptive tidal therapy mode may be employed during a standard tidal therapy. In this example, a slow-drain condition 760 is encountered below the maximum residual volume 710. As an optional feature of the cycler, the user or clinician has also chosen in this example to perform a complete drain 764 after every four tidal fill-dwell-drain cycles, comprising a cycle cluster during a therapy session. In this case, the cycler calculates that the Max IPV 700 will not be reached if the tidal fill volume 762 is maintained. The cycler may be programmed to continue the tidal therapy at a revised residual IP volume 760 in order to avoid another slow-drain condition. (Alternatively, the cycler may be programmed to attempt to drain back to the previously prescribed residual IP volume 742). Since tidal therapy can continue without risk of breaching Max IPV 700, the user need not be alerted to the institution of a revised or floating residual volume of the adaptive tidal therapy mode. A full drain 764 is initiated as prescribed, and if successful, the cycler controller may re-institute the originally prescribed tidal therapy parameters. In an embodiment, the cycler may be programmed to alert the user if a full drain cannot be achieved at the end of a tidal therapy cluster.

While aspects of the invention have been described in conjunction with specific embodiments thereof, it is evident that many alternatives, modifications, and variations will be apparent to those skilled in the art. Accordingly, embodiments of the invention as set forth herein are intended to be illustrative, not limiting. Various changes may be made without departing from the spirit and scope of the invention.

The invention claimed is:

1. A method of configuring heating elements of an electrical heater for a peritoneal dialysis apparatus, the electrical heater comprising two heating elements, an end of each heating element connected to a common point, the method comprising:

configuring the heating elements initially in a series configuration;

connecting the electrical heater to line voltage;

measuring electrical current flow through the electrical heater;

determining from the measured current flow whether the line voltage is in a range of about 100-120 volts, or in a range of about 200-240 volts;

providing a user of the peritoneal dialysis apparatus with information about the determined line voltage; and receiving a verification signal from the user before finally configuring the heating elements in either a series configuration or a parallel configuration based on the determined line voltage.

2. A heating system for a peritoneal dialysis apparatus comprising:

a heater bag containing dialysate solution and positioned on a heater pan;

a pumping apparatus configured to pump dialysate into and out of the heater bag;

an electrical heating element to heat the heater pan;

one or more heater pan temperature sensors to detect a temperature of the heater pan;

a dialysate temperature sensor mounted in the heater pan, thermally isolated from the heater pan, and configured to contact an outer surface of the heater bag to measure a dialysate temperature of dialysate in the heater bag; and a controller programmed to perform an inner control loop process that modulates electrical power provided to the heating element to achieve a target heater pan temperature as measured by the one or more heater pan temperature sensors, and programmed to perform an outer control loop process that determines the target heater pan temperature based on a difference between a pre-determined target dialysate temperature and the dialysate temperature as measured by the dialysate temperature sensor.

3. A liquid heating system comprising:

a heater bag containing a liquid and positioned on a heater pan;

a pumping apparatus configured to pump liquid into and out of the heater bag;

an electrical heating element to heat the heater pan;

one or more heating pan temperature sensors to detect a temperature of the heater pan;

a liquid temperature sensor mounted in the heater pan, thermally isolated from the heater pan, and configured to contact an outer surface of the heater bag to detect a liquid temperature of liquid in the heater bag; and a controller programmed to perform an inner control loop process that modulates electrical power provided to the heater element to achieve a target heater pan temperature as measured by the one or more heater pan temperature sensors, and programmed to perform an outer control loop process that determines the target heater pan temperature based on a difference between a pre-determined target liquid temperature and an equilibrium temperature, wherein the equilibrium temperature is a weighted average of the liquid temperature and the heater pan temperature, the liquid temperature being weighted by a thermal capacitance, mass, or volume of liquid present in the heater bag, and the heater pan temperature being weighted by a thermal capacitance, mass, or volume of the heater pan.

4. A liquid heating system comprising:
a heater bag containing a liquid and positioned on a heater pan;
a pumping apparatus configured to pump liquid into and out of the heater bag;
an electrical heating element to heat the heater pan;
one or more heating pan temperature sensors to detect the temperature of the heater pan;
a liquid temperature sensor mounted in the heater pan, thermally isolated from the heater pan, and configured to contact an outer surface of the heater bag to detect a liquid temperature of liquid in the heater bag; and
a controller programmed to perform an inner control loop process that modulates electrical power provided to the heater element to achieve a target heater pan temperature as measured by the one or more heater pan temperature sensors, and programmed to perform an outer control loop process that determines the target heater pan temperature based on a difference between a pre-determined target liquid temperature and an equilibrium temperature, wherein
the equilibrium temperature is a weighted average of the liquid temperature and the target heater pan temperature, the liquid temperature being weighted by a thermal capacitance, mass, or volume of liquid present in the heater bag, and the target heater pan temperature being weighted by the thermal capacitance, mass, or volume of the heater pan.

5. The liquid heating system of claim 4, wherein the inner control loop process includes an integrator element that generates a integral value with anti-windup logic to limit an integral value of a difference between the target heater pan temperature and the measured heater pan temperature.

6. The liquid heating system of claim 4, wherein the inner control loop process includes a maximum heater power command, the outer control loop process includes a maximum target heater pan temperature, and the outer control loop process includes an integrator element that is applied if:
  a rate of change of the liquid temperature is less than a pre-determined value;
  the liquid temperature is within a pre-determined range of the target liquid temperature;
  the amount of liquid in the heater bag is greater than a pre-determined value; or
  neither an output value of the inner control loop process, nor an output value of the outer control loop process are at pre-determined maximum values.

7. The liquid heating system of claim 4, wherein the controller is configured to set the electrical power to zero if the pan temperature exceeds a pre-determined value.

* * * * *